(12) United States Patent
Guzzo et al.

(10) Patent No.: US 8,575,186 B2
(45) Date of Patent: Nov. 5, 2013

(54) EPIMINOCYCLOALKYL[B] INDOLE DERIVATIVES AS SEROTONIN SUB-TYPE 6 (5-HT$_6$) MODULATORS AND USES THEREOF

(75) Inventors: Peter R. Guzzo, Niskayuna, NY (US); Alan J. Henderson, Albany, NY (US); Kassoum Nacro, Albany, NY (US); Matthew L. Isherwood, Delmar, NY (US); Animesh Ghosh, Singapore (SG); Kai Xiang, Singapore (SG)

(73) Assignee: Albany Molecular Research, Inc., Albany, NY (US)

( * ) Notice: Subject to any disclaimer, the term of this patent is extended or adjusted under 35 U.S.C. 154(b) by 301 days.

(21) Appl. No.: 12/898,271

(22) Filed: Oct. 5, 2010

(65) Prior Publication Data

US 2011/0112122 A1 May 12, 2011

Related U.S. Application Data

(60) Provisional application No. 61/248,529, filed on Oct. 5, 2009.

(51) Int. Cl.
*A61K 31/506* (2006.01)
*A61K 31/439* (2006.01)
*C07D 471/18* (2006.01)
*A61P 3/04* (2006.01)
*A61P 3/10* (2006.01)
*A61P 25/00* (2006.01)
*A61P 3/00* (2006.01)
*A61P 25/18* (2006.01)
*A61P 25/28* (2006.01)

(52) U.S. Cl.
USPC .............. 514/269; 514/286; 546/63; 544/298

(58) Field of Classification Search
USPC ...................... 514/269, 286; 546/63; 544/298
See application file for complete search history.

(56) References Cited

U.S. PATENT DOCUMENTS

| | | | |
|---|---|---|---|
| 2,894,942 A | 7/1959 | Hydro et al. | |
| 3,518,270 A | 6/1970 | Shavel et al. | |
| 3,914,421 A | 10/1975 | Rajagopalan | |
| 4,013,652 A | 3/1977 | Rajagopalan | |
| 4,115,577 A | 9/1978 | Rajagopalan | |
| 4,183,936 A | 1/1980 | Rajagopalan | |
| 4,219,550 A | 8/1980 | Rajagopalan | |
| 4,238,607 A | 12/1980 | Rajagopalan | |
| 5,187,180 A | 2/1993 | Gillard | |
| 5,250,537 A * | 10/1993 | Mewshaw et al. | 514/278 |
| 5,646,287 A | 7/1997 | Vedejs et al. | |
| 5,811,551 A | 9/1998 | Chen et al. | |
| 6,156,757 A | 12/2000 | Kennis et al. | |
| 6,469,020 B2 | 10/2002 | Batty et al. | |
| 6,548,493 B1 | 4/2003 | Robichaud et al. | |
| 6,552,017 B1 | 4/2003 | Robichaud et al. | |
| 6,951,881 B2 | 10/2005 | Cole et al. | |
| 6,995,176 B2 | 2/2006 | Bernotas et al. | |
| 2002/0119972 A1 | 8/2002 | Leftheris et al. | |
| 2003/0023085 A1 | 1/2003 | Chen et al. | |
| 2003/0176694 A1 | 9/2003 | Chen et al. | |
| 2003/0232843 A1 | 12/2003 | Cole et al. | |
| 2004/0087593 A1 | 5/2004 | Clark et al. | |
| 2004/0162332 A1 | 8/2004 | Fu | |
| 2004/0214815 A1 | 10/2004 | McWhorter, Jr. et al. | |
| 2006/0287299 A1 | 12/2006 | Sheldon | |
| 2007/0027178 A1 | 2/2007 | Lee | |
| 2007/0066608 A1 | 3/2007 | Bartolome-Nebreda et al. | |
| 2007/0123574 A1 | 5/2007 | De Kock et al. | |
| 2007/0197629 A1 | 8/2007 | Somei et al. | |
| 2007/0244145 A1 | 10/2007 | Kumagai et al. | |
| 2008/0194638 A1 | 8/2008 | Dedhiya et al. | |
| 2010/0249105 A1 | 9/2010 | Schrimpf et al. | |
| 2012/0184531 A1 | 7/2012 | Guzzo et al. | |

FOREIGN PATENT DOCUMENTS

| | | |
|---|---|---|
| EP | 0 203 505 A1 | 12/1986 |
| EP | 0473550 A1 | 8/1991 |
| EP | 1 505 061 A1 | 2/2005 |
| WO | 99/33800 A1 | 7/1999 |

(Continued)

OTHER PUBLICATIONS

Mewshaw et al., Journal of Medicinal Chemistry (1993), 36(3), 343-52.*
Mewshaw et al., Journal of Medicinal Chemistry (1993), 36(10), 1488-95.*
International Search Report and Written Opinion for PCT/US10/51485, dated Dec. 2, 2010.
Gremmen et al., "The Synthesis of New Heterocyclic Bridged Ring Systems. Analogs of Tetrahydro-beta-Carbolines," Tet. Lett. 39:1441-1444 (1998).

(Continued)

*Primary Examiner* — Niloofar Rahmani
(74) *Attorney, Agent, or Firm* — LeClairRyan, a Professional Corporation

(57) ABSTRACT

The present invention relates to epiminocycloalkyl[b]indole derivatives as serotonin sub-type 6 (5-HT$_6$) modulators, pharmaceutical compositions including these compounds, and methods of preparation and use thereof. These compounds are useful in the treatment of central nervous system disorders including obesity, metabolic syndrome, cognition, and schizophrenia. The subject compounds have the structure of formula (I)

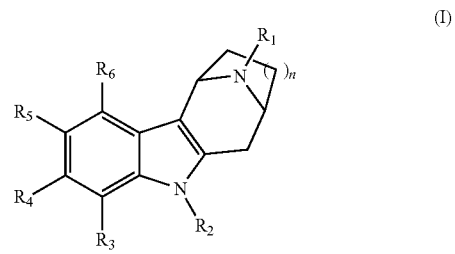

with the substituents being described herein.

53 Claims, No Drawings

(56) References Cited

FOREIGN PATENT DOCUMENTS

| WO | 00/35922 A1 | 6/2000 |
| WO | 00/77001 A1 | 12/2000 |
| WO | 00/77002 A1 | 12/2000 |
| WO | 00/77010 A2 | 12/2000 |
| WO | 01/58869 A2 | 8/2001 |
| WO | 01/87883 A1 | 11/2001 |
| WO | 02/089729 A2 | 11/2002 |
| WO | 03/014118 A1 | 2/2003 |
| WO | 03097598 A1 | 11/2003 |
| WO | 2004/056324 A2 | 7/2004 |
| WO | 2006/005063 A2 | 1/2006 |
| WO | 2006/064355 A2 | 6/2006 |
| WO | 2006/101434 A1 | 9/2006 |
| WO | 2007/050795 A2 | 5/2007 |
| WO | 2008/060190 A2 | 5/2008 |
| WO | 2008/060190 A3 | 5/2008 |
| WO | 2008/081282 A2 | 7/2008 |
| WO | 2009/055828 A1 | 4/2009 |
| WO | 2009/120720 A1 | 10/2009 |
| WO | 2011087712 A2 | 7/2011 |
| WO | 2012099952 A2 | 7/2012 |

OTHER PUBLICATIONS

Bailey et al., "New Asymmetric Route to Bridged Indole Alkaloids: Formal Enantiospecific Syntheses of (−)-Suaveoline, (−)-Raumacline and (−)-N(b)-Methylraumacline," J. Chem. Soc. Perkin Trans. 1:1209-1214 (1997).

Hoyer et al., "VII, International Union of Pharmacology Classification of Receptors for 5-Hydroxytryptamine (Serotonin)," Pharmacol. Rev. 46(2):157-203 (1994).

Hoffman et al., "Distribution of Serotonin 5-HT(1C) Receptor mRNA in Adult Rat Brain," FEBS Lett. 247(2):453-462 (1989).

Nonogaki et al., "Leptin-Independent Hyperphagia and Type 2 Diabetes in Mice with a Mutated Serotonin 5-HT(2C) Receptor Gene," Nat. Med. 4(10):1152-1156 (1998).

Vickers et al., "Reduced Satiating Effect of d-Fenfluramine in Serotonin 5-HT(2C) Receptor Mutant Mice," Psychopharmacol. 143:309-314 (1999).

Vickers et al., "Comparative Effects of Continuous Infusion of mCPP, Ro 60/0175 and d-Fenfluramine on Food Intake, Water Intake, Body Weight and Locomotor Activity in Rats," Br. J. Pharmacol. 130:1305-1314 (2000).

Vickers et al., "Evidence that Hypophagia Induced by d-Fenfluramine and d-Norfenfluramine in the Rat is Mediated by 5-HT(2C) Receptors," Neuropharmacol. 41:200-209 (2001).

Mazzola-Pomietto et al., "Evidence that m-Chlorophenylpiperazine-Induced Hyperthermia in Rats is Mediated by Stimulation of 5-HT(2C) Receptors," Psychopharmacol. 123:333-339 (1996).

Sharpley et al., "Slow Wave Sleep in Humans: Role of 5-HT(2A) and 5-HT(2C) Receptors," Neuropharmacol. 33:467-471 (1994).

Rittenhouse et al., "Evidence that ACTH Secretion is Regulated by Serotonin(2A/2C) (5-HT(2A/2C) Receptors," J. Pharmacol. Exp. Ther. 271:1647-1655 (1994).

Di Matteo et al., "Role of 5-HT(2C) Receptors in the Control of Central Dopamine Function," Trends Pharmacol. Sci. 22:229-232 (2001).

Cryan et al., "Antidepressant-Like Behavioral Effects Mediated by 5-Hydroxytryptamine(2C) Receptors," J. Pharmacol. Exp. Ther. 295(3):1120-1126 (2000).

Grottick et al., "Activation of 5-HT(2C) Receptors Reduces the Locomotor and Rewarding Effects of Nicotine," Psychopharmacol. 157:292-298 (2001).

Grottick et al., "Studies to Investigate the Role of 5-HT(2C) Receptors on Cocaine- and Food-Maintained Behavior," J. Pharmacol. Exp. Ther. 295(3):1183-1191 (2000).

Chojnacka-Wojcik et al., "Involvement of 5-HT(2C) Receptors in the m-CPP-Induced Antinociception in Mice," Pol. J. Pharmacol. 46:423-428 (1994).

Millan et al., "5-HT(2C) Receptors Mediate Penile Erections in Rats: Actions of Novel and Selective Agonists and Antagonists," Eur. J. Pharmacol. 325:9-12 (1997).

Kennis et al., "New 2-Substituted 1,2,3,4-Tetrahydrobenzofuro[3,2-c]pyridine Having Highly Active and Potent Central Alpha2-Antagonistic Activity as Potential Antidepressants," Bioorg. Med. Chem. Lett. 10:71-74 (2000).

International Search Report and Written Opinion for PCT/US2012/021708 dated Nov. 28, 2012.

\* cited by examiner

EPIMINOCYCLOALKYL[B] INDOLE DERIVATIVES AS SEROTONIN SUB-TYPE 6 (5-HT$_6$) MODULATORS AND USES THEREOF

This application claims benefit of U.S. Provisional Patent Application Ser. No. 61/248,529, filed Oct. 5, 2009, which is hereby incorporated by reference in its entirety.

FIELD OF THE INVENTION

The present invention relates to epiminocycloalkyl[b]indole derivatives as serotonin sub-type 6 (5-HT$_6$) modulators and uses thereof.

BACKGROUND OF THE INVENTION

Various central nervous system (CNS) disorders such as anxiety, depression, motor disorders, etc., are believed to involve a disturbance of the neurotransmitter 5-hydroxytryptamine (5-HT) or serotonin. Serotonin is localized in the central and peripheral nervous systems and is known to affect many types of conditions including psychiatric disorders, motor activity, feeding behavior, sexual activity, and neuroendocrine regulation among others. The effects of serotonin are regulated by the various 5-HT receptor subtypes. Known 5-HT receptors include the 5-HT$_1$ family (e.g. 5-HT$_{1A}$), the 5-HT$_2$ family (e.g. 5-HT$_{2A}$), 5-HT$_3$, 5-HT$_4$, 5-HT$_5$, 5-HT$_6$ and 5-HT$_7$ subtypes.

The biogenic amine serotonin (5-hydroxytryptamine; 5-HT) is a brain neurotransmitter that has been strongly implicated in the pathophysiology and treatment of a wide variety of neuropsychiatric disorders. It exerts its effects through a diverse family of serotonin receptor subtypes. Of the 14 different mammalian serotonin receptors to have been cloned, all but one are members of the G-protein coupled receptor superfamily. Several of these, including the serotonin 5-HT$_6$ receptor, stimulate adenylyl cyclase via G coupling. 5-HT$_6$ has a high affinity for several therapeutically important antidepressant, antianxiety, hallucinogenic, and antipsychotic drugs, particularly the atypical antipsychotics such as clozapine. The relevance of the 5-HT$_6$ receptor to psychotherapeutics is indicated both through its unique anatomical distribution and pharmacological properties.

The recently identified human 5-HT$_6$ receptor subtype has been cloned, and the extensive distribution of its mRNA has been reported. Highest levels of 5-HT$_6$ receptor mRNA have been observed in the olfactory tubercle, the striatum, nucleus accumbens, dentate gyms, and CA1, CA2, and CA3 regions of the hippocampus. Lower levels of 5-HT$_6$ receptor mRNA are seen in the granular layer of the cerebellum, several diencephalic nuclei, amygdalae, and in the cortex. Northern blots have revealed that 5-HT$_6$ receptor mRNA appears to be exclusively present in the brain, with little evidence for its presence in peripheral tissues. The high affinity of a number of antipsychotic agents for the 5-HT$_6$ receptor, in addition to its mRNA localization in striatum, olfactory tubercle and nucleus accumbens suggests that some of the clinical actions of these compounds may be mediated through this receptor. Therefore, 5-HT$_6$ receptor ligands are believed to be of potential use in the treatment of certain CNS disorders such as anxiety, depression, epilepsy, obsessive compulsive disorder, attention deficit disorder, migraine, cognitive memory enhancement (e.g. for the treatment of Alzheimer's disease), sleep disorders, feeding disorders (e.g. anorexia, obesity, or bulimia), neurodegenerative disorders (e.g. stroke or head trauma), panic attacks, withdrawal from drug abuse (e.g. cocaine, ethanol, nicotine or benzodiazepines), schizophrenia, or the like; or in the treatment of certain gastrointestinal disorders such as irritable bowel syndrome.

The high affinity of a number of antipsychotic agents for the 5-HT$_6$ receptor, in addition to its mRNA localization in striatum, olfactory tubercle and nucleus accumbens suggests that some of the clinical actions of these compounds may be mediated through this receptor. Compounds which interact with, stimulate, or inhibit the 5-HT$_6$ receptor are commonly referred to as 5-HT$_6$ ligands. In particular, 5-HT$_6$ selective ligands have been identified as potentially useful in the treatment of certain CNS disorders such as Parkinson's disease, Huntington's disease, anxiety, depression, manic depression, psychoses, epilepsy, obsessive compulsive disorders, migraine, Alzheimer's disease (enhancement of cognitive memory), sleep disorders, feeding disorders such as anorexia, obesity, and bulimia, panic attacks, attention deficit hyperactivity disorder (ADHD), attention deficit disorder (ADD), withdrawal from drug abuse such as cocaine, ethanol, nicotine and benzodiazepines, schizophrenia, bipolar disorder, and also disorders associated with spinal trauma and/or head injury such as hydrocephalus. Such compounds are also expected to be of use in the treatment of certain gastrointestinal (GI) disorders such as functional bowel disorder and irritable bowel syndrome (See for examples. Roth et al., *J. Pharmacol. Exp. Ther.* 268:1403-14120 (1994), Sibley et al., *Mol. Pharmacol.* 43:320-327 (1993), Sleight et al., *Neurotransmission* 11:1-5 (1995), and Sleight et al., *Serotonin ID Research Alert* 2(3):115-8 (1997)). Furthermore, the effect of 5-HT$_6$ antagonist and 5-HT$_6$ antisense oligonucleotides to reduce food intake in rats has been reported (Bentley et al., *Br. J. Pharmacol. Suppl.* 126:66 (1999) and Bentley et al., *J. Psychopharmacol. Suppl. A*64:255 (1997)).

Scientific research has revealed a potential therapeutic use for modulators of the 5-HT$_6$ receptor, especially with regard to various CNS disorders. Blocking 5-HT$_6$ receptor function has been shown to enhance cholinergic transmission (Bentley et al., *Br. J. Pharmacol.* 126:1537-1542 (1999) and Riemer et al., *J. Med. Chem.* 46:1273-1276 (2003)). 5-HT$_6$ antagonist have also been shown to reverse cognitive deficits in in vivo cognition models induced by the muscarinic antagonist scopolamine (Woolley et al., *Psychopharmacology* 170:358-367 (2003) and Foley et al., *Neuropsychopharmacology* 29:93-100 (2004)).

Studies have shown that 5-HT$_6$ antagonists increase levels of glutamate and aspartate in the frontal cortex and dorsal hippocampus as well as acetylcholine in the frontal cortex. These neurochemicals are known to be involved in memory and cognition (Dawson et al., *Neuropsychopharmacology* 25(5):662-668 (2001); Gerard et al., *Brain Res.* 746:207-219 (1997); and Riemer et al., *J. Med. Chem.* 46(7):1273-1276 (2003)).

Studies have also shown that 5-HT$_6$ antagonist increases the level of dopamine and noradrenaline in the medial prefrontal cortex (Lacroix et al., *Synapse* 51:158-164 (2004)). In addition, 5-HT$_6$ receptor antagonists have been shown to improve performance in the attentional set shifting task (Hatcher et al., *Psychopharmacology* 181(2):253-9 (2005)). Therefore, 5-HT$_6$ ligands are expected to be useful in the treatment of disorders where cognitive deficits are a feature, such as schizophrenia. Several antidepressants and atypical antipsychotics bind to the 5-HT$_6$ receptor and this may be a factor in their profile of activities (Roth et al., *J. Pharm. Exp. Therapeut.* 268:1402-1420 (1994); Sleight et al., *Exp. Opin. Ther. Patents* 8:1217-1224 (1998); Kohen et al., *J. Neurochem.* 66(1):47-56 (1996); Sleight et al., *Brit. J. Pharmacol.* 124:556-562 (1998); and Bourson et al., *Brit. J. Pharmacol.* 125:1562-1566 (1998)).

Stean et al., *Brit. J. Pharmacol.* 127 Proc. Supplement 131P (1999), have described the potential use of 5-HT$_6$ modulators in the treatment of epilepsy. 5-HT$_6$ receptors have also been linked to generalized stress and anxiety states (Yoshioka et al., *Life Sciences* 62(17/18):1473-1477 (1998)). 5-HT$_6$ agonists have been shown to elevate levels of GABA in brain regions associated with anxiety and shown positive effects in models predictive of obsessive-compulsive disorder (Schechter et al., *NeuroRx.* 2(4):590-611 (2005)). The use of modulators for this receptor is therefore expected for a wide range of CNS disorders.

Moreover, a reduction in food intake in rats has been reported using 5-HT$_6$ receptor modulators (Bentley et al., *Br. J. Pharmacol. Suppl.* 126:66 (1999); Bentley et al. *J. Psychopharmacol. Suppl.* A64:255 (1997); Pendharkar et al., *Society for Neuroscience* (2005); Heal et al. *Pharmacol. Ther.* 117, 207-231 (2008)). 5-HT$_6$ receptor modulators may therefore also be useful in the treatment of feeding disorders like anorexia, obesity, bulimia and similar disorders and also type 2 diabetes.

The importance of psychoactive drugs in present treatment of mental illness, and the presence of serious and undesirable side-effects with their use, makes the development of improved drugs of great interest. Furthermore, the need for a safe, efficacious treatment for obesity is highly desirable. Animal models useful in screening assays provide a benefit by determining candidate agents that have improved specificity of action.

Therefore, the present invention is directed to novel compounds which provide alternatives in overcoming these and other deficiencies in the art.

SUMMARY OF THE INVENTION

A first aspect of the present invention is directed to a compound of formula (I):

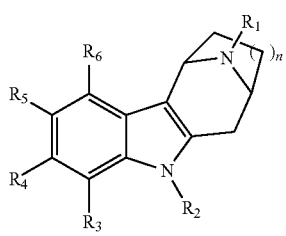

(I)

wherein:

n is an integer from 1 to 2; and $R_1$ is independently H, $C_1$-$C_6$ alkyl, $C_2$-$C_6$ alkenyl, $C_2$-$C_6$ alkynyl, $C_1$-$C_6$ alkoxy, $C_3$-$C_6$ cycloalkyl, $C_4$-$C_7$ cycloalkylalkyl, aryl $C_1$-$C_6$ alkyl, mono or polycyclic aryl, or mono or polycyclic heteroaryl containing from 1 to 5 heteroatoms selected from the group consisting of nitrogen, sulfur, and oxygen, each one of $R_1$ optionally substituted from 1 to 3 times with substituents selected from the group consisting of halogen, OH, OR$_8$, —C(O)R$_8$, —C(O)OR$_8$, —C(O)NR$_8$R$_9$, —NHR$_8$, —NR$_8$R$_9$, —SR$_8$, —S(O)R$_8$, —S(O)$_2$R$_8$, NH$_2$, CN, NO$_2$, $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, mono or polycyclic aryl, and mono or polycyclic heteroaryl containing from 1 to 5 heteroatoms selected from the group consisting of nitrogen, sulfur, and oxygen;

$R_2$ is independently —S(O)R$_8$, —S(O)$_2$R$_8$, $C_1$-$C_6$ alkyl, straight or branched $C_2$-$C_6$ alkenyl, $C_3$-$C_6$ cycloalkyl, mono or polycyclic aryl, or mono or polycyclic heteroaryl containing from 1 to 5 heteroatoms selected from the group consisting of nitrogen, sulfur, and oxygen, each optionally substituted from 1 to 3 times with substituents selected from the group consisting of halogen, OH, NO$_2$, $C_1$-$C_6$ linear alkyl, and $C_2$-$C_6$ alkenyl;

$R_3$ and $R_6$ are independently H, halogen, CF$_3$, CHF$_2$, CH$_2$F, OH, OR$_8$, —C(O)R$_8$, —C(O)OR$_8$, —C(O)NR$_8$R$_9$, —O—(CH$_2$)$_p$—C(O)NR$_8$R$_9$, —NHR$_8$, —NR$_8$R$_9$, —SR$_8$, —S(O)R$_8$, —S(O)$_2$R$_8$, NH$_2$, CN, NO$_2$, $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, mono or polycyclic aryl, wherein p is an integer from 0 to 6;

$R_4$ and $R_5$ are independently H, $C_1$-$C_6$ alkyl, halogen, or $R_7$SO$_2$—;

$R_7$ is independently a substituted or unsubstituted mono or polycyclic aryl or substituted or unsubstituted mono or polycyclic heteroaryl containing from 1 to 5 heteroatoms selected from the group consisting of oxygen, nitrogen, and sulfur, each one of $R_7$ optionally substituted from 1 to 4 times for each cyclic ring with substituents selected from the group consisting of H, OH, OR$_8$, —C(O)R$_8$, —C(O)OR$_8$, —C(O)NR$_8$R$_9$, —NHR$_8$, —NR$_8$R$_9$, —SR$_8$, —S(O)R$_8$, —S(O)$_2$R$_8$, NH$_2$, CN, NO$_2$, halogen, $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, mono or polycyclic aryl, and mono or polycyclic heteroaryl, each one of $R_7$ substituents optionally substituted from 1 to 3 times with substitutents selected from the group consisting of halogen, H, OH, OR$_8$, —C(O)R$_8$, —C(O)OR$_8$, —C(O)NR$_8$R$_9$, —NHR$_8$, —NR$_8$R$_9$, —SR$_8$, —S(O)R$_8$, —S(O)$_2$R$_8$, NH$_2$, CN, NO$_2$, $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, and mono or polycyclic aryl;

$R_8$ and $R_9$ are independently H, $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, a monocyclic aryl or a monocyclic heteroaryl containing from 1-5 heteroatoms selected from the group consisting of nitrogen, oxygen, and sulfur each one of $R_8$ and $R_9$ optionally substituted from 1 to 3 times with substituents selected from the group consisting of halogen, OH, CN, NO$_2$, NH$_2$, H, $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, a monocyclic aryl, and a monocyclic heteroaryl; or $R_8$ and $R_9$ can combine to form a 4- to 7-membered heterocyclyl or a mono heteroaryl each containing from 1 to 5 heteroatoms selected from the group consisting of nitrogen, sulfur, and oxygen, wherein the heterocyclyl or heteroaryl are optionally substituted from 1 to 3 times with substituents selected from the group consisting of halogen, OH, CN, NO$_2$, NH$_2$, H, $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, and a monocyclic aryl, with the proviso that at least one of $R_4$ and $R_5$, but not both, is $R_7$SO$_2$—;

or an oxide thereof, a pharmaceutically acceptable salt thereof, a solvate thereof, or prodrug thereof.

A second aspect of the present invention is directed to a method for modulating serotonin sub-type 6. The method involves providing the compound of formula (I) and contacting a serotonin receptor with said compound of formula (I) under conditions effective to modulate serotonin sub-type 6.

A third aspect of the present invention is directed to the process for preparation of a product compound of formula (I):

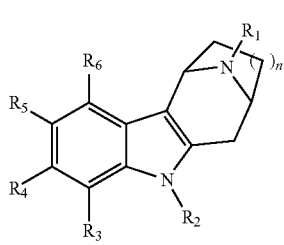

(I)

wherein n is an integer from 1 to 2; and $R_1$ is independently H, $C_1$-$C_6$ alkyl, $C_2$-$C_6$ alkenyl, $C_2$-$C_6$ alkynyl, $C_1$-$C_6$ alkoxy, $C_3$-$C_6$ cycloalkyl, $C_4$-$C_7$ cycloalkylalkyl, aryl $C_1$-$C_6$ alkyl, mono or polycyclic aryl, or mono or polycyclic heteroaryl containing from 1 to 5 heteroatoms selected from the group consisting of nitrogen, sulfur, and oxygen, each one of $R_1$ optionally substituted from 1 to 3 times with substituents selected from the group consisting of halogen, OH, $OR_8$, —$C(O)R_8$, —$C(O)OR_8$, —$C(O)NR_8R_9$, —$NHR_8$, —$NR_8R_9$, —$SR_8$, —$S(O)R_8$, —$S(O)_2R_8$, $NH_2$, CN, $NO_2$, $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, mono or polycyclic aryl, and mono or polycyclic heteroaryl containing from 1 to 5 heteroatoms selected from the group consisting of nitrogen, sulfur, and oxygen;

$R_2$ is independently —$C(O)R_8$, —$C(O)OR_8$, —$C(O)NR_8R_9$, —$S(O)R_8$, —$S(O)_2R_8$, $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, aryl $C_1$-$C_6$ alkyl, mono or polycyclic aryl, or mono or polycyclic heteroaryl containing from 1 to 5 heteroatoms selected from the group consisting of nitrogen, sulfur, and oxygen, each optionally substituted from 1 to 3 times with substituents selected from the group consisting of halogen, OH, $NH_2$, CN, $NO_2$, $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, mono or polycyclic aryl, and mono or polycyclic heteroaryl;

$R_3$ and $R_6$ are independently H, halogen, $CF_3$, $CHF_2$, $CH_2F$, OH, $OR_8$, —$C(O)R_8$, —$C(O)OR_8$, —$C(O)NR_8R_9$, —O—$(CH_2)_p$—$C(O)NR_8R_9$, —$NHR_8$, —$NR_8R_9$, —$SR_8$, —$S(O)R_8$, —$S(O)_2R_8$, $NH_2$, CN, $NO_2$, $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, mono or polycyclic aryl, wherein p is an integer from 0 to 6;

$R_4$ and $R_5$ are independently H, $C_1$-$C_6$ alkyl, halogen, or $R_7SO_2$—;

$R_7$ is independently a substituted or unsubstituted mono or polycyclic aryl or substituted or unsubstituted mono or polycyclic heteroaryl containing from 1 to 5 heteroatoms selected from the group consisting of oxygen, nitrogen, and sulfur, each one of $R_7$ optionally substituted from 1 to 4 times for each cyclic ring with substituents selected from the group consisting of H, OH, $OR_8$, —$C(O)R_8$, —$C(O)OR_8$, —$C(O)NR_8R_9$, —$NHR_8$, —$NR_8R_9$, —$SR_8$, —$S(O)R_8$, —$S(O)_2R_8$, $NH_2$, CN, $NO_2$, halogen, $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, mono or polycyclic aryl, and mono or polycyclic heteroaryl, each one of $R_7$ substituents optionally substituted from 1 to 3 times with substitutents selected from the group consisting of halogen, H, OH, $OR_8$, —$C(O)R_8$, —$C(O)OR_8$, —$C(O)NR_8R_9$, —$NHR_8$, —$NR_8R_9$, —$SR_8$, —$S(O)R_8$, —$S(O)_2R_8$, $NH_2$, CN, $NO_2$, $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, and mono or polycyclic aryl;

$R_8$ and $R_9$ are independently H, $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, a monocyclic aryl or a monocyclic heteroaryl containing from 1-5 heteroatoms selected from the group consisting of nitrogen, oxygen, and sulfur each one of $R_8$ and $R_9$ optionally substituted from 1 to 3 times with substituents selected from the group consisting of halogen, OH, CN, $NO_2$, $NH_2$, H, $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, a monocyclic aryl, and a monocyclic heteroaryl; or $R_8$ and $R_9$ can combine to form a 4- to 7-membered heterocyclyl or a mono heteroaryl each containing from 1 to 5 heteroatoms selected from the group consisting of nitrogen, sulfur, and oxygen, wherein the heterocyclyl or heteroaryl are optionally substituted from 1 to 3 times with substituents selected from the group consisting of halogen, OH, CN, $NO_2$, $NH_2$, H, $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, and a monocyclic aryl, with the proviso that at least one of $R_4$ and $R_5$, but not both, is $R_7SO_2$—;

or an oxide thereof, a pharmaceutically acceptable salt thereof, a solvate thereof, or prodrug thereof said process comprising:

providing a first intermediate having the structure:

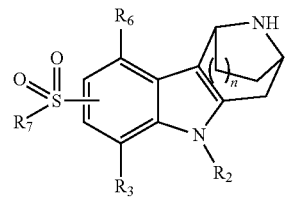

and reacting a first intermediate with an electrophile $R_1Z$ under conditions effective to form the compound of formula (I), wherein Z is a leaving group.

Another aspect of the present invention relates to a process for enantiomeric resolution. In this process, a mixture of diastereomers of the compound of formula (II) is provided

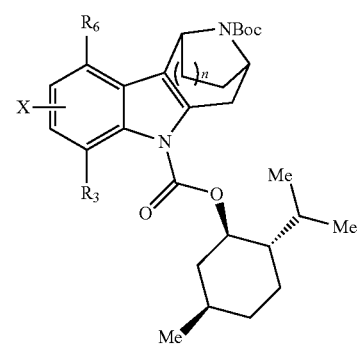

(II)

where:

$R_3$ and $R_6$ are independently H, halogen, $CF_3$, $CHF_2$, $CH_2F$, OH, $OR_8$, —$C(O)R_8$, —$C(O)OR_8$, —$C(O)NR_8R_9$, —$NHR_8$, —$NR_8R_9$, —$SR_8$, —$S(O)R_8$, —$S(O)_2R_8$, $NH_2$, CN, $NO_2$, $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, mono or polycyclic aryl; and X is independently chloro, bromo, iodo, or triflyl. The mixture is subjected to a resolution procedure under conditions effective to separate the diastereomers of the compound of formula (II) from one another.

Additional aspects of the present invention include pharmaceutical compositions comprising a compound of this invention and a pharmaceutically acceptable carrier and, optionally, one or more additional active agent(s) as discussed below. Further aspects include methods of treating a disease state related to or modulated by the 5-HT$_6$ receptor, in a patient, such as humans or animals (e.g. rat, mice, pigs, horses, monkeys, cows, sheep, guinea pigs, dogs, and cats).

The compounds of the present invention are effective in modulating the activity of the 5-HT$_6$ receptor in humans or animals, (e.g. rat, mice, pigs, horses, monkeys, cows, sheep, guinea pigs, dogs, and cats). These compounds exhibit excellent activity for 5-HT$_6$ receptors, especially where such activity affects states associated with CNS disorders including motor, mood, personality, behavioral, psychiatric, cognitive, and neurodegenerative disorders, such as, but not limited to, Alzheimer's disease (enhancement of cognitive memory), Parkinson's disease, Huntington's disease, anxiety, depression, manic depression, epilepsy, obsessive compulsive disorders, migraine, sleep disorders, feeding disorders such as obesity, anorexia, and bulimia, panic attacks, attention deficit hyperactivity disorder (ADUD), attention deficit disorder (ADD), withdrawal from drug abuse such as cocaine, ethanol, nicotine and benzodiazepines, psychoses, such as schizophrenia, bipolar disorder, and also disorders associated with spinal trauma and/or head injury such as hydrocephalus. Such compounds are also useful for the treatment of memory/cognitive impairment associated with Alzheimer's disease, schizophrenia, Parkinson's disease, Huntington's disease Pick's disease, Creutzfeld-Jakob disease, HIV, cardiovascular disease, head trauma or age-related cognitive decline. In addition, such compounds are also expected to be of use in the treatment of certain gastrointestinal (GI) disorders such as, but not limited to, functional bowel disorder, constipation, including chronic constipation, gastroesophageal reflux disease (GERD), nocturnal-GERD, and irritable bowel syndrome (IBS), including diarrhea-predominant IBS (IBS-c), constipation-predominant IBS (IBS-c) and alternating constipation/diarrhea IBS.

In addition to their use in therapeutic medicine, the compounds of formula I, salts, oxides thereof, solvates or solvated salts thereof, may also be useful as pharmacological tools in the development and standardization of in vitro and in vivo test systems for the evaluation of the effects of modulators of 5HT$_6$ related activity in laboratory animals such as cats, dogs, rabbits, monkeys, rats and mice, as part of the search for new therapeutics agents.

DETAILED DESCRIPTION OF THE INVENTION

A first aspect of the present invention is directed to a compound of formula (I):

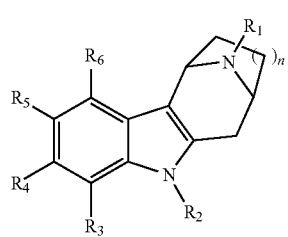

(I)

wherein:

n is an integer from 1 to 2; and $R_1$ is independently H, $C_1$-$C_6$ alkyl, $C_2$-$C_6$ alkenyl, $C_2$-$C_6$ alkynyl, $C_1$-$C_6$ alkoxy, $C_3$-$C_6$ cycloalkyl, $C_4$-$C_7$ cycloalkylalkyl, aryl $C_1$-$C_6$ alkyl, mono or polycyclic aryl, or mono or polycyclic heteroaryl containing from 1 to 5 heteroatoms selected from the group consisting of nitrogen, sulfur, and oxygen, each one of $R_1$ optionally substituted from 1 to 3 times with substituents selected from the group consisting of halogen, OH, OR$_8$, —C(O)R$_8$, —C(O)OR$_8$, —C(O)NR$_8$R$_9$, —NHR$_8$, —NR$_8$R$_9$, —SR$_8$, —S(O)R$_8$, —S(O)$_2$R$_8$, NH$_2$, CN, NO$_2$, $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, mono or polycyclic aryl, and mono or polycyclic heteroaryl containing from 1 to 5 heteroatoms selected from the group consisting of nitrogen, sulfur, and oxygen;

$R_2$ is independently —S(O)R$_8$, —S(O)$_2$R$_8$, $C_1$-$C_6$ alkyl, straight or branched $C_2$-$C_6$ alkenyl, $C_3$-$C_6$ cycloalkyl, mono or polycyclic aryl, or mono or polycyclic heteroaryl containing from 1 to 5 heteroatoms selected from the group consisting of nitrogen, sulfur, and oxygen, each optionally substituted from 1 to 3 times with substituents selected from the group consisting of halogen, OH, NO$_2$, $C_1$-$C_6$ linear alkyl, and $C_2$-$C_6$ alkenyl;

$R_3$ and $R_6$ are independently H, halogen, CF$_3$, CHF$_2$, CH$_2$F, OH, OR$_8$, —C(O)R$_8$, —C(O)OR$_8$, —C(O)NR$_8$R$_9$, —O—(CH$_2$)$_p$—C(O)NR$_8$R$_9$, —NHR$_8$, —NR$_8$R$_9$, —SR$_8$, —S(O)R$_8$, —S(O)$_2$R$_8$, NH$_2$, CN, NO$_2$, $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, mono or polycyclic aryl, wherein p is an integer from 0 to 6;

$R_4$ and $R_5$ are independently H, $C_1$-$C_6$ alkyl, halogen, or $R_7$SO$_2$—;

$R_7$ is independently a substituted or unsubstituted mono or polycyclic aryl or substituted or unsubstituted mono or polycyclic heteroaryl containing from 1 to 5 heteroatoms selected from the group consisting of oxygen, nitrogen, and sulfur, each one of $R_7$ optionally substituted from 1 to 4 times for each cyclic ring with substituents selected from the group consisting of H, OH, OR$_8$, —C(O)R$_8$, —C(O)OR$_8$, —C(O) NR$_8$R$_9$, —NHR$_8$, —NR$_8$R$_9$, —SR$_8$, —S(O)R$_8$, —S(O)$_2$R$_8$, NH$_2$, CN, NO$_2$, halogen, $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, mono or polycyclic aryl, and mono or polycyclic heteroaryl, each one of $R_7$ substituents optionally substituted from 1 to 3 times with substitutents selected from the group consisting of halogen, H, OH, OR$_8$, —C(O)R$_8$, —C(O)OR$_8$, —C(O)NR$_8$R$_9$, —NHR$_8$, —NR$_8$R$_9$, —SR$_8$, —S(O)R$_8$, —S(O)$_2$R$_8$, NH$_2$, CN, NO$_2$, $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, and mono or polycyclic aryl;

$R_8$ and $R_9$ are independently H, $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, a monocyclic aryl or a monocyclic heteroaryl containing from 1-5 heteroatoms selected from the group consisting of nitrogen, oxygen, and sulfur each one of $R_8$ and $R_9$ optionally substituted from 1 to 3 times with substituents selected from the group consisting of halogen, OH, CN, NO$_2$, NH$_2$, H, $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, a monocyclic aryl, and a monocyclic heteroaryl; or $R_8$ and $R_9$ can combine to form a 4- to 7-membered heterocyclyl or a mono heteroaryl each containing from 1 to 5 heteroatoms selected from the group consisting of nitrogen, sulfur, and oxygen, wherein the heterocyclyl or heteroaryl are optionally substituted from 1 to 3 times with substituents selected from the group consisting of halogen, OH, CN, NO$_2$, NH$_2$, H, $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, and a monocyclic aryl, with the proviso that at least one of $R_4$ and $R_5$, but not both, is $R_7SO_2$—;

or an oxide thereof, a pharmaceutically acceptable salt thereof, a solvate thereof, or prodrug thereof.

Unless defined otherwise, all technical and scientific terms used herein have the same meaning as its commonly understood by one of ordinary skill in the art to which this invention belongs. In the event that there is a plurality of definitions for a term herein, those in this section prevail unless stated otherwise.

As used herein, the term "halo" or "halogen" means fluoro, chloro, bromo, or iodo.

As used herein, the term "optionally substituted" indicates that a group may have a substituent at each substitutable atom of the group (including more than one substituent on a single atom), and the identity of each substituent is independent of the others.

The term "substituted" or "substitution" of an atom means that one or more hydrogen on the designated atom is replaced with a selection from the indicated group, provided that the designated atom's normal valency is not exceeded. "Unsubstituted" atoms bear all of the hydrogen atoms dictated by their valency. When a substituent is oxo (i.e., =O), then 2 hydrogens on the atom are replaced. Combinations of substituents and/or variables are permissible only if such combinations result in stable compounds; by "stable compound" or "stable structure" is meant a compound that is sufficiently robust to survive isolation to a useful degree of purity from a reaction mixture, and formulation into an efficacious therapeutic agent. Exemplary substitutents include, without limitation, oxo, thio (i.e. =S), nitro, cyano, halo, OH, $NH_2$, $C_1$-$C_6$ alkyl, $C_1$-$C_6$ alkoxy, $C_2$-$C_6$ alkenyl, $C_2$-$C_6$ alkynyl, $C_3$-$C_6$ cycloalkyl, $C_4$-$C_7$ cycloalkylalkyl, monocyclic aryl, monocyclic heteroaryl, polycyclic aryl, and polycyclic heteroaryl.

As used herein, the term "monocyclic" indicates a molecular structure having one ring.

As used herein, the term "polycyclic" indicates a molecular structure having two or more rings, including, but not limited to, fused, bridged, or spiro rings.

The term "alkyl" means an aliphatic hydrocarbon group which may be straight or branched having about 1 to about 6 carbon atoms in the chain. Branched means that one or more lower alkyl groups such as methyl, ethyl or propyl are attached to a linear alkyl chain. Exemplary alkyl groups include methyl, ethyl, n-propyl, i-propyl, n-butyl, t-butyl, n-pentyl, and 3-pentyl.

The term "alkenyl" means an aliphatic hydrocarbon group containing a carbon-carbon double bond and which may be straight or branched having about 2 to about 6 carbon atoms in the chain. Preferred alkenyl groups have 2 to about 4 carbon atoms in the chain. Branched means that one or more lower alkyl groups such as methyl, ethyl, or propyl are attached to a linear alkenyl chain. Exemplary alkenyl groups include ethenyl, propenyl, n-butenyl, and i-butenyl.

The term "alkynyl" means an aliphatic hydrocarbon group containing a carbon-carbon triple bond and which may be straight or branched having about 2 to about 6 carbon atoms in the chain. Preferred alkynyl groups have 2 to about 4 carbon atoms in the chain. Branched means that one or more lower alkyl groups such as methyl, ethyl, or propyl are attached to a linear alkynyl chain. Exemplary alkynyl groups include ethynyl, propynyl, n-butynyl, 2-butynyl, 3-methylbutynyl, and n-pentynyl.

The term "alkoxy" means an alkyl-O—, alkenyl-O—, or alkynyl-O— group wherein the alkyl, alkenyl, or alkynyl group is described above. Exemplary alkoxy groups include methoxy, ethoxy, n-propoxy, i-propoxy, n-butoxy, pentoxy, and hexoxy.

As used herein, "cycloalkyl" refers to a non-aromatic saturated or unsaturated mono- or polycyclic ring system which may contain 3 to 6 carbon atoms; and which may include at least one double bond. Exemplary cycloalkyl groups include, without limitation, cyclopropyl, cyclobutyl, cyclopentyl, cyclohexyl, cyclopropenyl, cyclobutenyl, cyclopentenyl, cyclohexenyl, anti-bicyclopropane, or syn-bicyclopropane.

As used herein, "cycloalkylalkyl" refers to a radical of the formula —$R^aR^b$ where $R^a$ is an alkyl radical as defined above and $R^b$ is a cycloalkyl radical as defined above. The alkyl radical and the cycloalkyl radical may be optionally substituted as defined above.

As used herein, "aryl" refers to aromatic monocyclic or polycyclic ring system containing from 6 to 19 carbon atoms, where the ring system may be optionally substituted. Aryl groups of the present invention include, but are not limited to, groups such as phenyl, naphthyl, azulenyl, phenanthrenyl, anthracenyl, fluorenyl, pyrenyl, triphenylenyl, chrysenyl, and naphthacenyl.

The term "arylalkyl" refers to a radical of the formula —$R^aR^b$ where $R^a$ is an alkyl radical as defined above and $R^b$ is an aryl radical as defined above. The alkyl radical and the aryl radical may be optionally substituted as defined above.

The term "aryarylalkyl" refers to a radical of the formula —$R^aR^bR^c$ where $R^a$ is an alkyl as defined above, $R^b$ is an aryl radical as defined above, and $R^c$ is an aryl radical as defined above. The alkyl radical and both aryl radicals may be optionally substituted as defined above.

As used herein, "heterocyclyl" refers to a stable 3- to 18-membered ring radical which consists of carbon atoms and from one to five heteroatoms selected from the group consisting of nitrogen, oxygen and sulfur. For purposes of this invention, the heterocyclyl radical may be a monocyclic, or a polycyclic ring system, which may include fused, bridged, or spiro ring systems; and the nitrogen, carbon, or sulfur atoms in the heterocyclyl radical may be optionally oxidized; the nitrogen atom may be optionally quaternized; and the ring radical may be partially or fully saturated. Examples of such heterocyclyl radicals include, without limitation, azepinyl, azocanyl, pyranyl dioxanyl, dithianyl, 1,3-dioxolanyl, tetrahydrofuryl, dihydropyrrolidinyl, decahydroisoquinolyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, 2-oxoazepinyl, oxazolidinyl, oxiranyl, piperidinyl, piperazinyl, 4-piperidonyl, pyrrolidinyl, pyrazolidinyl, thiazolidinyl, tetrahydropyranyl, thiamorpholinyl, thiamorpholinyl sulfoxide, and thiamorpholinyl sulfone.

As used herein, "heteroaryl" refers to an aromatic ring radical which consists of carbon atoms and from one to five heteroatoms selected from the group consisting of nitrogen, oxygen, and sulfur. For purposes of this invention the heteroaryl may be a monocyclic or polycyclic ring system; and the nitrogen, carbon, and sulfur atoms in the heteroaryl ring may be optionally oxidized; the nitrogen may optionally be quaternized. The mono or polycyclic ring system herein refers to 3 to 20 membered mono, bi, tri, tetra-aromatic ring partially or fully saturated containing one to five heteroatoms selected from the group consisting of oxygen, nitrogen, and sulfur. Examples of heteroaryl groups include, without limitation, pyrrolyl, pyrazolyl, imidazolyl, triazolyl, furyl, thiophenyl, oxazolyl, isoxazolyl, thiazolyl, isothiazolyl, oxadiazolyl, thiadiazolyl, pyridyl, pyrazinyl, pyrimidinyl, pyridazinyl, triazinyl, thienopyrrolyl, furopyrrolyl, indolyl, azaindolyl, isoindolyl, indolinyl, indolizinyl, indazolyl, benzimidazolyl, imidazopyridinyl, benzotriazolyl, benzoxazolyl, benzoxadiazolyl, benzothiazolyl, pyrazolopyridinyl, triazolopyridinyl, thienopyridinyl, benzothiadiazolyl, benzofuyl, benzothiophenyl, quinolinyl, isoquinolinyl, tetrahydroquinolyl, tetrahydroisoquinolyl, cinnolinyl, quinazolinyl, quinolizilinyl, phthalazinyl, benzotriazinyl, chromenyl, naphthyridinyl, acrydinyl, phenanzinyl, phenothiazinyl, phenoxazinyl, pteridinyl, and purinyl.

Further heterocycles and heteraryls are described in Katritzky et al., eds., "Comprehensive Heterocyclic Chemistry: The Structure, Reactions, Synthesis and Use of Heterocyclic Compounds," Vol. 1-8, Pergamon Press, N.Y. (1984), which is hereby incorporated by reference in its entirety.

The term "compounds of the invention", and equivalent expressions are meant to embrace compounds of general Formula (I) as herein before described, which expression includes the prodrugs, the pharmaceutically acceptable salts, and the solvates, e.g., hydrates, where the context so permits. Similarly, reference to intermediates, whether or not they themselves are claimed, is meant to embrace their salts and solvates, where the context so permits. For the sake of clarity, particular instances, when the context so permits, are sometimes indicated in the text, but these instances are purely illustrative and it is not intended to exclude other instances when the context so permits.

This invention also envisions the "quaternization" of any basic nitrogen-containing groups of the compounds disclosed herein. The basic nitrogen can be quaternized with any agents known to those of ordinary skill in the art including, for example, lower alkyl halides, such as methyl, ethyl, propyl and butyl chloride, bromides and iodides; dialkyl sulfates including dimethyl, diethyl, dibutyl and diamyl sulfates; long chain halides such as decyl, lauryl, myristyl and stearyl chlorides, bromides and iodides; and aralkyl halides including benzyl and phenethyl bromides. Water or oil-soluble or dispersible products may be obtained by such quaternization.

One embodiment of the present invention relates to the compound of formula (I) where
n is 1
$R_1$ is H or $C_1$-$C_6$ alkyl;
$R_2$ is —$CH_3$, —$CH_2CH_3$ or —$CH(CH_3)_2$;
$R_3$ is H, $C_1$-$C_6$ alkyl, or $OR_8$;
$R_4$ and $R_6$ are H;
$R_5$ is $R_7SO_2$—,
$R_7$ is substituted or unsubstituted phenyl, substituted or unsubstituted heteroaryl, substituted or unsubstituted polycyclic aryl, or substituted or unsubstituted polycyclic heteroaryl; and
$R_8$ is $C_1$-$C_6$ alkyl.
Exemplary groups of $R_3$ of this embodiment include, without limitation, H, methoxy, ethoxy, propoxy, isopropoxy, n-butoxy, sec-butoxy, i-butoxy, pentoxy, hexoxy, methyl, and ethyl.

Another embodiment of the present invention relates to compounds of formula (I) where
n is 1
$R_1$ is H or $C_1$-$C_6$ alkyl;
$R_2$ is —$CH_3$, —$CH_2CH_3$ or —$CH(CH_3)_2$;
$R_3$, $R_4$, and $R_6$ are H; and
$R_5$ is $R_7SO_2$—.
Particular examples of $R_1$ substituents of this embodiment include H, methyl, ethyl, propyl, isopropyl, or butyl.

Yet another embodiment includes compounds where
n is 1
$R_1$ is H or $C_1$-$C_6$ alkyl;
$R_2$ is —$CH_3$, —$CH_2CH_3$ or —$CH(CH_3)_2$;

$R_3$ is Br, Cl, F, or I;
$R_4$ and $R_6$ are H; and
$R_5$ is $R_7SO_2$—.
Preferred halogen groups of $R_3$ in this embodiment are Br, Cl, or F.

In another embodiment of the present invention, the compound of formula (I) is a compound where
n is 2
$R_1$ is H or $C_1$-$C_6$ alkyl;
$R_2$ is —$CH_3$, —$CH_2CH_3$ or —$CH(CH_3)_2$;
$R_3$, $R_4$, and $R_6$ are H; and
$R_5$ is $R_7SO_2$—.
Yet another embodiment includes compounds where
n is 1
$R_1$ is H or $C_1$-$C_6$ alkyl;
$R_2$ is —$CH_3$, —$CH_2CH_3$ or —$CH(CH_3)_2$;
$R_3$, $R_5$ and $R_6$ are H; and
$R_4$ is $R_7SO_2$—.
Yet another embodiment includes compounds where
n is 2
$R_1$ is H or $C_1$-$C_6$ alkyl;
$R_2$ is —$CH_3$, —$CH_2CH_3$ or —$CH(CH_3)_2$;
$R_3$, $R_5$ and $R_6$ are H; and
$R_4$ is $R_7SO_2$—.
In one embodiment, the compound of the present invention has the formula (Ia):

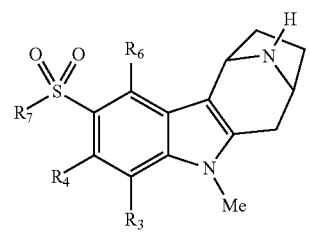

(Ia)

wherein
$R_3$ is H, Me, Et, or $OR_8$;
$R_4$ is H;
$R_6$ is H;
$R_7$ is substituted or unsubstituted phenyl, substituted or unsubstituted heteroaryl, substituted or unsubstituted polycyclic aryl, substituted or unsubstituted polycyclic heteroaryl, substituted or unsubstituted heteroaryl, or substituted or unsubstituted polycyclic heteroaryl;
$R_8$ is Me or Et.

Single enantiomers, any mixture of enantiomers, including racemic mixtures, or diastereomers (both separated and as any mixtures) of the compounds of the present invention are also included within the scope of the invention.

Another embodiment of the invention, described herein, involves the (+)-stereoisomer of the compound of formula I.

Another embodiment of the invention, described herein, involves the (−)-stereoisomer of the compound of formula I.

Within these embodiments, the selection of a particular preferred substituent at any one of $R_1$-$R_9$ of the compounds of the present invention does not affect the selection of a substituent at any of the others of $R_1$-$R_9$. That is, the specific compounds provided herein have any of the specific substituents at any of the positions. For example, as described hereinabove, $R_1$ is preferably $C_1$-$C_6$ alkyl; the selection of $R_1$ as any one of $C_1$, $C_2$, $C_3$, $C_4$, $C_5$, or $C_6$ alkyl, does not limit the choice of $R_2$ in particular to any one of $C_1$-$C_6$ alkyl. Rather, for $R_1$ as any of $C_1$, $C_2$, $C_3$, $C_4$, $C_5$, or $C_6$ alkyl, $R_2$ is any of $C_1$, $C_2$, $C_3$, $C_4$, $C_5$, or $C_6$ alkyl. Similarly, the selection of $R_2$ as any of $C_1$, $C_2$, $C_3$, $C_4$, $C_5$, or $C_6$ alkyl, does not limit the selection of $R_3$ in particular to any one of H, halogen, OH, $OR_8$, —$C(O)R_8$, —$C(O)OR_8$, —$C(O)NR_8R_9$, —$NHR_8$, —$NR_8R_9$, —$SR_8$, —$S(O)R_8$, —$S(O)_2R_8$, $NH_2$, CN, $NO_2$, $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, mono or polycyclic aryl.

Another aspect of the present invention is directed to a method for modulating serotonin sub-type 6. The method involves providing a compound of formula (I) and contacting a serotonin receptor with said compound of formula (I) under conditions effective to modulate serotonin sub-type 6.

According to the method of the present invention, contacting a serotonin sub-type 6 receptor is carried out by administering the compound of the present invention to a subject. The subject to whom the compound of the present invention is administered, presents or manifests a central nervous system disorder.

Administration of the compound of the present invention can be, without limitation, carried out systematically or at the site where the central nervous system is manifested. Exemplary methods of administering the compounds of the present invention include, without limitation, parental, oral, subcuteaneous, intravenous, intramuscular, extraperitoneal, intranasal instillation, by inhalation, or by application to mucuous membrane administration.

In view of their high degree of potency toward 5-$HT_6$ receptors, the compounds of the present invention can be administered to anyone requiring modulation of the 5-$HT_6$ receptor. Administration may be accomplished according to patient needs, for example, orally, nasally, parenterally (subcutaneously, intravenously, intramuscularly, intrasternally and by infusion) by inhalation, rectally, vaginally, topically and by ocular administration.

The serotonin sub-type-6 (5$HT_6$) receptor according to the present invention can be distributed throughout the entire body of the human or animal species (e.g. rat, mice, pigs, horses, monkeys, cows, sheep, guinea pigs, dogs, and cats). For example, 5-$HT_6$ receptor in rat brain can be localized in areas such as striatum, nucleus accumbens, olfactory tubercle, and hippocampal formation (Ward et al., *Neuroscience* 64:1105-1111 (1995), which is hereby incorporated by reference in its entirety). This receptor may also be mutated or modified. For purposes of modulating the 5$HT_6$ receptor, the compounds of formula (I) may be 5$HT_6$ receptor-agonists, antagonists, or partial agonists.

The central nervous system disorder according to the present invention is a condition associated or related to a brain and spinal cord ailment. Preferred central nervous system disorder treated according to the method of the present invention include obesity, metabolic syndrome, cognition, and schizophrenia. The method of the present invention may also be extended, without limitation, to other central nervous system disorders such as Alzheimer's disease, anxiety, depression, convulsive disorders such as epilepsy, personality disorders, obsessive compulsive disorders, migraine, cognitive disorders such as memory dysfunction, sleep disorders, feeding disorders such as anorexia, bulimia, panic attacks, withdrawal from drug abuse, attention deficit hyperactive disorder (ADHD), attention deficit disorder (ADD), dementia, memory loss, disorders associated with spinal trauma and/or head injury, stroke, diabetes type 2, binge disorders, bipolar disorders, psychoses, Parkinson's disease, Huntington's disease, neurodegenerative disorders characterized by impaired neuronal growth, and pain.

Additional aspects of the present invention include pharmaceutical compositions comprising a compound of this invention and a pharmaceutically acceptable carrier and, optionally, one or more additional active agent(s) as discussed below. Further aspects include methods of treating a disease state related to or modulated by the 5-$HT_6$ receptor, in a patient, such as humans or animals (e.g. rat, mice, pigs, horses, monkeys, cows, sheep, guinea pigs, dogs, and cats).

The amount of active ingredient that may be combined with the carrier materials to produce a single dosage form will vary depending upon the host treated and the particular mode of administration. For example, a formulation intended for the oral administration of humans may vary from about 5 to about 95% of the total composition. Dosage unit forms will generally contain between from about 1 mg to about 500 mg of active ingredient.

Any pharmaceutically acceptable liquid carrier suitable for preparing solutions, suspensions, emulsions, syrups and elixirs may be employed in the composition of the invention. Compounds of formula I may be dissolved or suspended in a pharmaceutically acceptable liquid carrier such as water, an organic solvent, or a pharmaceutically acceptable oil or fat, or a mixture thereof. The liquid composition may contain other suitable pharmaceutical additives such as solubilizers, emulsifiers, buffers, preservatives, sweeteners, flavoring agents, suspending agents, thickening agents, coloring agents, viscosity regulators, stabilizers, osmo-regulators, or the like. Examples of liquid carriers suitable for oral and parenteral administration include water (particularly containing additives as above, e.g., cellulose derivatives, preferably sodium carboxymethyl cellulose solution), alcohols (including monohydric alcohols and polyhydric alcohols, e.g., glycols) or their derivatives, or oils (e.g., fractionated coconut oil and arachis oil). For parenteral administration, the carrier may also be an oily ester such as ethyl oleate or isopropyl myristate.

Pharmaceutically acceptable salts include, but are not limited to, amine salts, such as but not limited to N,N'-dibenzylethylenediamine, chloroprocaine, choline, ammonia, diethanolamine and other hydroxyalkylamines, ethylenediamine, N-methylglucamine, procaine, N-benzylphenethylamine, 1-para-chlorobenzyl-2-pyrrolidin-1'-ylmethyl-benzimidazole, diethylamine and other alkylamines, piperazine, and tris (hydroxymethyl)aminomethane; alkali metal salts, such as but not limited to lithium, potassium, and sodium; alkali earth metal salts, such as but not limited to barium, calcium, and magnesium; transition metal salts, such as but not limited to zinc; and other metal salts, such as but not limited to sodium hydrogen phosphate and disodium phosphate; and also including, but not limited to, salts of mineral acids, such as but not limited to hydrochlorides and sulfates; and salts of organic acids, such as but not limited to acetates, lactates, malates, tartrates, citrates, ascorbates, succinates, butyrates, valerates and fumarates. Pharmaceutically acceptable esters include, but are not limited to, alkyl, alkenyl, alkynyl, aryl, heteroaryl, cycloalkyl and heterocyclyl esters of acidic groups, including, but not limited to, carboxylic acids, phosphoric acids, phosphinic acids, sulfonic acids, sulfinic acids, and boronic acids. Pharmaceutical acceptable enol ethers include, but are not limited to, derivatives of formula C=C (OR) where R is hydrogen, alkyl, alkenyl, alkynyl, aryl, heteroaryl, cycloalkyl, or heterocyclyl. Pharmaceutically acceptable enol esters include, but are not limited to, derivatives of formula C=C(OC(O) R) where R is hydrogen, alkyl, alkenyl, alkynyl, aryl, heteroaryl, cycloalkyl, or heterocyclyl. Pharmaceutical acceptable solvates and hydrates are complexes of a compound with one or more solvent or water molecules, or 1 to about 100, or 1 to about 10, or one to about 2, 3 or 4, solvent or water molecules.

It will be understood, however, that the specific dose level for any particular patient will depend upon a variety of factors including the activity of the specific compound employed, the age, body weight, general health, sex, diet time of administration, route of administration, rate of excretion, drug combination and the severity of the particular disease undergoing therapy.

As used herein, "treatment" or "treating" means any manner in which one or more of the symptoms of a disease or disorder are ameliorated or otherwise beneficially altered. Treatment also encompasses any pharmaceutical use of the compositions herein, such as use for treating central nervous system diseases or disorders, or diseases or disorders in which central nervous system receptor activity, including $5HT_6$ receptor activity, is implicated.

All methods comprise administering to the patient in need of such treatment an effective amount of one or more compounds of the invention.

A subject or patient in whom administration of the therapeutic compound is an effective therapeutic regimen for a disease or disorder is preferably a human, but can be any animal, including a laboratory animal in the context of a clinical trial or screening or activity experiment. Thus, as can be readily appreciated by one of ordinary skill in the art, the methods, compounds and compositions of the present invention are particularly suited to administration to any animal, particularly a mammal, and including, but by no means limited to, humans, domestic animals, such as feline or canine subjects, farm animals, such as but not limited to bovine, equine, caprine, ovine, and porcine subjects, wild animals (whether in the wild or in a zoological garden), research animals, such as mice, rats, rabbits, goats, sheep, pigs, dogs, cats, etc., avian species, such as chickens, turkeys, songbirds, etc., i.e., for veterinary medical use.

The compounds of the invention can be administered alone or as an active ingredient of a formulation. Thus, the present invention also includes pharmaceutical compositions of one or more compounds of Formula I containing, for example, one or more pharmaceutically acceptable carriers. The compounds of the invention can be administered in a form where the active ingredient is substantially pure.

Numerous standard references are available that describe procedures for preparing various formulations suitable for administering the compounds according to the invention. Examples of potential formulations and preparations are contained, for example, in the Handbook of Pharmaceutical Excipients, American Pharmaceutical Association (current edition); Pharmaceutical Dosage Forms: Tablets (Lieberman, Lachman and Schwartz, editors) current edition, published by Marcel Dekker, Inc., as well as Remington's Pharmaceutical Sciences (Arthur Osol, editor), 1553-1593 (current edition), which are hereby incorporated by reference in their entirety.

The compounds can be administered as the sole active agent or in combination with other pharmaceutical agents such as other agents used in the treatment of CNS disorders, such as psychoses, especially schizophrenia and bipolar disorder, obsessive-compulsive disorder, Parkinson's disease, cognitive impairment and/or memory loss, (e.g., nicotinic α-7 agonists, PDF4 inhibitors, PDE10 inhibitors, other 5-$HT_6$ receptor ligands), calcium channel blockers, muscarinic M1 and M2 modulators, adenosine receptor modulators, ampakines, NMDA-R modulators, mGluR modulators, dopamine modulators, serotonin modulators, canabinoid modulators, and cholinesterase inhibitors (e.g., donepezil, rivastigimine, and galanthanamine). In such combinations, each active ingredient can be administered either in accordance with their usual dosage range or in accordance with a dose below their usual dosage range.

The compounds can be administered in combination with other pharmaceutical agents used in the treatment of schizophrenia, e.g., Clozaril, Zyprexa, Risperidone, and Seroquel. Thus, the invention also includes methods for treating schizophrenia, including memory impairment associated with schizophrenia, comprising administering to a patient, simultaneously or sequentially, the compound of the invention and one or more additional agents used in the treatment of schizophrenia such as, but not limited to, Clozaril, Zyprexa, Risperidone, and Seroquel. In methods using simultaneous administration, the agents can be present in a combined composition or can be administered separately. As a result, the invention also includes compositions comprising a compound according to Formula I and one or more additional pharmaceutical agents used in the treatment of schizophrenia, e.g., Clozaril, Zyprexa, Risperidone, and Seroquel. Similarly, the invention also includes kits containing a composition comprising a compound according to Formula I and another composition comprising one or more additional pharmaceutical agents used in the treatment of schizophrenia, e.g., Clozaril, Zyprexa, Risperidone, and Seroquel.

Solid carriers suitable for use in the composition of the invention include one or more substances which may also act as flavoring agents, lubricants, solubilizers, suspending agents, fillers, glidants, compression aides, binders, tablet-disintegrating agents, or encapsulating materials. In powders, the carrier may be a finely divided solid which is in admixture with a finely divided compound of formula I. In tablets, the formula I compound may be mixed with a carrier having the necessary compression properties in suitable proportions and compacted in the shape and size desired. Said powders and tablets may contain up to 99% by weight of the formula I compound. Solid carriers suitable for use in the composition of the invention include calcium phosphate, magnesium stearate, talc, sugars, lactose, dextrin, starch, gelatin, cellulose, methyl cellulose, sodium carboxymethyl cellulose, polyvinylpyrrolidine, low melting waxes, and ion exchange resins.

Another aspect of the present invention is directed to the process for preparation of a product compound of formula (I):

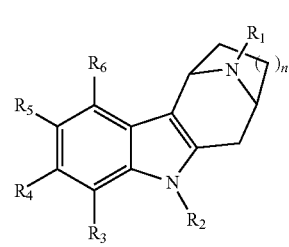

wherein n is an integer from 1 to 2; and $R_1$ is independently H, $C_1$-$C_6$ alkyl, $C_2$-$C_6$ alkenyl, $C_2$-$C_6$ alkynyl, $C_1$-$C_6$ alkoxy, $C_3$-$C_6$ cycloalkyl, $C_4$-$C_7$ cycloalkylalkyl, aryl $C_1$-$C_6$ alkyl, mono or polycyclic aryl, or mono or polycyclic heteroaryl containing from 1 to 5 heteroatoms selected from the group consisting of nitrogen, sulfur, and oxygen, each one of $R_1$ optionally substituted from 1 to 3 times with substituents selected from the group consisting of halogen, OH, $OR_8$, —$C(O)R_8$, —$C(O)OR_8$, —$C(O)NR_8R_9$, —$NHR_8$, —$NR_8R_9$, —$SR_8$, —$S(O)R_8$, —$S(O)_2R_8$, $NH_2$, CN, $NO_2$, $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, mono or polycyclic aryl, and mono or polycyclic heteroaryl containing from 1 to 5 heteroatoms selected from the group consisting of nitrogen, sulfur, and oxygen;

$R_2$ is independently —$C(O)R_8$, —$C(O)OR_8$, —$C(O)NR_8R_9$, —$S(O)R_8$, —$S(O)_2R_8$, $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, aryl $C_1$-$C_6$ alkyl, mono or polycyclic aryl, or mono or polycyclic heteroaryl containing from 1 to 5 heteroatoms selected from the group consisting of nitrogen, sulfur, and oxygen, each optionally substituted from 1 to 3 times with substituents selected from the group consisting of halogen, OH, $NH_2$, CN, $NO_2$, $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, mono or polycyclic aryl, and mono or polycyclic heteroaryl;

$R_3$ and $R_6$ are independently H, halogen, $CF_3$, $CHF_2$, $CH_2F$, OH, $OR_8$, —$C(O)R_8$, —$C(O)OR_8$, —$C(O)NR_8R_9$, —O—$(CH_2)_p$—$C(O)NR_8R_9$, —$NHR_8$, —$NR_8R_9$, —$SR_8$, —$S(O)R_8$, —$S(O)_2R_8$, $NH_2$, CN, $NO_2$, $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, mono or polycyclic aryl, wherein p is an interger from 0 to 6;

$R_4$ and $R_5$ are independently H, $C_1$-$C_6$ alkyl, halogen, or $R_7SO_2$—;

$R_7$ is independently a substituted or unsubstituted mono or polycyclic aryl or substituted or unsubstituted mono or polycyclic heteroaryl containing from 1 to 5 heteroatoms selected from the group consisting of oxygen, nitrogen, and sulfur, each one of $R_7$ optionally substituted from 1 to 4 times for each cyclic ring with substituents selected from the group consisting of H, OH, $OR_8$, —$C(O)R_8$, —$C(O)OR_8$, —$C(O)NR_8R_9$, —$NHR_8$, —$NR_8R_9$, —$SR_8$, —$S(O)R_8$, —$S(O)_2R_8$, $NH_2$, CN, $NO_2$, halogen, $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, mono or polycyclic aryl, and mono or polycyclic heteroaryl, each one of $R_7$ substituents optionally substituted from 1 to 3 times with substitutents selected from the group consisting of halogen, H, OH, $OR_8$, —$C(O)R_8$, —$C(O)OR_8$, —$C(O)NR_8R_9$, —$NHR_8$, —$NR_8R_9$, —$SR_8$, —$S(O)R_8$, —$S(O)_2R_8$, $NH_2$, CN, $NO_2$, $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, and mono or polycyclic aryl;

$R_8$ and $R_9$ are independently H, $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, a monocyclic aryl or a monocyclic heteroaryl containing from 1-5 heteroatoms selected from the group consisting of nitrogen, oxygen, and sulfur each one of $R_8$ and $R_9$ optionally substituted from 1 to 3 times with substituents selected from the group consisting of halogen, OH, CN, $NO_2$, $NH_2$, H, $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, a monocyclic aryl, and a monocyclic heteroaryl; or $R_8$ and $R_9$ can combine to form a 4- to 7-membered heterocyclyl or a mono heteroaryl each containing from 1 to 5 heteroatoms selected from the group consisting of nitrogen, sulfur, and oxygen, wherein the heterocyclyl or heteroaryl are optionally substituted from 1 to 3 times with substituents selected from the group consisting of halogen, OH, CN, $NO_2$, $NH_2$, H, $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, and a monocyclic aryl, with the proviso that at least one of $R_4$ and $R_5$, but not both, is $R_7SO_2$—;

or an oxide thereof, a pharmaceutically acceptable salt thereof, a solvate thereof, or prodrug thereof said process comprising:

providing a first intermediate having the structure:

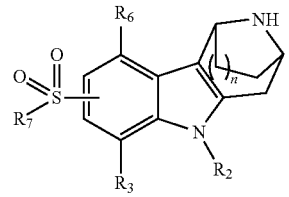

and reacting a first intermediate with an electrophile $R_1Z$ under conditions effective to form the compound of formula (I), wherein Z is a leaving group.

Palladium catalysts used in the synthesis of the compounds of the present invention may be of various oxidative state. Thus, the process for preparation of the compounds of the present invention would employ, without limitation, Pd (O), Pd (II), or Pd (IV). Examples of such Palladium catalysts include, without limitation, bis(benzonitrile) palladium (II) chloride, palladium diacetate, palladium dibenzylidene acetone, tetrakis(triphenylphosphine) palladium, bis(triphenylphosphine) palladium (II) dichloride, bis(diphenylphosphineferrocene) palladium (II) dichloride, and bis(diphenylphosphineferrocene) palladium.

Furthermore, the process of preparation according to the present invention employs various bases and acids depending on the reaction performed. For example, Brönsted or Lewis bases or acids may also be used for the present process of preparation. Exemplary bases include, without limitation, triethylamine, pyridine, piperidine, 2,6-lutidine, pyrrolidine, toludine, diisopropylamine, diisopropyl ethylamine, sodium hydride, sodium hydroxide, and sodium carbonate. Exemplary Lewis acid according to the present invention include without limitation titanium tetrachloride, aluminum chloride, boron trifluoride, boron tribromide, dimethylboron bromide, phosphorous pentachloride, tin dichloride, and tin tetrachloride.

For purposes of nucleophilic or electrophilic additions and substitutions identified in the process of preparation of the compounds of the present invention (including synthetic intermediate), various leaving or electrophilic groups have been used. Such groups include, without limitation, halogen, mesyl, triflate, acetyl, or tosyl.

The compounds according to the present invention may be prepared by the following process. In the description and formulae below, the various groups $R_1$-$R_7$ and other variables are as defined above, except where otherwise indicated. In such instances, removal of the protecting group may be the final step in a particular reaction. Suitable protecting groups for such functionality will be apparent to those skilled in the art. For specific details see Greene et al, "Protective Groups in Organic Synthesis", Wiley Interscience (1999), which is hereby incorporated by reference in its entirety.

It will also be appreciated by those skilled in the art that in the process described below the functional groups of intermediate compounds may need to be protected by suitable protecting groups. Such functional groups include hydroxy, amino, mercapto and carboxylic acid. Suitable protecting groups for hydroxy include trialkylsilyl or diarylalkylsilyl (e.g., t-butyldimethylsilyl, t-butyldiphenylsilyl or trimethylsilyl), tetrahydropyranyl, benzyl, and the like. Suitable protecting groups for amino, amidino and guanidino include t-butoxycarbonyl (t-Boc or Boc), benzyloxycarbonyl, and the like. Suitable protecting groups for mercapto include —C(O)—R (where R is alkyl, aryl or aralkyl), p-methoxybenzyl, trityl and the like. Suitable protecting groups for carboxylic acid include alkyl, aryl or aralkyl esters.

Protecting groups may be added or removed in accordance with standard techniques, which are well-known to those skilled in the art and as described herein. The use of protecting groups is described in detail in Green et al., *Protective Groups in Organic Synthesis,* 2nd Ed., Wiley-Interscience (1991), which is hereby incorporated by reference in its entirety.

It is also contemplated, for synthetic purposes, that compound 1 of scheme 1 is a representative radical of the mono or polycyclic aryl or mono or polycyclic heterorayl $R_7SO_2$— substituent of the compound of formula (I), which may be optionally substituted with substituents defined herein.

Synthetic Methods

Scheme 1

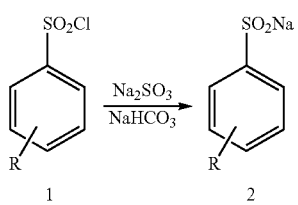

Compounds of formula 2 can be prepared from the corresponding sulfonyl chloride by treatment with aqueous sodium sulfite and sodium bicarbonate at 0° C. followed by heating to 65° C.

Scheme 2

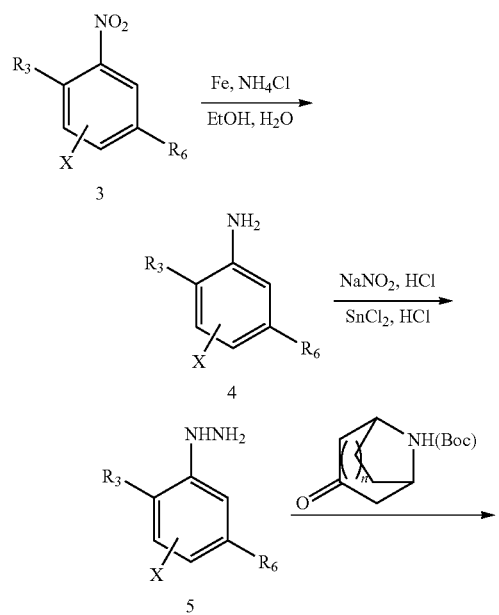

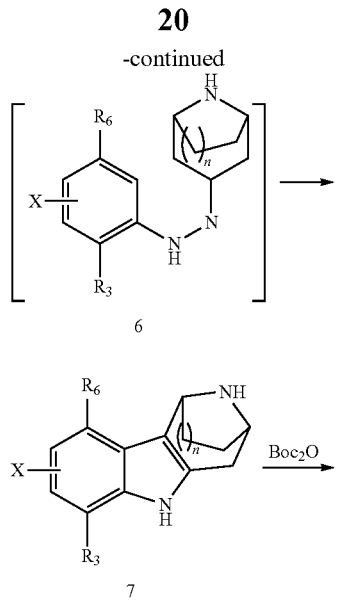

Compounds of formula 8 (where X=Br or I) can be prepared via a four (or five) step procedure starting from the corresponding nitroaromatic analog 3. Treatment with iron and ammonium chloride in an ethanol/water solution at reflux can be used to prepare compounds of formula 4. Subsequent treatment with sodium nitrite in aqueous HCl at 0° C. followed by tin(II)chloride in aqueous HCl at 0° C. can be used to prepare compounds of formula 5. Compounds of formula 5 can be subjected to Fisher indole forming conditions (conc. HCl, Ethanol, reflux) to directly prepare compounds of formula 7. Alternatively, the intermediate hydrazone of formula 6 can be isolated and converted to compounds of formula 7 using 10% sulfuric acid in acetic acid under refluxing conditions. Compounds of formula 7 can generally be transformed into compounds of formula 8 without purification via treatment with Boc anhydride, triethylamine and catalytic N,N-dimethylaminopyridine in methylene chloride at room temperature.

Scheme 3

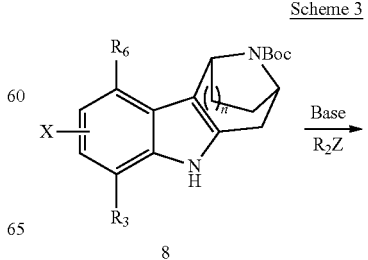

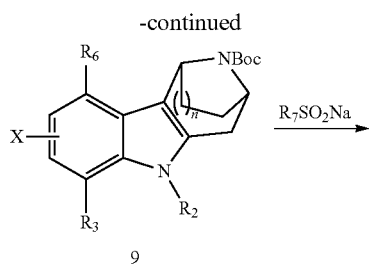

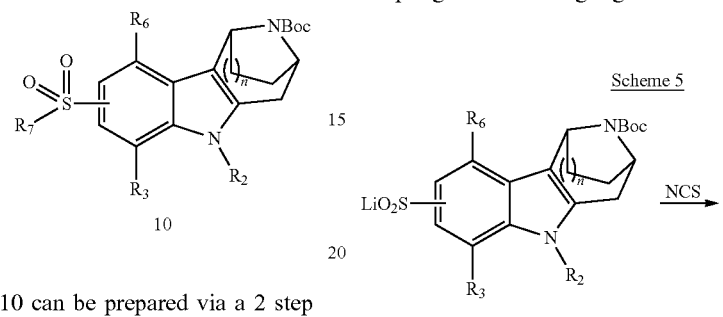

Compounds of formula 10 can be prepared via a 2 step procedure starting from compounds of formula 8. Treatment with sodium hydride in DMF (or THF) at room temperature followed by quenching with a suitable electrophile (where Z=Cl, Br, I, OSO$_2$Me, OSO$_2$CF$_3$, OTs) can be used to prepare compounds of formula 9. Alternatively, compound 9 can be prepared from the aforementioned electrophiles using a different base (potassium carbonate or cesium carbonate) in DMF at room temperature. Compounds of formula 9 can be converted to compounds of formula 10 via a palladium-catalyzed procedure using Pd$_2$(dba)$_3$ and xantphos with cesium carbonate and tetrabutylammonium chloride in toluene at reflux. Alternatively, in certain instances, the reaction is carried out in the absence of tetrabutylammonium chloride.

An alternative method for accessing compounds of formula 10 can also be used where compound 9 is converted to a lithiumsulfinate salt of formula 11 via lithium halogen-exchange using n-butyl lithium at −78° C. followed by quenching of the aryllithium intermediate with sulfur dioxide at −78° C. Conversion of compounds of formula 11 to compounds of formula 10 is achieved via reaction with an aryl halide (Z=Cl, Br, I) using the same palladium-catalyzed coupling conditions highlighted in scheme 3.

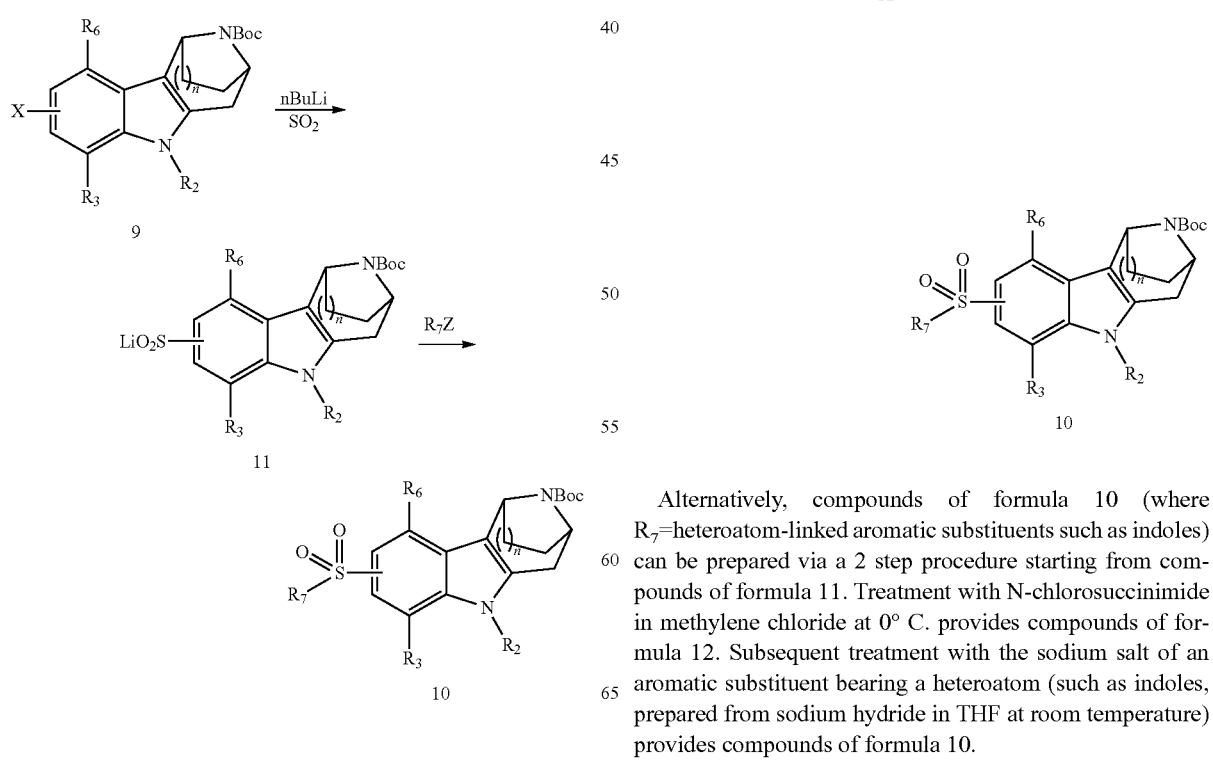

Alternatively, compounds of formula 10 (where R$_7$=heteroatom-linked aromatic substituents such as indoles) can be prepared via a 2 step procedure starting from compounds of formula 11. Treatment with N-chlorosuccinimide in methylene chloride at 0° C. provides compounds of formula 12. Subsequent treatment with the sodium salt of an aromatic substituent bearing a heteroatom (such as indoles, prepared from sodium hydride in THF at room temperature) provides compounds of formula 10.

Scheme 6

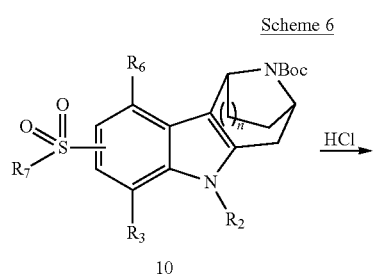

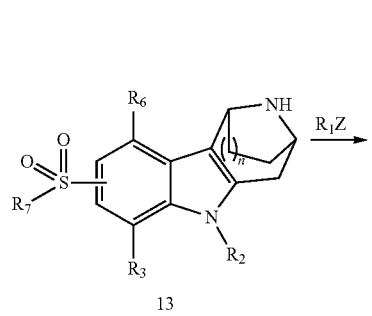

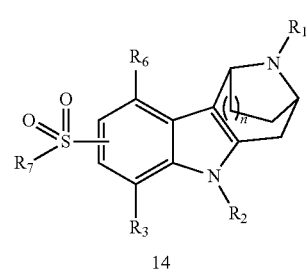

Compounds of formula 13 can be prepared from compounds of formula 10 via removal of the protecting group using HCl in a variety of different solvents. Alternatively, compounds of formula 13 can also be prepared using trifluoroacetic acid in methylene chloride. Compounds of formula 13 can also be elaborated to compounds of formula 14 via reaction with a suitable electrophile (Z=Cl, Br, I, $OSO_2Me$, $OSO_2CF_3$, OTs) in acetonitrile using triethylamine as a base under refluxing conditions.

Another aspect of the present invention relates to a process for enantiomeric resolution. In this process, a mixture of diastereomers of the compound of formula (II) is provided

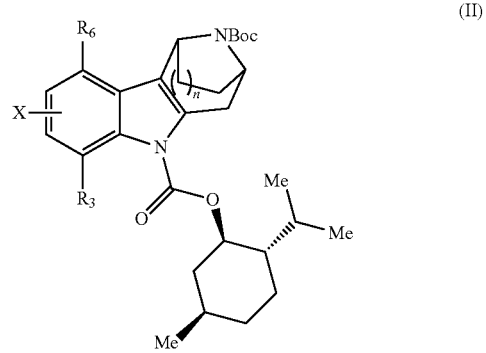

(II)

where:
$R_3$ and $R_6$ are independently H, halogen, $CF_3$, $CHF_2$, $CH_2F$, OH, $OR_8$, —$C(O)R_8$, —$C(O)OR_8$, —$C(O)NR_8R_9$, —$NHR_8$, —$NR_8R_9$, —$SR_8$, —$S(O)R_8$, —$S(O)_2R_8$, $NH_2$, CN, $NO_2$, $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, mono or polycyclic aryl; and X is independently chloro, bromo, iodo, or triflyl. The mixture is subjected to a resolution procedure under conditions effective to separate the diastereomers of the compound of formula (II) from one another.

Furthermore, the present invention contemplates the synthesis, isolation, and purification of enantiomerically pure stereoisomers of the compounds of the formula (I) and their synthetic intermediates (as outlined in scheme 7).

Scheme 7

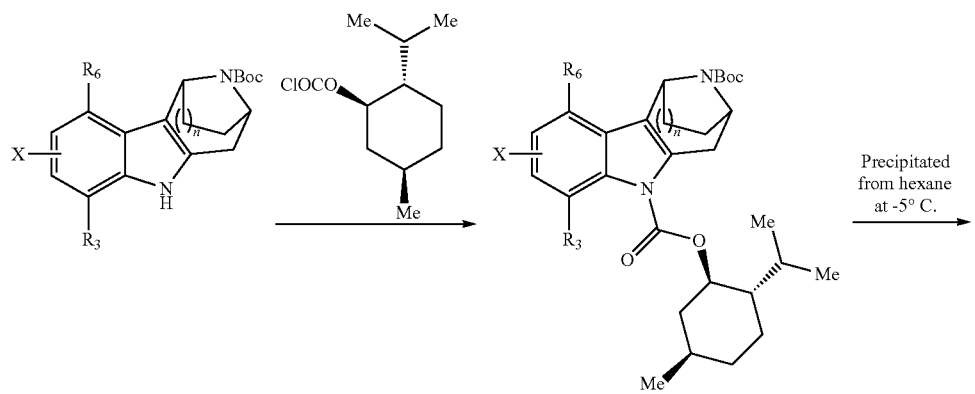

Precipitated from hexane at -5° C.

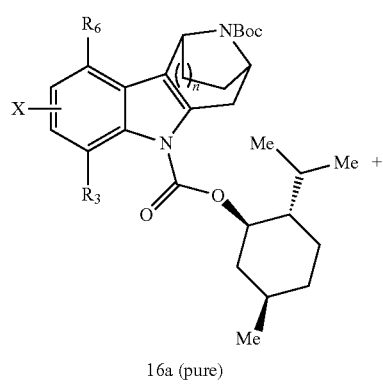

16a (pure)

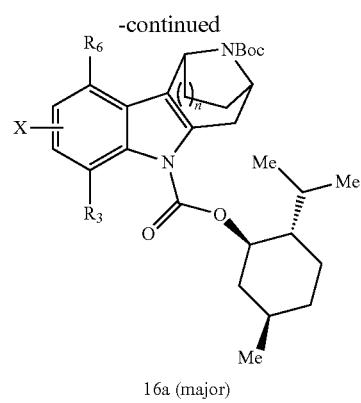

16a (major)

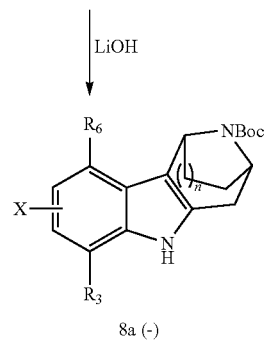

8a (−)

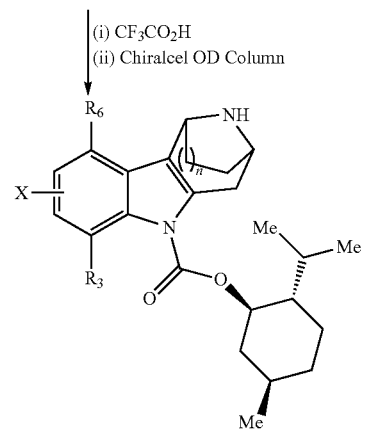

17

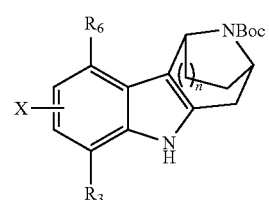

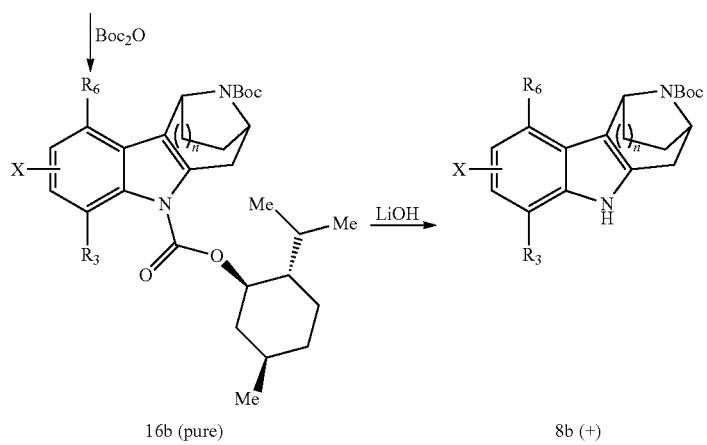

16b (pure)                                    8b (+)

Chiral resolution of intermediate 8 (where X=Br, R₃=H and R₆=H) can be achieved via synthesis of the chiral adduct 16. This can be dissolved in hexane and cooled to −5° C. leading to preferential precipitation of diastereomer 16a. The chiral auxiliary can then be removed providing the (−) enantiomer of intermediate 8 in >99% ee. The Boc protecting group can be removed from the material remaining in the supernatant, and this can be purified by chiral chromatography providing pure diastereomer 17. The Boc group can then be re-introduced, and the chiral auxiliary removed to provide the (+) enantiomer of intermediate 8 in >99% ee. Alternatively, where preferential precipitation of one diastereomer does not occur, diastereomeric mixture 16 can be purified by chiral chromatography and the separated products can have the Boc group re-introduced and the chiral auxiliary removed to provide the (+) and (−) enantiomers of intermediate 8 in >99% ee.

EXAMPLES

The Examples set forth below are for illustrative purposes only and are not intended to limit, in any way, the scope of the present invention.

Example 1

Analytical Methods and Materials

Unless otherwise noted, reagents and solvents were used as received from commercial suppliers. Proton nuclear magnetic resonance (NMR) spectra were obtained on Bruker spectrometers at 300, 400 or 500 MHz. Spectra are given in ppm (δ) and coupling constants, J, are reported in Hertz. Tetramethylsilane (TMS) was used as an internal standard. Mass spectra were collected using either a Finnigan LCQ Duo LCMS ion trap electrospray ionization (ESI) or a mass Varian 1200L single quadrapole mass spectrometer (ESI). High performance liquid chromatograph (HPLC) analyses were obtained using a Luna C18(2) column (250×4.6 mm, Phenomenex) with UV detection at 254 nm or 223 nm using a standard solvent gradient program (Method A or Method B).

| Method A: | | | |
|---|---|---|---|
| Time (min) | Flow (mL/min) | % A | % B |
| 0.0 | 1.0 | 90.0 | 10.0 |
| 20 | 1.0 | 10.0 | 90.0 |
| 30 | 1.0 | 10.0 | 90.0 |

A = Water with 0.05% Trifluoroacetic Acid
B = Acetonitrile with 0.05% Trifluoroacetic Acid

| Method B: | | | |
|---|---|---|---|
| Time (min) | Flow (mL/min) | % A | % B |
| 0.0 | 1.0 | 98.0 | 2.0 |
| 25 | 1.0 | 10.0 | 90.0 |
| 30 | 1.0 | 10.0 | 90.0 |

A = Water with 0.025% Trifluoroacetic Acid
B = Acetonitrile with 0.025% Trifluoroacetic Acid Example 2

Intermediate 1—Preparation of Sodium 3-chloro-benzenesulfinate

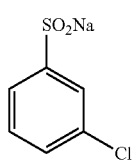

A solution of sodium sulphite (627 mg, 4.98 mmol) and sodium bicarbonate (418 mg, 4.98 mmol) in water (13 mL) was stirred vigorously with 3-chlorobenzenesulfonyl chloride (500 mg, 2.36 mmol) at 0° C. for 30 min then heated at 65° C. for 3 h. After cooling to ambient temperature, the reaction mixture was washed with dichloromethane (2×20 mL) and lyophilized. The resulting white solid was stirred with methanol (10 mL) for 5 min and the insoluble inorganic salts removed by filtration. The filtrate was concentrated in vacuo to approximately 3 mL and an equal volume of diethyl ether added. The precipitated solid containing residual inorganic salts was filtered and set aside. The remaining filtrate was diluted with excess diethyl ether, filtered and the filtered solid dried in vacuo to give sodium 3-chloro-benzenesulfinate (306 mg, 65%) as a white solid: $^1$H NMR (DMSO-$d_6$, 300 MHz) δ 7.43 (br s, 1H), 7.35-7.39 (m, 1H), 7.32 (d, J=7.2 Hz, 1H), 7.26 (dt, J=7.5, 1.8 Hz, 1H).

Example 3

Intermediate 2—Preparation of Sodium 3-fluoro-benzenesulfinate

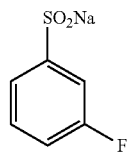

Sodium 3-fluoro-benzenesulfinate was prepared from 3-fluoro-benzenesulfonyl chloride following the procedure of Example 2 to give the product (9.3 g, 99%) as a white solid: $^1$H NMR (D$_2$O, 300 MHz) δ 7.51 (td, J=7.8, 5.1 Hz, 1H), 7.39-7.43 (m, 1H), 7.35 (ddd, J=8.6, 2.7 Hz, 1.5 Hz, 1H), 7.16-7.23 (m, 1H).

Example 4

Intermediate 3—Preparation of Sodium 3-trifluoromethoxybenzenesulfinate

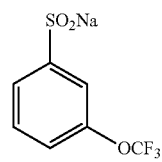

Sodium 3-trifluoromethoxy-benzenesulfinate was prepared from 3-trifluoromethoxy-benzenesulfonyl chloride following the procedure of Example 2 to give the product (219 mg, 46%) as a white solid: $^1$H NMR (CD$_3$OD, 300 MHz) δ 7.60-7.64 (m, 1H), 7.49-7.56 (m, 2H), 7.24-7.28 (m, 1H).

Example 5

Intermediate 4—Preparation of Sodium 3-methoxy-benzenesulfinate

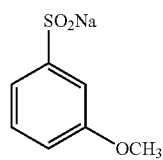

Sodium 3-methoxy-benzenesulfinate was prepared from 3-methoxy-benzenesulfonyl chloride following the procedure of Example 2 to give the product (205 mg, 43%) as a white solid: $^1$H NMR (CD$_3$OD, 300 MHz) δ 7.38-7.42 (m, 1H), 7.28-7.35 (m, 1H), 7.19-7.26 (m, 1H), 6.89-7.01 (m, 1H), 3.82 (s, 3H).

Example 6

Intermediate 5—Preparation of Sodium 3-cyano-benzenesulfinate

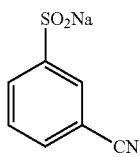

Sodium 3-cyano-benzenesulfinate was prepared from 3-cyano-benzenesulfonyl chloride following the procedure of Example 2 to give the product (750 mg, 80%) as a white solid: $^1$H NMR (CD$_3$OD, 300 MHz) δ 7.90-7.96 (m, 2H), 7.71-7.75 (m, 1H), 7.61 (t, J=7.2 Hz, 1H).

Example 7

Intermediate 6—Preparation of Sodium 3-difluoromethoxy-benzenesulfinate

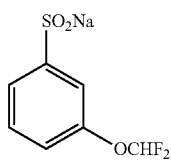

Sodium 3-difluoromethoxy-benzenesulfinate was prepared from 3-difluoromethoxy-benzenesulfonyl chloride following the procedure of Example 2 to give the product (780 mg, 80%) as a white solid: $^1$H NMR (CD$_3$OD, 300 MHz) δ 7.42-7.50 (m, 3H), 7.11-7.14 (m, 1H), 6.84 (t, J=74.1 Hz, 1H).

Example 8

Intermediate 7—Preparation of Sodium 3-methoxy-benzenesulfinate

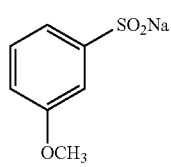

Sodium 3-methoxy-benzenesulfinate was prepared from 3-methoxy-benzenesulfonyl chloride following the procedure of Example 2 to give the product (0.58 g, 73%) as a white solid: $^1$H NMR (CD$_3$OD, 300 MHz) δ 7.31 (t, J=7.8 Hz, 1H), 7.25-7.26 (m, 1H), 7.21 (dt, J=7.5, 1.2 Hz, 1H), 6.91 (ddd, J=7.9, 2.7, 1.2 Hz, 1H), 3.83 (s, 3H).

Example 9

Intermediate 8—Preparation of Sodium 3-nitro-benzenesulfinate

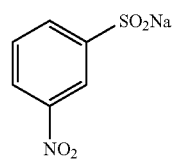

Sodium 3-nitro-benzenesulfinate was prepared from 3-nitro-benzenesulfonyl chloride following the procedure of Example 2 to give the product (1.7 g, 60%) as a yellow solid: $^1$H NMR (CD$_3$OD, 300 MHz) δ 8.42 (t, J=2.1 Hz, 1H), 8.29 (ddd, J=8.2, 1.8, 0.6 Hz, 1H), 7.98 (d, J=7.5 Hz, 1H), 7.72 (t, J=7.8 Hz, 1H).

Example 10

Intermediate 9—Preparation of Sodium 3-trifluoro-methylbenzenesulfinate

Sodium 3-trifluoromethyl-benzenesulfinate was prepared from 3-trifluoromethyl-benzenesulfonyl chloride following the procedure of Example 2 to give the product (1.0 g, 50%) as a white solid: $^1$H NMR (CD$_3$OD, 300 MHz) δ 7.96 (s, 1H), 7.88 (d, J=7.2 Hz, 1H), 7.58-7.68 (m, 2H).

Example 11

Intermediate 10—Preparation of Sodium 3-methyl-benzenesulfinate

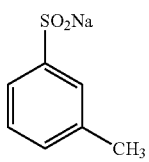

Sodium 3-methyl-benzenesulfinate was prepared from sodium 3-methyl-benzenesulfonyl chloride following the procedure of Example 2 to give the product (1.0 g, 50%) as a white solid: $^1$H NMR (CD$_3$OD, 300 MHz) δ 7.42-7.47 (m, 2H), 7.29 (t, J=7.5 Hz, 1H), 7.18 (d, J=7.8 Hz, 1H), 2.37 (s, 3H).

Example 12

Intermediate 11—Preparation of Sodium 4-cyano-benzenesulfinate

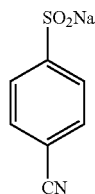

Sodium 4-cyano-benzenesulfinate was prepared from 4-cyano-benzenesulfonyl chloride following the procedure of Example 2 to give the product (1.87 g, 64%) as a white solid: $^1$H NMR (CD$_3$OD, 300 MHz) δ 7.78-7.80 (m, 4H).

Example 13

Intermediate 12—Preparation of Sodium 4-nitro-benzenesulfinate

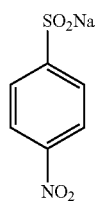

Sodium 4-nitro-benzenesulfinate was prepared from 4-nitro-benzenesulfonyl chloride following the procedure of Example 2 to give the product (0.98 g, 37%) as a yellow solid: $^1$H NMR (CD$_3$OD, 300 MHz) δ 8.28 (d, J=6.9 Hz, 2H), 7.86 (d, J=7.0 Hz, 2H).

Example 14

Intermediate 13—Preparation of Sodium 4-methyl-benzenesulfinate

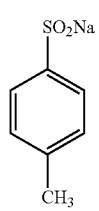

Sodium 4-methyl-benzenesulfinate was prepared from sodium 4-methyl-benzenesulfonyl chloride following the procedure of Example 2 to give the product (3.5 g, 75%) as a white solid: $^1$H NMR (D$_2$O, 300 MHz) δ 7.49 (d, J=8.1 Hz, 2H), 7.32 (d, J=8.1 Hz, 2H), 2.34 (s, 3H).

Example 15

Intermediate 14—Preparation of Sodium 4-methoxy-benzenesulfinate

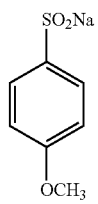

Sodium 4-methoxy-benzenesulfinate was prepared from 4-methoxybenzenesulfonyl chloride following the procedure of Example 2 to give the product (1.8 g, 99%) as a white solid $^1$H NMR (CD$_3$OD, 300 MHz) δ 7.57 (d, J=9.0 Hz, 2H), 6.95 (d, J=8.7 Hz, 2H), 3.80 (s, 3H).

Example 16

Intermediate 15—Preparation of Sodium 4-trifluoromethoxy-benzenesulfinate

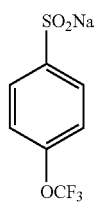

Sodium 4-trifluoromethoxy-benzenesulfinate was prepared from 4-trifluorobenzenesulfonyl chloride following the procedure of Example 2 to give the product (1.49 g, 96%) as a white solid: $^1$H NMR (CD$_3$OD, 300 MHz) δ 7.71-7.75 (m, 2H), 7.30-7.33 (m, 2H).

Example 17

Intermediate 16—Preparation of Sodium 4-fluoro-benzenesulfinate

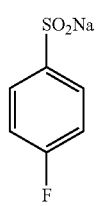

Sodium 4-fluoro-benzenesulfinate was prepared from 4-fluoro-benzenesulfonyl chloride following the procedure of Example 2 to give the product (1.6 g, 86%) as a white solid: $^1$H NMR (CD$_3$OD, 300 MHz) δ 7.63-7.68 (m, 2H), 7.08-7.16 (m, 2H)

Example 18

Intermediate 17—Preparation of Sodium 4-trifluoromethylbenzenesulfinate

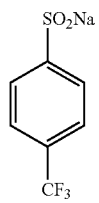

Sodium 4-trifluoromethyl-benzenesulfinate was prepared from 4-trifluoromethylbenzenesulfonyl chloride following the procedure of Example 2 to give the product (1.8 g, 94%) as a white solid: $^1$H NMR (CD$_3$OD, 300 MHz) δ 7.82 (d, J=8.4 Hz, 2H), 7.72 (d, J=8.1 Hz, 2H).

Example 19

Intermediate 18—Preparation of Sodium 4-chloro-benzenesulfinate

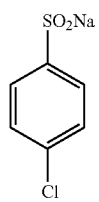

Sodium 4-chloro-benzenesulfinate was prepared from 4-chloro-benzenesulfonyl chloride following the procedure of Example 2 to give the product (5.0 g, 38%) as a white solid: $^1$H NMR (CD$_3$OD, 300 MHz) δ 7.54-7.57 (m, 2H), 7.47-7.51 (m, 2H).

Example 20

Intermediate 19—Preparation of Sodium 2-methyl-benzenesulfinate

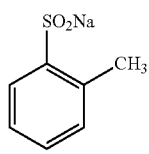

Sodium 2-methylbenzenesulfinate was prepared from sodium 2-methyl-benzenesulfonyl chloride following the procedure of Example 2 to give the product (1.0 g, 50%) as a white solid: $^1$H NMR (D$_2$O, 300 MHz) δ 7.54-7.63 (m, 2H), 7.02-7.07 (m, 2H), 3.84 (s, 3H).

Example 21

Intermediate 20—Preparation of Sodium 2,3-dichloro-benzenesulfinate

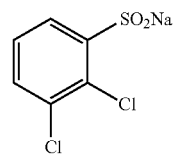

Sodium 2,3-dichloro-benzenesulfinate was prepared from 2,3-dichloro-benzenesulfonyl chloride following the procedure of Example 2 to give the product (0.85 g, 43%) as a white solid: $^1$H NMR (CD$_3$OD, 300 MHz) δ 7.79 (dd, J=7.5, 1.5 Hz, 1H), 7.49 (dd, J=7.8, 1.8 Hz, 1H), 7.36 (t, J=7.8 Hz, 1H).

Example 22

Intermediate 21—Preparation of Sodium 3,5-difluoro-benzenesulfinate

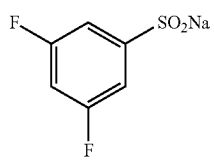

Sodium 3,5-difluoro-benzenesulfinate was prepared from 3,5-difluoro-benzenesulfonyl chloride following the procedure of Example 2 to give the product (0.46 g, 49%) as a white solid: $^1$H NMR (CD$_3$OD, 300 MHz) δ 7.18-7.23 (m, 2H), 6.91 (tt, J=9.0, 2.4 Hz, 1H).

Example 23

Intermediate 22—Preparation of Sodium 3,5-dichloro-benzenesulfinate

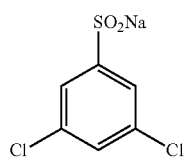

Sodium 3,5-dichloro-benzenesulfinate was prepared from 3,5-difluorobenzenesulfonyl chloride following the procedure of Example 2 to give the product (1.4 g, 77%) as a white solid: $^1$H NMR (CD$_3$OD, 300 MHz) δ 7.54-7.55 (m, 2H), 7.40-7.42 (m, 1H).

Example 24

Intermediate 23—Preparation of Sodium naphthalene-1-sulfinate

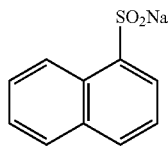

Sodium naphthalene-1-sulfinate was prepared from sodium naphthalene-1-sulfonyl chloride following the procedure of Example 2 to give the product (0.73 g, 51%) as a white solid: $^1$H NMR (D$_2$O, 300 MHz) δ 8.57-8.61 (m, 1H), 7.98-8.01 (m, 2H), 7.90 (dd, J=6.0, 1.2 Hz, 1H), 7.56-7.65 (m, 3H).

Example 25

Intermediate 24—Preparation of Sodium naphthalene-2-sulfinate

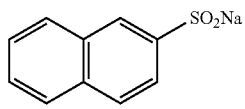

Sodium napthalene-2-sulfinate was prepared from naphalene-2-sulfonyl chloride following the procedure of Example 2 to give the product (3.83 g, 100%) as a white solid: $^1$H NMR (CD$_3$OD, 300 MHz) δ 8.09 (s, 1H), 7.78-7.95 (m, 4H), 7.46-7.55 (m 2H).

Example 26

Intermediate 25—Preparation of Sodium thiophene-3-sulfinate

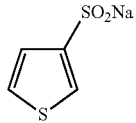

Sodium thiophene-3-sulfinate was prepared from thiophene-3-sulfonyl chloride following the procedure of Example 2 to give the product (400 mg, 86%) as a white solid: $^1$H NMR (CD$_3$OD, 300 MHz) δ 7.57 (dd, J=3.0, 1.2 Hz, 1H), 7.39 (dd, J=5.1, 3.0 Hz, 1H), 7.27 (dd, J=5.1, 1.2 Hz, 1H).

Example 27

Preparation of 2-Phenylsulfonyl-5-methyl-5,6,7,8,9,10-hexahydro-7,10-epiminocyclohepta[b]indole hydrochloride

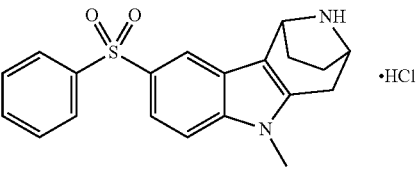 [SMILES: Cn1c2c(c3cc(S(=O)(=O)c4ccccc4)ccc31)C1CCC(C2)N1 ; Cl]

Step A: A slurry of 4-bromophenylhydrazine hydrochloride (55.3 g, 247 mmol) and nortropinone hydrochloride (40 g, 247 mmol) in ethanol (400 mL) was heated at reflux for 4 h. After cooling to ambient temperature the reaction mixture was treated with concentrated HCl (300 mL) and heated at reflux for 64 h. After concentrating in vacuo the reaction mixture was taken up in 2-propanol (600 mL) and water (400 mL) prior to the addition of potassium carbonate (100 g, 723 mmol) and di-tert-butyl dicarbonate (100 g, 458 mmol). The reaction mixture was stirred at 0° C. for 2 h then diluted with water (200 mL) and extracted three times with dichloromethane. The combined extracts were dried over sodium sulfate, filtered and concentrated in vacuo. The residue was diluted with dichloromethane stored in a refrigerator overnight and the resulting precipitate collected by filtration. The filter cake was rinsed with cold dichloromethane and dried in vacuo to the give tert-butyl 2-bromo-5,6,7,8,9,10-hexahydro-7,10-epiminocyclohepta[b]indole-carboxylate (21.6 g, 23%) as a grey solid: $^1$H NMR (DMSO-d$_6$, 300 MHz) δ 11.06 (s, 1H), 7.66 (d, J=1.8 Hz, 1H), 7.22 (d, J=8.7 Hz, 1H), 7.09 (dd, J=8.7, 1.8 Hz, 1H), 5.11 (d, J=5.1 Hz, 1H), 4.38-4.51 (br s, 1H), 3.18-3.30 (m, 1H), 2.54-2.61 (br s, 1H), 2.15-2.30 (m, 1H), 1.95-2.13 (m, 1H), 1.74-1.84 (m, 1H), 1.63-1.67 (m, 1H), 1.19-1.42 (m, 9H).

Step B: To a solution of the product of step A (11.7 g, 31.0 mmol) in DMF (200 mL) at 0° C. was added sodium hydride (3.72 g, 93.0 mmol). The mixture was stirred at 0° C. for 30 min prior to the addition of iodomethane (3.86 mL, 62.0 mmol). The reaction mixture was stirred overnight at ambient temperature, cooled to 0° C. and quenched by adding a saturated solution of ammonium chloride. The mixture was extracted three times with dichloromethane and the combined extracts dried over sodium sulfate. After concentration in vacuo the residue was purified by flash column chromatography (SiO$_2$, 4:1 to 2:1 hexanes/ethyl acetate) to give tert-butyl 2-bromo-5-methyl-5,6,7,8,9,10-hexahydro-7,10-epiminocyclohepta[b]indole-carboxylate (10.7 g, 88%) as a light yellow solid: $^1$H NMR (CDCl$_3$, 300 MHz) δ 7.61 (d, J=1.8 Hz, 1H), 7.21 (dd, J=8.7, 1.8 Hz, 1H), 7.10 (d, J=8.7 Hz, 1H), 5.08-5.30 (m, 1H), 4.54-4.75 (m, 1H), 3.56 (s, 3H), 3.21-3.49 (m, 1H), 2.47 (d, J=15.9 Hz, 1H), 2.10-2.38 (m, 2H), 1.86-1.98 (m, 1H), 1.56-1.68 (m, 1H), 1.40 (br s, 9H).

Step C: A mixture of product from step B (1.5 g, 3.84 mmol) and benzene sulfinic acid sodium salt (755 mg, 4.6 mmol) were suspended in toluene (30 mL) and N$_2$ was bubbled through the reaction mixture for 10-15 min. Di-palladium-tris(dibenzylideneacetone) (89 mg, 0.096 mmol), cesium carbonate (1.84 g, 5.76 mmol), xantphos (111 mg, 0.192 mmol) and tetrabutylammonium chloride (1.28 g, 4.6 mmol) were then added sequentially, and the reaction was heated to reflux for 12 h. The reaction mixture was cooled to ambient temperature, partitioned between ethyl acetate and sat. ammonium chloride solution and the organics removed. The aqueous was extracted with ethyl acetate (×2) and the combined organics dried over sodium sulfate and concentrated. Purification by flash column chromatography (silica gel, hexanes/EtOAc, 100:0 to 50:50) provided tert-butyl 2-phenylsulfonyl-5-methyl-5,6,7,8,9,10-hexahydro-7,10-epiminocyclohepta[b]indole-carboxylate (1.22 g, 71%) as a yellow solid: $^1$H NMR (300 MHz, CDCl$_3$) δ 8.20 (s, 1H), 7.96 (dd, J=7.7, 1.5 Hz, 2H), 7.68 (d, J=9.0 Hz, 1H), 7.47 (m, 3H), 7.30 (d, J=8.7 Hz, 1H), 5.25 (brs, 1H), 4.68 (m, 1H), 3.60 (s, 3H), 3.37 (m, 1H), 2.50 (d, J=16.7 Hz, 1H), 2.26 (m, 2H), 1.94 (t, J=10.3 Hz, 1H), 1.61 (m, 1H, partially masked by H$_2$O peak), 1.36 (s, 9H).

Step D: The product from step C (1.22 g, 2.7 mmol) was dissolved in methanol (7 mL) and dichloromethane (5 mL) and 2N HCl in diethylether (70 mL) was added. The reaction was stirred at room temperature for 12 h, after which a precipitate formed. The mixture was diluted with diethylether and filtered providing 2-phenylsulfonyl-5-methyl-5,6,7,8,9,10-hexahydro-7,10-epiminocyclohepta[b]indole hydrochloride (900 mg, 86%) as an off-white solid: Mpt 238-244° C. (dec.); $^1$H NMR (300 MHz, d$_6$-DMSO) δ 9.69 (brs, 1H), 9.15 (brs, 1H), 8.38 (s, 1H), 7.92 (dd, J=8.0, 1.7 Hz, 2H), 7.60 (m, 5H), 5.36 (d, J=4.8 Hz, 1H), 4.47 (brs, 1H), 3.68 (s, 3H), 3.34 (dd, 1H, partially masked by solvent), 3.00 (d, J=17.2 Hz, 1H), 2.25 (m, 2H), 2.08 (t, J=9.6 Hz, 1H), 1.80 (m, 1H); ESI MS m/z 353 [M+H]$^+$; HPLC (Method A)>99% (AUC), t$_R$=12.02 min.

The constituent enantiomers were separated by chiral HPLC purification and converted to the HCl salt:

Enantiomer 1 [(−)-enantiomer]: Off-white solid; [α]$^{20}_D$ (MeOH)=−27°; $^1$H NMR (500 MHz, d$_6$-DMSO) δ 9.46 (brs, 1H), 9.06 (brs, 1H), 8.37 (s, 1H), 7.93 (m, 2H), 7.60 (m, 5H), 5.36 (d, J=4.3 Hz, 1H), 4.48 (brs, 1H), 3.68 (s, 3H), 3.38 (dd, J=17.3, 4.4 Hz, 1H, partially masked by solvent), 3.01 (d, J=17.0 Hz, 1H), 2.26 (m, 2H), 2.09 (t, J=9.9 Hz, 1H), 1.80 (m, 1H); ESI MS m/z 353 [M+H]$^+$; HPLC (Method A)>99% (AUC), t$_R$=12.16 min; Chiral HPLC e.e >97% (AUC), t$_R$=11.09 min.

Enantiomer 2 [(+)-enantiomer]: Off-white solid; [α]$^{20}_D$ (MeOH)=−17°; $^1$H NMR (500 MHz, d$_6$-DMSO) δ 9.37 (brs, 1H), 9.03 (brs, 1H), 8.37 (s, 1H), 7.93 (d, J=7.3 Hz, 2H), 7.60 (m, 5H), 5.36 (brs, 1H), 4.48 (brs, 1H), 3.68 (s, 3H), 3.36 (m, 1H, partially masked by solvent), 3.01 (d, J=17.3 Hz, 1H), 2.26 (m, 2H), 2.10 (t, J=10.2 Hz, 1H), 1.80 (m, 1H); ESI MS m/z 353 [M+H]$^+$; HPLC (Method A)>99% (AUC), t$_R$=12.14 min; Chiral HPLC e.e >95% (AUC), t$_R$=14.72 min.

Example 28

Preparation of 2-(4-Fluorophenyl)sulfonyl-5-methyl-5,6,7,8,9,10-hexahydro-7,10-epiminocyclohepta[b]indole hydrochloride

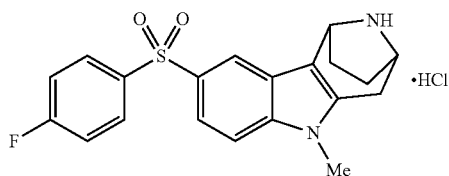 [SMILES: Cn1c2c(c3cc(S(=O)(=O)c4ccc(F)cc4)ccc31)C1CCC(C2)N1 ; Cl]

Step A: Prepared from the product of Example 27, step B and intermediate 16 according to the procedure of Example 27 (step C). Purification by flash column chromatography (SiO$_2$, 3:2 hexanes/ethyl acetate) provided tert-butyl 2-(4-fluorophenyl)sulfonyl-5-methyl-5,6,7,8,9,10-hexahydro-7,10-epiminocyclohepta[b]indole-carboxylate (100 mg, 24%) as a yellow solid: $^1$H NMR (CDCl$_3$, 300 MHz) δ 8.16 (s, 1H), 7.92-7.98 (m, 2H), 7.61-7.64 (m, 1H), 7.27-7.30 (m, 1H), 7.08-7.15 (m, 2H), 5.22-5.28 (m, 1H), 4.58-4.78 (m, 1H), 3.60 (s, 3H), 3.22-3.45 (m, 1H), 2.50 (d, J=15.0 Hz, 1H), 2.13-2.36 (m, 1H), 1.89-1.95 (m, 1H), 1.56-1.65 (m, 1H), 1.38 (br s, 9H).

Step B: To a solution of product from step B (150 mg, 0.31 mmol) in dichloromethane, cooled to 0° C. was added trifluoroacetic acid (0.4 ml, 5.13 mmol). The solution was stirred for 1.5 h then made basic (pH 10) by adding excess saturated sodium bicarbonate solution and extracted with dichloromethane. The organic layer was dried over sodium sulfate, filtered and concentrated in vacuo. The residue was purified by flash column chromatography (SiO$_2$, 9:1 dichloromethane/methanol) to give 2-(4-fluorophenyl)sulfonyl-5-methyl-5,6,7,8,9,10-hexahydro-7,10-epiminocyclohepta[b]indole (70 mg, 95%) as a white solid: $^1$H NMR (CDCl$_3$, 300 MHz) δ 8.17-8.18 (m, 1H), 7.96-8.03 (m, 2H), 7.65 (d, J=7.8 Hz, 1H), 7.48-7.51 (m, 1H), 7.22-7.30 (m, 2H), 4.80-4.90 (m, 1H), 4.18-4.22 (m, 1H), 3.66 (s, 3H), 3.22-3.33 (m, 1H), 2.76-2.81 (m, 1H), 2.04-2.28 (m, 3H), 1.71-1.77 (m, 1H).

Step C: The product of step B was treated with 1.25 M HCl in methanol (2 mL). The solution was concentrated in vacuo, dissolved in water and washed with dichloromethane. The aqueous layer was lyophilized to give 2-(4-fluorophenyl)sulfonyl-5-methyl-5,6,7,8,9,10-hexahydro-7,10-epiminocyclohepta[b]indole hydrochloride (25 mg, 73%, AUC HPLC 95.9%) as a white solid: mp 210-214° C.; $^1$H NMR (CD$_3$OD, 300 MHz) δ 8.27 (s, 1H), 7.99-8.03 (m, 2H), 7.72 (d, J=8.4 Hz, 1H), 7.57 (d, J=7.1 Hz, 1H), 7.24-7.30 (m, 2H), 5.30 (d, J=4.5 Hz, 1H), 4.59 (br s, 1H), 3.72 (s, 3H), 3.48 (dd, J=12.6, 4.5 Hz, 1H), 3.07 (d, J=17.4 Hz, 1H), 2.24-2.47 (m, 3H), 1.95-2.00 (m, 1H); ESI MS m/z 371 [M+H]$^+$.

Example 29

Preparation of 2-(4-Trifluoromethylphenyl)sulfonyl-5-methyl-5,6,7,8,9,10-hexahydro-7,10-epiminocyclohepta[b]indole hydrochloride

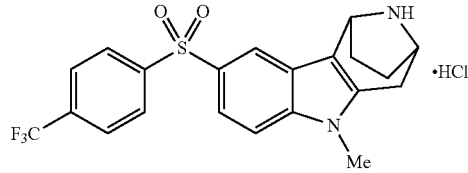 [SMILES: Cn1c2c(c3cc(S(=O)(=O)c4ccc(C(F)(F)F)cc4)ccc31)C1CCC(C2)N1 ; Cl]

Step A: Intermediate 17 was coupled with the product of Example 27, step B following the procedure of Example 27, step C. The crude product was purified by flash column chromatography (SiO$_2$, 3:2 hexane/ethyl acetate) to give tert-butyl 2-(4-trifluoromethylphenyl)sulfonyl-5-methyl-5,6,7,8,9,10-hexahydro-7,10-epiminocyclohepta[b]indole-carboxylate (130 mg, 24%) as a white solid: $^1$H NMR (CDCl$_3$, 300 MHz) δ 8.19 (s, 1H), 8.07 (d, J=8.4 Hz, 2H), 7.67-7.78 (m, 3H), 7.31-7.33 (m, 1H), 5.30 (br s, 1H), 4.70 (br s, 1H), 3.58 (s, 3H), 3.37-3.41 (m, 1H), 2.51 (d, J=16.3 Hz, 1H), 2.16-2.31 (m, 2H), 1.90-1.96 (m, 1H), 1.56-1.65 (m, 1H), 1.37 (s, 9H).

Step B: The product of step A was subjected to Boc-deprotection with TFA following the procedure of Example 28, step B to give 2-(4-trifluoromethylphenyl)sulfonyl-5-methyl-5,6,7,8,9,10-hexahydro-7,10-epiminocyclohepta[b]indole (100 mg, 95%) as an off-white solid: $^1$H NMR (CDCl$_3$, 300 MHz) δ 8.03-8.11 (m, 3H), 7.11-7.62 (m, 3H), 7.26-7.30 (m, 1H), 4.74-4.75 (m, 1H), 4.22 (br s, 1H), 3.56 (s, 3H), 3.26-3.31 (m, 1H), 2.56-2.62 (m, 1H), 1.99-2.28 (m, 3H), 1.59-1.64 (m, 1H).

Step C: The hydrochloride salt was prepared following the procedure of Example 28, step C to give 2-(4-trifluoromethylphenyl)sulfonyl-5-methyl-5,6,7,8,9,10-hexahydro-7,10-epiminocyclohepta[b]indole hydrochloride (80 mg, 73%, AUC HPLC >99%) as a white solid: mp 200-205° C.; $^1$H NMR (CD$_3$OD, 300 MHz) δ 8.31 (s, 1H), 8.15 (d, J=8.4 Hz, 2H), 7.86 (d, J=8.4 Hz, 2H), 7.75-7.80 (m, 1H), 7.59-7.62 (m, 1H), 5.29-5.30 (m, 1H), 4.52-4.53 (m, 1H), 3.72 (s, 3H), 3.47 (dd, J=12.6, 4.5 Hz, 1H), 3.05 (d, J=17.4 Hz, 1H), 2.28-2.43 (m, 3H), 1.95-2.05 (m, 1H); ESI MS m/z 421 [M+H]$^+$.

Example 30

Preparation of 2-(4-Cyanophenyl)sulfonyl-5-methyl-5,6,7,8,9,10-hexahydro-7,10-epiminocyclohepta[b]indole hydrochloride

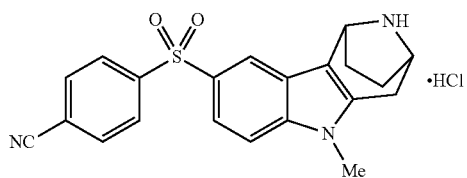 [SMILES: Cn1c2c(c3cc(S(=O)(=O)c4ccc(C#N)cc4)ccc31)C1CCC(C2)N1 ; Cl]

Step A: Intermediate 11 was coupled with the product of Example 27, step B following the procedure of Example 27, step C. The crude product was purified by flash column chromatography (SiO$_2$, 8:2 hexane/ethyl acetate) to give tert-butyl 2-(4-cyanophenyl)sulfonyl-5-methyl-5,6,7,8,9,10-hexahydro-7,10-epiminocyclohepta[b]indole-carboxylate (184 mg, 50%) as a yellow solid: $^1$H NMR (CDCl$_3$, 300 MHz) δ 8.18 (s, 1H), 8.05 (dd, J=6.9, 1.5 Hz, 2H), 7.75 (dd, J=6.9, 1.5 Hz, 2H), 7.66 (dd, J=8.7, 1.5 Hz, 1H), 7.33 (d, J=8.7 Hz, 1H), 5.26 (br s, 1H), 4.69 (br s, 1H), 3.62 (s, 3H), 3.37 (br s, 1H), 2.51 (d, J=15.9 Hz, 1H), 2.13-2.41 (m, 2H), 1.87-1.99 (m, 1H), 1.67-1.70 (m, 1H), 1.39 (br s, 9H).

Step B: The product of step A was subjected to Boc-deprotection with 2 M HCl in diethyl ether following the procedure of Example 28, step B. The crude material was purified by flash column chromatography (SiO$_2$, 80:18:2 chloroform/methanol/ammonium hydroxide) and the product treated directly with 1.25 M HCl in methanol (0.5 mL). After concentration in vacuo the residue was lyophilized to give 2-(4-cyanophenyl)sulfonyl-5-methyl-5,6,7,8,9,10-hexahydro-7,10-epiminocyclohepta[b]indole hydrochloride (38 mg, 49%, AUC HPLC >99%) as a white solid: mp 216-218° C.; $^1$H NMR (D$_2$O, 300 MHz) δ 8.23 (d, J=1.5 Hz, 1H), 7.97 (d, J=8.4 Hz, 2H), 7.78 (dd, J=8.4, 1.8 Hz, 2H), 7.62 (dd, J=8.7 Hz, 1.5 Hz, 1H), 7.49 (d, J=8.7 Hz, 1H), 5.23 (d, J=4.8 Hz, 1H), 4.52-4.57 (m, 1H), 3.51 (s, 3H), 3.46 (dd, J=17.7, 4.5 Hz, 1H), 3.01 (d, J=17.4 Hz, 1H), 2.20-2.48 (m, 3H), 1.78-1.94 (m, 1H); APCI MS m/z 378 [M+H]$^+$.

Example 31

Preparation of 2-(4-Methoxyphenyl)sulfonyl-5-methyl-5,6,7,8,9,10-hexahydro-7,10-epiminocyclohepta[b]indole hydrochloride

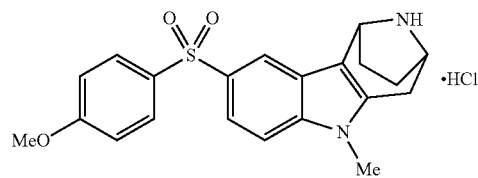 [SMILES: COc1ccc(S(=O)(=O)c2ccc3c(c2)c2c(n3C)CC3CCC2N3)cc1 ; Cl]

Step A: Intermediate 14 was coupled with the product of Example 27, step B following the procedure of Example 27, step C. The crude product was purified by flash column chromatography (8:2 hexanes/ethyl acetate) to give tert-butyl 2-(4-methoxyphenyl)sulfonyl-5-methyl-5,6,7,8,9,10-hexahydro-7,10-epiminocyclohepta[b]indole-carboxylate (106 mg, 34%) as a light-yellow solid: $^1$H NMR (CDCl$_3$, 300 MHz) δ 8.17 (s, 1H), 7.88 (d, J=8.7 Hz, 2H), 7.60-7.71 (m, 1H), 7.27-7.32 (m, 1H), 6.92 (d, J=9.0 Hz, 2H), 5.26 (br s, 1H), 4.69 (br s, 1H), 3.82 (s, 3H), 3.59 (s, 3H), 3.40 (br s, 1H), 2.49 (d, J=16.2 Hz, 1H), 2.12-2.39 (m, 2H), 1.88-2.01 (m, 1H), 1.53-1.72 (m, 1H), 1.38 (br s, 9H).

Step B: The product of step A was subjected to Boc-deprotection with 2 M HCl in diethyl ether following the procedure of Example 28, step B. The crude material was purified by flash column chromatography (SiO$_2$, 80:18:2 chloroform/methanol/ammonium hydroxide) and the product treated directly with 1.25 M HCl in methanol (0.5 mL). After concentration in vacuo the residue was lyophilized to give 2-(4-methoxyphenyl)sulfonyl-5-methyl-5,6,7,8,9,10-hexahydro-7,10-epiminocyclohepta[b]indole hydrochloride (49 mg, 34%, AUC HPLC 98.0%) as a light-yellow solid: mp 210-212° C.; $^1$H NMR (DMSO-d$_6$, 300 MHz) δ 9.34 (br s, 1H), 9.04 (br s, 1H), 8.32 (s, 1H), 7.85 (dd, J=7.2, 2.1 Hz, 2H), 7.63 (s, 2H), 7.09 (dd, J=7.2, 2.1 Hz, 2H), 5.35 (d, J=3.9 Hz, 1H), 4.48 (br s, 1H), 3.80 (s, 3H), 3.67 (s, 3H), 3.35-3.45 (m, 1H), 3.01 (d, J=17.1 Hz, 1H), 2.18-2.33 (m, 2H), 2.04-2.15 (m, 1H), 1.72-1.86 (m, 1H); ESI MS m/z 383 [M+H]$^+$.

Example 32

Preparation of 2-(4-Hydroxyphenyl)sulfonyl-5-methyl-5,6,7,8,9,10-hexahydro-7,10-epiminocyclohepta[b]indole hydrochloride

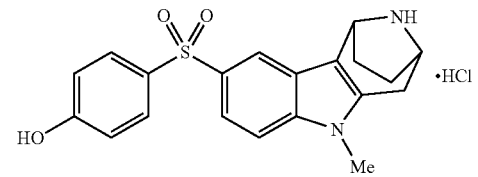

A mixture of the product of Example 31, step B (18 mg, 0.04 mmol) and 33% HBr in acetic acid (10 mL) was heated at 60° C. for 4 days. The reaction mixture was concentrated in vacuo and the resulting residue neutralized with saturated sodium bicarbonate solution before extracting with dichloromethane. The organic layer was dried over sodium sulfate, filtered and concentrated in vacuo. The crude material was purified by semi-preparative HPLC and the free base treated with 1.25 M HCl methanol solution (0.5 mL) to give 2-(4-hydroxyphenyl)sulfonyl-5-methyl-5,6,7,8,9,10-hexahydro-7,10-epiminocyclohepta[b]indole hydrochloride (2 mg, 12%, AUC HPLC 97.2%) as an off-white solid: mp 210-212° C.; ¹H NMR (CD₃OD, 300 MHz) δ 8.18-8.23 (m, 1H), 7.73-7.81 (m, 2H), 7.69 (dd, J=9.0 Hz, 1.8 Hz, 1H), 7.55 (d, J=8.7 Hz, 1H), 6.82-6.90 (m, 2H), 5.25-5.36 (m, 1H), 4.53 (br s, 1H), 3.71 (s, 3H), 3.40-3.55 (m, 1H), 3.46-3.55 (m, 1H), 3.01-3.11 (m, 1H), 2.23-2.51 (m, 2H), 1.92-2.11 (m, 1H); ESI MS m/z 369 [M+H]⁺.

Example 33

Preparation of 2-(4-Aminomethylphenyl)sulfonyl-5-methyl-5,6,7,8,9,10-hexahydro-7,10-epiminocyclohepta[b]indole dihydrochloride

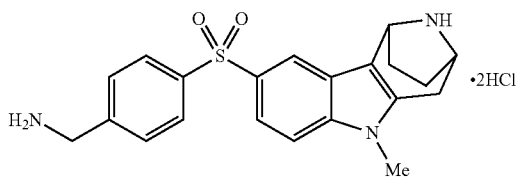 [SMILES: Cn1c2c(c3cc(S(=O)(=O)c4ccc(CN)cc4)ccc31)C1CCC(C2)N1 ; "·2HCl"]

Step A: A mixture of the product of Example 30, step A (92 mg, 0.19 mmol) and cobalt(II) chloride (25 mg, 0.19 mmol) in anhydrous methanol (1.5 mL), cooled to 0° C. was treated with sodium borohydride (22 mg, 0.58 mmol). The reaction mixture was stirred at 0° C. for 2 h then quenched with water and filtered through a celite bed. The filtrate was concentrated in vacuo and extracted with dichloromethane. The organic layer was dried over sodium sulfate and concentrated in vacuo. The residue was purified by flash column chromatography (SiO₂, 80:18:2 chloroform/methanol/ammonium hydroxide) to give tert-butyl 2-(4-aminomethylphenyl)sulfonyl-5-methyl-5,6,7,8,9,10-hexahydro-7,10-epiminocyclohepta[b]indole-carboxylate (40 mg, 43%) as a light-yellow solid: ESI MS m/z 382 [M+H]⁺

Step B: The product of step A was subjected to Boc-deprotection with 2 M HCl in diethyl ether following the procedure of Example 28, step B. The crude material was purified by flash column chromatography (SiO₂, 80:18:2 chloroform/methanol/ammonium hydroxide). The free base was treated with 1.25 M HCl in methanol (0.5 mL). The solution was concentrated in vacuo and the residue lyophilized to give 2-(4-Aminomethylphenyl)sulfonyl-5-methyl-5,6,7,8,9,10-hexahydro-7,10-epiminocyclohepta[b]indole dihydrochloride (13 mg, 76%, AUC HPLC 97.0%) as an off-white solid: mp 237-239° C.; ¹H NMR (DMSO-d₆, 300 MHz) δ 9.72 (br s, 1H), 9.26 (br s, 1H), 8.50 (br s, 3H), 8.38 (s, 1H), 7.97 (d, J=8.1 Hz, 2H), 7.58-7.74 (m, 4H), 5.34 (br s, 1H), 4.46 (br s, 1H), 4.07 (br s, 2H), 3.67 (s, 3H), 3.39-3.46 (m, 1H), 3.00 (d, J=17.4 Hz, 1H), 2.19-2.39 (m, 2H), 2.04-2.15 (m, 1H), 1.71-1.88 (m, 1H); ESI MS m/z 382 [M+H]⁺.

Example 34

Preparation of 2-[4-(N,N-Dimethylaminomethyl)phenyl]sulfonyl-5-methyl-5,6,7,8,9,10-hexahydro-7,10-epiminocyclohepta[b]indole dihydrochloride

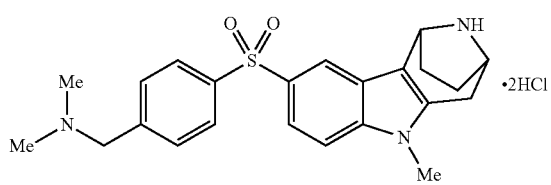 [SMILES: CN(C)Cc1ccc(S(=O)(=O)c2ccc3c(c2)c2c(n3C)CC3CCC2N3)cc1 ; "·2HCl"]

To a solution of the product of Example 33, step B (20 mg, 0.04 mmol) in 1,2-dichloroethane (4 mL) was added formaldehyde (20 μL, 37% in water). The mixture was stirred at ambient temperature for 10 min before addition of sodium triacetoxyborohydride (53 mg, 0.25 mmol). After stirring for 2 h the reaction mixture was quenched with saturated sodium bicarbonate solution and extracted with dichloromethane. The organic layer was dried over sodium sulfate and concentrated in vacuo. The residue was treated directly with 2 M HCl in diethyl ether (5 mL) and stirred at ambient temperature for 4 h. After concentration in vacuo the residue was neutralized with saturated sodium bicarbonate solution and extracted with dichloromethane. The organic layer was dried over sodium sulfate, filtered and concentrated in vacuo. The crude material was purified by flash column chromatography (SiO₂, 80:18:2 chloroform/methanol/ammonium hydroxide), followed by semi-preparative HPLC. The purified free base was treated directly with 1.25 M HCl methanol (0.5 mL). The solution was concentrated in vacuo and the residue lyophilized to give 2-[4-(N,N-dimethylaminomethyl)-phenyl]sulfonyl-5-methyl-5,6,7,8,9,10-hexahydro-7,10-epiminocyclohepta[b]indole dihydrochloride (8 mg, 46%, AUC HPLC 98.4%) as a white solid: mp 244-246° C.; ¹H NMR (DMSO-d₆, 300 MHz) δ 11.13 (br s, 1H), 9.50-9.85 (m, 1H), 9.10-9.30 (m, 1H), 8.41 (s, 1H), 8.01 (d, J=8.1 Hz, 2H), 7.80 (d, J=8.4 Hz, 2H), 7.62-7.72 (m, 2H), 5.35 (br s, 1H), 4.47 (br s, 1H), 4.32 (d, J=4.5 Hz, 2H), 3.67 (s, 3H), 3.46-3.37 (m, 1H), 3.00 (d, J=17.1 Hz, 1H), 2.64 (s, 6H), 2.19-2.37 (m, 2H), 2.13-2.02 (m, 1H), 1.72-1.87 (m, 1H); ESI MS m/z 410 [M+H]⁺.

Example 35

Preparation of 2-(3-Fluorophenyl)sulfonyl-5-methyl-5,6,7,8,9,10-hexahydro-7,10-epiminocyclohepta[b]indole hydrochloride

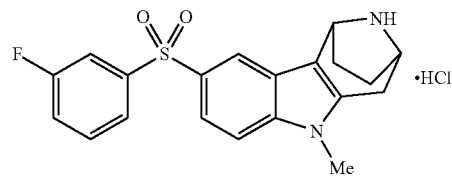 [SMILES: Cn1c2c(c3cc(S(=O)(=O)c4cccc(F)c4)ccc31)C1CCC(C2)N1 ; Cl]

Step A: Intermediate 2 was coupled with the product of Example 27, step B following the procedure of Example 27, step C. The crude material was purified by flash column chromatography (SiO₂, hexanes/ethyl acetate) to give tert-butyl 2-(3-fluorophenyl)sulfonyl-5-methyl-5,6,7,8,9,10- hexahydro-7,10-epiminocyclohepta[b]indole-carboxylate (110 mg, 46%) as a pale yellow solid: $^1$H NMR (CDCl$_3$, 300 MHz) δ 8.13-8.23 (m, 1H), 7.71-7.76 (m, 1H), 7.58-7.70 (m, 2H), 7.38-7.49 (m, 1H), 7.28-7.35 (m, 1H), 7.12-7.23 (m, 1H), 5.16-5.38 (m, 1H), 4.32-4.51 (m, 1H), 3.60 (s, 3H), 3.20-3.50 (m, 1H), 2.50 (d, J=16.2 Hz, 1H), 2.10-2.40 (m, 2H), 1.85-1.98 (m, 1H), 1.56-1.68 (m, 1H), 1.37 (br s, 9H).

Step B: The product of step A (105 mg, 0.22 mmol) was treated with a solution of 4 M HCl in dioxane (1.5 mL). After 1.5 h the mixture was concentrated in vacuo and the residue partitioned with saturated sodium bicarbonate solution and chloroform. The organic layer was dried over sodium sulfate, filtered and concentrated in vacuo. The residue was purified by flash column chromatography (SiO$_2$, 90:9:1 chloroform/methanol/ammonium hydroxide) to give 2-(3-fluorophenyl)sulfonyl-5-methyl-5,6,7,8,9,10-hexahydro-7,10-epiminocyclohepta[b]indole hydrochloride (45 mg, 50%, AUC HPLC 98.8%) as a white solid: mp 240-245° C.; $^1$H NMR (DMSO-d$_6$, 300 MHz) δ 8.20-8.70 (m, 3H), 7.74-7.81 (m, 2H), 7.59-7.71 (m, 3H), 7.45-7.55 (m, 1H), 5.15-5.24 (m, 1H), 4.31-4.43 (m, 1H), 3.66 (s, 3H), 3.21-3.39 (m, 1H), 2.92 (d, J=16.8 Hz, 1H), 2.12-2.29 (m, 2H), 1.96-2.09 (m, 1H), 1.66-1.80 (m, 1H); ESI MS m/z 371 [M+H]$^+$.

Example 36

Preparation of 2-(3-Chlorophenyl)sulfonyl-5-methyl-5,6,7,8,9,10-hexahydro-7,10-epiminocyclohepta[b]indole hydrochloride

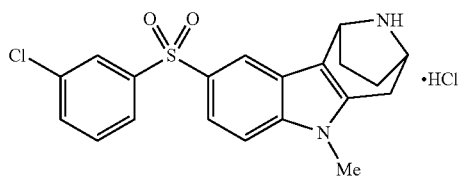 [SMILES: Cn1c2c(c3cc(S(=O)(=O)c4cccc(Cl)c4)ccc31)C1CCC(C2)N1 ; Cl]

Step A: Intermediate 1 was coupled with the product of Example 27, step B following the procedure of Example 27, step C. The crude material was purified by flash column chromatography (SiO$_2$, 8:2 hexanes/ethyl acetate) to give tert-butyl 2-(3-chlorophenyl)sulfonyl-5-methyl-5,6,7,8,9,10-hexahydro-7,10-epiminocyclohepta[b]indole-carboxylate (110 mg, 35%) as an off-white solid: $^1$H NMR (CDCl$_3$, 300 MHz) δ 8.17-8.23 (m, 1H), 7.92-7.96 (m, 1H), 7.83-7.88 (m, 1H), 7.65-7.73 (m, 1H), 7.46-7.50 (m, 1H), 7.41 (t, J=7.8 Hz, 1H), 7.34 (d, J=8.7 Hz, 1H), 5.20-5.36 (m, 1H), 4.60-4.73 (m, 1H), 3.63 (s, 3H), 3.30-3.50 (m, 1H), 2.52 (d, J=16.2 Hz, 1H), 2.15-2.42 (m, 2H), 1.90-2.01 (m, 1H), 1.58-1.60 (m, 1H), 1.39 (br s, 9H)

Step B: The product of step A was subjected to Boc-deprotection with 2 M HCl in diethyl ether following the procedure of example 28, step B. The crude material was purified by flash column chromatography (SiO$_2$, 90:9:1 chloroform/methanol/ammonium hydroxide) then converted to the HCl salt to give 2-(3-chlorophenyl)sulfonyl-5-methyl-5,6,7,8,9,10-hexahydro-7,10-epiminocyclohepta[b]indole hydrochloride (49 mg, 56%, AUC HPLC 95.7%) as an off white solid: mp 208-212° C.; $^1$H NMR (CD$_3$OD, 300 MHz) δ 8.30 (d, J=1.8 Hz, 1H), 7.86-7.95 (m, 2H), 7.72-7.78 (m, 1H), 7.57-7.63 (m, 2H), 7.49-7.56 (m, 1H), 5.32 (d, J=4.8 Hz, 1H), 4.51-4.58 (m, 1H), 3.72 (s, 3H), 3.43-3.55 (m, 1H), 3.03-3.12 (m, 1H), 2.24-2.52 (m, 3H), 1.90-2.04 (m, 1H); APCI MS m/z 387 [M+H]$^+$ Example 37

Preparation of 2-(3-Methylphenyl)sulfonyl-5-methyl-5,6,7,8,9,10-hexahydro-7,10-epiminocyclohepta[b]indole hydrochloride

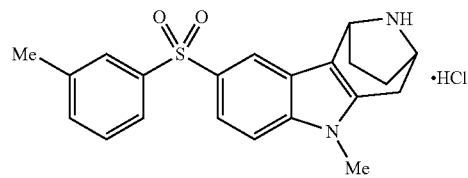

Step A: Intermediate 10 was coupled with the product of Example 27, step B following the procedure of Example 27, step C. The crude product was purified by flash column chromatography (SiO$_2$, 8:2 hexanes/ethyl acetate) to give tert-butyl 2-(3-methylphenyl)sulfonyl-5-methyl-5,6,7,8,9,10-hexahydro-7,10-epiminocyclohepta[b]indole-carboxylate (130 mg, 50%) as light yellow solid: $^1$H NMR (CDCl$_3$, 300 MHz) δ 8.19 (s, 1H), 7.72-7.78 (m, 2H), 7.67 (d, J=8.4 Hz, 1H), 7.27-7.35 (m, 3H), 5.26 (br s, 1H), 4.72 (br s, 1H), 3.60 (s, 3H), 3.35 (br s, 1H), 2.49 (d, J=15.8 Hz, 1H), 2.38 (s, 3H), 2.13-2.36 (m, 3H), 1.89-2.01 (m, 1H), 1.38 (br s, 9H).

Step B: The product of step A was subjected to Boc-deprotection with 2 M HCl in diethyl ether following the procedure of Example 28, step B. The crude material was purified by flash column chromatography (SiO$_2$, 80:18:2 chloroform/methanol/ammonium hydroxide). The free base was treated with 1.25 M HCl in methanol (0.5 mL). The solution was concentrated in vacuo and the residue lyophilized to give 2-(3-methylphenyl)sulfonyl-5-methyl-5,6,7,8,9,10-hexahydro-7,10-epiminocyclohepta[b]indole hydrochloride (52 mg, 46%, AUC HPLC >99%) as a white solid: mp 194-196° C.; $^1$H NMR (D$_2$O, 300 MHz) δ 8.18 (s, 1H), 7.61-7.73 (m, 2H), 7.58 (d, J=9.3 Hz, 1H), 7.30-7.49 (m, 3H), 5.20 (d, J=4.5 Hz, 1H), 4.54 (br s, 1H), 3.55 (s, 3H), 3.42 (dd, J=17.4, 4.2 Hz, 1H), 2.94 (d, J=17.7 Hz, 1H), 2.29-2.45 (m, 2H), 2.24 (s, 3H), 2.05-2.19 (m, 1H), 1.72-1.90 (m, 1H); APCI MS m/z 367 [M+H]$^+$.

Example 38

Preparation of 2-(3-Trifluoromethylphenyl)sulfonyl-5-methyl-5,6,7,8,9,10-hexahydro-7,10-epiminocyclohepta[b]indole hydrochloride

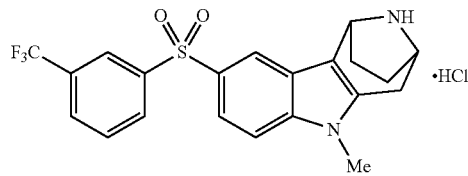 [SMILES: Cn1c2c(c3cc(S(=O)(=O)c4cccc(C(F)(F)F)c4)ccc31)C1CCC(C2)N1 ; Cl]

Step A: Intermediate 9 was coupled with the product of Example 27, step B following the procedure of Example 27, step C. The crude material was purified by flash column chromatography (SiO$_2$, 3:2 hexane/ethyl acetate) to give tert-butyl 2-(3-trifluoromethylphenyl)sulfonyl-5-methyl-5,6,7,8,9,10-hexahydro-7,10-epiminocyclohepta[b]indole-carboxylate (217 mg, 24%) as a white solid: $^1$H NMR (CDCl$_3$, 300 MHz) δ 8.20-8.22 (m, 2H), 8.13 (d, J=7.8 Hz, 1H), 7.58-7.70 (m, 3H), 7.33 (d, J=8.7 Hz, 1H), 5.26 (br s, 1H), 4.70 (br s, 1H), 3.61 (s, 3H), 3.38 (br s, 1H), 2.50 (d, J=16.8 Hz, 1H), 2.17-2.34 (m, 2H), 1.90-1.97 (m, 1H), 1.58-1.65 (m, 1H), 1.36 (br s, 9H).

Step B: The product of step A was subjected to Boc-deprotection with TFA following the procedure of Example 28, step B. The crude material was purified by flash column chromatography (SiO$_2$, 9:1 dichloromethane/methanol) to give 2-(3-trifluoromethylphenyl)sulfonyl-5-methyl-5,6,7,8,9,10-hexahydro-7,10-epiminocyclohepta[b]indole trifluoroacetate (130 mg, 95%) as a white solid: $^1$H NMR (CDCl$_3$, 300 MHz) δ 8.20 (s, 1H), 8.10-8.14 (m, 2H), 7.57-7.78 (m, 3H), 7.33 (d, J=8.7 Hz 1H), 4.89 (d, J=4.5 Hz, 1H), 4.30-4.34 (m, 1H), 3.60 (s, 3H), 3.40 (dd, J=12.0, 4.5 Hz, 1H), 2.65 (d, J=16.8 Hz, 1H), 2.30-2.39 (m, 2H), 2.08-2.16 (m, 1H), 1.66-1.72 (m, 1H).

Step C: The hydrochloride salt was prepared following the procedure of Example 28, step C to give 2-(3-trifluoromethylphenyl)sulfonyl-5-methyl-5,6,7,8,9,10-hexahydro-7,10-epiminocyclohepta[b]indole hydrochloride (80 mg, 73%, AUC HPLC 95.4%) as a white solid: mp 190-195° C.; $^1$H NMR (CD$_3$OD, 300 MHz) δ 8.34 (d, J=1.8 Hz, 1H), 8.19-8.24 (m, 2H), 7.89-7.92 (m, 1H), 7.73-7.79 (m, 2H), 7.60 (d, J=8.7 Hz, 1H), 5.31 (d, J=4.8 Hz, 1H), 4.54 (br s, 1H), 3.72 (s, 3H), 3.47 (dd, J=12.5 Hz, 4.2 Hz, 1H), 3.07 (d, J=17.4 Hz, 1H), 2.24-2.47 (m, 3H), 1.97-2.02 (m, 1H); ESI MS m/z 421 [M+H]$^+$.

Example 39

Preparation of 2-(3-Trifluoromethoxyphenyl)sulfonyl-5-methyl-5,6,7,8,9,10-hexahydro-7,10-epiminocyclohepta[b]indole hydrochloride

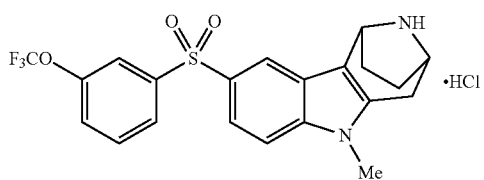

Step A: Intermediate 3 was coupled with the product of Example 27, step B following the procedure of Example 27, step C. The crude material was purified by flash column chromatography (SiO$_2$, 7:3 hexane/ethyl acetate) to give tert-butyl 2-(3-difluoromethoxyphenyl)sulfonyl-5-methyl-5,6,7,8,9,10-hexahydro-7,10-epiminocyclohepta[b]indole-carboxylate (110 mg, 32%) as an off-white solid: $^1$H NMR (CDCl$_3$, 300 MHz): δ 8.18 (s, 1H), 7.87 (d, J=7.8 Hz, 1H), 7.81 (s, 1H), 7.67 (dd, J=8.6, 1.4 Hz, 1H), 7.50 (t, J=8.1 Hz, 1H), 7.29-7.38 (m, 2H), 5.13-5.40 (m, 1H), 4.49-4.84 (m, 1H), 3.61 (s, 3H), 3.20-3.52 (m, 1H), 2.50 (d, J=16.2 Hz, 1H), 2.12-2.41 (m, 2H), 1.86-2.00 (m, 1H), 1.58-1.68 (m, 1H), 1.37 (br s, 9H).

Step B: The product of step A was subjected to Boc-deprotection with 2 M HCl in diethyl ether following the procedure of Example 28, step B. The crude material was purified by flash column chromatography (SiO$_2$, 90:9.9:0.1 dichloromethane/methanol/ammonium hydroxide). The free base was treated with 1.25 M HCl in methanol (1 mL) and the solution concentrated in vacuo to give 2-(3-trifluoromethoxyphenyl)sulfonyl-5-methyl-5,6,7,8,9,10-hexahydro-7,10-epiminocyclohepta[b]indole hydrochloride (30 mg, 34%, AUC HPLC >99%) as an off-white solid: mp 193-196° C.; $^1$H NMR (CD$_3$OD, 300 MHz): δ 8.31 (m, 1H), 7.91-7.99 (m, 1H), 7.79-7.85 (m, 1H), 7.71-7.78 (m, 1H), 7.58-7.70 (m, 2H), 7.48-7.57 (m, 1H), 5.26-5.34 (m, 1H), 4.50-4.60 (m, 1H), 3.72 (s, 3H), 3.49 (dd, J=17.4, J=4.2 Hz, 1H), 3.07 (d, J=17.7 Hz, 1H), 2.20-2.52 (m, 3H), 1.91-2.03 (m, 1H). ESI MS m/z 437 [M+H]$^+$ Example 40

Preparation of 2-(3-Difluoromethoxyphenyl)sulfonyl-5-methyl-5,6,7,8,9,10-hexahydro-7,10-epiminocyclohepta[b]indole hydrochloride

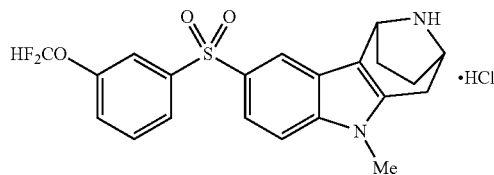

Step A: Intermediate 6 was coupled with the product of Example 27, step B following the procedure of Example 27, step C. The crude material was purified by flash column chromatography (SiO$_2$, 7:3 hexane/ethyl acetate) to give tert-butyl 2-(3-difluoromethoxyphenyl)sulfonyl-5-methyl-5,6,7,8,9,10-hexahydro-7,10-epiminocyclohepta[b]indole-carboxylate (155 mg, 43%) as an off-white solid: $^1$H NMR (CDCl$_3$, 300 MHz) δ 8.12-8.22 (m, 1H), 7.76-7.82 (m, 1H), 7.62-7.72 (m, 2H), 7.46 (t, J=8.1 Hz, 1H), 7.32 (d, J=8.7 Hz, 1H), 7.21-7.26 (m, 1H), 6.52 (t, J=72.9 Hz, 1H), 5.19-5.38 (m, 1H), 4.55-4.80 (m, 1H), 3.61 (s, 3H), 3.20-3.51 (m, 1H), 2.50 (d, J=8.1 Hz, 1H), 2.12-2.40 (m, 2H), 1.89-1.99 (m, 1H), 1.55-1.67 (m, 1H), 1.37 (s, 9H).

Step B: The product of step A was subjected to Boc-deprotection with TFA following the procedure of Example 28, step B. The crude material was purified by flash column chromatography (SiO$_2$, 90:9:1 dichloromethane/methanol/ammonium hydroxide) followed by conversion to the HCl salt to give 2-(3-difluoromethoxyphenyl)sulfonyl-5-methyl-5,6,7,8,9,10-hexahydro-7,10-epiminocyclohepta[b]indole hydrochloride (60 mg, 68%, AUC HPLC 98.0%) as an off-white solid: mp 186-190° C. dec; $^1$H NMR (DMSO-d$_6$, 300 MHz) δ 9.56 (br s, 1H), 9.10 (d, J=9.3 Hz, 1H), 8.39-8.44 (m, 1H), 7.76-7.82 (m, 1H), 7.66-7.74 (m, 3H), 7.61-7.66 (m, 1H), 7.41-7.48 (m, 1H), 7.35 (t, J=73.2 Hz, 1H), 5.32-5.39 (m, 1H), 4.42-4.53 (m, 1H), 3.68 (s, 3H), 3.32-3.45 (m, 1H), 3.00 (d, J=17.4 Hz, 1H), 2.20-2.32 (m, 2H), 2.03-2.14 (m, 1H), 1.72-1.84 (m, 1H); ESI MS m/z 419 [M+H$^+$]

Example 41

Preparation of 2-(3-Methoxyphenyl)sulfonyl-5-methyl-5,6,7,8,9,10-hexahydro-7,10-epiminocyclohepta[b]indole hydrochloride

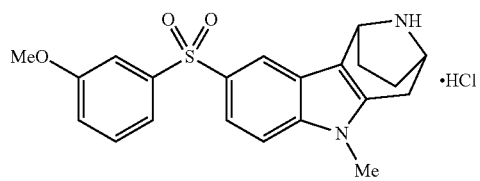 [SMILES: COc1cccc(S(=O)(=O)c2ccc3c(c2)c2c(n3C)CC3CCC2N3)c1 ; Cl]

Step A: Intermediate 7 was coupled with the product of Example 27, step B following the procedure of Example 27, step C. The crude product was purified by flash column chromatography (SiO$_2$, 7:3 hexanes/ethyl acetate) to give tert-butyl 2-(3-methoxyphenyl)sulfonyl-5-methyl-5,6,7,8,9,10-hexahydro-7,10-epiminocyclohepta[b]indole-carboxylate (194 mg, 63%) as an off-white solid: $^1$H NMR (CDCl$_3$, 300 MHz) δ 8.19 (s, 1H), 7.67 (d, J=8.1 Hz, 1H), 7.47-7.52 (m, 2H), 7.26-7.37 (m, 2H), 6.98-7.08 (m, 1H), 5.25-5.29 (m, 1H), 4.70 (br s, 1H), 3.82 (s, 3H), 3.60 (s, 3H), 3.36-3.49 (m, 1H), 2.49 (d, J=16.0 Hz, 1H), 2.25-2.33 (m, 1H), 2.16-2.23 (m, 1H), 1.90-1.97 (m, 1H), 1.50-1.70 (m, 1H), 1.37 (s, 9H).

Step B: The product of step A was subjected to Boc-deprotection with 2 M HCl in diethyl ether following the procedure of Example 28, step B. The crude material was purified by flash column chromatography (SiO$_2$, 95:5 dichloromethane/methanol). The free base was dissolved in methanol (0.5 mL) and treated with 1.25 M HCl in methanol (1.5 mL). The solution was concentrated in vacuo to give 2-(3-methoxyphenyl)sulfonyl-5-methyl-5,6,7,8,9,10-hexahydro-7,10-epiminocyclohepta[b]indole hydrochloride (19 mg, 85%, AUC HPLC >99%) as an off-white solid: mp 186-190° C.; $^1$H NMR (CD$_3$OD, 300 MHz) δ 8.27 (d, J=1.8 Hz 1H), 7.73 (dd, J=8.7, 1.8 Hz, 1H), 7.58 (d, J=8.7 Hz, 1H), 7.41-7.51 (m, 3H), 7.10-7.17 (m, 1H), 5.30 (d, J=4.8 Hz, 1H), 4.51-4.58 (m, 1H), 3.82 (s, 3H), 3.70 (s, 3H), 3.48 (dd, J=17.4, 4.5 Hz 1H), 2.25-2.47 (m, 3H), 2.16-2.23 (m, 1H), 1.94-2.23 (m, 1H). ESI MS m/z 383 [M+H]$^+$

Example 42

Preparation of 2-(3-Hydroxyphenyl)sulfonyl-5-methyl-5,6,7,8,9,10-hexahydro-7,10-epiminocyclohepta[b]indole hydrochloride

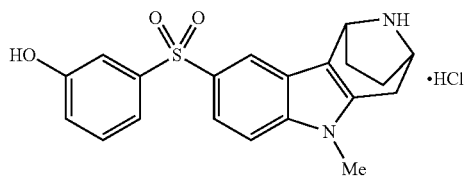 [SMILES: Cn1c2c(c3cc(S(=O)(=O)c4cccc(O)c4)ccc31)C1CCC(C2)N1 ; Cl]

Step A: A solution of the product of Example 41, step A (86 mg, 0.21 mmol) in dichloromethane (2.5 mL) at 0° C. was treated with boron tribromide (2.5 mL, 2.1 mmol). The reaction was stirred for 4 h then quenched with methanol followed by saturated sodium bicarbonate. The mixture was extracted with dichloromethane and the organic extract concentrated in vacuo. The residue was purified by flash column chromatography (SiO$_2$, 95:5 dichloromethane/methanol) and the residue dissolved in a minimum of methanol. The solution was treated with 1.25 M HCl in methanol (2 mL) then concentrated in vacuo to give 2-(3-hydroxyphenyl)sulfonyl-5-methyl-5,6,7,8,9,10-hexahydro-7,10-epiminocyclohepta[b]indole hydrochloride (21 mg, 23%, AUC HPLC >99%) as an off-white solid: mp 208-212° C.; $^1$H NMR (DMSO-d$_6$, 300 MHz) δ 10.20 (s, 1H), 8.90-9.40 (m, 2H), 8.32 (s, 1H), 7.60-7.67 (m, 2H), 7.29-7.39 (m, 2H), 7.25 (s, 1H), 6.98 (s, 1H), 5.32-5.39 (br s, 1H), 4.46 (br s, 1H), 3.70 (s, 3H), 3.37-3.39 (m, 1H), 3.01 (d, J=17.0 Hz, 1H), 2.26 (br s, 2H), 2.06-2.12 (m, 1H), 1.72-1.86 (m, 1H). ESI MS m/z 369 [M+H]$^+$

Example 43

Preparation of 2-(3-Cyanophenyl)sulfonyl-5-methyl-5,6,7,8,9,10-hexahydro-7,10-epiminocyclohepta[b]indole hydrochloride

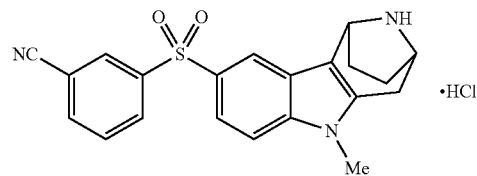 [SMILES: Cn1c2c(c3cc(S(=O)(=O)c4cccc(C#N)c4)ccc31)C1CCC(C2)N1 ; Cl]

Step A: Intermediate 5 was coupled with the product of Example 27, step B following the procedure of Example 27, step C. The crude material was purified by flash column chromatography (SiO$_2$, 7.5:2.5 hexane/ethyl acetate) to give tert-butyl 2-(3-cyanophenyl)sulfonyl-5-methyl-5,6,7,8,9,10-hexahydro-7,10-epiminocyclohepta[b]indole-carboxylate (106 mg, 35%) as a yellow solid: $^1$H NMR (CDCl$_3$, 300 MHz): δ 8.13-8.24 (m, 3H), 7.76 (td, J=7.8, 1.2 Hz, 1H), 7.66 (dd, J=8.7, 1.5 Hz, 1H), 7.60 (d, J=8.7 Hz, 1H), 7.34 (d, J=8.7 Hz, 1H), 5.20-5.37 (m, 1H), 4.58-4.82 (m, 1H), 3.62 (s, 3H), 3.25-3.50 (m, 1H), 2.52 (d, J=16.2 Hz, 1H), 2.13-2.42 (m, 2H), 1.88-2.00 (m, 1H), 1.55-1.68 (m, 1H), 1.38 (s, 9H).

Step B: The product of step A was subjected to Boc-deprotection with TFA following the procedure of Example 28, step B. The crude material was purified by flash column chromatography (SiO$_2$, 90:9.9:0.1 dichloromethane/methanol/ammonium hydroxide). The free base was treated with 1.25 M HCl in methanol (1 mL) and the solution concentrated in vacuo to give 2-(3-cyanophenyl)sulfonyl-5-methyl-5,6,7,8,9,10-hexahydro-7,10-epiminocyclohepta[b]indole hydrochloride (55 mg, 63%, AUC HPLC >99%) as a white solid: mp 211-214° C.; $^1$H NMR (DMSO d$_6$, 300 MHz): δ 9.00-9.60 (br s, 2H), 8.41-8.46 (m, 2H), 8.21-8.27 (m, 1H), 8.07-8.13 (m, 1H), 7.64-7.84 (m, 3H), 5.34 (d, J=3.6 Hz, 1H), 4.43-4.56 (m, 1H), 3.68 (s, 3H), 3.32-3.43 (m, 1H), 3.01 (d, J=17.1 Hz, 1H), 2.21-2.33 (m, 2H), 2.06-2.15 (m, 1H), 1.73-1.88 (m, 1H); APCI MS m/z 378 [M+H]$^+$

Example 44

Preparation of 2-(3-Aminophenyl)sulfonyl-5-methyl-5,6,7,8,9,10-hexahydro-7,10-epiminocyclohepta[b]indole hydrochloride

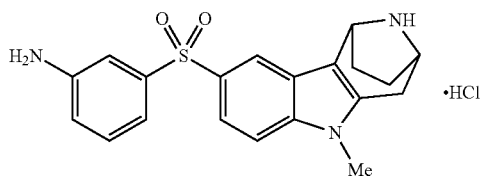 [SMILES: Cn1c2c(c3cc(S(=O)(=O)c4cccc(N)c4)ccc31)C1CCC(C2)N1 ; Cl]

Step A: Intermediate 8 was coupled with the product of Example 27, step B following the procedure of Example 27, step C. The crude material was purified by flash column chromatography (SiO$_2$, 3:2 hexane/ethyl acetate) to give tert-butyl 2-(3-nitrophenylsulfonyl)-5-methyl-5,6,7,8,9,10-hexahydro-7,10-epiminocyclohepta[b]indole-carboxylate (50 mg, 13%) as a yellow solid: $^1$H NMR (CDCl$_3$, 300 MHz) δ 8.76 (s, 1H), 8.25-8.38 (m, 1H), 8.21 (s, 1H), 7.67-7.72 (m, 2H), 7.65 (s, 1H), 7.35 d, J=8.7 Hz, 1H), 5.27 (br s, 1H) 4.70-4.73 (m, 1H), 3.62 (s, 3H), 3.38-3.42 (m, 1H), 2.51 (d, J=15 Hz, 1H), 2.15-2.42 (m, 2H), 1.97-1.90 (m, 1H), 1.54-1.67 (m, 1H), 1.37 (s, 9H).

Step B: To a solution of the product of step A (48 mg, 0.09 mmol) in EtOH (2 mL) and water (1 mL) was added iron powder (27 mg, 0.48 mmol) and ammonium chloride (5.7 mg, 0.10 mmol). The mixture was heated at reflux for 3 h, cooled to ambient temperature and filtered through a celite bed. The filtrate was extracted with chloroform and the organic layer dried over sodium sulfate then concentrated in vacuo. The residue was purified by flash column chromatography (SiO$_2$, 7:3 hexane/ethyl acetate) to give tert-butyl 2-(3-aminophenyl)sulfonyl-5-methyl-5,6,7,8,9,10-hexahydro-7,10-epiminocyclohepta[b]indole-carboxylate (28 mg, 62%) as a pale yellow solid: $^1$H NMR (CDCl$_3$, 300 MHz) δ 8.18 (s, 1H), 7.65 (d, J=7.2 Hz, 1H), 7.29 (d, J=8.7 Hz, 2H), 7.17-7.23 (m, 2H), 6.74 (dd, J=7.3, 1.2 Hz, 1H), 5.17-5.36 (m, 1H), 4.57-4.88 (m, 1H), 3.85 (s, 2H), 3.60 (s, 3H), 3.28-3.40 (m, 1H), 2.48 (d, J=16.5 Hz, 1H), 2.17-2.33 (m, 2H), 1.91-1.97 (m, 1H), 1.54-1.65 (m, 1H), 1.37 (br s, 9H).

Step C: The product of step A was subjected to Boc-deprotection with 2 M HCl in diethyl ether following the procedure of Example 28, step B. The crude material was purified by flash column chromatography (SiO$_2$, 96:4 dichloromethane/methanol). The free base was treated with 1.25 M HCl in methanol (1.5 mL). The solution was concentrated in vacuo and the residue lyophilized to give 2-(3-aminophenyl)sulfonyl-5-methyl-5,6,7,8,9,10-hexahydro-7,10-epiminocyclohepta[b]indole hydrochloride (14 mg, 91%, AUC HPLC >99%) as an off-white solid: mp 220-222° C.; $^1$H NMR (CD$_3$OD, 300 MHz) δ 8.27 (d, J=1.5 Hz, 1H), 7.72 (dd, J=8.7, 1.5 Hz, 1H), 7.54-7.60 (m, 3H), 7.41-7.46 (m, 1H), 7.18 (dd, J=7.8, 1.5 Hz 1H), 5.30 (d, J=4.2 Hz, 1H), 4.50 (br s, 1H), 3.72 (s, 3H), 3.52 (dd, J=18.0, 6.0 Hz, 1H), 3.07 (d, J=17.4 Hz, 1H), 2.25-2.50 (m, 3H), 1.97-2.00 (m, 1H); ESI MS m/z 368 [M+H]$^+$.

Example 45

Preparation of 2-[(3-N,N-Dimethylamino)phenyl]sulfonyl-5-methyl-5,6,7,8,9,10-hexahydro-7,10-epiminocyclohepta[b]indole hydrochloride

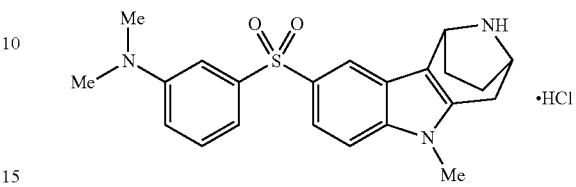

Step A: To a solution of the product of Example 44, step B (200 mg, 0.43 mmol), in DMF (2 mL) at 0° C. was added sodium hydride (60% dispersion in mineral oil) (26 mg, 0.64 mmol) followed by iodomethane (32 µL, 0.51 mmol). The reaction was stirred for 3.5 h at 0° C. then quenched with saturated ammonium chloride solution and extracted with ethyl acetate. The organic extract was concentrated in vacuo and the residue purified by flash column chromatography (SiO$_2$, 3:2 hexane/ethyl acetate) to give the dimethyl aniline derivative tert-butyl 2-[(3-N,N-dimethylamino)phenyl]sulfonyl-5-methyl-5,6,7,8,9,10-hexahydro-7,10-epiminocyclohepta[b]indole-carboxylate as an off-white solid (30 mg, 22%): $^1$H NMR (CDCl$_3$, 400 MHz) δ 8.19 (s, 1H), 7.66 (d, J=8.0 Hz, 1H), 7.26-7.27 (m, 2H), 7.23-7.25 (m, 1H), 7.18-7.19 (m, 1H), 6.76 (dd, J=8.0, 2.0 Hz, 1H), 5.24 (br s, 1H), 4.63-4.72 (m, 1H), 3.57 (s, 3H), 3.10-3.40 (m, 1H), 2.96 (s, 6H), 2.48 (d, J=16.4 Hz, 1H), 2.26-2.34 (m, 1H), 2.16-2.22 (m, 1H) 1.90-1.95 (m, 1H), 1.55-1.62 (m, 1H), 1.38 (br s, 9H); and monomethyl aniline derivative tert-butyl 2-[(3-N-methylamino)phenyl]sulfonyl-5-methyl-5,6,7,8,9,10-hexahydro-7,10-epiminocyclohepta[b]indole-carboxylate (39 mg, 30%) as an off-white solid: $^1$H NMR (CDCl$_3$, 400 MHz) δ 8.18 (s, 1H), 7.65 (dd, J=8.7 Hz, 1.2 Hz, 1H), 7.25-7.28 (m, 1H), 7.19-7.21 (m, 2H), 7.13-7.14 (m, 1H), 6.65-6.66 (m, 1H), 5.24 (br s, 1H), 4.70 (br s, 1H), 3.60 (s, 3H), 3.21-3.49 (m, 1H), 2.83 (s, 3H), 2.49 (d, J=16.2 Hz, 1H), 2.25-2.32 (m, 1H), 2.12-2.24 (m, 1H), 1.89-1.96 (m, 1H), 1.50-1.64 (m, 1H), 1.37 (br s, 9H).

Step B: The dimethyl aniline derivative obtained from step A was subjected to Boc-deprotection with TFA following the procedure of Example 28, step B. The crude product was purified by flash column chromatography (SiO$_2$, 90:9:1 dichloromethane/methanol/ammonium hydroxide) to give 2-[(3-N,N-dimethylamino)phenyl]sulfonyl-5-methyl-5,6,7,8,9,10-hexahydro-7,10-epiminocyclohepta[b]indole (23 mg, 77%) as a yellow solid: $^1$H NMR (CDCl$_3$, 300 MHz) δ 8.14 (s, 1H), 7.64 (d, J=8.7 Hz, 1H), 7.25-7.27 (m, 2H), 7.22 (s, 1H), 7.17 (d, J=7.8 Hz, 1H), 6.75 (dd, J=8.1, 2.4 Hz, 1H), 4.59 (d, J=4.8 Hz, 1H), 4.08-4.12 (m, 1H), 3.54 (s, 3H), 3.16 (dd, J=16.2, 4.2 Hz, 1H), 2.90 (s, 6H), 2.51 (d, J=16.5 Hz, 1H), 2.08-2.21 (m, 2H), 1.95-2.01 (m, 1H), 1.52-1.60 (m, 1H).

Step C: To a solution of the product of step B in dichloromethane (1 mL) was added 1.25 M HCl in methanol (1.5 mL). The solution was concentrated in vacuo and lyophilized to give 2-[(3-N,N-dimethylamino)phenyl]sulfonyl-5-methyl-5,6,7,8,9,10-hexahydro-7,10-epiminocyclohepta[b]indole hydrochloride (24 mg, 95%, AUC HPLC 98.3%) as an off-white solid: mp 204-208° C. dec; $^1$H NMR (CD$_3$OD, 400 MHz) δ 8.29 (d, J=1.2 Hz, 1H), 7.74 (dd, J=8.8, 1.6 Hz, 1H), 7.62 (s, 1H), 7.58 (d, J=8.8 Hz, 1H), 7.48-7.51 (m, 2H), 7.27

(d, J=7.2 Hz, 1H), 5.31 (d, J=4.8 Hz, 1H), 4.53-4.56 (m, 1H), 3.72 (s, 3H), 3.48 (dd, J=17.6, 4.4 Hz, 1H), 3.05-3.09 (m, 7H), 2.36-2.49 (m, 2H), 2.25-2.33 (m, 1H), 1.94-2.00 (m, 1H). ESI MS m/z 396 [M+H]⁺.

Example 46

Preparation of 2-[(3-N-Methylamino)phenyl]sulfonyl-5-methyl-5,6,7,8,9,10-hexahydro-7,10-epiminocyclohepta[b]indole hydrochloride

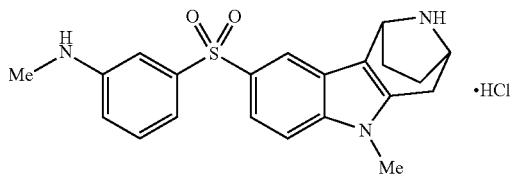 [SMILES: CNc1cccc(S(=O)(=O)c2ccc3c(c2)c2c(n3C)CC3CCC2N3)c1 ; Cl]

Step A: The mono-methyl aniline derivative obtained from Example 45, step A was subjected to Boc-deprotection with TFA following the procedure of Example 28, step B. The crude material was purified by flash column chromatography (SiO₂, 90:9:1 dichloromethane/methanol/ammonium hydroxide) to give 2-[(3-N-methylamino)phenyl]sulfonyl-5-methyl-5,6,7,8,9,10-hexahydro-7,10-epiminocyclohepta[b]indole (13 mg, 65%) as an off-white solid: ¹H NMR (CD₃OD, 400 MHz) δ 8.08 (d, J=1.6 Hz, 1H), 7.60 (dd, J=8.8, 2.1 Hz, 1H), 7.43 (d, J=8.8 Hz, 1H), 7.20-7.24 (m, 1H), 7.07-7.10 (m, 2H), 6.72 (ddd, J=8.0, 2.4, 0.8 Hz, 1H), 4.60 (d, J=4.8 Hz, 1H), 4.02-4.05 (m, 1H), 3.62 (s, 3H), 3.19 (dd, J=16.8, 4.8 Hz, 1H), 2.75 (s, 3H), 2.64 (dd, J=16.4, 1.2 Hz, 1H), 2.15-2.21 (m, 1H), 2.14-2.06 (m, 1H), 1.97 (dd, J=11.6, 2.4 Hz, 1H), 1.64-1.67 (m, 1H).

Step B: To a solution of the product of step B in dichloromethane (1 mL) was added 1.25 M HCl in methanol (1.5 mL). The solution was concentrated in vacuo and lyophilized to give 2-[(3-N-methylamino)phenyl]sulfonyl-5-methyl-5,6,7,8,9,10-hexahydro-7,10-epiminocyclohepta[b]indole hydrochloride (11 mg, 77%, AUC HPLC 98.8%) as an off-white solid: mp 208-212° C. dec; ¹H NMR (DMSO-d₆, 300 MHz) δ 9.30 (br s, 1H), 9.00 (br s, 1H), 8.30 (s, 1H), 7.59-7.66 (m, 2H), 7.21-7.29 (m, 1H), 6.95-7.02 (m, 2H), 6.70 (dd, J=7.5, 1.8 Hz, 1H), 6.30 (br s, 1H), 5.30 (s, 1H), 4.47 (br s, 1H), 3.72 (s, 3H), 3.38-3.39 (m, 1H), 3.01 (d, J=17.7 Hz, 1H), 2.73 (s, 3H), 2.20-2.26 (m, 2H), 2.06-2.15 (m, 1H), 1.79-1.82 (m, 1H); APCI MS m/z 382 [M+H]⁺.

Example 47

Preparation of 2-[(3-N-Isopropylamino)phenyl]sulfonyl-5-methyl-5,6,7,8,9,10-hexahydro-7,10-epiminocyclohepta[b]indole hydrochloride

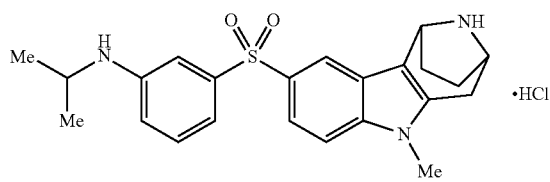 [SMILES: CC(C)Nc1cccc(S(=O)(=O)c2ccc3c(c2)c2c(n3C)CC3CCC2N3)c1 ; Cl]

Step A: To a solution of the product of Example 44, step B (90 mg, 0.19 mmol) in DMF (1 mL) at 0° C. was added sodium hydride (15 mg, 0.38 mmol) followed by 2-iodopropane (40 µL, 0.38 mmol). The reaction mixture was stirred for 3 h then quenched with saturated ammonium chloride solution and extracted with ethyl acetate. The organic layer was concentrated in vacuo and the residue purified by flash column chromatography (SiO₂, 6.5:3.5 hexane/ethyl acetate) to give tert-butyl 2-[(3-N-isopropylylamino)phenyl]sulfonyl-5-methyl-5,6,7,8,9,10-hexahydro-7,10-epiminocyclohepta[b]indole-carboxylate (17 mg, 17%) as an off-white solid: ¹H NMR (CDCl₃, 400 MHz) δ 8.18 (s, 1H), 7.68 (d, J=6.6 Hz, 1H), 7.29 (d, J=5.4 Hz 1H), 7.16-7.19 (m, 2H), 7.12 (s, 1H) 6.62 (dt, J=5.4, 1.5 Hz, 1H), 5.24-5.40 (m, 1H), 4.56-4.80 (m, 1H), 3.67-3.72 (m, 1H), 3.60-3.64 (m, 1H), 3.60 (s, 3H), 3.34-3.40 (m, 1H), 2.48 (d, J=16.0 Hz, 1H), 2.17-2.33 (m, 2H), 1.91-1.97 (m, 1H), 1.55-1.66 (m, 1H), 1.39-1.47 (m, 9H), 1.19 (dd, J=4.5, 1.8 Hz, 6H).

Step B: The product of step A was subjected to Boc-deprotection with TFA following the procedure of Example 28, step B. The crude material was purified by flash column chromatography (SiO₂, 90:9:1 dichloromethane/methanol/ammonium hydroxide) to give 2-[(3-N-isopropylamino)phenyl]sulfonyl-5-methyl-5,6,7,8,9,10-hexahydro-7,10-epiminocyclohepta[b]indole (10 mg, 74%): ¹H NMR (CDCl₃, 300 MHz) δ 8.13 (s, 1H), 7.64 (d, J=4.8 Hz, 1H), 7.24-7.27 (m, 1H), 7.15-7.19 (m, 2H), 7.11-7.12 (m, 1H) 6.62 (dt, J=7.2, 2.1 Hz, 1H), 4.63 (d, J=4.8 Hz, 1H), 4.65-4.69 (m, 1H), 4.02-4.05 (m, 1H), 3.59-3.66 (m, 1H), 3.55 (s, 3H), 3.19 (dd, J=16.5, 4.5 Hz, 1H), 2.53 (d, J=16.2 Hz, 1H), 2.17-2.33 (m, 2H), 1.91-1.97 (m, 1H), 1.52-1.67 (m, 1H), 1.18 (d, J=6.0 Hz, 6H).

Step C: To a solution of the product of step B in dichloromethane (1 mL) was added 1.25 M HCl in methanol (1.5 mL). The solution was concentrated in vacuo and lyophilized to give 2-[(3-N-isopropylamino)phenyl]sulfonyl-5-methyl-5,6,7,8,9,10-hexahydro-7,10-epiminocyclohepta[b]indole hydrochloride (8 mg, 75%, AUC HPLC >99%) as an off-white solid: mp 208-212° C. dec; ¹H NMR (CD₃OD, 400 MHz) δ 8.26 (d, J=0.8 Hz 1H), 7.72 (dd, J=8.0, 1.8 Hz, 1H), 7.58 (d, J=8.7 Hz, 1H), 7.37-7.40 (m, 3H), 7.00-7.06 (m, 1H), 5.30 (d, J=4.8 Hz, 1H), 4.53-4.56 (m, 1H), 3.72 (s, 3H), 3.63-3.69 (m, 1H), 3.47-3.51 (m, 1H), 3.07 (d, J=17.6 Hz, 1H), 2.25-2.49 (m, 3H), 1.96-2.00 (m, 1H), 1.22 (d, J=4.8 Hz, 6H); ESI MS m/z 410 [M+H]⁺.

Example 48

Preparation of 2-[(3-N-Cyclopentylamino)phenyl]sulfonyl-5-methyl-5,6,7,8,9,10-hexahydro-7,10-epiminocyclohepta[b]indole hydrochloride

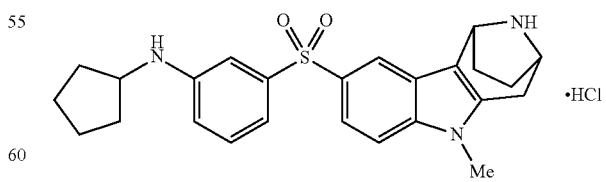

Step A: To a solution of the product of Example 44, step B (110 mg, 0.23 mmol) cyclopentanone (21 µl, 0.23 mmol) in 1,2-dichloroethane (1 mL) under a nitrogen atmosphere at 0° C. was added sodium triacetoxyborohydride (69 mg, 0.33 mmol) followed by acetic acid (13 µl, 0.23 mmol). The reaction mixture was allowed to warm to ambient temperature and stirred for 24 h. The reaction mixture was made basic by addition of 2 N NaOH solution and extracted with chloroform. The organic extract was washed with brine, dried over sodium sulfate and concentrated in vacuo. The residue was purified by flash column chromatography (SiO$_2$, 7:3 hexane/ethyl acetate) to give tert-butyl 2-[(3-N-cyclopentylylylamino)phenyl]sulfonyl-5-methyl-5,6,7,8,9,10-hexahydro-7,10-epiminocyclohepta[b]indole-carboxylate (25 mg, 20%) as an off-white solid: $^1$H NMR (CDCl$_3$, 300 MHz) δ 8.18 (s, 1H), 7.65 (dd, J=8.7, 1.5 Hz, 1H), 7.27 (d, J=8.7 Hz, 1H), 7.13-7.19 (m, 3H), 6.60-6.68 (m, 1H), 5.24-5.30 (m, 1H), 4.65-4.73 (m, 1H), 3.90 (br s, 1H), 3.72-3.83 (m, 1H), 3.58 (s, 3H), 3.34-3.40 (m, 1H), 2.48 (d, J=16.2 Hz, 1H), 2.17-2.33 (m, 2H), 1.91-2.10 (m, 3H), 1.52-1.78 (m, 7H), 1.37 (br s, 9H).

Step B: Boc-Deprotection was carried out following the procedure of Example 28, Step B. The crude product was purified by flash column chromatography (SiO$_2$, 80:18:2 dichloromethane/methanol/ammonium hydroxide) to give 2-[(3-N-cyclopentylamino)phenyl]sulfonyl-5-methyl-5,6,7,8,9,10-hexahydro-7,10-epiminocyclohepta[b]indole as an off-white solid (12 mg, 70%): $^1$H NMR (CD$_3$OD, 400 MHz) δ 8.09 (d, J=1.6 Hz, 1H), 7.59 (dd, J=8.4, 1.6 Hz, 1H), 7.44 (d, J=8.8 Hz, 1H), 7.19 (t, J=8.0 Hz, 1H), 7.05-7.09 (m, 2H), 6.72-6.75 (m, 1H), 4.65 (d, J=4.8 Hz, 1H), 4.07-4.09 (m, 1H), 3.70-3.73 (m, 1H), 3.62 (s, 3H), 3.22 (dd, J=16.8, 4.4 Hz, 1H), 2.67 (d, J=16.4, 1.2 Hz, 1H), 2.07-2.23 (m, 2H), 1.90-2.04 (m, 3H), 1.55-1.75 (m, 5H), 1.40-1.49 (m, 2H).

Step C: To a solution of the product of step B (12 mg, 0.03 mmol) in dichloromethane (1 mL) was added 1.25 M HCl in MeOH (1 ml). The solution was concentrated in vacuo and lyophilized from water/acetonitrile to give 2-[(3-N-cyclopentylamino)phenyl]sulfonyl-5-methyl-5,6,7,8,9,10-hexahydro-7,10-epiminocyclohepta[b]indole hydrochloride (12 mg, 91%, AUC HPLC >99%) as an off-white solid: mp 211-217° C.; $^1$H NMR (CD$_3$OD, 300 MHz) δ 8.26 (s, 1H), 7.70 (d, J=8.7 Hz, 1H), 7.54-7.68 (m, 3H), 7.43-7.48 (m, 1H), 7.20-7.27 (m, 1H), 5.27-5.29 (d, J=6.0 Hz, 1H), 4.49-4.55 (m, 1H), 3.82-3.90 (m, 1H), 3.70 (s, 3H), 3.41-3.52 (m, 1H), 3.04 (d, J=17.4 Hz, 1H), 2.20-2.49 (m, 3H), 1.88-2.00 (m, 3H), 1.51-1.82 (m, 6H); ESI MS m/z 436 [M+H]$^+$.

Example 49

Preparation of 2-(1-Napthyl)sulfonyl-5-methyl-5,6,7,8,9,10-hexahydro-7,10-epiminocyclohepta[b]indole hydrochloride

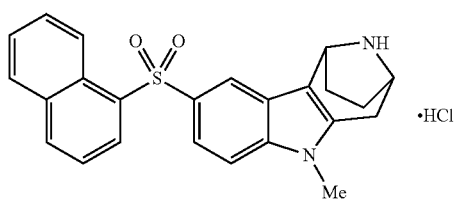 [SMILES: Cn1c2c(c3cc(S(=O)(=O)c4cccc5ccccc45)ccc31)C1CCC(C2)N1 ; Cl]

Step A: Intermediate 23 was coupled with the product of Example 27, step B following the procedure of Example 27, Step C. The crude product was purified by flash column chromatography (SiO$_2$, 8:2 hexanes/ethyl acetate) to give tert-butyl 2-(1-napthyl)sulfonyl-5-methyl-5,6,7,8,9,10-hexahydro-7,10-epiminocyclohepta[b]indole-carboxylate (120 mg, 26%) as a light yellow solid: $^1$H NMR (CDCl$_3$, 300 MHz) δ 8.48 (dd, J=7.5, 1.2 Hz, 1H), 8.20 (s, 1H), 8.04 (d, J=8.4 Hz, 1H), 7.86 (dd, J=8.6, 1.5 Hz, 1H), 7.67 (d, J=8.7 Hz, 1H), 7.59 (t, J=7.8 Hz, 1H), 7.40-7.52 (m, 4H), 5.25 (br s, 1H), 4.69 (br s, 1H), 3.59 (s, 3H), 3.36 (br s, 1H), 2.45 (d, J=6.0 Hz, 1H), 2.14-2.38 (m, 2H), 1.87-1.96 (m, 1H), 1.59-1.67 (m, 1H), 1.37 (br s, 9H).

Step B: The product of step A was subjected to Boc-deprotection with 2 M HCl in diethyl ether following the procedure of Example 28, step C. The crude material was purified by flash column chromatography (SiO$_2$, 80:18:2 chloroform/methanol/ammonium hydroxide) followed by semi-preparative HPLC. The free base was treated with 1.25 M HCl in methanol (0.5 mL) and lyophilized to give 2-(1-napthyl)sulfonyl-5-methyl-5,6,7,8,9,10-hexahydro-7,10-epiminocyclohepta[b]indole hydrochloride (5 mg, 12%, AUC HPLC 97.9%) as a white solid: mp 229-231° C.; $^1$H NMR (DMSO-d$_6$, 300 MHz) δ 9.38 (br s, 1H), 9.02 (br s, 1H), 8.63 (d, J=8.7 Hz, 1H), 8.48 (s, 1H), 8.43 (dd, J=7.2, 1.2 Hz, 1H), 8.28 (d, J=8.1 Hz, 1H), 8.03-8.09 (m, 1H), 8.76 (t, J=7.8 Hz, 1H), 7.57-7.65 (m, 4H), 5.38 (d, J=3.9 Hz, 1H), 4.47 (br s, 1H), 3.64 (s, 3H), 3.34-3.40 (m, 1H), 2.49 (d, J=17.4 Hz, 1H), 2.18-2.33 (m, 2H), 2.03-2.12 (m, 1H), 1.71-1.89 (m, 1H); ESI MS m/z 403 [M+H]$^+$.

Example 50

Preparation of 2-(2-Napthyl)sulfonyl-5-methyl-5,6,7,8,9,10-hexahydro-7,10-epiminocyclohepta[b]indole hydrochloride

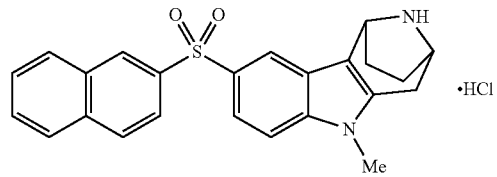 [SMILES: Cn1c2c(c3cc(S(=O)(=O)c4ccc5ccccc5c4)ccc31)C1CCC(C2)N1 ; Cl]

Step A: Intermediate 24 was coupled with the product of Example 27, step B following the procedure of Example 27, step C. The crude material was purified by flash column chromatography (SiO$_2$, 8:2 hexanes/ethyl acetate) to give tert-butyl 2-(2-napthyl)sulfonyl-5-methyl-5,6,7,8,9,10-hexahydro-7,10-epiminocyclohepta[b]indole-carboxylate (113 mg, 24%) as a light-yellow solid: $^1$H NMR (CDCl$_3$, 300 MHz) δ 8.58 (d, J=0.9 Hz, 1H), 8.26 (s, 1H), 7.93-8.04 (m, 1H), 7.81-7.88 (m, 2H), 7.71 (d, J=9.9 Hz, 1H), 7.52-7.63 (m, 2H), 7.42-7.51 (m, 1H), 7.29 (d, J=8.7 Hz, 1H), 5.26 (br s, 1H), 4.71 (br s, 1H), 3.59 (s, 3H), 3.39 (br s, 1H), 2.49 (d, J=16.2 Hz, 1H), 2.20-2.48 (m, 2H), 1.88-1.99 (m, 1H), 1.59-1.67 (m, 1H), 1.37 (br s, 9H).

Step B: The product of step A was subjected to Boc-deprotection with 2 M HCl in diethyl ether following the procedure of Example 28, step B. The crude material was purified by flash column chromatography (SiO$_2$, 80:18:2 chloroform/methanol/ammonium hydroxide) followed by semi-preparative HPLC. The free base was treated with 1.25 M HCl in methanol (0.5 mL) and lyophilized to give 2-(2-napthyl)sulfonyl-5-methyl-5,6,7,8,9,10-hexahydro-7,10-epiminocyclohepta[b]indole hydrochloride (41 mg, 45%, AUC HPLC >99%) as an off-white solid: mp 220-222° C.; $^1$H NMR (DMSO-d$_6$, 300 MHz) δ 9.42 (br s, 1H), 9.16 (br s, 1H), 8.66 (d, J=1.5 Hz, 1H), 8.43 (d, J=1.5 Hz, 1H), 8.19 (dd, J=8.0 Hz, 2.1 Hz, 1H), 8.08 (d, J=8.7 Hz, 1H), 8.01 (dd, J=8.0 Hz, 2.1 Hz, 1H), 7.88 (dd, J=8.7 Hz, 2.1 Hz, 1H), 7.64-7.75 (m, 4H), 5.36 (d, J=3.9 Hz, 1H), 4.47 (br s, 1H), 3.67 (s, 3H), 3.30-3.42 (m, 1H), 3.00 (d, J=17.1 Hz, 1H), 2.18-2.34 (m, 2H), 2.05-2.15 (m, 1H), 1.70-1.87 (m, 1H); ESI MS m/z 403 [M+H]$^+$.

Example 51

Preparation of 2-(4-Chlorophenyl)sulfonyl-5-methyl-5,6,7,8,9,10-hexahydro-7,10-epiminocyclohepta[b]indole hydrochloride

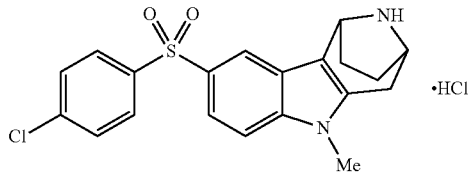 [SMILES: Cn1c2c(c3cc(S(=O)(=O)c4ccc(Cl)cc4)ccc31)C1CCC(C2)N1 ; Cl]

Step A: Intermediate 18 was coupled with the product of Example 27, step B following the procedure of Example 27, step C. The crude material was purified by flash column chromatography (SiO$_2$, 3:2 hexanes/ethyl acetate) to give tert-butyl 2-(4-chlorophenyl)sulfonyl-5-methyl-5,6,7,8,9,10-hexahydro-7,10-epiminocyclohepta[b]indole-carboxylate (100 mg, 40%) as a yellow solid: $^1$H NMR (CDCl$_3$, 300 MHz) δ 8.16 (s, 1H), 7.86-7.90 (m, 2H), 7.62-7.66 (m, 1H), 7.43-7.45 (m, 1H), 7.32-7.42 (m, 1H), 7.29-7.32 (m, 1H), 5.25 (br s, 1H), 4.68 (br s, 1H), 4.70 (s, 1H), 3.60 (s, 3H), 2.50 (d, J=16.3 Hz, 1H), 2.17-2.33 (m, 2H), 1.89-1.97 (m, 1H), 1.55-1.65 (m, 1H), 1.37 (br s, 9H).

Step B: The product of step A was subjected to Boc-deprotection with TFA following the procedure of Example 28, Step B. The crude product was purified by flash column chromatography (SiO$_2$, 1:9 methanol/dichloromethane) to give 2-(4-chlorophenyl)sulfonyl-5-methyl-5,6,7,8,9,10-hexahydro-7,10-epiminocyclohepta[b]indole (20 mg, 26%) as a white solid. $^1$H NMR (CDCl$_3$, 300 MHz) δ 8.12-8.14 (m, 1H), 7.83-7.94 (m, 2H), 7.61 (d, J=7.8 Hz, 1H), 7.51-7.55 (m, 2H), 7.45-7.48 (m, 1H), 4.59 (d, J=2.7 Hz, 1H), 4.01-4.05 (m, 1H), 3.64 (s, 3H), 3.16-3.23 (m, 1H), 2.61-2.67 (m, 1H), 1.94-2.23 (m, 3H), 1.59-1.67 (m, 1H).

Step C: The product of step B was converted to the hydrochloride salt following the procedure of Example 28, Step C to give 2-(4-chlorophenyl)sulfonyl-5-methyl-5,6,7,8,9,10-hexahydro-7,10-epiminocyclohepta[b]indole hydrochloride (16 mg, 73%, AUC HPLC 95.5%) as a yellow brown solid: mp 310-320° C.; $^1$H NMR (CD$_3$OD, 300 MHz) δ 8.27 (d, J=1.8 Hz, 1H), 7.91-7.95 (m, 2H), 7.73 (d, J=8.4 Hz, 1H), 7.54-7.70 (m, 3H), 5.29 (d, J=4.5 Hz, 1H), 4.54 (br s, 1H), 3.72 (s, 3H), 3.47 (dd, J=4.5, 12.6 Hz, 1H), 3.04-3.29 (d, J=17.4 Hz, 1H), 2.24-2.28 (m, 1H), 1.95 (s, 1H); ESI MS m/z 387 [M+H]$^+$.

Example 52

Preparation of 2-(2-Methylphenyl)sulfonyl-5-methyl-5,6,7,8,9,10-hexahydro-7,10-epiminocyclohepta[b]indole hydrochloride

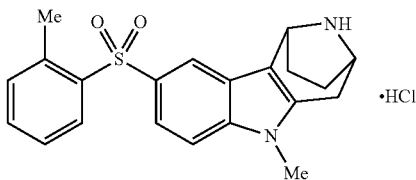 [SMILES: Cc1ccccc1S(=O)(=O)c1ccc2c(c1)c1c(n2C)CC2CCC1N2 ; Cl]

Step A: Intermediate 19 was coupled with the product of Example 27, step B following the procedure of Example 27, step C. The crude product was purified by flash column chromatography (SiO$_2$, 8:2 hexanes/ethyl acetate) to give tert-butyl 2-(2-methylphenyl)sulfonyl-5-methyl-5,6,7,8,9,10-hexahydro-7,10-epiminocyclohepta[b]indole-carboxylate (45 mg, 17%) as a light-yellow solid: $^1$H NMR (CDCl$_3$, 300 MHz) δ 8.18 (dd, J=7.4, 1.5 Hz, 1H), 7.95 (dd, J=7.8, 1.8 Hz, 1H), 7.16-7.71 (m, 5H), 5.24 (br s, 1H), 4.70 (br s, 1H), 3.60 (s, 3H), 3.38 (br s, 1H), 2.50 (d, J=15.9 Hz, 1H), 2.49 (s, 3H), 2.26-2.47 (m, 1H), 2.13-2.26 (m, 1H), 1.88-1.99 (m, 1H), 1.59-1.67 (m, 1H), 1.37 (br s, 9H).

Step B: The product of step A was subjected to Boc-deprotection with 2 M HCl in diethyl ether following the procedure of Example 28, Step B. The crude material was purified by flash column chromatography (SiO$_2$, 80:18:2 chloroform/methanol/ammonium hydroxide) followed by semi-preparative HPLC. The free base was treated with 1.25 M HCl in methanol (0.5 mL) and lyophilized to give 2-(2-methylphenyl)sulfonyl-5-methyl-5,6,7,8,9,10-hexahydro-7,10-epiminocyclohepta[b]indole hydrochloride (6 mg, 17%, AUC HPLC 96.3%) as a white solid: mp 186-188° C.; $^1$H NMR (DMSO-d$_6$, 300 MHz) δ 9.18 (br s, 2H), 8.30 (d, J=1.5 Hz, 1H), 8.06 (dd, J=7.8, 1.5 Hz, 1H), 7.65 (d, J=8.7 Hz, 1H), 7.45-7.60 (m, 3H), 7.33 (d, J=7.2 Hz, 1H), 5.36 (d, J=3.9 Hz, 1H), 4.47 (br s, 1H), 3.69 (s, 3H), 3.01 (d, J=17.1 Hz, 1H), 2.39 (s, 3H), 2.20-2.33 (m, 2H), 2.07-2.14 (m, 2H), 1.73-1.90 (m, 1H); ESI MS m/z 367 [M+H]$^+$.

Example 53

Preparation of 2-(4-Aminophenyl)sulfonyl-5-methyl-5,6,7,8,9,10-hexahydro-7,10-epiminocyclohepta[b]indole hydrochloride

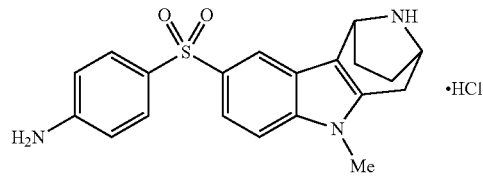 [SMILES: Cn1c2c(c3cc(S(=O)(=O)c4ccc(N)cc4)ccc31)C1CCC(C2)N1 ; Cl]

Step A: Intermediate 12 was coupled with the product of Example 27, step B following the procedure of Example 27, step C. The crude material was purified by flash column chromatography (SiO$_2$, 1:1 hexane/ethyl acetate) to give tert-butyl 2-(4-nitrophenyl)sulfonyl-5-methyl-5,6,7,8,9,10-hexahydro-7,10-epiminocyclohepta[b]indole-carboxylate (150 mg, 54%) as a white solid: $^1$H NMR (CDCl$_3$, 300 MHz) δ 8.27-8.31 (m, 2H), 8.19 (s, 1H), 8.09-8.11 (m, 2H), 7.68 (d, J=8.4 Hz, 1H), 7.33 (d, J=8.0 Hz, 1H), 5.26 (br s, 1H), 4.70 (br s, 1H), 3.62 (s, 3H), 3.40 (br s, 1H), 2.50 (d, J=16.2 Hz, 1H), 2.17-2.31 (m, 2H), 1.89-1.97 (m, 1H), 1.54-1.65 (m, 1H), 1.38 (br s, 9H).

Step B: A mixture of the product of step A (145 mg, 0.29 mmol), iron powder (82 mg, 1.45 mmol) and ammonium chloride (17 mg, 0.32 mmol) was taken up in ethanol (2.3 mL) and water (1.1 mL). The mixture was refluxed for 3 h then diluted with water and extracted with dichloromethane. The organic extract was dried over sodium sulfate and concentrated in vacuo to give tert-butyl 2-(4-aminophenyl)sulfonyl-5-methyl-5,6,7,8,9,10-hexahydro-7,10-epiminocyclohepta[b]indole-carboxylate (130 mg, 96%) as a pale yellow solid: $^1$H NMR (CDCl$_3$, 300 MHz) δ 8.15 (s, 1H), 7.69-7.71 (m, 2H), 7.62 (d, J=9.3 Hz, 1H), 7.27 (d, J=8.7 Hz, 1H), 6.60-6.65 (m, 2H), 5.24 (br s, 1H), 4.69 (br s, 1H), 4.04 (br s, 2H), 3.58 (s, 3H), 3.48 (br s, 1H), 2.48 (d, J=16.5 Hz, 1H), 2.12-2.32 (m, 2H), 1.89-1.97 (m, 1H), 1.52-1.64 (m, 1H), 1.37 (br s, 9H).

Step C: The product of step A was subjected to Boc-deprotection with TFA following the procedure of Example 28, step B. The crude material was purified by flash column chromatography (SiO$_2$, 1:9 methanol/dichloromethane) to give 2-(4-aminophenyl)sulfonyl-5-methyl-5,6,7,8,9,10-hexahydro-7,10-epiminocyclohepta[b]indole (25 mg, 25%) as a yellow oil: $^1$H NMR (CDCl$_3$, 300 MHz) δ 8.16 (s, 1H), 7.49-7.65 (m, 4H), 6.62-6.67 (m, 2H), 5.24-5.25 (m, 1H), 4.51-4.53 (m, 1H), 3.68 (s, 3H), 3.34-3.50 (m, 1H), 2.97-3.05 (m, 1H), 2.34-2.45 (m, 2H), 2.20-2.27 (m, 1H), 1.96-1.98 (m, 1H).

Step D: To the product of step C (25 mg, 0.06 mmol) was added 1.25 M HCl in methanol (1 mL). The solution was concentrated in vacuo and the residue triturated with ethyl acetate before it was lyophilized from water to give 2-(4-aminophenyl)sulfonyl-5-methyl-5,6,7,8,9,10-hexahydro-7,10-epiminocyclohepta[b]indole hydrochloride (15 mg, 62%, AUC HPLC 98.3%) as a white solid: mp 220-225° C.; $^1$H NMR (CD$_3$OD, 300 MHz) δ 8.21 (s, 1H), 7.78 (d, J=7.8 Hz, 1H), 7.75 (s, 2H), 7.66-7.70 (m, 1H), 7.55 (d, J=9.0 Hz, 1H), 6.96 (d, J=8.1 Hz, 1H), 5.28 (d, J=4.8 Hz, 1H), 4.54 (br s, 1H), 3.72 (s, 3H), 3.44-3.53 (m, 1H), 3.03-3.07 (m, 1H), 2.24-2.47 (m, 3H), 1.95-2.01 (m, 1H); ESI MS m/z 368 [M+H]$^+$.

Example 54

Preparation of 2-(3,5-Dichlorophenyl)sulfonyl-5-methyl-5,6,7,8,9,10-hexahydro-7,10-epiminocyclohepta[b]indole hydrochloride

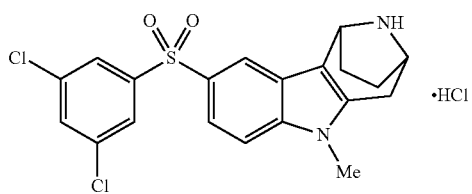 [SMILES: Cn1c2c(c3cc(S(=O)(=O)c4cc(Cl)cc(Cl)c4)ccc31)C1CCC(C2)N1 ; Cl]

Step A: Intermediate 20 was coupled with the product of Example 27, step B following the procedure of Example 27, step C. The crude product was purified by flash column chromatography (SiO$_2$, dichloromethane) to give tert-butyl 2-(3,5-dichlorophenyl)sulfonyl-5-methyl-5,6,7,8,9,10-hexahydro-7,10-epiminocyclohepta[b]indole-carboxylate (55 mg, 19%) as an off-white solid: $^1$H NMR (CDCl$_3$, 300 MHz) δ 8.18 (s, 1H), 7.60-8.02 (m, 3H), 7.30-7.50 (m, 2H), 5.30 (br s, 1H), 4.70 (br s, 1H), 3.62 (s, 3H), 3.27-3.50 (m, 1H), 2.50 (d, J=16.2 Hz, 1H), 2.15-2.40 (m, 2H), 1.91-2.01 (m, 1H), 1.55-1.70 (m, 1H), 1.39 (br s, 9H).

Step B: The product of step A was Boc-deprotected with TFA following the procedure of Example 28, Step B. The crude material was purified by flash column chromatography (SiO$_2$, 90:9:1 dichloromethane/methanol/ammonium hydroxide) followed by semi-preparative HPLC. The free base was treated directly with 1.25 M HCl in methanol (2 mL) and the solution concentrated in vacuo to give 2-(3,5-dichlorophenyl)sulfonyl-5-methyl-5,6,7,8,9,10-hexahydro-7,10-epiminocyclohepta[b]indole hydrochloride (15 mg, 31%, AUC HPLC 98.9%) as an off-white solid: mp 190-195° C.; $^1$H NMR (CD$_3$OD, 300 MHz) δ 8.32 (s, 1H), 7.88 (d, J=1.8 Hz, 2H), 7.58-7.78 (m, 3H), 5.28-5.38 (m, 1H), 4.55 (br s, 1H), 3.72 (s, 3H), 3.40-3.60 (m, 1H), 3.02-3.17 (m, 1H), 2.22-2.55 (m, 3H), 1.92-2.07 (m, 1H); ESI MS m/z 421 [M+H]$^+$.

Example 55

Preparation of 2-(3,5-Difluorophenyl)sulfonyl-5-methyl-5,6,7,8,9,10-hexahydro-7,10-epiminocyclohepta[b]indole hydrochloride

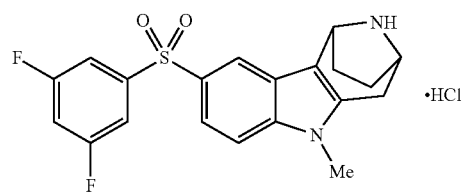 [SMILES: Cn1c2c(c3cc(S(=O)(=O)c4cc(F)cc(F)c4)ccc31)C1CCC(C2)N1 ; Cl]

Step A: Intermediate 21 was coupled with the product of Example 27, step B following the procedure of Example 27, step C. The crude product was purified by flash column chromatography (SiO$_2$, 8:2 hexanes/ethyl acetate) to give tert-butyl 2-(3,5-difluorophenyl)sulfonyl-5-methyl-5,6,7,8,9,10-hexahydro-7,10-epiminocyclohepta[b]indole-carboxylate (40 mg, 13%) as an off-white solid: $^1$H NMR (CDCl$_3$, 300 MHz) δ 8.17 (s, 1H), 7.67 (d, J=8.7 Hz, 1H), 7.44-7.50 (m, 2H), 7.34 (d, J=8.7 Hz, 1H), 6.91-6.96 (m, 1H), 5.26 (br s, 1H), 4.71 (br s, 1H), 3.62 (s, 3H), 3.39 (br s, 1H), 2.48 (d, J=16.0 Hz, 1H), 2.18-2.35 (m, 2H), 1.91-1.99 (m, 1H), 1.50-1.68 (m, 1H), 1.37 (s, 9H)

Step B: To a solution of the product of step A in dichloromethane (0.9 mL) and methanol (0.1 mL) was added 2M HCl in diethyl ether (5 mL). The reaction mixture was stirred at ambient temperature overnight, filtered, washed with diethyl ether and dried in vacuo to give 2-(3,5-difluorophenyl)sulfonyl-5-methyl-5,6,7,8,9,10-hexahydro-7,10-epiminocyclohepta[b]indole hydrochloride (15 mg, 50%, AUC HPLC 98.0%) as an off-white solid: mp 230-235° C. dec; $^1$H NMR (CD$_3$OD, 300 MHz) δ 8.32 (d, J=1.8 Hz, 1H), 7.77 (dd, J=8.7, 1.8 Hz, 1H), 7.57-7.61 (m, 3H), 7.20-7.28 (m, 1H), 5.32 (d, J=4.8 Hz, 1H), 4.55 (br s, 1H), 3.73 (s, 3H), 3.49 (dd, J=17.4, 4.5 Hz, 1H), 3.25-3.40 (m, 1H), 3.08 (d, J=17.4 Hz, 1H), 2.26-2.48 (m, 2H), 1.96-2.00 (m, 1H); ESI MS m/z 389 [M+H]$^+$.

Example 56

Preparation of 2-(3-Thienyl)sulfonyl-5-methyl-5,6,7,8,9,10-hexahydro-7,10-epiminocyclohepta[b]indole hydrochloride

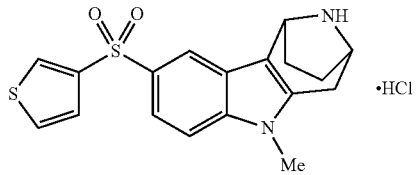 [SMILES: Cn1c2c(c3cc(S(=O)(=O)c4ccsc4)ccc31)C1CCC(C2)N1 ; Cl]

Step A: Intermediate 25 was coupled with the product of Example 27, step B following the procedure of Example 27, step C. The crude material was purified by flash column chromatography (SiO$_2$, hexane/ethyl acetate 55:45) to give tert-butyl 2-(3-thienyl)sulfonyl-5-methyl-5,6,7,8,9,10-hexahydro-7,10-epiminocyclohepta[b]indole-carboxylate (130 mg, 31%) as a yellow solid: $^1$H NMR (CDCl$_3$, 300 MHz) δ 8.20 (s, 1H), 8.02-8.53 (m, 1H), 7.66-7.74 (m, 1H), 7.28-7.37 (m, 3H), 5.26 (br s, 1H), 4.70 (br s, 1H), 3.61 (s, 3H), 3.38 (br s, 1H), 2.50 (d, J=15.9 Hz, 1H), 2.12-2.41 (m, 2H), 1.89-2.00 (m, 1H), 1.57-1.68 (m, 1H), 1.48 (s, 9H).

Step B: The product of step A was subjected to Boc-deprotection with 2 M HCl in diethyl ether following the procedure of Example 28, step B. The crude material was purified by flash column chromatography (SiO$_2$, 88:12 chloroform/methanol) to give 2-(3-thienyl)sulfonyl-5-methyl-5,6,7,8,9,10-hexahydro-7,10-epiminocyclohepta[b]indole (84 mg, 83%) as a yellow solid: $^1$H NMR (CDCl$_3$, 300 MHz) δ 8.18 (d, J=1.8 Hz, 1H), 8.00-8.05 (m, 1H), 7.68 (dd, J=8.7, 1.8 Hz, 1H), 7.28-7.35 (m, 3H), 4.60 (d, J=5.1 Hz, 1H), 4.05-4.15 (m, 1H), 3.60 (s, 3H), 3.17 (dd, J=16.5, 4.5 Hz, 1H), 2.53 (d, J=16.5 Hz, 1H), 1.95-2.29 (m, 3H), 1.51-1.65 (m, 1H).

Step C: To a solution of product from step B (25 mg, 0.07 mmol) in methanol (0.5 mL) and dichloromethane (0.5 mL) was added 1.25 M HCl in methanol (0.22 mL). The solution was concentrated in vacuo and the residue lyophilized to give 2-(3-thienyl)sulfonyl-5-methyl-5,6,7,8,9,10-hexahydro-7,10-epiminocyclohepta[b]indole hydrochloride (26 mg, 94%; AUC HPLC 98.5%) as a white solid. mp 208-212° C. dec; $^1$H NMR (DMSO-d$_6$, 300 MHz) δ 9.56 (br s, 1H), 9.30 (br s, 1H), 8.30-8.39 (m, 2H), 7.63-7.76 (m, 3H), 7.39 (dd, J=5.1, 1.5 Hz, 1H), 5.31-5.39 (m, 1H), 4.42-4.52 (m, 1H), 3.68 (s, 3H), 3.31-3.44 (m, 1H), 3.01 (d, J=17.4 Hz, 1H), 2.20-2.36 (m, 2H), 2.01-2.14 (m, 1H), 1.72-1.89 (m, 1H); ESI, m/z 359 [M+H]$^+$

Example 57

Preparation of 2-[(3-Phenyl)-phenyl]sulfonyl-5-methyl-5,6,7,8,9,10-hexahydro-7,10-epiminocyclohepta[b]indole hydrochloride

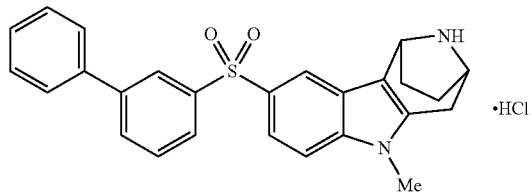 [SMILES: Cn1c2c(c3cc(S(=O)(=O)c4cccc(-c5ccccc5)c4)ccc31)C1CCC(C2)N1 ; Cl]

Step A: The product of Example 27, step B was coupled with 3-phenyl-bromobenzene following the procedure of Example 27, step C. The crude material was purified by flash column chromatography (SiO$_2$, 4:1 to 1:1 hexane/ethyl acetate) to give tent-butyl 2-[(3-phenyl)-phenyl]sulfonyl-5-methyl-5,6,7,8,9,10-hexahydro-7,10-epiminocyclohepta[b]indole-carboxylate (0.32 g) as a yellow foam.

Step B: To a solution of the product of step A (0.30 g, 0.56 mmol) in ethanol (20 mL) was added concentrated HCl (8.0 mL). The reaction mixture was stirred at ambient temperature overnight then concentrated in vacuo. The residue was purified by semi-preparative HPLC. The free base was dissolved in methanol and treated with concentrated HCl then concentrated to dryness in vacuo to give 2-[(3-phenyl)-phenyl]sulfonyl-5-methyl-5,6,7,8,9,10-hexahydro-7,10-epiminocyclohepta[b]indole hydrochloride (98 mg, 38%, AUC HPLC 97.7%) as a light brown solid: mp 230-235° C. dec; $^1$H NMR (CDCl$_3$, 300 MHz) δ 9.71 (s, 1H), 9.12 (s, 1H), 8.45 (d, J=1.2 Hz, 1H), 8.15 (t, J=1.2 Hz, 1H), 7.89-7.94 (m, 2H), 7.75 (dd, J=6.6, 1.2 Hz, 1H), 7.63-7.71 (m, 4H), 7.48-7.53 (m, 2H), 7.40-7.46 (m, 1H), 5.36 (d, J=3.0 Hz, 1H), 4.45 (br s, 1H), 3.67 (s, 3H), 3.37 (dd, J=12.9, 3.3 Hz, 1H), 2.99 (d, J=12.9 Hz, 1H), 2.23-2.31 (m, 2H), 1.99-2.11 (m, 1H), 1.74-1.81 (m, 1H); ESI MS m/z 429 [M+H]$^+$.

Example 58

Preparation of 2-[3-(5-Chloro)-pyridine]sulfonyl-5-methyl-5,6,7,8,9,10-hexahydro-7,10-epiminocyclohepta[b]indole hydrochloride

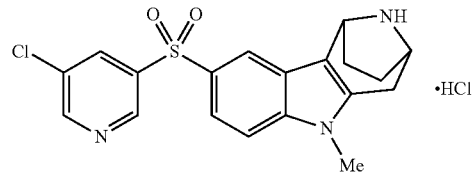 [SMILES: Cn1c2c(c3cc(S(=O)(=O)c4cncc(Cl)c4)ccc31)C1CCC(C2)N1 ; Cl]

Step A: To a solution of the product of Example 27, step B (4.97 g, 12.70 mmol) in anhydrous THF (40 mL) at −78° C. under an argon atmosphere was added n-butyl lithium (1.6M in hexane, 10.3 mL, 16.51 mmol) dropwise. The resulting solution was stirred for 15 min then sulfur dioxide gas bubbled into the reaction mixture for 15 min. The reaction mixture was stirred for another 30 min. at −78° C. under a sulfur dioxide atmosphere then allowed to warm to ambient temperature. After 30 min the reaction mixture was concentrated in vacuo and the residue triturated with diethyl ether (100 mL) to give crude tert-butyl 5-methyl-5,6,7,8,9,10-hexahydro-7,10-epiminocyclohepta[b]indole-carboxylate-2-sulfinic acid lithium salt (4.71 g) as a yellow solid: $^1$H NMR (CD$_3$OD, 300 MHz) δ 7.79 (s, 1H), 7.46 (dd, J=8.7, 1.5 Hz, 1H), 7.34 (d, J=8.7 Hz, 1H), 5.20-5.30 (m, 1H), 4.56-4.69 (m, 1H), 3.68-3.77 (m, 1H), 3.62 (s, 3H), 2.61 (d, J=16.2 Hz, 1H), 2.10-2.38 (m, 2H), 1.81-1.99 (m, 1H), 1.62-1.75 (m, 1H), 1.34 (s, 9H).

Step B: To a mixture of product of step A (165 mg, 0.46 mmol), 3-bromo-5-chloropyridine (89 mg, 0.46 mmol), Pd$_2$(dba)$_3$ (42 mg, 0.04 mmol), xanthphos (54 mg, 0.09 mmol), cesium carbonate (226 mg, 0.69 mmol) and tetrabutylammonium chloride (154 mg, 0.55 mmol) under an argon atmosphere was added anhydrous toluene (3 mL). The mixture was heated to reflux for 1.5 h, cooled to ambient temperature, diluted with ethyl acetate and filtered through a celite bed. The filtrate was concentrated in vacuo and the residue purified by flash column chromatography (SiO$_2$, 65:35 hexane/ethyl acetate) to give tert-butyl 2-[3-(5-chloro)-pyridine]sulfonyl- 5-methyl-5,6,7,8,9,10-hexahydro-7,10-epiminocyclohepta[b]indole-carboxylate (14 mg, 6%) as a yellow solid: $^1$H NMR (CDCl$_3$, 300 MHz) δ 9.00 (d, J=1.8 Hz, 1H), 8.66 (d, J=2.4 Hz, 1H), 8.15-8.23 (m, 2H), 7.63-7.74 (m, 1H), 7.32-7.40 (m, 1H), 5.26 (br s, 1H), 4.71 (br s, 1H), 3.62 (s, 3H), 3.40 (br s, 1H), 2.45-2.58 (m, 1H), 2.12-2.41 (m, 2H), 1.88-2.00 (m, 1H), 1.54-1.73 (m, 1H), 1.38 (s, 9H).

Step C: The product of step B was subjected to Boc-deprotection with 2 M HCl in diethyl ether following the procedure of Example 28, step B. The crude material was purified by flash column chromatography (SiO$_2$, 93:6:1 dichloromethane/methanol/ammonium hydroxide) to give 2-[3-(5-chloro)-pyridine]sulfonyl-5-methyl-5,6,7,8,9,10-hexahydro-7,10-epiminocyclohepta[b]indole (7 mg, 62%) as a yellow solid: $^1$H NMR (CDCl$_3$, 300 MHz) δ 8.99 (d, J=1.8 Hz, 1H), 8.65 (d, J=2.1 Hz, 1H), 8.14-8.21 (m, 2H), 7.66 (dd, J=8.7, 1.8 Hz, 1H), 7.34 (d, J=9.0 Hz, 1H), 4.61 (d, J=4.8 Hz, 1H), 4.05-4.15 (m, 1H), 3.62 (s, 3H), 3.16 (dd, J=16.8, 4.8 Hz, 1H), 2.54 (d, J=16.5 Hz, 1H), 1.95-2.29 (m, 3H), 1.52-1.64 (m, 1H).

Step D: To a solution of product from step C (7 mg, 0.018 mmol) in dichloromethane (1 ml) was added 1.25 M HCl in methanol (58 μl). The solution was concentrated in vacuo and the residue lyophilized from water/acetonitrile to give 2-[3-(5-chloro)-pyridine]sulfonyl-5-methyl-5,6,7,8,9,10-hexahydro-7,10-epiminocyclohepta[b]indole hydrochloride (8 mg, 100%; AUC HPLC 98.8%) as a white solid: mp 202-205° C. dec; $^1$H NMR (DMSO-d$_6$, 300 MHz) δ 9.41 (br s, 1H), 8.98-9.13 (m, 2H), 8.88 (d, J=2.4 Hz, 1H), 8.45-8.52 (m, 2H), 7.79 (dd, J=8.7, 1.8 Hz, 1H), 7.70 (d, J=8.7 Hz, 1H), 5.31-5.39 (m, 1H), 4.49 (s, 1H), 3.69 (s, 3H), 3.31-3.44 (m, 1H), 3.02 (d, J=17.1 Hz, 1H), 2.20-2.35 (m, 2H), 2.06-2.18 (m, 1H), 1.76-1.90 (m, 1H); ESI, m/z 388 [M+H]$^+$ Example 59

Preparation of 2-[3-(5-Fluoro)-pyridine]sulfonyl-5-methyl-5,6,7,8,9,10-hexahydro-7,10-epiminocyclohepta[b]indole hydrochloride

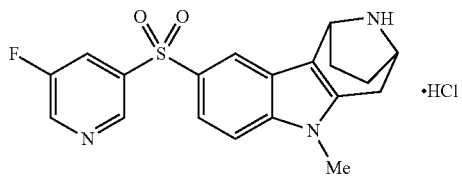 [SMILES: Cn1c2c(c3cc(S(=O)(=O)c4cncc(F)c4)ccc31)C1CCC(C2)N1 ; Cl]

Step A: The product of Example 58, step A was coupled with 3-bromo-5-fluoropyridine following the procedure of Example 58, step B. The crude material was purified by flash column chromatography (SiO$_2$, 60:40 hexane/ethyl acetate) to give 2-[3-(5-fluoro)-pyridine]sulfonyl-5-methyl-5,6,7,8,9,10-hexahydro-7,10-epiminocyclohepta[b]indole-carboxylate (38 mg, 17%) as a yellow solid: $^1$H NMR (CDCl$_3$, 300 MHz) δ 8.56 (d, J=1.2 Hz, 1H), 8.57 (d, J=2.7 Hz, 1H), 8.19 (s, 1H), 7.88-7.96 (m, 1H), 7.60-7.63 (m, 1H), 7.35 (d, J=8.7 Hz, 1H), 5.26 (br s, 1H), 4.70 (br s, 1H), 3.62 (s, 3H), 3.39 (br s, 1H), 2.51 (d, J=16.2 Hz, 1H), 2.14-2.41 (m, 2H), 1.88-2.00 (m, 1H), 1.55-1.69 (m, 1H), 1.38 (s, 9H).

Step C: The product of step B was subjected to Boc-deprotection with 2 M HCl in diethyl ether following the procedure of Example 28, step B. The crude material was purified by flash column chromatography (SiO$_2$, 96:3:1 dichloromethane/methanol/ammonium hydroxide) to give 2-[3-(5-fluoro)-pyridine]sulfonyl-5-methyl-5,6,7,8,9,10-hexahydro-7,10-epiminocyclohepta[b]indole (11 mg, 37%) as a yellow solid: $^1$H NMR (CDCl$_3$, 300 MHz) δ 8.92-8.98 (m, 1H), 8.56 (d, J=2.7 Hz, 1H), 8.17 (d, J=1.8 Hz, 1H) 7.87-7.94 (m, 1H), 7.67 (dd, J=8.7, 2.1 Hz, 1H), 7.34 (d, J=8.7 Hz, 1H), 4.61 (d, J=4.8 Hz, 1H), 4.06-4.16 (m, 1H), 3.61 (s, 3H), 3.17 (dd, J=16.5, 4.5 Hz, 1H), 2.54 (dd, J=16.5, 0.9 Hz, 1H), 1.95-2.29 (m, 3H), 1.51-1.65 (m, 1H).

Step D: To a solution of product from step C (11 mg, 0.07 mmol) in methanol (1 mL) and dichloromethane (1 mL) was added 1.25 M HCl in methanol (94 μl). The solution was concentrated in vacuo and the residue was dissolved lyophilized from water/acetonitrile to give 2-[3-(5-fluoro)-pyridine]sulfonyl-5-methyl-5,6,7,8,9,10-hexahydro-7,10-epiminocyclohepta[b]indole hydrochloride (12 mg, 99%; AUC HPLC >99%) as a white solid: mp 212-215° C.; $^1$H NMR (DMSO-d$_6$, 300 MHz) δ 9.30 (br s, 1H), 9.21 (br s, 1H), 8.99 (t, J=1.5 Hz, 1H), 8.85 (d, J=2.7 Hz, 1H), 8.47 (d, J=1.8 Hz, 1H), 8.30-8.38 (m, 1H), 7.78 (dd, J=8.7, 1.8 Hz, 1H), 7.70 (d, J=8.7 Hz, 1H), 5.34 (d, J=3.9 Hz, 1H), 4.44-4.54 (m, 1H), 3.69 (s, 3H), 3.30-3.43 (m, 1H), 3.02 (d, J=17.4 Hz, 1H), 2.20-2.34 (m, 2H), 2.05-2.17 (m, 1H), 1.72-1.89 (m, 1H); ESI m/z 372 [M+H]$^+$.

Example 60

Preparation of 2-(2-Pyridine)sulfonyl-5-methyl-5,6,7,8,9,10-hexahydro-7,10-epiminocyclohepta[b]indole hydrochloride

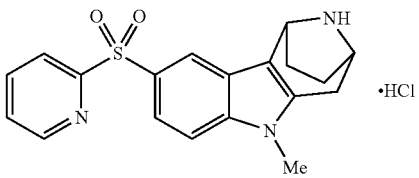 [SMILES: Cn1c2c(c3cc(S(=O)(=O)c4ccccn4)ccc31)C1CCC(C2)N1 ; Cl]

Step A: The product of Example 58, step A was coupled with 2-bromo-pyridine following the procedure of Example 58, step B. The crude material was purified by flash column chromatography (SiO$_2$, 40:60 hexane/ethyl acetate) to give tert-butyl 2-(2-pyridine)sulfonyl-5-methyl-5,6,7,8,9,10-hexahydro-7,10-epiminocyclohepta[b]indole-carboxylate (30 mg, 21%) as a yellow solid. $^1$H NMR (CDCl$_3$, 300 MHz) δ 8.61-8.67 (m, 1H), 8.29 (s, 1H), 8.20 (d, J=7.8 Hz, 1H), 7.88 (dt, J=7.8, 1.8 Hz, 1H), 7.81 (s, 1H), 7.36-7.43 (m, 1H), 7.32 (d, J=8.7 Hz, 1H), 5.26 (br s, 1H), 4.71 (br s, 1H), 3.60 (s, 3H), 3.37 (br s, 1H), 2.49 (d, J=15.6 Hz, 1H), 2.11-2.38 (m, 2H), 1.88-1.99 (m, 1H), 1.52-1.66 (m, 1H), 1.37 (s, 9H).

Step B: The product of step A was subjected Boc-deprotection with TFA following the procedure of Example 28, step B. The crude material was purified by flash column chromatography (SiO$_2$, 88:11:1 dichloromethane/methanol/ammonium hydroxide) to give 2-(2-pyridine)sulfonyl-5-methyl-5,6,7,8,9,10-hexahydro-7,10-epiminocyclohepta[b]indole (11 mg, 47%) as a yellow solid: $^1$H NMR (CDCl$_3$, 300 MHz) δ 8.60-8.67 (m, 1H), 8.25 (d, J=1.8 Hz, 1H), 8.19 (dd, J=8.1, 0.9 Hz, 1H), 7.88 (dt, J=7.8, 1.5 Hz, 1H), 7.77 (dt, J=8.7, 1.8 Hz, 1H), 7.35-7.43 (m, 1H), 7.31 (d, J=9.0 Hz, 1H), 4.62 (d, J=4.8 Hz, 1H), 4.06-4.16 (m, 1H), 3.58 (s, 3H), 3.18 (dd, J=16.5, 4.5 Hz, 1H), 2.53 (d, J=16.5 Hz, 1H), 1.96-2.29 (m, 3H), 1.51-1.64 (m, 1H).

Step C: The product of step B in MeOH (1 mL) and dichloromethane (1 mL) was treated with 1.25 M HCl in methanol (0.1 mL). The solution was concentrated in vacuo and the residue lyophilized from water/acetonitrile to give 2-(2-pyridine)sulfonyl-5-methyl-5,6,7,8,9,10-hexahydro-7,10-epiminocyclohepta[b]indole hydrochloride (11 mg, 91%; AUC HPLC >99%) as a while mp 222-225° C.; $^1$H NMR (DMSO-$d_6$, 300 MHz) δ 9.33-9.47 (m, 1H), 9.00-9.13 (m, 1H), 8.60-8.66 (m, 1H), 8.34 (t, J=1.2 Hz, 1H), 8.23-8.08 (m, 2H), 7.58-7.71 (m, 3H), 5.36 (d, J=2.7 Hz, 1H), 4.47 (s, 1H), 3.69 (s, 3H), 3.31-3.43 (m, 1H), 3.01 (d, J=17.1 Hz, 1H), 2.18-2.33 (m, 2H), 2.03-2.13 (m, 1H), 1.72-1.87 (m, 1H); ESI, m/z 354 [M+H]$^+$.

Example 61

Preparation of 2-(3-Pyridine)sulfonyl-5-methyl-5,6,7,8,9,10-hexahydro-7,10-epiminocyclohepta[b]indole hydrochloride

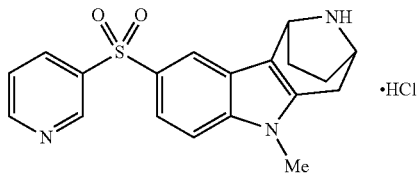 [SMILES: Cn1c2c(c3cc(S(=O)(=O)c4cccnc4)ccc31)C1CCC(C2)N1 ; Cl]

Step A: The product of Example 58, step A was coupled with 3-bromo-pyridine following the procedure of Example 58, step B. The crude material was purified by flash column chromatography (SiO$_2$, 45:55 hexane/ethyl acetate) to give tert-butyl 2-(3-pyridine)sulfonyl-5-methyl-5,6,7,8,9,10-hexahydro-7,10-epiminocyclohepta[b]indole-carboxylate (95 mg, 25%) as a yellow solid: $^1$H NMR (CDCl$_3$, 300 MHz) δ 9.15 (dd, J=2.4, 0.6 Hz, 1H), 8.71 (dd, J=5.1, 1.8 Hz, 1H), 8.16-8.26 (m, 2H), 7.68 (dd, J=8.7, 1.5 Hz, 1H), 7.30-7.46 (m, 2H), 5.26 (br s, 1H), 4.71 (br s, 1H), 3.61 (s, 3H), 3.38 (br s, 1H), 2.51 (d, J=16.2 Hz, 1H), 2.12-2.40 (m, 2H), 1.88-1.99 (m, 1H), 1.54-1.68 (m, 1H), 1.38 (s, 9H).

Step B: The product of step A was subjected to Boc-deprotection with TFA following the procedure of Example 28, step B. The crude material was purified by column chromatography (SiO$_2$, 85:15 dichloromethane/methanol) to give 2-(3-pyridine)sulfonyl-5-methyl-5,6,7,8,9,10-hexahydro-7,10-epiminocyclohepta[b]indole (34 mg, 46%) as a yellow solid: $^1$H NMR (CDCl$_3$, 300 MHz) δ 9.13 (d, J=1.8 Hz, 1H), 8.70 (dd, J=4.8, 1.5 Hz, 1H), 8.13-8.24 (m, 2H), 7.66 (dd, J=8.7, 1.8 Hz, 1H), 7.28-7.43 (m, 2H), 4.59 (d, J=5.1 Hz, 1H), 4.06-4.13 (m, 1H), 3.60 (s, 3H), 3.15 (dd, J=16.5, 4.5 Hz, 1H), 2.53 (d, J=16.2 Hz, 1H), 2.04-2.27 (m, 3H), 1.52-1.63 (m, 1H).

Step C: The product of step B in MeOH (1 mL) and dichloromethane (1 mL) was treated with 1.25 M HCl in methanol (0.1 mL). The solution was concentrated in vacuo and the residue lyophilized from water/acetonitrile to give 2-(3-pyridine)sulfonyl-5-methyl-5,6,7,8,9,10-hexahydro-7,10-epiminocyclohepta[b]indole hydrochloride (35 mg, 94%; AUC HPLC >99%) as a light yellow solid: mp 226-228° C.; $^1$H NMR (DMSO-$d_6$, 300 MHz) δ 9.59 (br s, 1H), 9.04-9.18 (m, 2H), 8.79 (dd, J=4.8, 1.5 Hz, 1H), 8.44 (d, J=1.5 Hz, 1H), 8.28-8.37 (m, 1H), 7.58-7.78 (m, 3H), 5.35 (br s, 1H), 4.47 (s, 1H), 3.68 (s, 3H), 3.37 (dd, J=17.1, 4.5 Hz, 1H), 3.01 (d, J=17.4 Hz, 1H), 2.19-2.34 (m, 2H), 2.04-2.14 (m, 1H), 1.71-1.88 (m, 1H); ESI, m/z 354 [M+H]$^+$.

Example 62

Preparation of 2-(1-indole)sulfonyl-5-methyl-5,6,7,8,9,10-hexahydro-7,10-epiminocyclohepta[b]indole hydrochloride

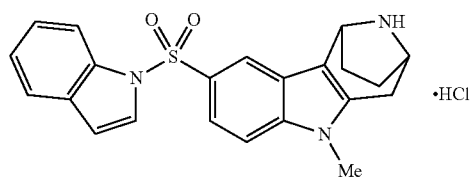 [SMILES: Cn1c2c(c3cc(S(=O)(=O)n4ccc5ccccc54)ccc31)C1CCC(C2)N1 ; Cl]

Step A: To a solution of the product of Example 58, step A (302 mg, 0.85 mmol) in dichloromethane (5 mL) at 0° C. under an argon atmosphere was added N-chlorosuccinimide (120 mg, 0.89 mmol). The reaction mixture was stirred at 0° C. for 2 h then for a further 30 min at ambient temperature. Water (10 mL) was added and the product was extracted with dichloromethane. The organic extract was dried over sodium sulfate, filtered and concentrated in vacuo. The residue was purified by flash column chromatography (SiO$_2$, 60:40 hexane/ethyl acetate) to give tert-butyl 2-chlorosulfonyl-5-methyl-5,6,7,8,9,10-hexahydro-7,10-epiminocyclohepta[b]indole-carboxylate (142 mg, 42%) as a yellow solid: $^1$H NMR (CDCl$_3$, 300 MHz) δ 8.24 (d, J=1.5 Hz, 1H), 7.80 (dd, J=9.0, 1.8 Hz, 1H), 7.39 (d, J=8.7 Hz, 1H), 5.26 (br s, 1H), 4.73 (br s, 1H), 3.67 (s, 3H), 3.43 (br s, 1H), 2.53 (d, J=16.2 Hz, 1H), 2.16-2.42 (m, 2H), 1.90-2.02 (m, 1H), 1.57-1.69 (m, 1H), 1.39 (s, 9H).

Step B: To a solution of indole (19 mg, 0.16 mmol) in anhydrous THF (2 mL) under an argon atmosphere was added NaH (60% dispersion in mineral oil, 8 mg, 0.19 mmol) portionwise. After stirring for 1 h at ambient temperature the product of step A (65 mg, 0.16 mmol) was added. The reaction mixture was stirred for an additional 1.5 h then quenched with 5% aqueous sodium bicarbonate solution (10 mL) and extracted with chloroform. The organic extract was dried over sodium sulfate, filtered and concentrated in vacuo. The residue was purified by flash column chromatography (SiO$_2$, hexane/ethyl acetate) to give tert-butyl 2-(1-indole)sulfonyl-5-methyl-5,6,7,8,9,10-hexahydro-7,10-epiminocyclohepta[b]indole-carboxylate (49 mg, 61%) as a yellow solid: $^1$H NMR (CDCl$_3$, 300 MHz) δ 8.15 (d, J=1.2 Hz, 1H), 8.21 (d, J=8.4 Hz, 1H), 7.63 (d, J=3.9 Hz, 1H), 7.59 (dd, J=8.7, 1.5 Hz, 1H), 7.48 (d, J=7.8 Hz, 1H), 7.11-7.31 (m, 3H), 6.61 (d, J=3.6 Hz, 1H), 5.19 (br s, 1H), 4.67 (br s, 1H), 3.53 (s, 3H), 3.34 (br s, 1H), 2.44 (d, J=16.2 Hz, 1H), 2.12-2.36 (m, 2H), 1.82-1.94 (m, 1H), 1.49-1.63 (m, 1H), 1.34 (s, 9H).

Step C: To a solution of product from step B (49 mg, 0.09 mmol) in dichloromethane (2 mL) was added 2M HCl in diethyl ether (2 mL). After stirring overnight at ambient temperature the reaction mixture was quenched with 10% aqueous sodium bicarbonate solution (10 mL) and extracted with dichloromethane. The organic extract was dried over sodium sulfate, filtered and concentrated in vacuo. The residue was purified by flash column chromatography (SiO$_2$, 88:12 chloroform/methanol) to give 2-(1-indole)sulfonyl-5-methyl-5,6,7,8,9,10-hexahydro-7,10-epiminocyclohepta[b]indole (19 mg, 49%) as a yellow solid: $^1$H NMR (CDCl$_3$, 300 MHz) δ 8.11 (d, J=1.8 Hz, 1H), 8.04 (d, J=8.1 Hz, 1H), 7.62 (d, J=3.9

Hz, 1H), 7.58 (dd, J=8.7, 1.8 Hz, 1H), 7.48 (d, J=7.8 Hz, 1H), 7.25-7.31 (m, 1H), 7.12-7.21 (m, 2H), 6.58-6.63 (m, 1H), 4.59 (d, J=5.1 Hz, 1H), 4.05-4.15 (m, 1H), 3.47 (s, 3H), 3.13 (dd, J=16.5, 4.5 Hz, 1H), 2.47 (d, J=16.5 Hz, 1H), 2.07-2.23 (m, 2H), 1.89-2.00 (m, 1H), 1.48-1.61 (m, 1H).

Step D: To a solution of product from step C (19 mg, 0.07 mmol) in dichloromethane (1 mL) was added 1.25 M HCl in methanol solution (155 µl). The solution was concentrated in vacuo and the residue lyophilized from water/acetonitrile to give 2-(1-indole)sulfonyl-5-methyl-5,6,7,8,9,10-hexahydro-7,10-epiminocyclohepta[b]indole hydrochloride (20 mg, 97%; AUC HPLC >99%) as a white solid: mp 207-210° C.; $^1$H NMR (DMSO-$d_6$, 300 MHz) δ 9.44 (br s, 1H), 9.00 (br s, 1H), 8.48 (d, J=1.2 Hz, 1H), 7.99 (dd, J=8.1, 0.6 Hz, 1H), 7.80 (d, J=3.6 Hz, 1H), 7.50-7.68 (m, 3H), 7.13-7.34 (m, 2H), 6.79 (dd, J=3.6, 0.6 Hz, 1H), 5.30-5.38 (m, 1H), 4.40-4.51 (m, 1H), 3.62 (s, 3H), 3.30-3.38 (m, 1H), 2.97 (d, J=17.1 Hz, 1H), 2.18-2.32 (m, 2H), 1.96-2.09 (m, 1H), 1.70-1.84 (m, 1H); ESI MS m/z 392 [M+H]$^+$.

Example 63

Preparation of 2-[1-(5-Fluoro)-indole]sulfonyl-5-methyl-5,6,7,8,9,10-hexahydro-7,10-epiminocyclohepta[b]indole hydrochloride

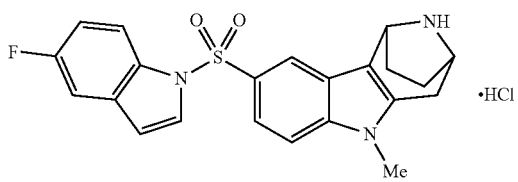 [SMILES: Cn1c2c(c3cc(S(=O)(=O)n4ccc5cc(F)ccc54)ccc31)C1CCC(C2)N1 ; Cl]

Step A: The product of Example 62, step A and 5-fluoroindole were coupled following the procedure of Example 62, step B. The crude product was purified by flash column chromatography (SiO$_2$, 60:40 hexane/ethyl acetate) to give tert-butyl 2-[1-(5-fluoro)-indole]sulfonyl-5-methyl-5,6,7,8,9,10-hexahydro-7,10-epiminocyclohepta[b]indole-carboxylate (58 mg, 70%) as a yellow solid: $^1$H NMR (CDCl$_3$, 300 MHz) δ 8.16 (d, J=1.8 Hz, 1H), 7.94-8.04 (m, 1H), 7.65 (d, J=3.6 Hz, 1H), 7.56 (dd, J=8.7, 1.8 Hz, 1H), 7.20 (d, J=8.7 Hz, 1H), 7.12 (dd, J=8.7, 2.4 Hz, 1H), 6.93-7.06 (m, 1H), 6.56 (d, J=3.3 Hz, 1H), 5.19 (br s, 1H), 4.67 (br s, 1H), 3.53 (s, 3H), 3.34 (br s, 1H), 2.45 (d, J=16.2 Hz, 1H), 2.12-2.38 (m, 2H), 1.81-1.93 (m, 1H), 1.50-1.61 (m, 1H), 1.33 (s, 9H).

Step B: To a solution of product from step B (58 mg, 0.12 mmol) in dichloromethane (2 mL) at 0° C. under an argon atmosphere was added trifluoroacetic acid (0.18 mL). After stirring for 90 min the reaction was quenched with 10% aqueous sodium bicarbonate solution (10 mL) and extracted with dichloromethane. The organic extract was dried over sodium sulfate, filtered and concentrated in vacuo. The residue was purified by flash column chromatography (SiO$_2$, 90:10 dichloromethane/methanol) to give 2-[1-(5-fluoro)-indole]sulfonyl-5-methyl-5,6,7,8,9,10-hexahydro-7,10-epiminocyclohepta[b]indole (22 mg, 46%) as a yellow solid: $^1$H NMR (CDCl$_3$, 300 MHz) δ 8.08 (d, J=1.8 Hz, 1H), 7.94-8.01 (m, 1H), 7.65 (d, J=3.9 Hz, 1H), 7.55 (dd, J=8.7, 1.8 Hz, 1H), 7.19 (d, J=9.0 Hz, 1H), 7.12 (dd, J=9.0, 2.7 Hz, 1H), 7.00 (dt, J=9.0, 2.7 Hz, 1H), 6.56 (d, J=3.6 Hz, 1H), 4.58 (d, J=4.8 Hz, 1H), 4.05-4.14 (m, 1H), 3.51 (s, 3H), 3.14 (dd, J=16.5, 4.5 Hz, 1H), 2.49 (d, J=16.5 Hz, 1H), 1.90-2.28 (m, 3H), 1.49-1.61 (m, 1H).

Step C: To a solution of product from step C (22 mg, 0.05 mmol) in dichloromethane (2 mL) was added 1.25 M HCl in methanol solution (171 µA). The solution was concentrated in vacuo and the residue lyophilized from water/acetonitrile to give 2-[1-(5-fluoro)-indole]sulfonyl-5-methyl-5,6,7,8,9,10-hexahydro-7,10-epiminocyclohepta[b]indole hydrochloride (22 mg, 92%; AUC HPLC 97.9%) as an off-white solid: mp 218-220° C.; $^1$H NMR (DMSO-$d_6$, 300 MHz) δ 9.46 (br s, 1H), 9.02 (br s, 1H), 8.48 (d, J=0.6 Hz, 1H), 7.95-8.04 (m, 1H), 7.88 (d, J=3.6 Hz, 1H), 7.58-7.68 (m, 2H), 7.37 (dd, J=9.3, 2.7 Hz, 1H), 7.14 (dt, J=9.0, 2.4 Hz, 1H), 6.78 (d, J=3.3 Hz, 1H), 5.33 (d, J=3.3 Hz, 1H), 4.46 (s, 1H), 3.63 (s, 3H), 3.30-3.41 (m, 1H), 2.98 (d, J=17.1 Hz, 1H), 2.17-2.35 (m, 2H), 1.97-2.09 (m, 1H), 1.70-1.87 (m, 1H); ESI, m/z 410 [M+H]$^+$.

Example 64

Preparation of 2-[1-(4-Fluoro)-indole]sulfonyl-5-methyl-5,6,7,8,9,10-hexahydro-7,10-epiminocyclohepta[b]indole hydrochloride

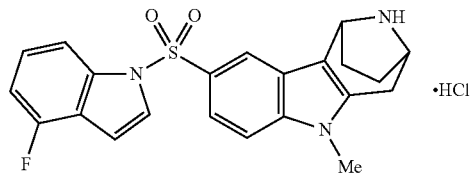 [SMILES: Cn1c2c(c3cc(S(=O)(=O)n4ccc5c(F)cccc54)ccc31)C1CCC(C2)N1 ; Cl]

Step A: The product of Example 62, step A and 4-fluoroindole were coupled following the procedure of Example 62, step B. The crude product was purified by flash column chromatography (SiO$_2$, 4:1 hexanes/ethyl acetate) to give tert-butyl 2-[1-(4-fluoro)-indolesulfonyl]-5-methyl-5,6,7,8,9,10-hexahydro-7,10-epiminocyclohepta[b]indole-carboxylate (83 mg, 53%) as a light yellow solid: $^1$H NMR (CDCl$_3$, 300 MHz) δ 8.14 (d, J=1.8 Hz, 1H), 7.83 (d, J=8.1 Hz, 1H), 7.61 (s, 1H), 7.59 (dd, J=6.9, 1.8 Hz, 1H), 7.16-7.24 (m, 2H), 6.85 (dd, J=9.4, 8.4 Hz, 1H), 6.71 (dd, J=3.9, 0.9 Hz, 1H), 5.19 (br s, 1H), 4.67 (br s, 1H), 3.56 (s, 3H), 3.32-3.35 (m, 1H), 2.46 (d, J=16.2 Hz, 1H), 2.14-2.36 (m, 2H), 1.86-1.92 (m, 1H), 1.48-1.59 (m, 1H), 1.55 (s, 9H).

Step B: The product of step A was subjected to Boc-deprotection following the procedure of Example 28, step B. The crude material was purified by flash column chromatography (SiO$_2$, 90:9:0.5 dichloromethane/methanol/ammonium hydroxide). The purified free base was dissolved directly in dichloromethane (1 mL) and treated with 1.25M HCl in MeOH (0.33 mL). The solution was concentrated in vacuo to give 2-[1-(4-fluoro)-indolesulfonyl]-5-methyl-5,6,7,8,9,10-hexahydro-7,10-epiminocyclohepta[b]indole hydrochloride (43 mg, 94%, AUC HPLC >99%) as a light yellow solid: $^1$H NMR (CD$_3$OD, 300 MHz) δ 8.35 (s, 1H), 7.87 (d, J=8.4 Hz, 1H), 7.72-7.76 (m, 2H), 7.54 (d, J=9.0 Hz, 1H), 7.24-7.31 (m, 1H), 6.92 (t, J=8.7 Hz, 1H), 6.78 (d, J=3.3 Hz, 1H), 5.32 (d, J=4.2 Hz, 1H), 4.56 (br s, 1H), 3.70 (s, 3H), 3.47 (dd, J=17.4, 4.5 Hz, 1H), 3.07 (d, J=17.7 Hz, 1H), 2.49-2.38 (m, 2H), 2.23-2.29 (m, 1H), 1.96-2.00 (m, 1H); ESI MS m/z 410 [M+H]$^+$.

Example 65

Preparation of 2-[1-(6-fluoro)-indole]sulfonyl-5-methyl-5,6,7,8,9,10-hexahydro-7,10-epiminocyclohepta[b]indole hydrochloride

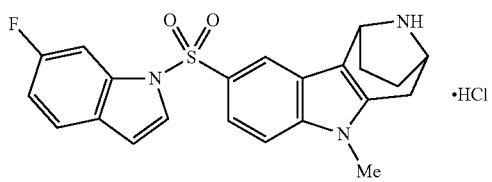 [SMILES: Cn1c2c(c3cc(S(=O)(=O)n4ccc5ccc(F)cc54)ccc31)C1CCC(C2)N1 ; Cl]

Step A: The product of example 62, step A and 6-fluoroindole were coupled following the procedure of example 62, step B. The crude product was purified by flash column chromatography (SiO$_2$, 4:1 hexanes/ethyl acetate) to give tert-butyl 2-[1-(6-fluoro)-indole]sulfonyl-5-methyl-5,6,7,8,9,10-hexahydro-7,10-epiminocyclohepta[b]indole-carboxylate (70 mg, 80%) as a light yellow solid: $^1$H NMR (CDCl$_3$, 300 MHz) δ 8.14 (s, 1H), 7.78 (dd, J=9.9, 2.1 Hz, 1H), 7.60-7.64 (m, 2H), 7.40 (dd, J=8.7, 5.4 Hz, 1H), 7.23 (d, J=8.7 Hz, 1H), 6.93 (td, J=9.2, 2.4 Hz, 1H), 6.58 (dd, J=3.6, 0.6 Hz, 1H), 5.21 (br s, 1H), 4.69 (br s, 1H), 3.56 (s, 3H), 3.32-3.40 (m, 1H), 2.46 (d, J=16.2 Hz, 1H), 2.17-2.36 (m, 2H), 1.88-1.92 (m, 1H), 1.53-1.59 (m, 1H), 1.34 (s, 9H).

Step B: The product of step A was subjected to Boc-deprotection following the procedure of Example 28, step B. The crude material was purified by flash column chromatography (SiO$_2$, 90:9:0.5 dichloromethane/methanol/ammonium hydroxide). The purified free base was dissolved directly in dichloromethane (1 mL) and treated with 1.25M HCl in MeOH (0.33 mL). The solution was concentrated in vacuo to give 2-[1-(6-fluoro)-indole]sulfonyl-5-methyl-5,6,7,8,9,10-hexahydro-7,10-epiminocyclohepta[b]indole hydrochloride (18 mg, 92%, AUC HPLC 98.7%) as a light yellow solid: $^1$H NMR (CD$_3$OD, 300 MHz) δ 8.32 (s, 1H), 7.66-7.75 (m, 3H), 7.46-7.53 (m, 2H), 6.96 (t, J=9.3 Hz, 1H), 6.68 (br s, 1H), 5.30 (br s, 1H), 4.53 (br s, 1H), 3.67 (s, 3H), 3.44 (d, J=18.6 Hz, 1H), 3.04 (d, J=17.4 Hz, 1H), 2.40-2.44 (m, 2H), 2.21-2.24 (m, 1H), 1.94-1.97 (m, 1H); ESI MS m/z 410 [M+H]$^+$.

Example 66

Preparation of 2-[1-(5-Methoxy)-indole]sulfonyl-5-methyl-5,6,7,8,9,10-hexahydro-7,10-epiminocyclohepta[b]indole hydrochloride

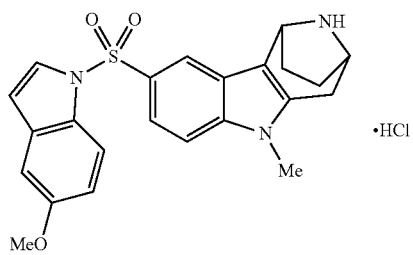 [SMILES: COc1ccc2c(ccn2S(=O)(=O)c2ccc3c(c2)c2c(n3C)CC3CCC2N3)c1 ; Cl]

Step A: The product of Example 62, step A and 5-methoxyindole were coupled following the procedure of Example 62, step B. The crude product was purified by flash column chromatography (SiO$_2$, 70:30 hexane/ethyl acetate) to give tert-butyl 2-[1-(5-methoxy)-indole]sulfonyl-5-methyl-5,6,7,8,9,10-hexahydro-7,10-epiminocyclohepta[b]indole-carboxylate (70 mg, 50%) as a light yellow solid: $^1$H NMR (CDCl$_3$, 300 MHz) δ 8.11 (d, J=1.2 Hz, 1H), 7.93 (d, J=9.0 Hz, 1H), 7.54-7.60 (m, 2H), 7.17-7.20 (m, 1H), 6.87-6.93 (m, 2H), 6.53 (d, J=3.6 Hz, 1H), 5.19 (s, 1H), 4.68 (s, 1H), 3.78 (s, 3H), 3.54 (s, 3H), 3.35 (s, 1H), 2.35-2.42 (m, 1H), 2.13-2.31 (m, 2H), 1.85-1.89 (m, 1H), 1.50-1.60 (m, 1H), 1.34 (s, 9H).

Step B: The product of step A was subjected to Boc-deprotection following the procedure of Example 28, step B. The crude material was purified by flash column chromatography (SiO$_2$, 92:8 dichloromethane/methanol) and the material treated directly with 1.25 M HCl in methanol (0.7 mL). The solution was concentrated in vacuo to give 2-[1-(5-methoxy)-indole]sulfonyl-5-methyl-5,6,7,8,9,10-hexahydro-7,10-epiminocyclohepta[b]indole hydrochloride (25 mg, 45%, HPLC AUC 96.7%) as a pink solid: mp 206-209° C.; $^1$H NMR (CD$_3$OD, 400 MHz) δ 8.24 (d, J=1.2 Hz, 1H), 7.88 (d, J=6.6 Hz, 1H), 7.56-7.67 (m, 2H), 7.46-7.47 (m, 1H), 6.99 (d, J=2.4 Hz, 1H), 6.87 (d, J=9.0 Hz, 1H), 6.61 (d, J=3.6 Hz, 1H), 5.26 (d, J=3.6 Hz, 1H), 4.49-4.53 (m, 1H), 3.75 (s, 3H), 3.65 (s, 3H), 3.39-3.47 (m, 1H), 3.00-3.04 (m, 1H), 2.36-2.41 (m, 2H), 2.20-2.25 (m, 1H), 2.00-1.89 (m, 1H); ESI MS m/z 422 [M+H]$^+$

Example 67

Preparation of 2-[1-(3-Chloro)-indole]sulfonyl-5-methyl-5,6,7,8,9,10-hexahydro-7,10-epiminocyclohepta[b]indole hydrochloride

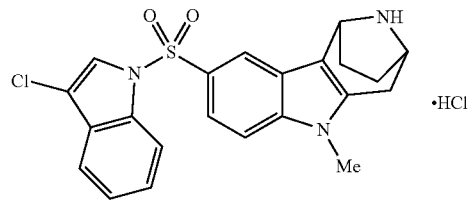 [SMILES: Cn1c2c(c3cc(S(=O)(=O)n4cc(Cl)c5ccccc54)ccc31)C1CCC(C2)N1 ; Cl]

Step A: To a solution of indole (2.0 g, 17.0 mmol) in DMF (12 mL) at 10° C. under a nitrogen atmosphere was added N-chlorosuccinimide (2.49 g, 18.7 mmol). The reaction was stirred for 4 h then quenched with 10% sodium bisulfite solution. After stirring for 15 min the precipitated solid was collected by vacuum filtration. The filtered solid was washed with water then dissolved in dichloromethane. The solution was washed with water, brine and dried over sodium sulfate then concentrated in vacuo to give 3-chloroindole (1.8 g, 70%) as a yellow-brown solid: $^1$H NMR (CDCl$_3$, 300 MHz) δ 8.06 (s, 1H), 7.64 (d, J=7.8 Hz, 1H), 7.34-7.37 (m, 1H), 7.16-7.22 (m, 2H).

Step B: The product of Example 62, step A and 3-chloroindole were coupled following the procedure of Example 62, step B. The crude product was purified by flash column chromatography (SiO$_2$, 70:30 hexane/ethyl acetate) to give tert-butyl 2-[1-(3-chloro)-indole]sulfonyl-5-methyl-5,6,7,8,9,10-hexahydro-7,10-epiminocyclohepta[b]indole-carboxylate (50 mg, 50%) as a light yellow solid: $^1$H NMR (CDCl$_3$, 300 MHz) δ 8.14 (d, J=1.8 Hz, 1H), 8.07 (d, J=8.4 Hz, 1H), 7.57-7.61 (m, 2H), 7.49-7.51 (m, 1H), 7.32-7.37 (m, 1H), 7.20-7.28 (m, 2H), 5.19 (s, 1H), 4.68 (s, 1H), 3.54 (s, 3H), 3.35 (s, 1H), 2.45 (d, J=16.3 Hz, 1H), 2.19-2.37 (m, 2H), 1.85-1.91 (m, 1H), 1.50-1.63 (m, 1H), 1.33 (s, 9H).

Step C: The product of step B was subjected to Boc-deprotection following the procedure of Example 28, step B. The crude material was purified by flash column chromatography (SiO$_2$, 92:8 dichloromethane/methanol) and the material treated directly with 1.25 M HCl in methanol (0.7 mL). The solution was concentrated in vacuo to give 2-[1-(3-chloro)-indole]sulfonyl-5-methyl-5,6,7,8,9,10-hexahydro-7,10-epiminocyclohepta[b]indole hydrochloride (10 mg, 30%, HPLC AUC 97.4%) as a yellow solid: mp 204-206° C.; $^1$H NMR (CD$_3$OD, 400 MHz) δ 8.31 (d, J=1.7 Hz, 1H), 8.07 (d, J=8.4 Hz, 1H), 7.79 (s, 1H), 7.70 (dd, J=6.9, 1.8 Hz, 1H), 7.47-7.51 (m, 2H), 7.35-7.40 (m, 1H), 7.26-7.30 (m, 1H), 5.28-5.29 (m, 1H), 4.50-4.53 (m, 1H), 3.65 (s, 3H), 3.40-3.48 (m, 1H), 3.00-3.05 (m, 1H), 2.33-2.47 (m, 2H), 2.20-2.25 (m, 1H), 1.91-1.98 (m, 1H); APCI MS m/z 426 [M+H]$^+$ Example 68

Preparation of 2-[1-(3-Methyl)-indole]sulfonyl-5-methyl-5,6,7,8,9,10-hexahydro-7,10-epiminocyclohepta[b]indole hydrochloride

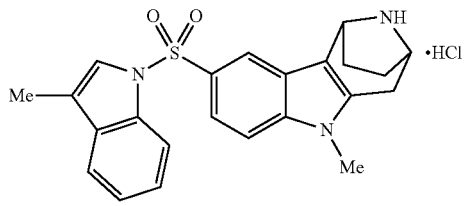 [SMILES: Cc1cn(S(=O)(=O)c2ccc3c(c2)c2c(n3C)CC3CCC2N3)c2ccccc12 ; Cl]

Step A: The product of Example 62, step A and 3-methylindole were coupled following the procedure of Example 62, step B. The crude product was purified by flash column chromatography (SiO$_2$, 70:30 hexane/ethyl acetate) to give tert-butyl 2-[1-(3-methyl)-indole]sulfonyl-5-methyl-5,6,7,8,9,10-hexahydro-7,10-epiminocyclohepta[b]indole-carboxylate (60 mg, 50%) as a light yellow solid: $^1$H NMR (CDCl$_3$, 300 MHz) δ 8.12 (d, J=1.5 Hz, 1H), 8.04 (d, J=8.1 Hz, 1H), 7.57 (dd, J=7.2, 1.5 Hz, 1H), 7.36-7.41 (m, 2H), 7.25-7.30 (m, 1H), 7.16-7.20 (m, 2H), 5.19 (s, 1H), 4.67 (s, 1H), 3.52 (s, 3H), 3.33 (s, 1H), 2.44 (d, J=16.2, 1H), 2.12-2.37 (m, 5H), 1.84-1.91 (m, 1H), 1.63-1.76 (m, 1H), 1.33 (s, 9H).

Step B: The product of step A was subjected to Boc-deprotection following the procedure of Example 28, step B. The crude material was purified by flash column chromatography (SiO$_2$, 92:8 dichloromethane/methanol) and the material treated directly with 1.25 M HCl in methanol (0.7 mL). The solution was concentrated in vacuo to give 2-[1-(3-methyl)-indole]sulfonyl-5-methyl-5,6,7,8,9,10-hexahydro-7,10-epiminocyclohepta[b]indole hydrochloride (25 mg, 45%, HPLC AUC 97.5%) as an off-white solid: mp 212-215° C.; $^1$H NMR (CD$_3$OD, 400 MHz) δ 8.24 (d, J=2.4 Hz, 1H), 7.99 (d, J=10.8 Hz, 1H), 7.63 (dd, J=9.2, 2.4 Hz, 1H), 7.41-7.46 (m, 3H), 7.23-7.29 (m, 1H), 7.15-7.20 (m, 1H), 5.25-5.27 (m, 1H), 4.51-4.52 (m, 1H), 3.64 (s, 3H), 3.42 (dd, J=16.8, 6.0 Hz, 1H), 2.98-3.04 (m, 1H), 2.35-2.44 (m, 2H), 2.24-2.21 (m, 1H), 2.21 (s, 3H), 1.95-1.90 (m, 1H); ESI MS m/z 406 [M+H]$^+$.

Example 69

Preparation of 2-Phenylsulfonyl-5-methyl-5,6,7,8,9,10-hexahydro-7,10-N-methyl-epiminocyclohepta[b]indole hydrochloride

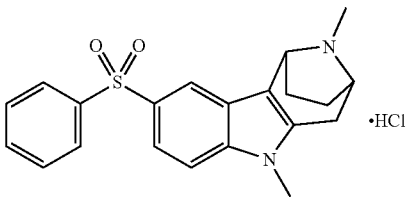 [SMILES: CN1C2CCC1c1c(n(C)c3ccc(S(=O)(=O)c4ccccc4)cc13)C2 ; Cl]

To a solution of the product of Example 27, step D (32 mg, 0.082 mmol) in methanol (2 mL) was added formaldehyde (37% in H$_2$O, 20 µL, 0.31 mmol). After stirring for 1 h sodium triacetoxyborohydride (35 mg, 0.165 mmol) was added. After 1 h the reaction was quenched by addition of water and extracted with dichloromethane. The organic extract was dried over sodium sulfate, filtered and concentrated in vacuo. Purification by flash column chromatography (silica gel, methylene chloride/methanol:ammonia mixture (10:1); 100:0 to 85:25) followed by conversion to the HCl salt provided 2-phenylsulfonyl-5-methyl-5,6,7,8,9,10-hexahydro-7,10-N-methyl-epiminocyclohepta[b]indole hydrochloride (16 mg, 48%) as a yellow solid: $^1$H NMR (500 MHz, d$_6$-DMSO) δ 10.90 (brs, 0.5H), 10.29 (brs, 0.5H), 8.29 (2×s, 1H), 7.92 (2×d, 2H), 7.63 (m, 5H), 5.25 (brs, 1H), 4.28 (2×brs, 1H), 3.69 (2×s, 3H), 3.41 (m, 1H, partially masked by solvent), 3.06 (m, 1H), 2.83 (2×s, 1.7H), 2.64 (2×s, 1.3H), 2.45 (m, 1H), 2.33 (m, 1H), 2.10 (m, 1H), 1.85 (m, 1H); ESI MS m/z 367 [M+H]$^+$; HPLC (Method A)>99% (AUC), t$_R$=12.12 min.

Example 70

Preparation of 2-(3-thienyl)sulfonyl-5-methyl-5,6,7,8,9,10-hexahydro-7,10-N-methyl-epiminocyclohepta[b]indole hydrochloride

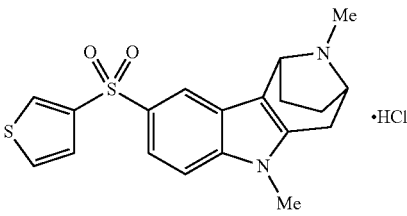 [SMILES: CN1C2CCC1c1c(n(C)c3ccc(S(=O)(=O)c4ccsc4)cc13)C2 ; Cl]

Step A: To a solution of the product of Example 56, step B (59 mg, 0.16 mmol) in 1,2-dichloroethane (4 mL) was added formaldehyde (37% in H$_2$O, 37 µL, 0.49 mmol). After stirring for 30 min sodium triacetoxyborohydride (208 mg, 0.98 mmol) was added. After 3 h the reaction was quenched by addition of 5% aqueous sodium bicarbonate and extracted with ethyl acetate. The organic extract was dried over sodium sulfate, filtered and concentrated in vacuo. The residue was purified by flash column chromatography (SiO$_2$, 92:8 chloroform/methanol) to give 2-(3-thienyl)sulfonyl-5-methyl-5,6,7,8,9,10-hexahydro-7,10-N-methyl-epiminocyclohepta[b]indole (48 mg, 78%) as a yellow solid: $^1$H NMR (CDCl$_3$, 300 MHz) δ 8.16 (d, J=1.8 Hz, 1H), 8.03 (dd, J=1.5, 2.7 Hz, 1H), 7.69 (dd, J=1.8, 8.7 Hz, 1H), 7.28-7.36 (m, 3H), 4.23 (d, J=5.1 Hz, 1H), 3.58-3.68 (m, 4H), 3.16 (dd, J=16.5, 4.5 Hz, 1H), 2.24-2.39 (m, 6H), 1.82-1.92 (m, 1H), 1.47-1.57 (m, 1H).

Step B: To a solution of product from step A in methanol (0.5 mL) and dichloromethane (0.5 mL) was added 1.25 M HCl in methanol (0.41 mL). The solution was concentrated in vacuo and the residue lyophilized from water/acetonitrile to give 2-(3-thienyl)sulfonyl-5-methyl-5,6,7,8,9,10-hexahydro-7,10-N-methyl-epiminocyclohepta[b]indole hydrochloride (49 mg, 94%, AUC HPLC 96.9%) as a white solid: mp 238-240° C.; $^1$H NMR (D$_2$O, 300 MHz) δ 8.15-8.23 (m, 2H), 7.63-7.71 (m, 1H), 7.46-7.55 (m, 2H), 7.28-7.34 (m, 1H), 5.00-5.13 (m, 1H), 4.25-4.36 (m, 1H), 3.58-3.67 (m, 3H), 3.34-3.57 (m, 1H), 2.97-3.09 (m, 1H), 2.92 (s, 1.7H), 2.72 (s, 1.3H), 2.32-2.60 (m, 2H), 2.10-2.24 (m, 1H), 1.86-1.98 (m, 1H); ESI, m/z 373 [M+H]$^+$.

Example 71

Preparation of 2-Phenylsulfonyl-4,5-dimethyl-5,6,7,8,9,10-hexahydro-7,10-epiminocyclohepta[b]indole hydrochloride

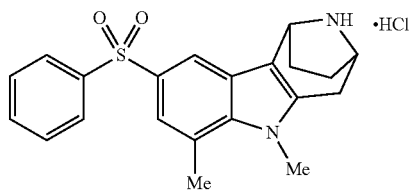

Step A: To a solution of 4-bromo-2-methylaniline (2.50 g, 13.44 mmol) in concentrated HCl (5.4 mL) at 0° C. was added a cold solution of sodium nitrite (1.02 g, 14.78 mmol) in water (5.1 mL). Stirring was continued at 0° C. for 45 min then the mixture was filtered. To the filtrate at 0° C. was added a solution of tin(II) chloride in concentrated HCl (9.5 mL). The reaction mixture was allowed to warm to ambient temperature and stirred overnight. The reaction mixture was made basic at 0° C. with 40% NaOH solution and extracted three times with diethyl ether. The combined organic extracts was washed with brine, dried over anhydrous sodium sulfate, filtered and concentrated in vacuo. The resulting solid was treated with 1.25 M HCl in methanol (30 mL), stirred for 10 min at 0° C. then concentrated in vacuo to give a pale yellow solid. The solid was triturated with diethyl ether and dried in vacuo to give (4-bromo-2-methylphenyl)hydrazine hydrochloride (2.26 g, 71%) as an off-white solid: $^1$H NMR (DMSO-d$_6$, 300 MHz): δ 10.27 (br s, 3H), 7.97 (br s, 1H), 7.35 (m, 2H), 6.89 (d, J=8.2 Hz, 1H), 2.18 (s, 3H).

Step B: A mixture of (4-bromo-2-methylphenyl)hydrazine hydrochloride (2.04 g, 8.60 mmol), concentrated HCl and nortropinone hydrochloride (1.60 g, 9.89 mmol) in ethanol was heated to reflux for 48 h. The reaction mixture was cooled to ambient temperature, concentrated in vacuo and made basic with 10% ammonium hydroxide in methanol. The mixture was concentrated in vacuo, dissolved in methanol (75 mL) and treated with di-tert-butyl dicarbonate (2.81 g, 12.90 mmol) and triethylamine (2.4 mL, 17.20 mmol). The reaction mixture was stirred overnight at ambient temperature, concentrated in vacuo, diluted with water and extracted with ethyl acetate. The organic phase was dried over anhydrous sodium sulfate and concentrated in vacuo. The residue was purified by flash column chromatography (SiO$_2$, 7:3 hexanes/ethyl acetate) to give tert-butyl 2-bromo-4-methyl-5,6,7,8,9,10-hexahydro-7,10-epiminocyclohepta[b]indole-carboxylate (0.43 g, 13%) as light-pink solid. $^1$H NMR (CDCl$_3$, 300 MHz): δ 7.76 (br s, 1H), 7.47 (s, 1H), 7.04 (s, 1H), 5.05-5.38 (m, 1H), 4.48-4.76 (m, 1H), 3.30-3.57 (br s, 1H), 2.48 (d, J=16.2 Hz, 1H), 2.41 (s, 3H), 2.24-2.35 (m, 1H), 2.10-2.21 (m, 1H), 1.89-1.96 (m, 1H), 1.59-1.64 (m, 1H), 1.38 (br s, 9H).

Step C: To a solution of the product of step B (410 mg, 1.05 mmol) in DMF (3.5 ml) at 0° C., under nitrogen was added sodium hydride (60% dispersion in mineral oil, 51 mg, 2.09 mmol). The mixture was stirred for 45 min at 0-5° C. before iodomethane (0.13 mL, 2.09 mmol) was added. The mixture was stirred for a further 90 min then quenched with ice water. The mixture was diluted with ethyl acetate, washed with water, brine and dried over anhydrous sodium sulfate. Concentration in vacuo afforded a viscous oil which was dissolved in a minimal amount of ethyl acetate and precipitated by addition of hexanes. The separated solid was filtered and dried in vacuo to give tert-butyl 2-bromo-4,5-dimethyl-5,6,7,8,9,10-hexahydro-7,10-epiminocyclohepta[b]indole-carboxylate (340 mg, 80%) as an off-white solid. $^1$H NMR (CDCl$_3$, 300 MHz): δ 7.43 (d, J=1.2 Hz, 1H), 6.94 (d, J=1.2 Hz, 1H), 5.05-5.30 (m, 1H), 4.52-4.70 (m, 1H), 3.80 (s, 3H), 3.15-3.47 (m, 1H), 2.69 (s, 3H), 2.43 (dd, J=15.9, 0.9 Hz, 1H), 2.23-2.30 (m, 1H), 2.08-2.22 (m, 1H), 1.85-1.95 (m, 1H), 1.58-1.64 (m, 1H), 1.39 (br s, 9H).

Step D: A mixture of the product of step C (230 mg, 0.57 mmol), sodium benzenesulfinate (112 mg, 0.68 mmol), di-palladium-tris(dibenzylideneacetone) (52 mg, 0.057 mmol), cesium carbonate (277 mg, 0.85 mmol), xantphos (66 mg, 0.11 mmol) and tetrabutyl ammonium chloride (189 mg, 0.68 mmol) was taken up in toluene (3.2 mL). The reaction flask was purged with nitrogen and heated at reflux for 4 h under a nitrogen atmosphere. After cooling to ambient temperature the reaction mixture was filtered through a celite pad and the resulting filtrate concentrated in vacuo. The crude product was purified by flash column chromatography (SiO$_2$, 7.5:2.5 hexanes/ethyl acetate) to give tert-butyl 2-phenylsulfonyl-4,5-dimethyl-5,6,7,8,9,10-hexahydro-7,10-epiminocyclohepta[b]indole-carboxylate (110 mg, 41%) as an off-white solid: $^1$H NMR (CDCl$_3$, 300 MHz): δ 8.02 (br s, 1H), 7.93-7.96 (m, 2H), 7.40-7.52 (m, 3H), 7.34 (br s, 1H), 5.13-5.33 (m, 1H), 4.53-4.80 (m, 1H), 3.83 (s, 3H), 3.14-3.47 (m, 1H), 2.74 (s, 3H), 2.45 (d, J=15.9 Hz, 1H), 2.10-2.38 (m, 2H), 1.86-1.98 (m, 1H), 1.58-1.67 (m, 1H), 1.37 (br s, 9H).

Step E: To a solution of the product of step D (104 mg, 0.22 mmol) in chloroform (1 mL) was added 2 M HCl in diethyl ether solution (5 mL). The reaction was stirred at 0° C. for 1 h then allowed to warm to ambient temperature overnight. The mixture was concentrated in vacuo, made basic with sat. sodium bicarbonate solution and extracted with chloroform. The organic extract was dried over anhydrous sodium sulfate, concentrated in vacuo and the resulting residue purified by flash column chromatography (SiO$_2$, 90:9.9:0.1 dichloromethane/methanol/ammonium hydroxide). The free-base was treated directly with 1.25 M HCl in methanol (2 mL) and the resulting solution concentrated in vacuo to give 2-phenyl-sulfonyl-4,5-dimethyl-5,6,7,8,9,10-hexahydro-7,10-epiminocyclohepta[b]indole hydrochloride (65 mg, 72%, AUC HPLC 98.7%) as a white solid: mp 244-248° C.; $^1$H NMR (CD$_3$OD, 300 MHz): δ 8.08 (d, J=1.5 Hz, 1H), 7.90-7.98 (m, 2H), 7.49-7.63 (m, 3H), 7.38-7.43 (m, 1H), 5.26 (d, J=4.8 Hz, 1H), 4.49-4.58 (m, 1H), 3.94 (s, 3H), 3.44 (dd, J=17.1 Hz, J=4.5 Hz, 1H), 3.02 (d, J=17.4 Hz, 1H), 2.99 (s, 3H), 2.19-2.52 (m, 3H), 1.91-2.20 (m, 1H); APCI MS m/z 367 [M+H]$^+$.

Example 72

Preparation of 2-(3-Fluorophenyl)sulfonyl-4,5-dimethyl-5,6,7,8,9,10-hexahydro-7,10-epiminocyclohepta[b]indole hydrochloride

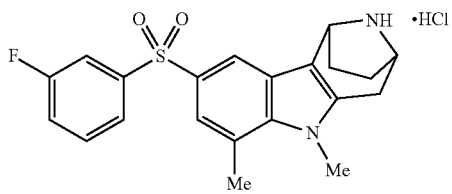 [SMILES: Cl ; Cc1cc(S(=O)(=O)c2cccc(F)c2)cc2c3c(n(C)c12)CC1CCC3N1]

Step A: Intermediate 2 was coupled to the product of Example 71, step C following the procedure of Example 71, step D. The crude product was purified by flash column chromatography (SiO$_2$, 8:2 hexanes/ethyl acetate) to give tert-butyl 2-(3-fluorophenyl)sulfonyl)-4,5-dimethyl-5,6,7,8,9,10-hexahydro-7,10-epiminocyclohepta[b]indole-carboxylate (137 mg, 41%) as a light-yellow solid: $^1$H NMR (CDCl$_3$, 300 MHz) δ 8.02 (s, 1H), 7.74 (dd, J=7.8, 0.9 Hz, 1H), 7.59-7.67 (m, 1H), 7.39-7.49 (m, 1H), 7.34 (s, 1H), 7.14-7.23 (m, 1H), 5.22 (br s, 1H), 4.70 (br s, 1H), 3.84 (s, 3H), 3.34 (br s, 1H), 2.75 (s, 3H), 2.46 (d, J=15.6 Hz, 1H), 2.10-2.39 (m, 2H), 1.85-1.97 (m, 1H), 1.52-1.66 (m, 1H), 1.37 (br s, 9H).

Step B: A solution of the product of step A (137 mg, 0.28 mmol) in dichloromethane (5 mL) was treated with trifluoroacetic acid (5 mL) and stirred at 0-5° C. for 2 h. The reaction mixture was concentrated in vacuo and the residue made basic by addition of saturated sodium bicarbonate solution. The mixture was extracted with dichloromethane and the organic layer dried over sodium sulfate, filtered and concentrated in vacuo. The crude material was purified by flash column chromatography (SiO$_2$, 80:18:2 chloroform/methanol/ammonium hydroxide) and semi-preparative HPLC. The purified free-base was treated directly with 1.25M HCl in methanol solution (0.5 mL) and lyophilized to give 2-(3-fluorophenyl)sulfonyl-4,5-dimethyl-5,6,7,8,9,10-hexahydro-7,10-epiminocyclohepta[b]indole hydrochloride (70 mg, 58%, AUC HPLC 96.4%) as a white solid: mp 254-256° C.; $^1$H NMR (DMSO-d$_6$, 300 MHz) δ 9.32 (br s, 2H), 8.22 (d, J=1.8 Hz, 1H), 7.77 (dd, J=8.4, 1.5 Hz, 2H), 7.45-7.69 (m, 1H), 7.44-7.53 (m, 1H), 7.42 (d, J=0.9 Hz, 1H), 5.23 (d, J=3.9 Hz, 1H), 4.46 (br s, 1H), 3.87 (s, 3H), 3.37 (d, J=5.4 Hz, 1H), 2.97 (d, J=17.1 Hz, 1H), 2.77 (s, 3H), 2.19-2.35 (m, 2H), 2.02-2.13 (m, 1H), 1.68-1.87 (m, 1H); ESI MS m/z 385 [M+H]$^+$.

Example 73

Preparation of 2-(3-Chloro-phenyl)sulfonyl-4,5-dimethyl-5,6,7,8,9,10-hexahydro-7,10-epiminocyclohepta[b]indole hydrochloride

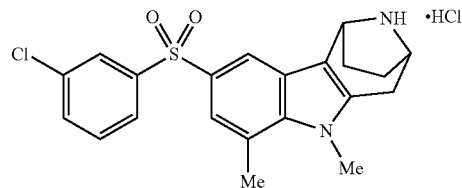 [SMILES: Cl ; Cc1cc(S(=O)(=O)c2cccc(Cl)c2)cc2c3c(n(C)c12)CC1CCC3N1]

Step A: Intermediate 1 was coupled to the product of Example 71, step C following the procedure of Example 71, step D. The crude product was purified by flash column chromatography (SiO$_2$, 8:2 hexanes/ethyl acetate) to give tert-butyl 2-(3-chlorophenyl)sulfonyl-4,5-dimethyl-5,6,7,8,9,10-hexahydro-7,10-epiminocyclohepta[b]indole-carboxylate (136 mg, 39%) as a light-yellow solid: $^1$H NMR (CDCl$_3$, 300 MHz) δ 8.02 (s, 1H), 7.92 (t, J=1.8 Hz, 1H), 7.83 (dt, J=7.5, 1.5 Hz, 1H), 7.43-7.49 (m, 1H), 7.41 (d, J=7.8 Hz, 1H), 7.33 (s, 1H), 5.22 (br s, 1H), 4.71 (br s, 1H), 3.85 (s, 3H), 3.35 (br s, 1H), 2.76 (s, 3H), 2.45 (d, J=15.9 Hz, 1H), 2.12-2.38 (m, 2H), 1.86-1.97 (m, 1H), 1.52-1.66 (m, 1H), 1.37 (br s, 9H).

Step B: The product of step A was Boc-deprotected and converted to the hydrochloride salt following the procedure of Example 72, step B to give 2-(3-chlorophenyl)sulfonyl-4,5-dimethyl-5,6,7,8,9,10-hexahydro-7,10-epiminocyclohepta[b]indole hydrochloride (66 mg, 56%, AUC HPLC 96.5%) as a white solid: mp 227-229° C.; $^1$H NMR (DMSO-d$_6$, 300 MHz) δ 9.63 (br s, 1H), 9.13 (br s, 1H), 8.24 (d, J=1.5 Hz, 1H), 7.95 (t, J=1.8 Hz, 1H), 7.86-7.93 (m, 1H), 7.68-7.74 (m, 1H), 7.61 (t, J=7.8 Hz, 1H), 7.42 (d, J=0.9 Hz, 1H), 5.33 (d, J=3.9 Hz, 1H), 4.46 (br s, 1H), 3.87 (s, 3H), 3.37 (d, J=3.6 Hz, 1H), 2.97 (d, J=17.1 Hz, 1H), 2.77 (s, 3H), 2.18-2.36 (m, 2H), 2.01-2.12 (m, 1H), 1.70-1.86 (m, 1H); ESI MS m/z 401 [M+H]$^+$.

Example 74

Preparation of 2-(3-Methyl-phenyl)sulfonyl-4,5-dimethyl-5,6,7,8,9,10-hexahydro-7,10-epiminocyclohepta[b]indole hydrochloride

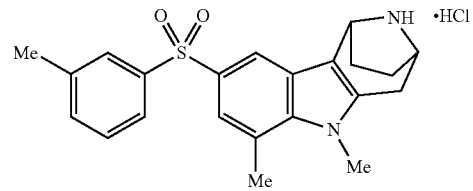 [SMILES: Cl ; Cc1cccc(S(=O)(=O)c2cc(C)c3c(c2)c2c(n3C)CC3CCC2N3)c1]

Step A: Intermediate 10 was coupled to the product of Example 71, step C following the procedure of Example 71, step D. The crude product was purified by flash column chromatography (SiO$_2$, (8:2 hexanes/ethyl acetate) to give tert-butyl 2-(3-methyl-phenyl)sulfonyl-4,5-dimethyl-5,6,7,8,9,10-hexahydro-7,10-epiminocyclohepta[b]indole-carboxylate (85 mg, 29%) as a light-yellow solid: $^1$H NMR (CDCl₃, 300 MHz) δ 7.97-8.05 (m, 1H), 7.71-7.78 (m, 2H), 7.29-7.38 (m, 3H), 5.23 (br s, 1H), 4.72 (br s, 1H), 3.83 (s, 3H), 3.33 (br s, 1H), 2.74 (s, 3H), 2.45 (d, J=16.2 Hz, 1H), 2.38 (s, 3H), 2.11-2.35 (m, 2H), 1.88-1.97 (m, 1H), 1.55-1.64 (m, 1H), 1.37 (br s, 9H).

Step B: The product of step A was Boc-deprotected and converted to the hydrochloride salt following the procedure of Example 72, step B to give 2-(3-methyl-phenyl)sulfonyl-4,5-dimethyl-5,6,7,8,9,10-hexahydro-7,10-epiminocyclohepta[b]indole hydrochloride (60 mg, 82%, AUC HPLC 96.1%) as a white solid: mp 228-230° C.; ¹H NMR (DMSO-d₆, 300 MHz) δ 9.52 (br s, 1H), 9.08 (br s, 1H), 8.16 (d, J=1.8 Hz, 1H), 7.66-7.76 (m, 2H), 7.39-7.50 (m, 2H), 7.35 (d, J=0.9 Hz, 1H), 5.32 (d, J=3.0 Hz, 1H), 4.46 (br s, 1H), 3.87 (s, 3H), 3.44-3.49 (m, 1H), 2.96 (d, J=17.4 Hz, 1H), 2.76 (s, 3H), 2.36 (s, 3H), 2.19-2.30 (m, 2H), 2.01-2.11 (m, 1H), 1.71-1.84 (m, 1H); ESI MS m/z 381 [M+H]⁺.

Example 75

Preparation of 2-(3-Trifluoromethyl-phenyl)sulfonyl-4,5-dimethyl-5,6,7,8,9,10-hexahydro-7,10-epiminocyclohepta[b]indole hydrochloride

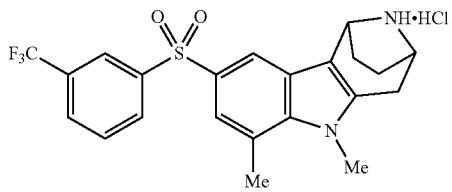

Step A: Intermediate 9 was coupled to the product of Example 71, step C following the procedure of Example 71, step D. The crude product was purified by flash column chromatography (SiO₂, (8:2 hexanes/ethyl acetate) to give tert-butyl 2-(3-trifluoromethyl-phenyl)sulfonyl-4,5-dimethyl-5,6,7,8,9,10-hexahydro-7,10-epiminocyclohepta[b]indole-carboxylate (87 mg, 33%) as a light-yellow solid: ¹H NMR (CDCl₃, 300 MHz) δ 8.22 (s, 1H), 8.13 (d, J=7.8 Hz, 1H), 8.03 (s, 1H), 7.71-7.78 (m, 1H), 7.57-7.65 (m, 1H), 7.35 (s, 1H), 5.23 (br s, 1H), 4.71 (br s, 1H), 3.85 (s, 3H), 3.37 (br s, 1H), 2.76 (s, 3H), 2.46 (d, J=16.2 Hz, 1H), 2.12-2.39 (m, 2H), 1.86-1.96 (m, 1H), 1.53-1.65 (m, 1H), 1.36 (br s, 9H).

Step B: The product of step A was Boc-deprotected and converted to the hydrochloride salt following the procedure of Example 72, step B to give 2-(3-trifluoromethyl-phenyl)sulfonyl-4,5-dimethyl-5,6,7,8,9,10-hexahydro-7,10-epiminocyclohepta[b]indole hydrochloride (63 mg, 82%, AUC HPLC 95.6%) as an off-white solid: mp 227-229° C.; ¹H NMR (DMSO-d₆, 300 MHz) δ 9.50 (br s, 1H), 8.96-9.15 (m, 1H), 8.16-8.32 (m, 3H), 8.04 (d, J=7.8 Hz, 1H), 7.84 (t, J=7.8 Hz, 1H), 7.46 (d, J=0.9 Hz, 1H), 5.34 (br s, 1H), 4.47 (br s, 1H), 3.87 (s, 3H), 3.32-3.40 (m, 1H), 2.97 (d, J=17.1 Hz, 1H), 2.77 (s, 3H), 2.17-2.34 (m, 2H), 2.03-2.10 (m, 1H), 1.69-1.84 (m, 1H); ESI MS m/z 435 [M+H]⁺.

Example 76

Preparation of 2-(3-Trifluoromethoxy-phenyl)sulfonyl-4,5-dimethyl-5,6,7,8,9,10-hexahydro-7,10-epiminocyclohepta[b]indole hydrochloride

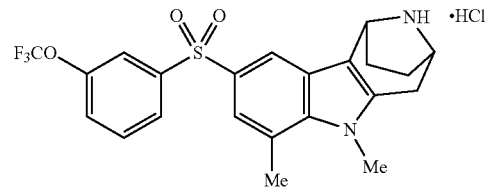 [SMILES: Cl ; Cc1cc(S(=O)(=O)c2cccc(OC(F)(F)F)c2)cc2c3c(n(C)c12)CC1CCC3N1]

Step A: Intermediate 3 was coupled to the product of Example 71, step C following the procedure of Example 71, step D. The crude product was purified by flash column chromatography (SiO₂, 8:2 hexanes/ethyl acetate) to give tert-butyl 2-(3-trifluoromethoxy-phenyl)sulfonyl-4,5-dimethyl-5,6,7,8,9,10-hexahydro-7,10-epiminocyclohepta[b]indole-carboxylate (58 mg, 26%) as a light-yellow solid: ¹H NMR (CDCl₃, 300 MHz) δ 8.02 (br s, 1H), 7.85-7.90 (m, 1H), 7.81 (br s, 1H), 7.50 (t, J=8.1 Hz, 1H), 7.31-7.37 (m, 2H), 5.21 (br s, 1H), 4.72 (br s, 1H), 3.85 (s, 3H), 3.35 (br s, 1H), 2.76 (s, 3H), 2.45 (d, J=15.6 Hz, 1H), 2.24-2.49 (m, 1H), 2.12-2.24 (m, 1H), 1.85-1.96 (m, 1H), 1.57-1.66 (m, 1H), 1.37 (br s, 9H).

Step B: The product of step A was Boc-deprotected and converted to the hydrochloride salt following the procedure of Example 72, step B to give 2-(3-trifluoromethoxy-phenyl)sulfonyl-4,5-dimethyl-5,6,7,8,9,10-hexahydro-7,10-epiminocyclohepta[b]indole hydrochloride (31 mg, 60%, AUC HPLC 98.0%) as a light-pink solid: mp 220-222° C.; ¹H NMR (DMSO-d₆, 300 MHz) δ 9.72 (br s, 1H), 9.05-9.23 (m, 1H), 8.25 (d, J=1.8 Hz, 1H), 7.92-8.02 (m, 1H), 7.90 (s, 1H), 7.74 (t, J=7.8 Hz, 1H), 7.63-7.69 (m, 1H), 7.43 (d, J=0.9 Hz, 1H), 5.32 (br s, 1H), 4.46 (br s, 1H), 3.87 (s, 3H), 3.28-3.34 (m, 1H), 2.96 (d, J=17.1 Hz, 1H), 2.77 (s, 3H), 2.18-2.34 (m, 2H), 1.97-2.11 (m, 1H), 1.68-1.84 (m, 1H); ESI MS m/z 451 [M+H]⁺.

Example 77

Preparation of 2-(4-Amino-phenyl)sulfonyl-4,5-dimethyl-5,6,7,8,9,10-hexahydro-7,10-epiminocyclohepta[b]indole hydrochloride

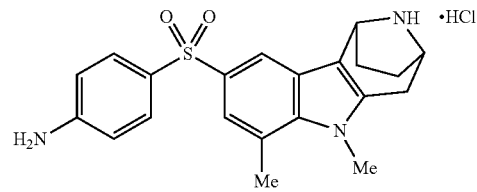 [SMILES: Cl ; Cc1cc(S(=O)(=O)c2ccc(N)cc2)cc2c3c(n(C)c12)CC1CCC3N1]

Step A: Intermediate 12 was coupled to the product of Example 71, step C following the procedure of Example 71, step D. The crude product was purified by flash column chromatography (SiO₂, 8:2 hexanes/ethyl acetate) to give tert-butyl 2-(4-nitro-phenyl)sulfonyl-4,5-dimethyl-5,6,7,8,9,10-hexahydro-7,10-epiminocyclohepta[b]indole-carboxylate (44 mg, 6%) as a yellow solid: ¹H NMR (CDCl₃, 300 MHz)

δ 8.86-8.33 (m, 2H), 8.08-8.16 (m, 2H), 8.03 (s, 1H), 7.34 (s, 1H), 5.23 (br s, 1H), 4.71 (br s, 1H), 3.85 (s, 3H), 3.36 (br s, 1H), 2.76 (s, 3H), 2.46 (d, J=16.2 Hz, 1H), 2.11-2.39 (m, 2H), 1.85-1.97 (m, 1H), 1.53-1.67 (m, 1H), 1.36 (br s, 9H).

Step B: To a solution of the product of step A (43 mg, 0.08 mmol) in ethanol (5 mL) was added 5% palladium on carbon (60 mg). The reaction flask was purged with hydrogen and the reaction mixture was stirred at ambient temperature for 4 h before it was filtered through a celite bed. The filtrate was concentrated in vacuo to give tert-butyl 2-(4-amino-phenyl)sulfonyl-4,5-dimethyl-5,6,7,8,9,10-hexahydro-7,10-epiminocyclohepta[b]indole-carboxylate (29 mg, 72%) as a yellow solid: $^1$H NMR (CDCl$_3$, 300 MHz) δ 8.00 (s, 1H), 7.71 (dd, J=6.9, 1.8 Hz, 2H), 7.29 (s, 1H), 6.62 (dd, J=6.9, 1.8 Hz, 2H), 5.22 (br s, 1H), 4.69 (br s, 1H), 4.04 (s, 2H), 3.82 (s, 3H), 3.34 (br s, 1H), 2.72 (s, 3H), 2.44 (d, J=15.9 Hz, 1H), 2.08-2.37 (m, 2H), 1.86-1.97 (m, 1H), 1.52-1.65 (m, 1H), 1.37 (br s, 9H).

Step C: The product of step A was Boc-deprotected and converted to the hydrochloride salt following the procedure of Example 72, step B to give 2-(4-amino-phenyl)sulfonyl-4,5-dimethyl-5,6,7,8,9,10-hexahydro-7,10-epiminocyclohepta[b]indole hydrochloride (21 mg, 78%, AUC HPLC 97.0%) as an off-white solid: mp 244-246° C.; $^1$H NMR (CD$_3$OD, 300 MHz) δ 8.02 (s, 1H), 7.78 (d, J=8.4 Hz, 2H), 7.36 (s, 1H), 6.97 (d, J=8.4 Hz, 2H), 5.25 (d, J=4.8 Hz, 1H), 4.46-4.58 (m, 1H), 3.93 (s, 3H), 3.39-3.50 (m, 1H), 2.94-3.08 (m, 1H), 2.79 (s, 3H), 2.31-2.50 (m, 2H), 2.14-2.28 (m, 1H), 1.87-2.03 (m, 1H); ESI MS m/z 382 [M+H]$^+$.

Example 78

Preparation of 2-(5-Pyrimidine)sulfonyl-4,5-dimethyl-5,6,7,8,9,10-hexahydro-7,10-epiminocyclohepta[b]indole

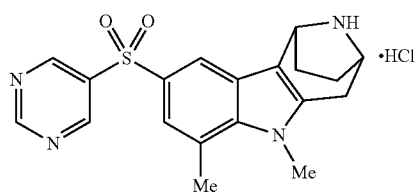 [SMILES: Cc1cc(S(=O)(=O)c2cncnc2)cc2c3c(n(C)c12)CC1CCC3N1 ; Cl]

Step A: To a mixture of Example 71, step C (300 mg, 0.81 mmol), 5-bromo-pyrimidine (129 mg, 0.81 mmol), Pd$_2$(dba)$_3$ (74 mg, 0.08 mmol), xanthphos (94 mg, 0.16 mmol), cesium carbonate (396 mg, 1.21 mmol) and tetrabutyl-ammonium chloride (270 mg, 0.97 mmol) under an argon atmosphere was added anhydrous toluene (3 mL). The mixture was heated to reflux for 1 h, cooled to ambient temperature, diluted with ethyl acetate and filtered through a celite bed. The filtrate was concentrated in vacuo and the residue purified by flash column chromatography (SiO$_2$, 60:40 hexane/ethyl acetate) to give tert-butyl 2-(5-pyrimidine)sulfonyl-4,5-dimethyl-5,6,7,8,9,10-hexahydro-7,10-epiminocyclohepta[b]indole-carboxylate (22 mg, 6%) as a yellow solid: $^1$H NMR (CDCl$_3$, 300 MHz) δ 9.30 (s, 1H), 9.19 (s, 2H), 8.04 (d, J=1.2 Hz, 1H), 7.35 (s, 1H), 5.23 (br s, 1H), 4.70 (br s, 1H), 3.86 (s, 3H), 3.34 (br s, 1H), 2.77 (s, 3H), 2.47 (d, J=16.2 Hz, 1H), 2.11-2.40 (m, 2H), 1.85-1.98 (m, 1H), 1.54-1.63 (m, 1H), 1.38 (s, 9H).

Step B: The product of step A was subjected to Boc-deprotection with TFA following the procedure of Example 28, step B. The crude material was purified by flash column chromatography (SiO$_2$, 88:12 dichloromethane/methanol) to give 245-pyrimidine)sulfonyl-4,5-dimethyl-5,6,7,8,9,10-hexahydro-7,10-epiminocyclohepta[b]indole (10 mg, 58%) as a yellow solid: $^1$H NMR (CDCl$_3$, 300 MHz) δ 9.29 (s, 1H), 9.19 (s, 2H), 8.01 (d, J=1.5 Hz, 1H), 7.36 (d, J=0.6 Hz, 1H), 4.69 (d, J=4.8 Hz 1H), 4.15-4.24 (m, 1H), 3.85 (s, 3H), 3.26 (dd, J=16.2, 4.5 Hz, 1H), 2.76 (s, 3H), 2.54 (d, J=16.5 Hz, 1H), 2.15-2.34 (m, 2H), 1.96-2.07 (m, 1H), 1.55-1.67 (m, 1H).

Step C: The product of step B in MeOH (1 mL) and dichloromethane (1 mL) was treated with 1.25 M HCl in methanol (0.1 mL). The solution was concentrated in vacuo and the residue lyophilized from water/acetonitrile to give 2-(5-pyrimidine)sulfonyl-4,5-dimethyl-5,6,7,8,9,10-hexahydro-7,10-epiminocyclohepta[b]indole hydrochloride (10 mg, 96%; AUC HPLC 99%) as an off-white solid: mp 226-228° C.: $^1$H NMR (DMSO-d$_6$, 300 MHz) δ 9.38-9.50 (m, 2H), 9.34 (s, 2H), 9.00-9.12 (m, 1H), 8.30 (d, J=1.8 Hz 1H), 7.52 (d, J=0.9 Hz 1H), 5.31 (s, 1H), 4.48 (s, 1H), 3.88 (s, 3H), 3.33 (dd, J=17.4, 4.5 Hz, 1H), 2.97 (d, J=17.4 Hz, 1H), 2.78 (s, 3H), 2.18-2.34 (m, 2H), 2.02-2.13 (m, 1H), 1.70-1.85 (m, 1H); ESI, m/z 369 [M+H]$^+$.

Example 79

Preparation of 2-[1-Indolesulfonyl]-4,5-dimethyl-5,6,7,8,9,10-hexahydro-7,10-epiminocyclohepta[b]indole

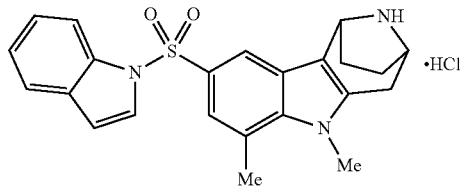 [SMILES: Cc1cc(S(=O)(=O)n2ccc3ccccc32)cc2c3c(n(C)c12)CC1CCC3N1 ; Cl]

Step A: To a solution of Example 71, step C (3.67 g, 9.05 mmol) in anhydrous THF (28 mL) at –78° C. under an argon atmosphere was added n-butyl lithium (1.6M in hexane, 6.8 mL, 10.86 mmol) dropwise. The resulting solution was stirred for 15 min while the temperature was maintained at –78° C. Sulfur dioxide gas was bubbled into the reaction mixture for 15 min. The reaction mixture was then stirred for another 30 min. at –78° C. while maintaining a sulfur dioxide atmosphere. The reaction mixture was allowed to warm to ambient temperature and stirred for a further 30 min. The reaction mixture was concentrated to dryness in vacuo and triturated with diethyl ether (75 mL) to give crude tert-butyl 4,5-dimethyl-5,6,7,8,9,10-hexahydro-7,10-epiminocyclohepta[b]indole-carboxylate-2-sulfinic acid lithium salt (3.08 g, 86%) as a yellow solid: $^1$H NMR (CD$_3$OD, 300 MHz) δ 7.59 (s, 1H), 7.14 (s, 1H), 5.15-5.25 (m, 1H), 4.55-4.67 (m, 1H), 3.84 (s, 3H), 3.28-3.35 (m, 1H), 2.76 (s, 3H), 2.56 (d, J=15.9 Hz, 1H), 2.10-2.36 (m, 2H), 1.82-1.96 (m, 1H), 1.61-1.72 (m, 1H), 1.34 (s, 9H).

Step B: To a solution of the product of step A (580 mg, 1.56 mmol) in dichloromethane (9.7 mL) at 0° C. under an argon atmosphere was added N-chlorosuccinimide (220 mg, 1.64 mmol). The reaction mixture was stirred at 0° C. for 2 h then at ambient temperature for 30 min. Water (10 ml) was added and the mixture extracted with dichloromethane. The extract was dried over sodium sulfate, filtered and concentrated in vacuo. The residue was purified by flash column chromatography (SiO$_2$, 60:40 hexane/ethyl acetate) to give tert-butyl 2-chlorosulfonyl-4,5-dimethyl-5,6,7,8,9,10-hexahydro-7,10-epiminocyclohepta[b]indole-carboxylate (310 mg, 47%) as a yellow solid: $^1$H NMR (CDCl$_3$, 300 MHz) δ 8.06 (d, J=1.5 Hz, 1H), 7.48 (s, 1H), 5.20 (br s, 1H), 4.72 (br s, 1H), 3.90 (s, 3H), 3.73 (br s, 1H), 2.81 (s, 3H), 2.48 (d, J=16.2 Hz, 1H), 2.14-2.41 (m, 2H), 1.89-1.99 (m, 1H), 1.57-1.68 (m, 1H), 1.39 (s, 9H).

Step C: To a solution of indole (19 mg, 0.16 mmol) in anhydrous THF (2 ml) under an argon atmosphere was added sodium hydride (60% dispersion in mineral oil) (8 mg, 0.19 mmol) portionwise. After stirring for 1 h, the product of step B (65 mg, 0.16 mmol) was added. The reaction mixture was stirred for an additional 3 h and then quenched with 5% aqueous sodium bicarbonate solution (10 ml) and extracted with dichloromethane. The organic extract was dried over sodium sulfate, filtered and concentrated in vacuo. The residue was purified by flash column chromatography (SiO$_2$, 60:40 hexane/ethyl acetate) to give tert-butyl 2-(1-indole)sulfonyl-4,5-dimethyl-5,6,7,8,9,10-hexahydro-7,10-epiminocyclohepta[b]indole-carboxylate (70 mg, 88%) as a yellow solid: $^1$H NMR (CDCl$_3$, 300 MHz) δ 8.03 (dd, J=16.2, 0.6 Hz, 1H), 7.98 (d, J=1.2 Hz, 1H), 7.60 (d, J=3.6 Hz, 1H), 7.48 (d, J=7.8 Hz, 1H), 7.22-7.32 (m, 2H), 7.15 (t, J=7.8 Hz, 1H), 6.60 (dd, J=3.6, 0.6 Hz, 1H), 5.15 (br s, 1H), 4.67 (br s, 1H), 3.76 (s, 3H), 3.30 (br s, 1H), 2.65 (s, 3H), 2.10-2.45 (m, 3H), 1.79-1.91 (m, 1H), 1.48-1.58 (m, 1H), 1.34 (s, 9H).

Step D: The product of step C was subjected to Boc-deprotection with TFA following the procedure of Example 72, step B. The crude material was purified by flash column chromatography (SiO$_2$, 90:10 dichloromethane/methanol) to give 2(1-indole)sulfonyl-4,5-dimethyl-5,6,7,8,9,10-hexahydro-7,10-epiminocyclohepta[b]indole (35 mg, 62%) as an off-white solid: $^1$H NMR (CDCl$_3$, 300 MHz) δ 8.02 (d, J=8.1 Hz, 1H), 7.94 (d, J=1.8 Hz, 1H), 7.62 (d, J=3.6 Hz, 1H), 7.48 (d, J=7.5 Hz, 1H), 7.25-7.32 (m, 2H), 7.16 (t, J=6.9 Hz, 1H), 6.60 (d, J=3.6 Hz, 1H), 4.55 (d, J=4.8 Hz, 1H), 4.05-4.14 (m, 1H), 3.65 (s, 3H), 3.06 (dd, J=16.5, 4.5 Hz, 1H), 2.62 (s, 3H), 2.42 (dd, J=16.2, 0.6 Hz, 1H), 2.03-2.19 (m, 2H), 1.86-1.97 (m, 1H), 1.46-1.58 (m, 1H).

Step E: To a solution of product from step D (19 mg, 0.07 mmol) in dichloromethane (2 mL) was added 1.25 M HCl in methanol (0.28 mL). The solution was concentrated in vacuo and the residue lyophilized to give 2-(1-indole)sulfonyl-4,5-dimethyl-5,6,7,8,9,10-hexahydro-7,10-epiminocyclohepta[b]indole hydrochloride (34 mg, 89%; AUC HPLC 97.9%) as a white solid: mp 225-228° C.; $^1$H NMR (DMSO-d$_6$, 300 MHz) δ 9.36 (br s, 1H), 8.99 (br s, 1H), 8.30 (d, J=1.8 Hz, 1H), 7.99 (d, J=8.1 Hz, 1H), 7.76-7.83 (m, 1H), 7.56 (d, J=7.8 Hz, 1H), 7.35 (s, 1H), 7.29 (t, J=7.5 Hz, 1H), 7.19 (d, J=7.5 Hz, 1H), 6.78 (d, J=3.3 Hz, 1H), 5.32 (s, 1H), 4.46 (s, 1H), 3.81 (s, 3H), 3.20-3.30 (m, 1H), 2.96 (d, J=17.1 Hz, 1H), 2.70 (s, 3H), 2.17-2.33 (m, 2H), 1.95-2.05 (m, 1H), 1.68-1.81 (m, 1H); ESI, m/z 406 [M+H]$^+$.

Example 80

Preparation of 2-Phenylsulfonyl-4-ethyl-5-methyl-5, 6,7,8,9,10-hexahydro-7,10-epiminocyclohepta[b] indole hydrochloride

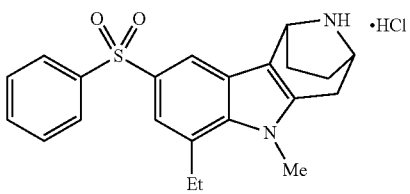 [SMILES: CCc1cc(S(=O)(=O)c2ccccc2)cc2c3c(n(C)c12)CC1CCC3N1 ; Cl]

Step A: 4-Bromo-2-ethyl-phenylhydrazine hydrochloride was prepared from 4-bromo-2-ethylaniline following the procedure of Example 71, step A to give the product (4.27 g, 80%) as a light yellow solid. $^1$H NMR (CDCl$_3$, 300 MHz) δ 7.27 (dd, J=6.6, 2.1 Hz, 1H), 7.17 (m, 1H), 6.90 (d, J=8.7 Hz, 1H), 2.42 (q, J=7.5 Hz, 2H), 1.21 (t, J=7.5 Hz, 3H).

Step B: Prepared from 4-bromo-2-ethyl-phenylhydrazine hydrochloride and nortropinone hydrochloride then protected with a Boc group following the procedure of example 47, step B. The crude material was purified by flash chromatography (SiO$_2$, 4:1 hexanes/ethyl acetate) to give tert-butyl 2-bromo-4-ethyl-5,6,7,8,9,10-hexahydro-7,10-epiminocyclohepta[b]indole-carboxylate (300 mg, 12%) as a light brown solid: $^1$H NMR (CDCl$_3$, 300 MHz) δ 7.87 (br s, 1H), 7.47-7.48 (m, 1H), 7.06 (s, 1H), 5.12 (br s, 1H), 4.64 (br s, 1H), 3.44 (s, 1H), 2.74-2.81 (m, 2H), 2.47 (d, J=15.9 Hz, 1H), 2.12-2.30 (m, 2H), 1.90-1.97 (m, 1H), 1.58-1.60 (m, 1H), 1.33 (br s, 9H), 1.31-1.33 (m, 3H).

Step C: The product of step B was methylated following the procedure of Example 71, step C to give tert-butyl 2-bromo-4-ethyl-5-methyl-5,6,7,8,9,10-hexahydro-7,10-epiminocyclohepta[b]indole-carboxylate (330 mg, 97%) as a light yellow solid: $^1$H NMR (CDCl$_3$, 300 MHz) δ 7.44 (d, J=1.8 Hz, 1H), 6.99 (d, J=1.8 Hz, 1H), 5.12 (s, 1H), 4.69 (s, 1H), 3.76 (s, 3H), 3.34 (s, 1H), 3.03 (q, J=7.5 Hz, 2H), 2.44 (d, J=15.9, 1H), 2.10-2.35 (m, 2H), 1.80-1.97 (m, 1H), 1.55-1.70 (m, 1H), 1.39 (br s, 9H), 1.31-1.38 (m, 3H).

Step D: The product of step C was converted to the sulfone derivative following the procedure of Example 71, step D. The crude was purified by flash column chromatography (SiO$_2$, 3:1 hexane/ethyl acetate) to give tert-butyl 2-phenylsulfonyl-4-ethyl-5-methyl-5,6,7,8,9,10-hexahydro-7,10-epiminocyclohepta[b]indole-carboxylate (46 mg, 12%) as an off-white solid: mp 201-203° C.; $^1$H NMR (CDCl$_3$, 300 MHz), δ 8.02 (s, 1H), 7.94 (dd, J=6.3, 1.5 Hz, 2H), 7.43-7.52 (m, 4H), 5.23 (br s, 1H), 4.72 (br s, 1H), 3.80 (s, 3H), 3.05-3.12 (m, 2H), 2.45 (d, J=15.9 Hz, 1H), 2.32-2.48 (m, 2H), 1.92-1.95 (m, 1H), 1.85-1.98 (m, 1H), 1.52-1.68 (m, 1H), 1.37 (br s, 9H), 1.30-1.35 (m, 3H).

Step E: The product of step D was subjected to Boc-deprotection with TFA following the procedure of Example 28, step B. The crude free base was purified by flash column chromatography (SiO$_2$, 92:8 dichloromethane/methanol) and the product treated directly with 1.25 M HCl in methanol. The solution was concentrated in vacuo to give 2-phenylsulfonyl-4-ethyl-5-methyl-5,6,7,8,9,10-hexahydro-7,10-epiminocyclohepta[b]indole hydrochloride as a pink solid (22 mg, 60%, HPLC, AUC >99%): $^1$H NMR (CD$_3$OD, 300 MHz) δ 8.09 (m, 1H), 7.93-7.96 (m, 2H), 7.48-7.61 (m, 4H), 5.26-5.27 (m, 1H), 4.53-4.55 (m, 1H), 3.91 (s, 3H), 3.41-3.48 (m, 1H), 3.11-3.24 (m, 2H), 3.04 (d, J=17.4 Hz, 1H), 2.35-2.49 (m, 2H), 2.22-2.35 (m, 1H), 1.94-2.01 (m, 1H), 1.28-1.34 (m, 3H).

Example 81

Preparation of 2-(Phenylsulfonyl)-4-fluoro-5-methyl-5,6,7,8,9,10-hexahydro-7,10-epiminocyclohepta[b]indole hydrochloride

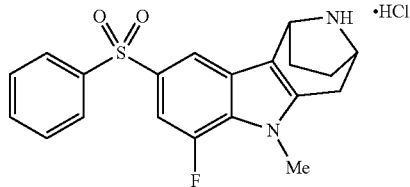

Step A: Prepared from 4-bromo-2-fluoro-aniline following the procedure of Example 71, step A to give 4-Bromo-2-fluoro-phenylhydrazine hydrochloride as a white solid (4.0 g, 79%): $^1$H NMR (DMSO-$d_6$, 300 MHz) δ 10.40 (br s, 3H), 8.45 (br s, 1H), 7.53 (dd, J=11.1, 2.1 Hz, 1H), 7.38 (dd, J=8.7, 0.9 Hz, 1H), 7.16 (t, J=8.9 Hz, 1H).

Step B: Prepared from 4-bromo-2-fluoro-phenylhydrazine hydrochloride and nortropinone hydrochloride followed by Boc protection following the procedure of Example 71, step B. The crude material was purified by flash column chromatography (SiO$_2$, 70:30 hexane/ethyl acetate) to give tert-butyl 2-bromo-4-fluoro-5,6,7,8,9,10-hexahydro-7,10-epiminocyclohepta[b]indole-carboxylate (225 mg, 7%) as a brown solid: $^1$H NMR (CDCl$_3$, 300 MHz) δ 8.02 (br s, 1H), 7.40 (d, J=1.2 Hz, 1H), 6.99 (dd, J=11.2, 1.2 Hz, 1H), 5.06-5.28 (m, 1H), 4.01-4.21 (m, 1H), 3.30-3.60 (m, 1H), 2.50 (d, J=15.9 Hz, 1H), 2.24-2.38 (m, 1H), 2.10-2.23 (m, 1H), 1.86-1.98 (m, 1H), 1.59-1.70 (m, 1H), 1.38 (br s, 9H).

Step C: The product of step B was methylated following the procedure of Example 71, step C. The crude product was purified by flash chromatography (SiO$_2$, 100:0 to 60:40 hexane/ethyl acetate) to give tert-butyl 2-bromo-4-fluoro-5-methyl-5,6,7,8,9,10-hexahydro-7,10-epiminocyclohepta[b]indole-carboxylate (214 mg, 79%) as a brown solid: $^1$H NMR (CDCl$_3$, 300 MHz): δ 7.36 (d, J=1.5 Hz, 1H), 6.93 (dd, J=12.0, 1.5 Hz, 1H), 5.01-5.27 (m, 1H), 4.28-4.54 (m, 1H), 3.75 (s, 3H), 3.14-3.47 (m, 1H), 2.46 (d, J=16.0 Hz, 1H), 2.23-2.38 (m, 1H), 2.08-2.22 (m, 1H), 1.84-1.96 (m, 1H), 1.56-1.68 (m, 1H), 1.39 (br s, 9H).

Step D: The product of step C was converted to the phenylsulfone derivative following the procedure of Example 71, step D. The crude product was purified by flash column chromatography (SiO$_2$, 75:25 hexane/ethyl acetate) to give tert-butyl 2-phenylsulfonyl-4-fluoro-5-methyl-5,6,7,8,9,10-hexahydro-7,10-epiminocyclohepta[b]indole-carboxylate (61 mg, 26%) as an off-white solid: $^1$H NMR (CDCl$_3$, 300 MHz): δ 7.91-7.99 (m, 3H), 7.43-7.55 (m, 3H), 7.28-7.36 (m, 1H), 5.13-5.31 (m, 1H), 4.58-4.70 (m, 1H), 3.78 (s, 3H), 3.14-3.50 (m, 1H), 2.41 (d, J=19.2 Hz, 1H), 2.12-2.40 (m, 2H), 1.86-1.97 (m, 1H), 1.58-1.68 (m, 1H), 1.38 (br s, 9H).

Step E: The product of step D was subjected to Boc-deprotection with 2 N HCl in diethyl ether following the procedure of Example 28, step B. The crude material was purified by flash column chromatography (90:9:1 dichloromethane/methanol/ammonium hydroxide) to give 2-phenylsulfonyl-4-fluoro-5-methyl-5,6,7,8,9,10-hexahydro-7,10-epiminocyclohepta[b]indole hydrochloride (40 mg, 84%, HPLC, AUC 97.8%.) as a white solid: mp 251-256° C. dec; $^1$H NMR (DMSO-$d_6$, 300 MHz): δ 8.24 (d, J=1.5 Hz, 1H), 7.94-8.00 (m, 2H), 7.56-7.70 (m, 3H), 7.48 (dd, J=12.0, 1.5 Hz, 1H), 5.36 (d, J=3.9 Hz, 1H), 4.44-4.52 (m, 1H), 3.82 (s, 3H), 3.34-3.39 (m, 1H), 3.00 (d, J=17.1 Hz, 1H), 2.18-2.30 (m, 2H), 2.03-2.12 (m, 1H), 1.70-1.87 (m, 1H); APCI MS m/z 371 [M+H]$^+$ Example 82

Preparation of 2-Phenylsulfonyl-4-chloro-5-methyl-5,6,7,8,9,10-hexahydro-7,10-epiminocyclohepta[b]indole hydrochloride

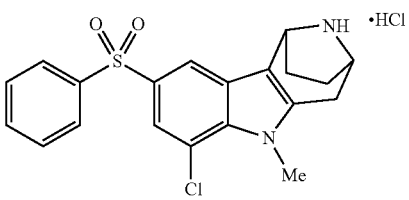 [SMILES: Cl ; Cn1c2c(c3cc(S(=O)(=O)c4ccccc4)cc(Cl)c31)C1CCC(C2)N1]

Step A: Prepared from 4-bromo-2-chloro-aniline following the procedure of Example 71, step A to give 4-bromo-2-chloro-phenylhydrazine hydrochloride (3.30 g, 88%) as a pink solid: $^1$H NMR (CD$_3$OD, 300 MHz): δ 7.62 (d, J=2.1 Hz, 1H), 7.50 (dd, J=8.7, 2.1 Hz, 1H), 6.96 (d, J=8.7 Hz, 1H).

Step B: A mixture of 4-bromo-2-chloro-phenylhydrazine hydrochloride (3.30 g, 12.81 mmol) and nortropinone hydrochloride (2.38 g, 14.73 mmol) in ethanol (30 mL) was heated at reflux for 3 h. Concentrated HCl (3.3 mL) was added and the reaction mixture heated at reflux for 2 days. After cooling to ambient temperature, the reaction mixture was concentrated in vacuo, diluted with methanol and made basic by addition of potassium carbonate (3.45 g, 25.62 mmol). Di-tert-butyl-dicarbonate (4.20 g, 19.21 mmol) was added and the mixture stirred for 14 h at ambient temperature. The reaction mixture was concentrated in vacuo, diluted with water and extracted with ethyl acetate. The organic extract was washed with brine, dried over anhydrous sodium sulfate and concentrated in vacuo. The crude material was purified by flash column chromatography (SiO$_2$, 8:2 hexanes/ethyl acetate) to give tert-butyl 3-(2-(4-bromo-2-chlorophenyl)hydrazono)-8-azabicyclo[3.2.1]octane-8-carboxylate (2.80 g, 51%) as a light yellow solid: $^1$H NMR (CDCl$_3$, 300 MHz): δ 7.50 (br s, 1H), 7.34-7.40 (m, 2H), 7.26-7.31 (dd, J=8.7, 2.1 Hz, 1H), 4.40 (br s, 2H), 2.30-2.85 (m, 4H), 1.94-2.12 (m, 2H), 1.67-1.80 (m, 1H), 1.52-1.60 (m, 1H), 1.48 (s, 9H).

Step C: A mixture of the product of step B (1.90 g, 4.44 mmol) and 10% sulfuric acid in acetic acid (20 mL) was heated at 110° C. for 16 h. The reaction mixture was cooled to ambient temperature and concentrated in vacuo. The residue was made basic with saturated sodium bicarbonate solution and extracted with ethyl acetate. The organic extract was washed with brine, dried over anhydrous sodium sulfate and concentrated in vacuo. The crude material was purified by flash column chromatography (SiO$_2$, 90:9:1 dichloromethane/methanol/ammonium hydroxide) to give 2-bromo-4-chloro-5,6,7,8,9,10-hexahydro-7,10-epiminocyclohepta[b]indole (0.49 g, 36%) as a light brown solid: $^1$H NMR (CDCl$_3$, 300 MHz): δ 8.11 (br s, 1H), 7.51 (d, J=1.5 Hz, 1H), 7.22 (d, J=1.8 Hz, 1H), 4.47 (d, J=5.1 Hz, 1H), 4.01-4.07 (m, 1H), 3.21 (dd, J=16.2, 4.5 Hz, 1H), 2.54 (dd, J=16.2, 1.0 Hz, 1H), 2.04-2.26 (m, 2H), 1.92-2.03 (m, 1H), 1.52-1.68 (m, 1H).

Step D: To a solution of the product of step C (490 mg, 1.57 mmol) in 2-propanol (5 mL) and water (5 mL) at 0° C. was added di-tert-butyl-dicarbonate (379 mg, 1.73 mmol) and potassium carbonate (239 mg, 1.73 mmol). The reaction mixture was stirred for 3 h at 0-5° C. then concentrated in vacuo. The residue was diluted with water and extracted with ethyl acetate. The organic extract was washed with brine, dried over anhydrous sodium sulfate and concentrated in vacuo. The residue was triturated with hexane and dried in vacuo to give tert-butyl 2-bromo-4-chloro-5,6,7,8,9,10-hexahydro-7,10-epiminocyclohepta[b]indole-carboxylate (531 mg, 82%) as a brown solid: $^1$H NMR (CDCl$_3$, 300 MHz): δ 8.05 (br s, 1H), 7.53 (d, J=0.9 Hz, 1H), 7.24 (d, J=1.5 Hz, 1H), 5.04-5.28 (m, 1H), 4.52-4.72 (m, 1H), 3.30-3.62 (m, 1H), 2.51 (d, J=16.2 Hz, 1H), 2.24-2.39 (m, 1H), 2.10-2.24 (m, 1H), 1.86-1.98 (m, 1H), 1.58-1.69 (m, 1H), 1.38 (br s, 9H).

Step E: The product of step D was methylated following the procedure of Example 71, step C. The crude product was purified by flash column chromatography (SiO$_2$, 9:1 hexane/ethyl acetate) to give tert-butyl 2-bromo-4-chloro-5-methyl-5,6,7,8,9,10-hexahydro-7,10-epiminocyclohepta[b]indole-carboxylate (490 mg, 91%) as a light yellow solid: $^1$H NMR (CDCl$_3$, 300 MHz): δ 7.47 (d, J=1.2 Hz, 1H), 7.17 (d, J=1.2 Hz, 1H), 5.00-5.28 (m, 1H), 4.55-4.57 (m, 1H), 3.90 (s, 3H), 3.17-3.48 (m, 1H), 2.46 (d, J=16.2 Hz, 1H), 2.12-2.38 (m, 1H), 2.08-2.11 (m, 1H), 1.83-1.95 (m, 1H), 1.55-1.67 (m, 1H), 1.39 (br s, 9H)

Step F: The product of step E was converted to the phenylsulfone derivative following the procedure of Example 71, step D. The crude product was purified by flash column chromatography (SiO$_2$, 75:25 hexanes/ethyl acetate) to give tert-butyl 2-phenylsulfonyl-4-chloro-5-methyl-5,6,7,8,9,10-hexahydro-7,10-epiminocyclohepta[b]indole-carboxylate (165 mg, 63%) as an off-white solid: $^1$H NMR (CDCl$_3$, 300 MHz): δ 8.02-8.07 (m, 1H), 7.91-7.97 (m, 2H), 7.42-7.62 (m, 4H), 5.10-5.32 (m, 1H), 4.55-4.80 (m, 1H), 3.94 (s, 3H), 3.15-3.48 (m, 1H), 2.47 (d, J=16.2 Hz, 1H), 2.10-2.40 (m, 2H), 1.85-1.96 (m, 1H), 1.52-1.65 (m, 1H), 1.38 (br s, 9H).

Step G: The product of step F was subjected to Boc-deprotection with TFA following the procedure of Example 28, step B. The crude free base was purified by flash column chromatography (SiO$_2$, 90:9:1 dichloromethane/methanol/ammonium hydroxide) and the product treated directly with 1.25 M HCl in methanol. The solution was concentrated in vacuo to give 2-phenylsulfonyl-4-chloro-5-methyl-5,6,7,8,9,10-hexahydro-7,10-epiminocyclohepta[b]indole hydrochloride (123 mg, 97%, HPLC, AUC >99%.) as a white solid: mp 258-264° C. dec; $^1$H NMR (DMSO-d$_6$, 300 MHz): δ 9.70 (br s, 1H), 9.20 (br s, 1H), 8.38 (d, J=1.2 Hz, 1H), 7.94-8.02 (m, 2H), 7.58-7.69 (m, 4H), 5.37 (d, J=3.3 Hz, 1H), 4.42-4.57 (m, 1H), 3.82 (s, 3H), 3.30-3.40 (m, 1H), 3.00 (d, J=12.6 Hz, 1H), 2.20-2.33 (m, 2H), 2.03-2.12 (m, 1H), 1.73-1.86 (m, 1H); ESI MS m/z 387 [M+H]$^+$ Example 83

Preparation of 2-Phenylsulfonyl-4-methoxy-5-methyl-5,6,7,8,9,10-hexahydro-7,10-epiminocyclohepta[b]indole hydrochloride

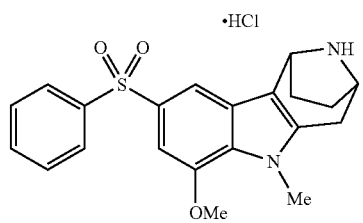

Step A: To a solution of concentrated sulfuric acid (32.6 mL) in water (105 mL) was added potassium nitrate (51.5 g, 509 mmol) at 10° C. The reaction mixture was stirred for 5 min before adding 3-bromophenol (49.35 g, 285 mmol) dropwise so that the temperature of the reaction was maintained around 10° C. The reaction mixture was stirred at ambient temperature for an additional 2 h, diluted with water (350 mL) and extracted with diethyl ether. The organic layer was washed with brine, dried over sodium sulfate and concentrated in vacuo. The crude material was purified by flash column chromatography (SiO$_2$, 19:1 hexanes/ethyl acetate) to give 5-bromo-2-nitrophenol (11.3 g, 18%) as a yellow-green solid: $^1$H NMR (DMSO-d$_6$, 300 MHz) δ 11.44 (s, 1H), 7.84 (d, J=8.7 Hz, 1H), 7.33 (d, J=2.1 Hz, 1H), 7.18 (dd, J=8.7, 2.1 Hz, 1H).

Step B: A mixture of 5-bromo-2-nitrophenol (10.4 g, 47.7 mmol), benzyl bromide (9.8 g, 57.2 mmol) and potassium carbonate (9.9 g, 71.5 mmol) was taken up in acetone (50 mL) and heated to reflux for 5 h. After cooling to ambient temperature, the reaction mixture was concentrated in vacuo, diluted with water and extracted with ethyl acetate. The organic layer was washed with brine, dried over sodium sulfate and concentrated in vacuo. The crude material was purified by flash column chromatography (9:1 hexanes/ethyl acetate) to give 2-(benzyloxy)-4-bromo-1-nitrobenzene (14.19 g, 97%) as a light-yellow solid: $^1$H NMR (CDCl$_3$, 300 MHz) δ 7.76 (d, J=8.4 Hz, 1H), 7.32-7.48 (m, 5H), 7.30 (d, J=1.8 Hz, 1H), 7.19 (dd, J=8.7, 1.8 Hz, 1H), 5.23 (s, 2H).

Step C: A mixture of 2-(benzyloxy)-4-bromo-1-nitrobenzene (14.1 g, 45.8 mmol), iron powder (12.8 g, 229.12 mmol) and ammonium chloride (2.9 g, 55.0 mmol) was taken up in ethanol (60 mL) and water (30 mL) and heated at 90° C. for 3 h. After cooling to ambient temperature, the reaction mixture was filtered through a celite bed and the filtrate concentrated in vacuo. The aqueous residue was extracted with dichloromethane and the organic layer washed with brine, dried over sodium sulfate and concentrated in vacuo to give 2-(benzyloxy)-4-bromoaniline (12.6 g, 99%) as a purple oil: $^1$H NMR (CDCl$_3$, 300 MHz) δ 7.31-7.46 (m, 5H), 6.98 (d, J=2.1 Hz, 1H), 6.92 (dd, J=8.4, 2.1 Hz, 1H), 6.60 (d, J=8.4 Hz, 1H), 5.05 (s, 2H), 3.81 (br s, 2H).

Step D: To a stirred slurry of 2-(benzyloxy)-4-bromoaniline (12.60 g, 45.3 mmol) in concentrated HCl (150 mL) was added a solution of sodium nitrite (3.44 g, 49.9 mmol) in water (20 mL). The reaction mixture was stirred at 0° C. for 30 min before adding a slurry of tin dichloride (25.8 g, 136.0 mmol) in concentrated HCl (35 mL). The reaction mixture was stirred at 0° C. overnight, warmed to ambient temperature, made basic to pH 10 by addition of sodium hydroxide and extracted with diethyl ether. The organic layer was washed with brine, dried over sodium sulfate and treated with 1.25M HCl in methanol (10 mL). The solution was concentrated in vacuo to give (2-(benzyloxy)-4-bromophenyl)hydrazine hydrochloride (5.64 g, 38%) as a brown solid: $^1$H NMR (CD$_3$OD, 300 MHz) δ 7.31-7.47 (m, 5H), 7.06 (dd, J=8.4, 2.1 Hz, 1H), 6.96 (d, J=2.1 Hz, 1H), 6.86 (d, J=8.4 Hz, 1H), 5.01 (s, 2H).

Step E: A solution of (2-(benzyloxy)-4-bromophenyl)hydrazine hydrochloride (1.00 g, 3.03 mmol) and nortropinone hydrochloride (0.49 g, 3.03 mmol) in ethanol (10 mL) was refluxed at 90° C. overnight. Concentrated HCl (2 mL) was then added and the reaction mixture was refluxed for a further 14 h. After cooling to ambient temperature, the reaction mixture was made basic by addition of 10% ammonium hydroxide solution in methanol and concentrated under reduced pressure. The residue was suspended in methanol (20 mL) and treated with di-tert-butyl dicarbonate (0.73 g, 3.34 mmol) and triethylamine (0.61 g, 10.70 mmol). The reaction mixture was stirred at ambient temperature overnight, concentrated in vacuo, washed with 0.5 N HCl (50 mL) and extracted with dichloromethane twice. The combined organic layers were washed with brine, dried over sodium sulfate and concentrated in vacuo. The crude material was purified by flash column chromatography (3:1 hexanes/ethyl acetate) to give tert-butyl 2-bromo-4-benzyloxy-5,6,7,8,9,10-hexahydro-7,10-epiminocyclohepta[b]indole-carboxylate (412 mg, 28%) as a light-yellow solid: $^1$H NMR (CDCl$_3$, 300 MHz) δ 8.08 (br s, 1H), 7.35-7.48 (m, 5H), 7.28 (s, 1H), 6.80 (s, 1H), 5.07-5.25 (m, 3H), 4.52 (br s, 1H), 3.43 (br s, 1H), 2.44 (d, J=15.9 Hz, 1H), 2.22-2.36 (m, 1H), 2.08-2.22 (m, 1H), 1.87-1.97 (m, 1H), 1.58-1.67 (m, 1H), 1.38 (br s, 9H).

Step F: To a solution of the product of step E (412 mg, 0.85 mmol) in DMF (10 mL) under a nitrogen atmosphere was added sodium hydride (60% dispersion in mineral oil, 69 mg, 1.70 mmol) at 0° C. The reaction mixture was stirred at ambient temperature for 1 h before addition of iodomethane (181 mg, 1.28 mmol). After stirring for an additional 2 h, the reaction mixture was quenched with water (50 mL) and extracted with dichloromethane. The organic layer was washed with brine, dried over sodium sulfate and concentrated in vacuo to give tert-butyl 2-bromo-4-benzyloxy-5-methyl-5,6,7,8,9,10-hexahydro-7,10-epiminocyclohepta[b]indole-carboxylate (420 mg, 99%) as a light-yellow solid: $^1$H NMR (CDCl$_3$, 300 MHz) δ 7.31-7.50 (m, 5H), 7.21-7.27 (m, 1H), 6.75 (d, J=1.2 Hz, 1H), 5.05-5.23 (m, 3H), 4.67 (br s, 1H), 3.79 (s, 3H), 3.32 (br s, 1H), 2.42 (d, J=15.9 Hz, 1H), 2.21-2.36 (m, 1H), 2.07-2.21 (m, 1H), 1.85-1.96 (m, 1H), 1.55-1.65 (m, 1H), 1.39 (br s, 9H).

Step G: A mixture of the product of step F (420 mg, 0.84 mmol), sodium benzenesulfinate (222 mg, 1.35 mmol), di-palladium-tris(dibenzylideneacetone) (77 mg, 0.08 mmol), cesium carbonate (413 mg, 1.27 mmol), xantphos (98 mg, 0.17 mmol) and tetrabutylammonium chloride (282 mg, 1.01 mmol) was taken up in anhydrous toluene (10 mL). The reaction flask was purged with argon and heated at 120° C. overnight. After cooling to ambient temperature, the reaction mixture was diluted with dichloromethane and filtered through a celite bed. The filtrate was concentrated in vacuo and the residue purified by flash column chromatography (SiO$_2$, 3:1 hexanes/ethyl acetate) to give tert-butyl 2-phenyl-sulfone-4-benzyloxy-5-methyl-5,6,7,8,9,10-hexahydro-7,10-epiminocyclohepta[b]indole-carboxylate (197 mg, 42%) as a light-yellow solid: $^1$H NMR (CDCl$_3$, 300 MHz) δ 7.92-7.85 (m, 2H), 7.83 (s, 1H), 7.53-7.31 (m, 8H), 7.13 (s, 1H), 5.28-5.13 (m, 3H), 4.69 (br s, 1H), 3.83 (s, 3H), 3.31 (br s, 1H), 2.43 (d, J=16.2 Hz, 1H), 2.38-2.23 (m, 1H), 2.23-2.10 (m, 1H), 1.96-1.85 (m, 1H), 1.65-1.53 (m, 1H), 1.37 (br s, 9H).

Step H: To a suspension of the product of step G (70 mg, 0.13 mmol) in ethanol (10 mL) was added 10% palladium on carbon (18 mg). The reaction flask was purged with hydrogen and stirred at ambient temperature for 48 h. The reaction mixture was diluted with DMF (10 mL), methanol (5 mL) and dichloromethane (5 mL), sonicated and heated at 40° C. The reaction mixture was filtered through a glass-wool plug and the filtrate was concentrated in vacuo to give tert-butyl 2-phenylsulfone-4-hydroxy-5-methyl-5,6,7,8,9,10-hexahydro-7,10-epiminocyclohepta[b]indole-carboxylate as an off-white solid: $^1$H NMR (DMSO-d$_6$, 300 MHz) δ 10.29 (s, 1H), 7.87 (d, J=6.6 Hz, 2H), 7.48-7.67 (m, 4H), 6.91 (d, J=1.5 Hz, 1H), 5.14 (d, J=5.4 Hz, 1H), 4.50 (br s, 1H), 3.84 (s, 3H), 3.16 (br s, 1H), 2.59 (d, J=15.0 Hz, 1H), 2.15-2.31 (m, 1H), 2.02-2.15 (m, 1H), 1.73-1.85 (m, 1H), 1.51-1.66 (m, 1H), 1.35 (br s, 9H).

Step I: To a solution of the product of step H (45 mg, 0.10 mmol) in DMF (10 mL) under a nitrogen atmosphere was added sodium hydride (dispersion in mineral oil) (8 mg, 0.19 mmol) at 0° C. The reaction mixture was stirred at ambient temperature for 1 h before addition of iodomethane (15 mg, 0.11 mmol). Stirring was continued for an additional 2 h before the reaction mixture was quenched with water and extracted with dichloromethane. The organic extract was washed with brine, dried over sodium sulfate and concentrated in vacuo to give tert-butyl 2-phenylsulfone-4-methoxy-5-methyl-5,6,7,8,9,10-hexahydro-7,10-epiminocyclohepta[b]indole-carboxylate (40 mg, 87%) as a light-yellow solid: $^1$H NMR (CDCl$_3$, 300 MHz) δ 7.91-7.98 (m, 2H), 7.82 (s, 1H), 7.41-7.54 (m, 3H), 7.03 (s, 1H), 5.20 (br s, 1H), 4.69 (br s, 1H), 3.93 (s, 3H), 3.84 (s, 3H), 3.31 (br s, 1H), 2.44 (d, J=16.2 Hz, 1H), 2.23-2.36 (m, 1H), 2.10-2.23 (m, 1H), 1.85-1.96 (m, 1H), 1.51-1.65 (m, 1H), 1.38 (br s, 9H).

Step J: To a solution of the product of step I (40 mg, 0.08 mmol) in dichloromethane (5 mL) was added trifluoroacetic acid (5 mL) at 0° C. The reaction mixture was stirred at 0° C. for 4 h then concentrated in vacuo. The residue was neutralized with saturated sodium bicarbonate solution and extracted with dichloromethane. The organic layer was dried over sodium sulfate, filtered and concentrated in vacuo. The crude material was purified by flash column chromatography (SiO$_2$, 80:18:2 chloroform/methanol/ammonium hydroxide) followed by semi-preparative HPLC. The purified free-base was treated with 1.25M HCl in methanol solution (0.5 mL) and lyophilized to give 2-phenylsulfonyl-4-methoxy-5-methyl-5,6,7,8,9,10-hexahydro-7,10-epiminocyclohepta[b]indole hydrochloride (12 mg, 34%, AUC HPLC >99%) as an off-white solid: mp 175-177° C.; $^1$H NMR (DMSO-d$_6$, 400 MHz) δ 9.52 (br s, 1H), 9.07 (br s, 1H), 7.94-8.04 (m, 3H), 7.54-7.70 (m, 3H), 7.10 (d, J=1.2 Hz, 1H), 5.30 (d, J=2.8 Hz, 1H), 4.45 (br s, 1H), 3.95 (s, 3H), 3.86 (s, 3H), 3.22-3.48 (m, 1H), 2.95 (d, J=16.8 Hz, 1H), 2.15-2.38 (m, 2H), 1.95-2.15 (m, 1H), 1.70-1.86 (m, 1H); ESI MS m/z 383 [M+H]$^+$.

Example 84

2-Phenylsulfonyl-4-ethoxy-5-methyl-5,6,7,8,9,10-hexahydro-7,10-epiminocyclohepta[b]indole hydrochloride

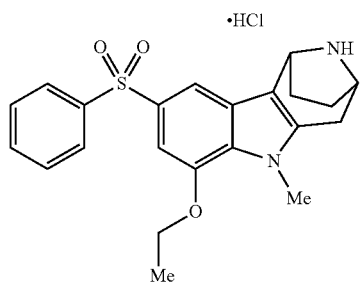 [SMILES: Cl ; CCOc1cc(S(=O)(=O)c2ccccc2)cc2c3c(n(C)c12)CC1CCC3N1]

The product of Example 83, step H was O-alkylated with iodoethane following the procedure of Example 83, step I. The crude product was subjected to Boc-deprotection and hydrochloride salt formation following the procedure of Example 83, Step J to give 2-phenylsulfonyl-4-ethoxy-5-methyl-5,6,7,8,9,10-hexahydro-7,10-epiminocyclohepta[b]indole hydrochloride (12 mg, 27%, AUC HPLC >99%) as a white solid: mp 182-184° C.; $^1$H NMR (DMSO-$d_6$, 300 MHz) δ 9.67 (br s, 1H), 9.15 (br s, 1H), 7.87-8.03 (m, 3H), 7.52-7.67 (m, 3H), 7.08 (d, J=1.2 Hz, 1H), 5.29 (d, J=3.3 Hz, 1H), 4.45 (br s, 1H), 4.13-4.27 (m, 2H), 3.87 (s, 3H), 3.22-3.31 (m, 1H), 2.94 (d, J=17.1 Hz, 1H), 2.15-2.33 (m, 2H), 1.97-2.09 (m, 1H), 1.63-1.85 (m, 1H), 1.41 (t, J=6.9 Hz, 3H); ESI MS m/z 397 [M+H]$^+$.

Example 85

2-Phenylsulfonyl-4-isopropoxy-5-methyl-5,6,7,8,9,10-hexahydro-7,10-epiminocyclohepta[b]indole hydrochloride

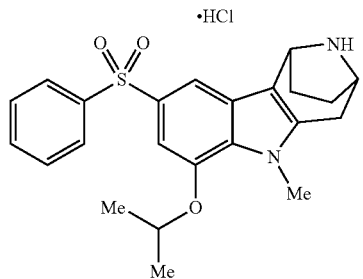 [SMILES: Cl ; CC(C)Oc1cc(S(=O)(=O)c2ccccc2)cc2c3c(n(C)c12)CC1CCC3N1]

The product of Example 83, step H was O-alkylated with 2-iodopropane following the procedure of Example 83, step I. The crude product was subjected to Boc-deprotection and hydrochloride salt formation following the procedure of Example 83, Step J to give 2-phenylsulfonyl-4-isopropoxy-5-methyl-5,6,7,8,9,10-hexahydro-7,10-epiminocyclohepta[b]indole hydrochloride (29 mg, 68%, AUC HPLC 97.7%) as an off-white solid: mp 187-189° C.; $^1$H NMR (DMSO-$d_6$, 300 MHz) δ 9.17 (br s, 2H), 7.86-7.99 (m, 3H), 7.52-7.68 (m, 3H), 7.80 (d, J=1.2 Hz, 1H), 5.27 (d, J=3.3 Hz, 1H), 4.83 (hept, J=6.0 Hz, 1H), 4.44 (br s, 1H), 3.85 (s, 3H), 3.19-3.30 (m, 1H), 2.93 (d, J=16.8 Hz, 1H), 2.16-2.34 (m, 2H), 1.97-2.11 (m, 1H), 1.68-1.84 (m, 1H), 1.33 (dd, J=6.0, 4.2 Hz, 6H); ESI MS m/z 411 [M+H]$^+$.

Example 86

2-Phenylsulfonyl-4-benzyloxy-5-methyl-5,6,7,8,9,10-hexahydro-7,10-epiminocyclohepta[b]indole hydrochloride

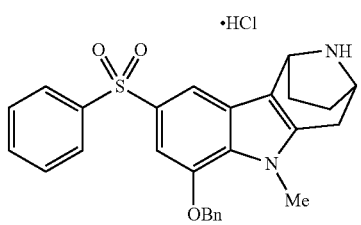 [SMILES: Cl ; Cn1c2c(c3cc(S(=O)(=O)c4ccccc4)cc(OCc4ccccc4)c31)C1CCC(C2)N1]

The product of Example 83, step H was O-alkylated with benzyl bromide following the procedure of Example 83, step I. The crude product was subjected to Boc-deprotection and hydrochloride salt formation following the procedure of Example 83, step J to give 2-phenylsulfonyl-4-benzyloxy-5-methyl-5,6,7,8,9,10-hexahydro-7,10-epiminocyclohepta[b]indole hydrochloride (23 mg, 53%, AUC HPLC >99%) as a light-yellow solid: mp 178-180° C.; $^1$H NMR (DMSO-$d_6$, 300 MHz) δ 9.56 (br s, 1H), 9.08 (br s, 1H), 7.95 (d, J=0.9 Hz, 1H), 7.84-7.93 (m, 2H), 7.47-7.67 (m, 5H), 7.34-7.44 (m, 3H), 7.25 (d, J=0.9 Hz, 1H), 5.34 (d, J=1.8 Hz, 2H), 5.30 (br s, 1H), 4.45 (br s, 1H), 3.87 (s, 3H), 3.24-3.30 (m, 1H), 2.94 (d, J=16.8 Hz, 1H), 2.17-2.35 (m, 2H), 1.96-2.11 (m, 1H), 1.67-1.85 (m, 1H); ESI MS m/z 459 [M+H]$^+$.

Example 87

Preparation of 2-Phenylsulfonyl-5-isopropyl-5,6,7,8,9,10-hexahydro-7,10-epiminocyclohepta[b]indole hydrochloride

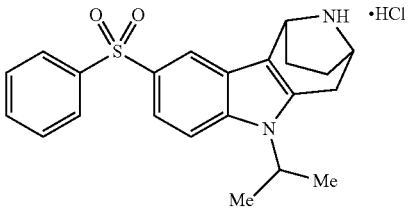 [SMILES: Cl ; CC(C)n1c2c(c3cc(S(=O)(=O)c4ccccc4)ccc31)C1CCC(C2)N1]

Step A: To a solution of the product of Example 27, step A (300 mg, 0.79 mmol) in anhydrous DMF (4 ml) at 0° C., was added sodium hydride (60% dispersion in mineral oil, 106 mg, 1.59 mmol) and 18-crown-6 (21 mg, 0.08 mmol). The reaction mixture was stirred for 30 min before 2-iodopropane was added. The reaction mixture then heated at 60° C. for 4 h, quenched with water and extracted with ethyl acetate. The ethyl acetate layer was dried over sodium sulfate, filtered and concentrated in vacuo to give tert-butyl 2-bromo-5-isopropyl-5,6,7,8,9,10-hexahydro-7,10-epiminocyclohepta[b]indole-carboxylate (270 mg, 81%) as an off-white solid: $^1$H NMR (CDCl$_3$, 300 MHz) δ 7.61 (d, J=1.8 Hz, 1H), 7.25 (d, J=8.7 Hz, 1H), 7.15 (d, J=8.7 Hz, 1H), 5.13 (br s, 1H), 4.66 (br s, 1H), 4.41-4.55 (m, 1H), 3.44 (br s, 1H), 2.52 (d, J=15.9 Hz, 1H), 2.22-2.26 (m, 1H), 2.07-2.19 (m, 1H), 1.89-1.96 (m, 1H), 1.57-1.64 (m, 1H), 1.53 (d, J=7.2 Hz, 3H), 1.48 (d, J=6.9 Hz, 3H), 1.35 (br s, 9H).

Step B: To a mixture of the product of step A (270 mg, 0.64 mmol), sodium benzenesulfinate (211 mg, 1.29 mmol), di-palladium-tris(dibenzylideneacetone) (59 mg, 0.06 mmol), cesium carbonate (314 mg, 0.96 mmol) and xantphos (74 mg, 0.12 mmol) under an argon atmosphere was added anhydrous toluene (4 mL). The mixture was heated at 115° C. overnight, cooled to ambient temperature, diluted with dichloromethane and filtered through celite bed. The filtrate was concentrated in vacuo and the residue was purified by flash column chromatography (SiO$_2$, 3:2 hexanes/ethyl acetate) to give tert-butyl 2-phenylsulfonyl-5-isopropyl-5,6,7,8,9,10-hexahydro-7,10-epiminocyclohepta[b]indole-carboxylate (100 mg, 38%) as a yellow solid: $^1$H NMR (CDCl$_3$, 300 MHz) δ 8.18 (s, 1H), 7.94-7.97 (m, 2H), 7.62 (d, J=8.7 Hz, 1H), 7.43-7.52 (m, 4H), 5.24 (br s, 1H), 4.69 (br s, 1H), 4.46-4.61 (m, 1H), 3.46 (br s, 1H), 2.54 (d, J=15.9 Hz, 1H), 2.25-2.35 (m, 1H), 2.12-2.23 (m, 1H), 1.95 (t, J=9.9 Hz, 1H), 1.56-1.63 (m, 1H), 1.54 (d, J=6.9 Hz, 3H), 1.50 (d, J=6.9 Hz, 3H), 1.33 (s, 9H).

Step C: To a solution of the product of step B (100 mg, 0.06 mmol) in dichloromethane was added 2M HCl in diethylether (2 mL). After stirring at ambient temperature for 5 h the reaction mixture was concentrated in vacuo, triturated with ethyl acetate and lyophilized from water to give 2-phenylsulfonyl-5-isopropyl-5,6,7,8,9,10-hexahydro-7,10-epiminocyclohepta[b]indole hydrochloride (50 mg, 57%, AUC HPLC >99%) as a white solid: mp 260-265° C., $^1$H NMR (CD$_3$OD, 300 MHz) δ 8.26 (d, J=1.5 Hz, 1H), 7.93-7.97 (m, 2H), 7.67-7.76 (m, 2H), 7.51-7.59 (m, 3H), 5.28-5.30 (m, 1H), 4.69-4.75 (m, 1H), 4.52 (br s, 1H), 3.55 (dd, J=17.2, 5.1 Hz, 1H), 3.11 (d, J=17.4 Hz, 1H), 2.28-2.43 (m, 3H), 1.93-2.02 (m, 1H), 1.59 (d, J=7.2 Hz, 3H), 1.56 (d, J=6.9 Hz, 3H); ESI, m/z 381 [M+H]$^+$.

Example 88

Preparation of 2-Phenylsulfonyl-5-phenyl-5,6,7,8,9,10-hexahydro-7,10-epiminocyclohepta[b]indole hydrochloride

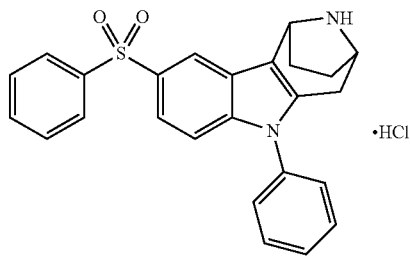 [SMILES: O=S(=O)(c1ccccc1)c1ccc2c(c1)c1c(n2-c2ccccc2)CC2CCC1N2 ; Cl]

Step A: To a solution the product of Example 27, step A (2.80 g, 7.42 mmol) in DMF (50 mL) at 0° C. was added a sodium hydride (60% suspension in mineral oil, 1.33 g, 33.25 mmol). After 30 min SEM-Cl (2.6 mL, 14.84 mmol) was added and the reaction mixture stirred at ambient temperature overnight. The reaction mixture was cooled to 0° C. and quenched with saturated aqueous ammonium chloride. The mixture was diluted with water and extracted with dichloromethane. The organic phase was dried over sodium sulfate, filtered and concentrated in vacuo. The residue was purified by flash column chromatography (SiO$_2$, 4:1 to 1:1 hexane/ethyl acetate) to give tert-butyl 2-bromo-5-[(trimethylsilyl)ethoxy]methyl-5,6,7,8,9,10-hexahydro-7,10-iminocyclohept[b]indole-carboxylate (3.0 g, 81%) as a viscous yellow oil: $^1$H NMR (CDCl$_3$, 300 MHz) δ 7.69 (s, 1H), 7.28-7.38 (m, 2H), 5.41 (d, J=11.4 Hz, 1H), 5.35 (d, J=11.4 Hz, 1H), 5.18-5.32 (m, 1H), 4.63-4.82 (m, 1H), 3.40-3.60 (m, 3H), 2.61 (d, J=16.2 Hz, 1H), 2.31-2.43 (m, 1H), 2.19-2.30 (m, 1H), 1.97-2.08 (m, 1H), 1.64-1.75 (m, 1H), 1.45 (br s, 9H), 0.91 (ddd, J=8.4, 7.5, 1.2 Hz, 2H), −0.11 (s, 9H).

Step B: The product of step A was converted to the phenyl sulfone derivative following the procedure of example 1, step C. The crude material was purified by flash column chromatography (SiO$_2$ 98:2 to 65:35 hexane/ethyl acetate) to give tert-butyl 2-phenylsulfonyl-5-[(trimethylsilyl)ethoxy]methyl-5,6,7,8,9,10-hexahydro-7,10-iminocyclohept[b]indole-carboxylate (1.30 g, 58%) as a brown foam: $^1$H NMR (CDCl$_3$, 300 MHz) δ 8.28 (s, 1H), 8.03-8.09 (m, 2H), 7.75-7.83 (m, 1H), 7.51-7.62 (m, 4H), 5.28-5.49 (m, 3H), 4.66-4.89 (m, 1H), 3.45-3.68 (m, 3H), 2.64 (d, J=16.2 Hz, 1H), 2.45-2.52 (m, 1H), 2.25-2.38 (m, 1H), 2.01-2.11 (m, 1H), 1.64-1.75 (m, 1H), 1.46 (br s, 9H), 0.88-0.95 (m, 2H), −0.11 (s, 9H).

Step C: To a solution of the product of step B (1.28 g, 2.25 mmol) in THF (30 mL) was added a 1M solution of TBAF in THF (12 mL, 12.0 mmol) and the resulting solution heated to reflux overnight. The reaction was concentrated in vacuo to a reduced volume and diluted with a saturated aqueous solution of ammonium chloride followed by water. The mixture was extracted with dichloromethane and the organic phase dried over sodium sulfate, filtered, and concentrated in vacuo. The residue was purified by flash column chromatography (SiO$_2$, 4:1 to 1:1 hexane/ethyl acetate) to give tert-butyl 2-phenylsulfonyl-5,6,7,8,9,10-hexahydro-7,10-iminocyclohept[b]indole-carboxylate (0.91 g, 93%) as a white foam: $^1$H NMR (CD$_3$OD, 300 MHz) δ 8.12 (s, 1H), 7.91-7.96 (m, 2H), 7.48-7.62 (m, 4H), 7.41 (d, J=8.7 Hz, 1H), 5.19-5.28 (m, 1H), 4.52-4.61 (m, 1H), 3.35-3.48 (m, 1H), 2.58 (d, J=16.2 Hz, 1H), 2.15-2.41 (m, 2H), 1.90-1.99 (m, 1H), 1.64-1.75 (m, 1H), 1.27-1.49 (m, 9H).

Step D: To a solution of the product of step C (100 mg, 0.27 mmol) in dimethylsulfoxide (2 mL) was added copper iodide (51 mg, 0.02 mmol), L-proline (6.2 mg, 0.05 mmol), iodobenzene (33 μL, 0.29 mmol) and potassium carbonate (75 mg, 0.54 mmol). The resulting mixture was heated to 115° C. for 40 h, diluted with water and extracted with ethyl acetate. The organic extract was dried over sodium sulfate, filtered, and concentrated in vacuo. The crude material was purified by flash chromatography (SiO$_2$, 3:2 hexanes/ethyl acetate) to give tert-butyl 2-phenylsulfonyl-5-phenyl-5,6,7,8,9,10-hexahydro-7,10-epiminocyclohepta[b]indole-carboxylate (70 mg, 50%) as a white solid: $^1$H NMR (CDCl$_3$, 300 MHz) δ 8.26 (s, 1H), 7.95-7.98 (m, 2H), 7.63 (d, J=8.7 Hz, 1H), 7.42-7.54 (m, 6H), 7.21-7.26 (m, 3H), 5.33 (br s, 1H), 4.65 (br s, 1H), 2.20-2.33 (m, 3H), 2.00-2.06 (m, 1H), 1.60-1.69 (m, 2H), 1.40 (s, 9H).

Step E: To a solution of the product of step D (70 mg, 0.13 mmol) in methanol was added 2M HCl in diethylether (4 mL). After stirring for 2 h, the solution was concentrated in vacuo, triturated with ethyl acetate, and lyophilized from water to give 2-phenylsulfonyl-5-phenyl-5,6,7,8,9,10-hexahydro-7,10-epiminocyclohepta[b]indole hydrochloride (50 mg, 57%, AUC HPLC >99%) as a white solid: mp 195-200° C.; $^1$H NMR (CD$_3$OD, 300 MHz) δ 8.38 (d, J=1.8 Hz, 1H), 7.95-7.99 (m, 2H), 7.72 (dd, J=8.8, 1.5 Hz, 1H), 7.51-7.64 (m, 6H), 7.39-7.42 (m, 2H), 7.32 (d, J=9.0 Hz, 1H), 5.39-5.40 (m, 1H), 4.49 (br s, 1H), 3.39 (dd, J=8.7, 4.5 Hz, 1H), 2.81 (d, J=17.7 Hz, 1H), 2.37-2.46 (m, 3H), 1.98-2.08 (m, 1H); ESI, m/z 415 [M+H]+.

Example 89

Preparation of 2-Phenylsulfonyl-5-(2-hydroxy)ethyl-5,6,7,8,9,10-hexahydro-7,10-epiminocyclohepta[b]indole hydrochloride

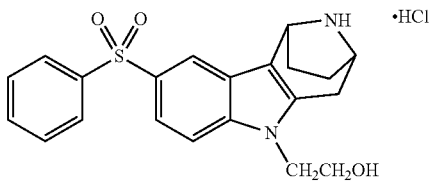

Step A: To a solution of the product of Example 88, step C (120 mg, 0.27 mmol) in anhydrous DMF (3 mL) at 0° C. was added sodium hydride (60% dispersion in mineral oil, 22 mg, 0.54 mmol), tetrabutylammonium iodide (51 mg, 0.13 mmol) and 18-crown-6 (7 mg, 0.02 mmol). The resulting mixture was stirred for 30 min before 2-bromoethoxy-tert-butyldimethylsilane (0.07 ml, 0.32 mmol) was added. The reaction mixture was stirred at room temperature for 4 h, quenched with water and extracted with ethyl acetate. The organic extract was dried over sodium sulfate, filtered, and concentrated to give tert-butyl 2-phenylsulfonyl-5-[2-(tert-butyldimethylsilyloxy)]ethyl-5,6,7,8,9,10-hexahydro-7,10-epiminocyclohepta[b]indole-carboxylate (160 mg, quant) as a yellow-brown solid: $^1$H NMR (CDCl$_3$, 300 MHz), δ 8.39 (s, 1H), 8.14-8.18 (m, 2H), 7.86 (d, J=8.4 Hz, 1H), 7.63-7.71 (m, 3H), 7.56 (d, J=8.7 Hz, 1H), 5.47 (br s, 1H), 4.91 (br s, 1H), 4.25-4.38 (m, 2H), 4.03 (t, J=5.4 Hz, 2H), 2.76 (d, J=16.2 Hz, 1H), 2.34-2.57 (m, 2H), 2.10-2.22 (m, 1H), 1.79-1.86 (m, 2H), 1.58 (s, 9H), 0.93 (s, 9H), 0.04 (s, 3H), 0.01 (s, 3H).

Step B: To a solution of the product of step A (110 mg, 0.30 mmol) in dichloromethane at 0° C. was added trifluoroacetic acid (0.57 ml, 7.5 mmol) and the reaction was stirred overnight. The reaction mixture was made basic with saturated sodium bicarbonate solution and extracted with dichloromethane. The dichloromethane layer was dried over sodium sulfate, filtered, and concentrated in vacuo. The crude material was crystallized from dichloromethane to give 2-phenylsulfonyl-5-(2-hydroxy)ethyl-5,6,7,8,9,10-hexahydro-7,10-epiminocyclohepta[b]indole (100 mg, 87%) as a white crystalline solid: $^1$H NMR (CDCl$_3$, 300 MHz), δ 8.27 (s, 1H), 7.93-7.96 (m, 2H), 7.71 (dd, J=9.0, 1.2 Hz, 1H), 7.52-7.62 (m, 4H), 5.29-5.31 (m, 1H), 4.53 (br s, 1H), 4.24 (t, J=5.1 Hz, 2H), 3.81 (t, J=5.1 Hz, 2H), 3.54 (dd, J=17.4, 4.5 Hz, 1H), 3.12 (d, J=20.7 Hz, 1H), 2.23-2.46 (m, 3H), 1.93-1.97 (m, 1H).

Step C: The product of step B (100 mg, 0.26 mmol) was treated with 1.25 M HCl in methanol (2 mL). The solution was concentrated in vacuo and lyophilized from water to give 2-phenylsulfonyl-5-(2-hydroxy)ethyl-5,6,7,8,9,10-hexahydro-7,10-epiminocyclohepta[b]indole hydrochloride (90 mg, 74%, AUC HPLC >99%) as a white solid: mp 185-190° C.; $^1$H NMR (CD$_3$OD, 300 MHz) δ 8.26 (s, 1H), 7.93-7.96 (m, 2H), 7.71 (dd, J=8.8, 1.8 Hz, 1H), 7.51-7.62 (m, 4H), 5.25-5.26 (m, 1H), 4.49 (br s, 1H), 4.24 (t, J=5.1 Hz, 2H), 3.80 (t, J=5.1 Hz, 2H), 3.48-3.53 (m, 1H), 3.10 (d, J=18.0 Hz, 1H), 2.23-2.44 (m, 3H), 1.91-1.96 (m, 1H); ESI, m/z 383 [M+H]+.

Example 90

Preparation of 2-Phenylsulfonyl-5-ethyl-5,6,7,8,9,10-hexahydro-7,10-epiminocyclohepta[b]indole hydrochloride

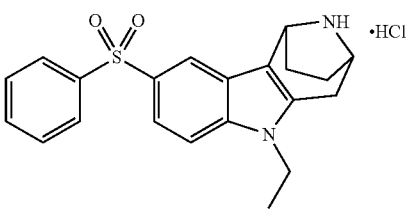 [SMILES: CCn1c2c(c3cc(S(=O)(=O)c4ccccc4)ccc31)C1CCC(C2)N1 ; Cl]

Step A: The product of Example 27, step A was alkylated with iodoethane following the procedure of Example 27, step B. The crude material was purified by flash column chromatography (SiO$_2$, 4:1 to 1:1 hexanes/ethyl acetate) to give tert-butyl 2-bromo-5-ethyl-5,6,7,8,9,10-hexahydro-7,10-epiminocyclohepta[b]indole-carboxylate (0.5 g, 94%) as a white foam: $^1$H NMR (CDCl$_3$, 300 MHz) δ 7.61 (d, J=1.5 Hz, 1H), 7.24 (dd, J=8.7, 1.5 Hz, 1H), 7.12 (d, J=8.7 Hz, 1H), 5.08-5.28 (m, 1H), 4.55-4.78 (m, 1H), 3.91-4.00 (m, 2H), 3.22-3.50 (m, 1H), 2.45 (d, J=15.9 Hz, 1H), 2.23-2.37 (m, 1H), 2.09-2.21 (m, 1H), 1.89-1.98 (m, 1H), 1.51-1.67 (m, 1H), 1.36 (br s, 9H), 1.24-1.37 (m, 3H).

Step B: The product of step A was coupled with sodium benzenesulfinate following the procedure of Example 27, step C. The crude material was purified by flash column chromatography (SiO$_2$, 4:1 to 1:1 hexane/ethyl acetate) to give tert-butyl 2-phenylsulfonyl-5-ethyl-5,6,7,8,9,10-hexahydro-7,10-epiminocyclohepta[b]indole-carboxylate (0.12 g, 36%) as a white solid: $^1$H NMR (CDCl$_3$, 300 MHz) δ 8.20 (s, 1H), 7.94-7.99 (m, 2H), 7.40-7.53 (m, 4H), 7.31 (d, J=8.7 Hz, 1H), 5.20-5.33 (m, 1H), 4.55-4.81 (m, 1H), 3.95-4.11 (m, 2H), 3.19-3.50 (m, 1H), 2.47 (d, J=16.2 Hz, 1H), 2.15-2.38 (m, 2H), 1.91-2.01 (m, 1H), 1.53-1.62 (m, 1H), 1.34 (s, 9H), 1.25-1.31 (m, 3H).

Step C: The product of step B was subjected to Boc-deprotection with 2 M HCl in diethyl ether following the procedure of Example 27, step D. The crude material was purified by flash column chromatography (SiO$_2$, 99:0.9:0.1 to 80:18:2 dichloromethane/methanol/ammonium hydroxide) and semi-preparative HPLC. The free base was dissolved in methanol and treated with an excess of HCl in diethyl ether. The solution was concentrated in vacuo and the residue lyophilized from water/acetonitrile to give 2-phenylsulfonyl-5-ethyl-5,6,7,8,9,10-hexahydro-7,10-epiminocyclohepta[b]indole hydrochloride (28 mg, 100%, AUC HPLC >99%) as a white solid: mp 200-204° C. dec; $^1$H NMR (CD$_3$OD, 300 MHz) δ 8.28 (d, J=1.8 Hz, 1H), 7.91-7.98 (m, 2H), 7.72 (dd, J=8.7; 1.8 Hz, 1H), 7.49-7.63 (m, 4H), 5.25-5.32 (m, 1H), 4.49-4.58 (m, 1H), 4.10-4.28 (m, 2H), 3.42-3.56 (m, 1H), 3.00-3.11 (m, 1H), 2.23-2.52 (m, 3H), 1.88-2.05 (m, 1H), 1.32 (t, J=7.2 Hz, 3H); ESI MS m/z 367 [M+H]+

Example 91

Preparation of 3-Phenylsulfonyl-5-methyl-5,6,7,8,9,10-hexahydro-7,10-epiminocyclohepta[b]indole hydrochloride

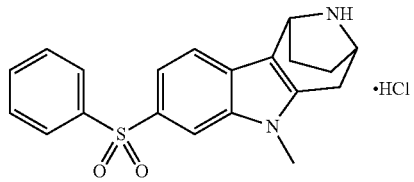 [SMILES: Cn1c2c(c3ccc(S(=O)(=O)c4ccccc4)cc31)C1CCC(C2)N1 ; Cl]

Step A: 3-Bromophenylhydrazine hydrochloride (919 mg, 4.12 mmol) and nortropanone hydrochloride (1000 mg, 6.18 mmol) were dissolved in ethanol (5 mL), and conc. HCl (2 mL) was added. The reaction mixture was then heated to reflux for 18 h and then concentrated. The residue was suspended in isopropanol (25 mL) and water (15 ml) and $K_2CO_3$ (1.70 g, 12.3 mmol) and $Boc_2O$ (1.79 g, 8.24 mmol) were added. After 18 h the mixture was diluted with $CH_2Cl_2$ and the organic phase removed, dried over $Na_2SO_4$ and concentrated. The resulting mixture of regioisomers was purified by flash column chromatography (silica gel, hexanes/EtOAc, 100:0 to 50:50) to give tert-butyl 3-bromo-5,6,7,8,9,10-hexahydro-7,10-epiminocyclohepta[b]indole-carboxylate (240 mg, 15%) as a yellow solid: $^1$H NMR (500 MHz, $CDCl_3$) δ 7.92-7.64 (br s, 1H), 7.42 (s, 1H), 7.34 (d, J=8.4 Hz, 1H), 7.19 (d, J=8.4 Hz, 1H), 5.29-5.11 (br m, 1H), 4.69-4.65 (br m, 1H), 3.52-3.27 (br m, 1H), 2.44 (d, J=15.9 Hz, 1H), 2.34-2.24 (m, 1H), 2.19-2.14 (m, 1H), 1.93 (t, J=9.8 Hz, 1H), 1.46-1.43 (m, 1H), 1.43 (s, 9H).

Step B: Sodium hydride (38 mg, 0.950 mmol) was added to a solution of the product of step A (240 mg, 0.636 mol) in DMF (4 mL) at room temperature under $N_2$. After 1 h, methyl iodide (134 mg, 0.058 mL, 0.943 mol) was added, and the reaction allowed to proceed for an additional 1 h. The mixture was quenched with $H_2O$, upon which a solid precipitated out of solution. The solids were filtered off to provide tert-butyl 3-bromo-5-methyl-5,6,7,8,9,10-hexahydro-7,10-epiminocyclohepta[b]indole-carboxylate (248 mg, 100%) as a brown solid: $^1$H NMR (300 MHz, $CDCl_3$) δ 7.40 (s, 1H), 7.35 (d, J=8.5 Hz, 1H), 7.19 (d, J=8.5 Hz, 1H), 5.30-5.10 (br m, 1H), 4.76-4.56 (br m, 1H), 3.54 (s, 3H), 3.49-3.19 (br m, 1H), 2.46 (d, J=16.0 Hz, 1H), 2.37-2.08 (m, 2H), 1.97-1.86 (m, 1H), 1.69-1.57 (m, 1H), 1.50 (s, 9H).

Step C: Prepared from the product of step B and benzene sulfinic acid sodium salt according to the procedure of Example 27, step C. Purification by flash column chromatography (silica gel, hexanes/EtOAc, 100:0 to 50:50) provided tert-butyl 3-phenylsulfonyl-5-methyl-5,6,7,8,9,10-hexahydro-7,10-epiminocyclohepta[b]indole-carboxylate (53 mg, 35%) as a white solid: $^1$H NMR (300 MHz, $CDCl_3$) δ 7.95 (m, 3H), 7.52 (m, 5H), 5.21 (m, 1H), 4.68 (m, 1H), 3.67 (s, 3H), 3.39 (m, 1H), 2.53 (d, J=17.0 Hz, 1H), 2.32 (m, 2H), 2.17 (m, 1H), 1.88 (t, J=10.1 Hz, 1H), 1.37 (brs, 9H).

Step D: Prepared from the product of step C according to the procedure of Example 27, step D giving 3-phenylsulfonyl-5-methyl-5,6,7,8,9,10-hexahydro-7,10-epiminocyclohepta[b]indole hydrochloride (34 mg, 74%) as an off-white solid: Mpt 252-256° C.; $^1$H NMR (500 MHz, $d_6$-DMSO) δ 9.56 (brs, 1H), 9.13 (brs, 1H), 8.16 (d, J=1.4 Hz, 1H), 7.95 (d, J=1.5 Hz, 2H), 7.78 (d, J=8.4 Hz, 1H), 7.63 (m, 1H), 7.58 (m, 3H), 5.21 (d, J=4.4 Hz, 1H), 4.47 (t, J=6.0 Hz, 1H), 3.76 (s, 3H), 3.40 (dd, J=18.0, 4.6 Hz, 1H, partially masked by solvent), 3.04 (d, J=17.0 Hz, 1H), 2.24 (m, 2H), 2.01 (m, 1H), 1.76 (m, 1H); ESI MS m/z 353 [M+H]$^+$; HPLC (Method A) 95.8% (AUC), $t_R$=12.20 min.

Example 92

Preparation of 2-(Phenylsulfonyl)-5-methyl-6,7,8,9,10,11-hexahydro-5H-7,11-epiminocycloocta[b]indole hydrochloride

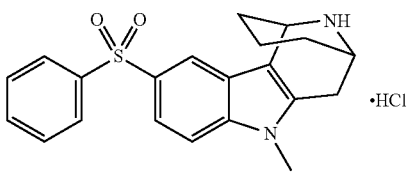 [SMILES: Cn1c2c(c3cc(S(=O)(=O)c4ccccc4)ccc31)C1CCCC(C2)N1 ; Cl]

Step A: ACE Chloride (904 mg, 5.27 mmol) was added to a solution of pseudopelletierine hydrochloride (1.0 g, 5.27 mmol) in methanol (20 mL) and the mixture refluxed for 64 h. The mixture was then concentrated and methylene chloride (30 mL) followed by triethylamine (997 µL, 7.18 mmol), DMAP (10 mg) and $Boc_2O$ (1.18 g, 5.39 mmol) were added. After stirring for 1 h at room temperature, the mixture was washed with 0.5 N HCl, dried over $Na_2SO_4$ and concentrated. Purification by flash column chromatography (silica gel, hexanes/EtOAc, 100:0 to 50:50) provided tert-butyl norpseudopelletierine carboxylate (122 mg, 9.2%) as a white solid: $^1$H NMR (300 MHz, $CDCl_3$) δ 4.72 (brs, 1H), 4.65 (brs, 1H), 2.60 (m, 2H), 2.36 (d, J=16.3 Hz, 2H), 1.72 (m, 6H, partially masked by $H_2O$ peak), 1.49 (s, 9H).

Step B: 4-Bromophenylhydrazine hydrochloride (106 mg, 0.48 mmol) and tert-butyl norpseudopelletierine carboxylate (120 mg, 0.48 mmol) were dissolved in ethanol (5 mL), and conc. HCl (1 mL) was added. The reaction mixture was then heated to reflux for 18 h and then concentrated. The residue was suspended in methylene chloride (5 mL) containing triethylamine (197 uL) and DMAP (10 mg) and $Boc_2O$ (124 mg, 0.569 mmol) was added. After 2 h, the mixture was washed with 0.5 N HCl, dried over $Na_2SO_4$, and concentrated. Purification by flash column chromatography (silica gel, hexanes/EtOAc, 100:0 to 50:50) provided tert-butyl 2-bromo-6,7,8,9,10,11-hexahydro-5H-7,11-epiminocycloocta[b]indole-carboxylate (60 mg, 32%) as a yellow solid: $^1$H NMR (500 MHz, $CDCl_3$) δ 7.97 (2×brs, 1H), 7.55 (s, 1H), 7.19 (m, 2H), 5.47 (2×brs, 1H), 4.70 (2×brt, 1H), 3.33 (td, J=16.8, 7.2 Hz, 1H), 2.56 (d, J=17.0 Hz, 1H), 1.85 (m, 2H), 1.66 (t, J=6.5 Hz, 2H, partially masked by $H_2O$ peak), 1.46 (s+m, 11H).

Step C: Prepared from the product of step B and methyl iodide according to the procedure outlined in Example 27, step B. tert-Butyl 2-bromo-5-methyl-6,7,8,9,10,11-hexahydro-5H-7,11-epiminocycloocta[b]indole-carboxylate was recovered as a yellow solid (50 mg, 81%): LC MS $t_R$=4.00 min, ESI MS m/z 349 [M−t-Bu+2H]$^+$.

Step D: Prepared from the product of step C and benzene sulfinic acid sodium salt according to the procedure outlined in Example 27, step C. Purification by flash column chromatography (silica gel, hexanes/EtOAc, 100:0 to 50:50) provided tert-butyl 2-phenylsulfonyl-5-methyl-6,7,8,9,10,11-hexahydro-5H-7,11-epiminocycloocta[b]indole-carboxylate (6 mg, 10%) as an oil: $^1$H NMR (300 MHz, $CDCl_3$) δ 8.12

(2×s, 1H), 7.95 (d, J=6.8 Hz, 2H), 7.69 (m, 1H), 7.47 (m, 3H), 7.33 (m, 1H), 5.52 (2×brs, 1H), 4.76 (2×brt, 1H), 3.69 (s, 3H), 3.21 (m, 1H), 2.57 (d, J=17.1 Hz, 1H), 1.88 (m, 2H), 1.68 (t, J=6.4 Hz, 2H, partially masked by H$_2$O peak), 1.45 (s+m, 11H).

Step E: Prepared from the product of step D according to the procedure outlined in Example 27, step D providing 2-phenylsulfonyl-5-methyl-6,7,8,9,10,11-hexahydro-5H-7,11-epiminocycloocta[b]indole hydrochloride (5.2 mg, 100%) as a beige solid: $^1$H NMR (500 MHz, d$_6$-DMSO) δ 9.37 (br d, 1H), 8.90 (br d, 1H), 8.30 (s, 1H), 7.93 (d, J=4.4 Hz, 2H), 7.62 (m, 5H), 5.19 (s, 1H), 4.10 (br s, 1H), 3.73 (s, 3H), 3.37 (m, 1H, partially masked by solvent), 3.05 (d, J=18.0 Hz, 1H), 2.03 (2×m, 2H), 1.78 (dd, J=37.2, 12.9 Hz, 2H), 1.45 (d, J=13.0 Hz, 1H), 1.22 (m, 1H); ESI MS m/z 367 [M+H]$^+$; HPLC (Method A) 95.2% (AUC), $t_R$=12.44 min.

Example 93

Chiral Resolution of tert-Butyl 2-bromo-5,6,7,8,9,10-hexahydro-7,10-epiminocyclohepta[b]indole-carboxylate

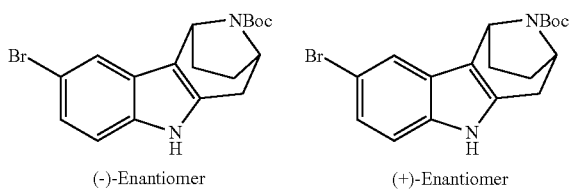 [SMILES: CC(C)(C)OC(=O)N1C2CCC1c1c([nH]c3ccc(Br)cc13)C2 ; CC(C)(C)OC(=O)N1C2CCC1c1c([nH]c3ccc(Br)cc13)C2]

(−)-Enantiomer          (+)-Enantiomer

Step A: To a stirred suspension of powdered NaOH (10.6 g, 265 mmol) in CH$_2$Cl$_2$ (750 mL) and water (50 µl, 2.7 mmol) was added the product from Example 27, step A (25.0 g, 66.2 mmol), followed by (−)-(1R,2S,5R)-menthyl chloroformate (50.7 g, 232 mmol) and tetrabutylammonium hydrogensulfate (450 mg, 1.32 mmol) respectively at ambient temperature. The mixture was stirred vigorously for 8 h, quenched with aqueous saturated NH$_4$Cl solution (150 mL) and extracted with CH$_2$Cl$_2$ (2×200 mL). The combined extracts were dried (Na$_2$SO$_4$), filtered, and concentrated in vacuo. The residue was purified by column chromatography (SiO$_2$, hexane/ethyl acetate, 95:5) to afford tert-butyl 2-bromo-5-[(1R,2S,5R)-2-isopropyl-5-methylcyclohexyl]-5,6,7,8,9,10-hexahydro-7,10-epiminocyclohepta[b]indole-carboxylate (37.0 g, 99%) as a foam, which was used directly in the next step.

Step B: The product from step A (37.0 g, 66.12 mmol) was dissolved in hexane (740 mL) at ambient temperature. The solution was stored at −5° C. for 72 h. The resulting precipitate was filtered, washed with cold hexane (50 mL), and dried to give 18.0 g of a pinkish solid. The solid was suspended in hexane (360 mL) and heated to 60° C. for 40 min. The resultant slurry was cooled to ambient temperature and stored at −5° C. for 72 h. The precipitate was filtered, washed with cold hexane (50 mL), and dried to give a pure, single diastereomer of tert-butyl 2-bromo-5-[(1R,2S,5R)-2-isopropyl-5-methylcyclohexyl]-5,6,7,8,9,10-hexahydro-7,10-epiminocyclohepta[b]indole-carboxylate (diastereomer A) (15.65 g) as a pink solid: $^1$H NMR (CDCl$_3$, 400 MHz) δ 8.02 (d, J=8.4 Hz, 1H), 7.57 (d, J=1.6 Hz, 1H), 7.35 (dd, J=8.8, 1.6 Hz, 1H), 5.11 (s, 1H), 4.92 (dt, J=11.2, 4.4 Hz, 1H), 4.44-4.79 (m, 1H), 3.42-3.63 (m, 1H), 2.81 (d, J=17.6 Hz, 1H), 2.09-2.38 (m, 3H), 1.89-2.04 (m, 2H), 1.51-1.80 (m, 6H), 1.42 (s, 9H), 1.07-1.23 (m, 2H), 0.94 (t, J=6.4 Hz, 6H), 0.80 (d, J=6.8 Hz, 3H). The remaining mother liquor was concentrated in vacuo to afford 21.3 g of crude tert-butyl 2-bromo-5-[(1R,2S,5R)-2-isopropyl-5-methylcyclohexyl]-5,6,7,8,9,10-hexahydro-7,10-epiminocyclohepta[b]indole-carboxylate (major isomer: diastereomer B) as a foam.

Step C: To a solution of diastereomer A obtained from step B (15.6 g, 27.8 mmol) in tetrahydrofuran (186 mL) and MeOH (93 mL) was added a solution of lithium hydroxide monohydrate (3.51 g, 83.64 mmol) in water (47 mL) at ambient temperature. The mixture was stirred vigorously for 2.5 h, quenched with aqueous saturated NH$_4$Cl solution (100 mL), and extracted with ethyl acetate (2×250 mL). The combined extracts were dried (Na$_2$SO$_4$), filtered, and concentrated in vacuo. The residue was purified by column chromatography (SiO$_2$, hexane/ethyl acetate, 70:30) to afford (−)-tert-butyl 2-bromo-5,6,7,8,9,10-hexahydro-7,10-epiminocyclohepta[b]indole-carboxylate (10.2 g, 97%) as a white solid: $[α]_D$=−137.2° (c 0.03, MeOH); $^1$H NMR (CDCl$_3$, 300 MHz) δ 7.82 (s, 1H), 7.62 (d, J=1.5 Hz, 1H), 7.11-7.23 (m, 2H), 5.14 (s, 1H), 4.65 (s, 1H), 3.46 (s, 1H), 2.47 (d, J=15.9 Hz, 1H), 2.09-2.38 (m, 2H), 1.88-1.98 (m, 1H), 1.56-1.69 (m, 1H), 1.38 (s, 9H).

Step D: To a solution of major isomer:diastereomer B obtained from step B (21.3 g, 38.1 mmol) in CH$_2$Cl$_2$ (348 mL) was added CF$_3$CO$_2$H (38.8 mL) at 0° C. under an argon atmosphere. After stirring for 3 h at 0° C., the mixture was concentrated in vacuo. The residue was dissolved in CH$_2$Cl$_2$ (100 mL), quenched with 10% aqueous NaHCO$_3$ solution (40 mL), and extracted with CH$_2$Cl$_2$ (2×100 mL). The combined extracts were dried (Na$_2$SO$_4$), filtered, and concentrated in vacuo. The residue was purified by column chromatography (SiO$_2$, CH$_2$Cl$_2$/MeOH, 70:30) to afford 2-bromo-5-[(1R,2S,5R)-2-isopropyl-5-methylcyclohexyl]-5,6,7,8,9,10-hexahydro-7,10-epiminocyclohepta[b]indole (13.3 g, 76%) as a foam. A quantity of this amine (9.0 g) was eluted through a Chiralcel OD preparative column (heptane/isopropanol, 99:1+0.1% v/v diethylamine) to afford chirally pure 2-bromo-5-[(1R,2S,5R)-2-isopropyl-5-methylcyclohexyl]-5,6,7,8,9,10-hexahydro-7,10-epiminocyclohepta[b]indole (diastereomer B) (7.93 g) as a foam: $^1$H NMR (CDCl$_3$, 300 MHz) δ 7.99 (d, J=8.7 Hz, 1H), 7.55 (d, J=1.8 Hz, 1H), 7.30-7.38 (m, 1H), 4.94 (dt, J=11.1, 4.5 Hz, 1H), 4.46 (d, J=4.8 Hz, 1H), 3.99-4.10 (m, 1H), 3.39 (dd, J=18.0, 4.5 Hz, 1H), 2.84 (d, J=18.0 Hz, 1H), 1.90-2.29 (m, 6H), 1.46-1.83 (m, 5H), 1.05-1.23 (m, 2H), 0.94 (dd, J=7.2, 1.2 Hz, 6H), 0.81 (d, J=6.9 Hz, 3H).

Step E: To a solution of the product from step D (7.0 g, 15.2 mmol) in isopropanol (55 mL) and H$_2$O (47 mL) was added K$_2$CO$_3$ (6.31 g, 45.7 mmol) followed by di-tert-butyl dicarbonate (4.15 g, 19.0 mmol) at 0° C. The mixture was stirred for 2 h, diluted with H$_2$O (100 mL) and extracted with CH$_2$Cl$_2$ (2×150 mL). The combined extracts were dried (Na$_2$SO$_4$), filtered, and concentrated in vacuo to afford tert-butyl 2-bromo-5-[(1R,2S,5R)-2-isopropyl-5-methylcyclohexyl]-5,6,7,8,9,10-hexahydro-7,10-epiminocyclohepta[b]indole-carboxylate (diastereomer B) (8.51 g) as a white solid. The crude product was used in the next step without further purification: $^1$H NMR (CDCl$_3$, 300 MHz) δ 8.0 (s, 1H), 7.57 (d, J=1.8 Hz, 1H), 7.31-7.39 (m, 1H), 5.11 (s, 1H), 4.94 (dt, J=11.1, 4.5 Hz, 1H), 4.63 (s, 1H), 3.41-3.68 (m, 1H), 2.82 (d, J=17.7 Hz, 1H), 2.07-2.38 (m, 3H), 1.90-2.05 (m, 2H), 1.50-1.83 (m, 6H), 1.42 (s, 9H), 1.05-1.30 (m, 2H), 0.95 (dd, J=7.2, 1.2 Hz, 6H), 0.82 (d, J=6.9 Hz, 3H).

Step F: To a solution of the product from step E (8.51 g, 15.23 mmol) in tetrahydrofuran (102 mL) and MeOH (51 mL) was added a solution of lithium hydroxide monohydrate (1.92 g, 45.69 mmol) in water (25 mL) at ambient temperature. The mixture was stirred vigorously for 2.5 h, quenched with aqueous saturated NH$_4$Cl solution (75 mL), and extracted with ethyl acetate (2×200 mL). The combined extracts were dried (Na$_2$SO$_4$), filtered, and concentrated in vacuo. The residue was purified by column chromatography (SiO$_2$, hexane/ethyl acetate, 70:30) to afford (+)-tert-butyl 2-bromo-5,6,7,8,9,10-hexahydro-7,10-epiminocyclohepta[b]indole-carboxylate (5.29 g, 92%) as a white solid: [α]$_D$=+142.4° (c 0.33, MeOH); $^1$H NMR (CDCl$_3$, 300 MHz) δ 7.93 (s, 1H), 7.61 (d, J=0.9 Hz, 1H), 7.11-7.23 (dd, J=16.8, 8.4 Hz, 2H), 5.14 (s, 1H), 4.65 (s, 1H), 3.28-3.57 (m, 1H), 2.47 (d, J=16.2 Hz, 1H), 2.10-2.38 (m, 2H), 1.88-1.98 (m, 1H), 1.54-1.70 (m, 1H), 1.38 (s, 9H).

By methods as described above, the compounds listed in TABLE 1 were synthesized.

TABLE 1

| Ex. No. | Structure | Mass Spec | $^1$H NMR Data |
|---|---|---|---|
| 94 | (structure) •HCl | 392 | $^1$H NMR (DMSO-d$_6$, 300 MHz) δ 11.58 (s, 1H), 9.28 (br s, 1H), 9.00 (br s, 1H), 8.32 (d, J = 1.2 Hz, 1H), 8.20 (d, J = 1.8 Hz, 1H), 7.68-7.50 (m, 5H), 6.65-6.60 (m, 1H), 5.36 (br s, 1H), 4.47 (br s, 1H), 3.73 (s, 3H), 3.40-3.28 (m, 1H), 3.00 (d, J = 17.1 Hz, 1H), 2.30-2.20 (m, 2H), 2.14-2.04 (m, 1H), 1.83-1.73 (m, 1H) |
| 95 | (structure) •HCl | 392 | $^1$H NMR (DMSO-d$_6$, 300 MHz) δ 11.69 (s, 1H), 9.58 (br s, 1H), 9.11 (br s, 1H), 8.40 (s, 1H), 8.02 (s, 1H), 7.68 (d, J = 8.4 Hz, 1H), 7.65-7.59 (m, 3H), 7.47 (dd, J = 8.4, 1.5 Hz, 1H), 6.56-6.50 (m, 1H), 5.35 (d, J = 3.9 Hz, 1H), 4.45 (br s, 1H), 3.65 (s, 3H), 3.38-3.28 (m, 1H), 2.99 (d, J = 17.4 Hz, 1H), 2.32-2.21 (m, 2H), 2.13-2.04 (m, 1H), 1.84-1.73 (m, 1H) |
| 96 | (structure) •HCl | 372 | $^1$H NMR (DMSO-d$_6$, 300 MHz) δ 9.30 (br s, 2H), 8.67 (d, J = 2.7 Hz, 1H), 8.36-8.26 (m, 2H), 8.03 (td, J = 8.7, 2.7 Hz, 1H), 7.68 (d, J = 0.9 Hz, 2H), 5.35 (d, J = 4.2 Hz, 1H), 4.51-4.42 (m, 1H), 3.69 (s, 3H), 3.38 (dd, J = 17.4, 4.5 Hz, 1H), 3.01 (d, J = 17.1 Hz, 1H), 2.31-2.22 (m, 2H), 2.12-2.02 (m, 1H), 1.83-1.73 (m, 1H) |
| 97 | (structure) •HCl | 388 | $^1$H NMR (DMSO-d$_6$, 300 MHz) δ 9.47 (br s, 1H), 9.13-9.05 (m, 1H), 8.62 (d, J = 5.7 Hz, 1H), 8.37 (s, 1H), 8.26 (d, J = 1.5 Hz, 1H), 7.81 (dd, J = 5.1, 1.8 Hz, 1H), 7.72-7.69 (m, 2H), 5.36 (br s, 1H), 4.48 (br s, 1H), 3.69 (s, 3H), 3.42-3.32 (m, 1H), 3.02 (d, J = 17.4 Hz, 1H), 2.32-2.21 (m, 2H), 2.13-2.04 (m, 1H), 1.88-1.75 (m, 1H) |
| 98 | (structure) •HCl | 392 | $^1$H NMR (CD$_3$OD, 300 MHz) δ 8.31 (d, J = 1.8 Hz, 1H), 7.97 (s, 1H), 7.85-7.75 (m, 2H), 7.56-7.41 (m, 2H), 7.26-7.10 (m, 2H), 5.29 (d, J = 4.8 Hz, 1H), 4.58-4.48 (m, 1H), 3.68 (s, 3H), 3.45 (dd, J = 17.4, 4.8 Hz, 1H), 3.04 (dd, J = 17.4, 1.2 Hz, 1H), 2.52-2.21 (m, 3H), 2.02-1.90 (m, 1H) |
| 99 | (structure) •HCl | 392 | $^1$H NMR (DMSO-d$_6$, 300 MHz) δ 11.26 (s, 1H), 9.16 (br s, 2H), 8.59 (d, J = 1.5 Hz, 1H), 7.88-7.69 (m, 3H), 7.60 (d, J = 8.7 Hz, 1H), 7.43 (t, J = 2.7 Hz, 1H), 7.18 (t, J = 7.8 Hz, 1H), 6.62-6.55 (m, 1H), 5.26 (d, J = 4.2 Hz, 1H), 4.52-4.42 (m, 1H), 3.64 (s, 3H), 3.40-3.28 (m, 1H), 2.98 (d, J = 17.1 Hz, 1H), 2.35-2.20 (m, 2H), 2.13-2.03 (m, 1H), 1.87-1.71 (m, 1H) |

TABLE 1-continued

| Ex. No. | Structure | Mass Spec | ¹H NMR Data |
|---|---|---|---|
| 100 | 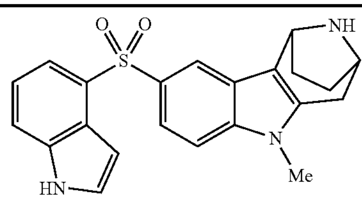 | 392 | ¹H NMR (DMSO-d₆, 300 MHz) δ 11.63 (s, 1H), 9.13 (br s, 2H), 8.40 (d, J = 1.5 Hz, 1H), 7.77-7.50 (m, 5H), 7.27 (t, J = 7.8 Hz, 1H), 6.87-6.81 (m, 1H), 5.35 (d, J = 3.9 Hz, 1H), 4.50-4.40 (m, 1H), 3.63 (s, 3H), 3.39-3.28 (m, 1H), 2.97 (d, J = 17.7 Hz, 1H), 2.31-2.18 (m, 2H), 2.10-1.99 (m, 1H), 1.83-1.70 (m, 1H) |
| 101 | 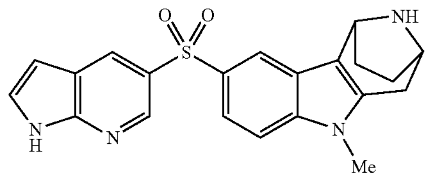 | 393 | ¹H NMR (DMSO-d₆, 300 MHz) δ 12.23 (s, 1H), 9.34 (br s, 1H), 9.00 (br s, 1H), 8.74 (d, J = 2.1 Hz, 1H), 8.53 (d, J = 2.1 Hz, 1H), 8.40 (d, J = 1.5 Hz, 1H), 7.76-7.60 (m, 3H), 6.63 (dd, J = 3.3, 1.8 Hz, 1H), 5.36 (d, J = 3.6 Hz, 1H), 4.53-4.41 (m, 1H), 3.66 (s, 3H), 3.40-3.30 (m, 1H), 3.00 (d, J = 17.1 Hz, 1H), 2.32-2.20 (m, 2H), 2.15-2.06 (m, 1H), 1.86-1.72 (m, 1H) |
| 102 | 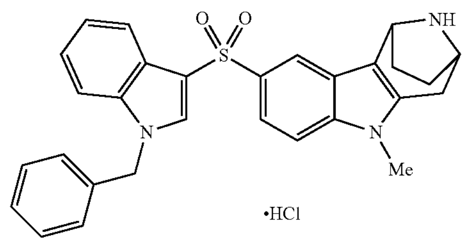 [SMILES: Cn1c2c(c3cc(S(=O)(=O)c4cn(Cc5ccccc5)c5ccccc45)ccc31)C1CCC(C2)N1 ; Cl] | 482 | ¹H NMR (DMSO-d₆, 400 MHz) δ 9.09 (br s, 2H), 8.39 (d, J = 1.6 Hz, 1H), 8.38 (s, 1H), 7.79 (dd, J = 7.2, 0.8 Hz, 1H), 7.68 (dd, J = 8.8, 1.6 Hz, 1H), 7.60 (d, J = 8.8 Hz, 1H), 7.54 (d, J = 8.0 Hz, 1H), 7.36-7.13 (m, 7H), 5.52 (s, 2H), 5.35 (d, J = 4.0 Hz, 1H), 4.50-4.42 (m, 1H), 3.64 (s, 3H), 3.29-3.38 (m, 1H), 2.98 (d, J = 17.2 Hz, 1H), 2.30-2.20 (m, 2H), 2.10-2.02 (m, 1H), 1.84-1.72 (m, 1H) |
| 103 | 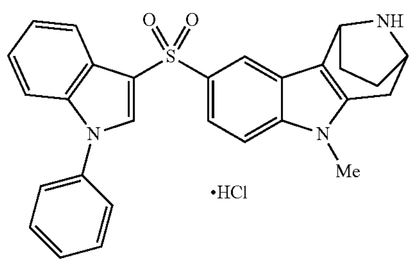 [SMILES: Cn1c2c(c3cc(S(=O)(=O)c4cn(-c5ccccc5)c5ccccc45)ccc31)C1CCC(C2)N1 ; Cl] | 468 | ¹H NMR (DMSO-d₆, 400 MHz) δ 9.13 (br s, 2H), 8.47 (d, J = 1.6 Hz, 1H), 8.39 (s, 1H), 7.95-7.90 (m, 1H), 7.79 (dd, J = 8.8, 1.6 Hz, 1H), 7.69-7.60 (m, 5H), 7.56-7.49 (m, 2H), 7.34-7.26 (m, 2H), 5.36 (d, J = 4.0 Hz, 1H), 4.51-4.43 (m, 1H), 3.65 (s, 3H), 3.39-3.30 (m, 1H), 2.99 (d, J = 17.2 Hz, 1H), 2.30-2.20 (m, 2H), 2.12-2.04 (m, 1H), 1.84-1.73 (m, 1H) |
| 104 | 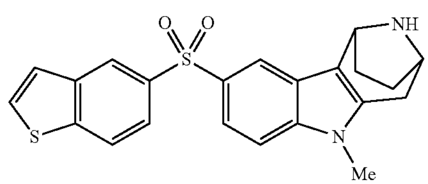 | 409 | ¹H NMR (DMSO-d₆, 300 MHz) δ 9.21 (br s, 2H), 8.53 (d, J = 1.5 Hz, 1H), 8.39 (d, J = 1.2 Hz, 1H), 8.21 (d, J = 8.4 Hz, 1H), 7.97 (d, J = 5.4 Hz, 1H), 7.82 (dd, J = 8.7, 1.8 Hz, 1H), 7.72-7.62 (m, 3H), 5.33 (d, J = 3.6 Hz, 1H), 4.45 (br s, 1H), 3.66 (s, 3H), 3.43-3.35 (m, 1H), 2.99 (d, J = 17.4 Hz, 1H), 2.36-2.18 (m, 2H), 2.17-1.99 (m, 1H), 1.86-1.69 (m, 1H) |
| 105 | 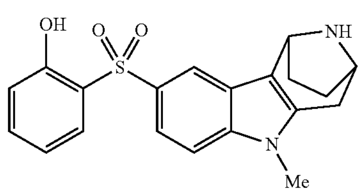 | 369 | ¹H NMR (DMS0-d₆, 300 MHz) δ 10.62 (br s, 1H), 9.29 (br s, 2H), 8.25 (s, 1H), 7.91 (dd, J = 8.1, 1.8 Hz, 1H), 7.66-7.54 (m, 2H), 7.43 (t, J = 8.7 Hz, 1H), 6.98 (t, J = 7.2 Hz, 1H), 6.91 (d, J = 8.1 Hz, 1H), 5.31 (d, J = 3.6 Hz, 1H), 4.46 (br s, 1H), 3.68 (s, 3H), 3.46-3.35 (m, 1H), 3.00 (d, J = 17.1 Hz, 1H), 2.35-2.18 (m, 2H), 2.16-1.97 (m, 1H), 1.89-1.65 (m, 1H) |
| 106 | 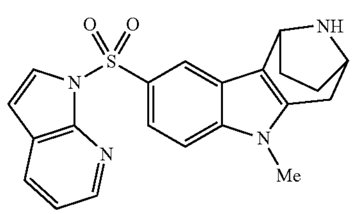 | 393 | ¹H NMR (CD₃OD, 300 MHz) δ 8.49 (d, J = 1.2 Hz, 1H), 8.32 (s, 1H), 8.04 (br s, 1H), 7.92-7.88 (m, 1H), 7.85 (dd, J = 8.8, 1.6 Hz, 1H), 7.52 (d, J = 8.8 Hz, 1H), 7.32-7.24 (m, 1H), 6.74 (br s, 1H), 5.31 (d, J = 5.2 Hz, 1H), 4.53 (t, J = 4.8 Hz, 1H), 3.68 (s, 3H), 3.48-3.42 (m, 1H), 3.04 (dd, J = 17.4, 1.2 Hz, 1H), 2.51-2.33 (m, 2H), 2.29-2.21 (m, 1H), 2.01-1.91 (m, 1H) |

TABLE 1-continued

| Ex. No. | Structure | Mass Spec | ¹H NMR Data |
|---|---|---|---|
| 107 | (structure) ·HCl | 393 | ¹H NMR (CD₃OD, 300 MHz) δ 9.22 (d, J = 8.7 Hz, 1H), 8.73 (d, J = 5.7 Hz, 1H), 8.60 (d, J = 3.9 Hz, 1H), 8.56 (d, J = 1.8 Hz, 1H), 7.86-7.93 (m, 2H), 7.62 (d, J = 9.0 Hz, 1H), 7.11 (d, J = 4.2 Hz, 1H), 5.35 (d, J = 4.8 Hz, 1H), 4.59-4.51 (m, 1H), 3.71 (s, 3H), 3.47 (dd, J = 17.4, 5.1 Hz, 1H), 3.07 (d, J = 17.7 Hz, 1H), 2.48-2.34 (m, 2H), 2.28-2.21 (m, 1H), 1.98-1.91 (m, 1H) |
| 108 | (structure) ·HCl | 393 | ¹H NMR (CD₃OD, 300 MHz) δ 9.67 (s, 1H), 8.61 (s, 2H), 8.49 (d, J = 5.7 Hz, 1H), 8.22 (d, J = 6.0 Hz, 1H), 7.92 (d, J = 8.4 Hz, 1H), 7.63 (d, J = 8.4 Hz, 1H), 7.19 (s, 1H), 5.38 (br s, 1H), 4.56 (br s, 1H), 3.72 (s, 3H), 3.49 (d, J = 14.7 Hz, 1H), 3.09 (d, J = 9.3 Hz, 1H), 2.51-2.37 (m, 2H), 2.32-2.20 (m, 1H), 2.02-1.88 (m, 1H) |
| 109 | (structure) ·HCl | 420 | ¹H NMR (DMSO-d₆, 400 MHz) δ 9.17 (br s, 2H), 8.38 (d, J = 1.6 Hz, 1H), 8.22 (s, 1H), 7.80 (d, J = 8.0 Hz, 1H), 7.66 (d, J = 8.0 Hz, 1H), 7.60-7.56 (m, 2H), 7.25-7.23 (m, 1H), 7.20-7.16 (m, 1H), 5.36 (d, J = 4.0 Hz, 1H), 4.45 (br s, 1H), 4.29 (dd, J = 16.0, 7.5 Hz, 2H), 3.65 (s, 3H), 3.00 (d, J = 15.0 Hz, 1H), 2.70-2.50 (m, 1H), 2.24-2.21 (m, 2H), 2.06 (t, J = 8.0 Hz, 1H), 1.80-1.76 (m, 1H), 1.39 (t, J = 7.2 Hz, 3H) |
| 110 | (structure) ·HCl | 404 | ¹H NMR (DMSO-d₆, 300 MHz) δ 9.41 (br s, 1H), 9.10-8.94 (m, 3H), 8.55-8.44 (m, 2H), 8.34 (d, J = 8.4 Hz, 1H), 8.00 (t, J = 7.5 Hz, 1H), 7.66-7.56 (m, 3H), 5.38 (br s, 1H), 4.46 (br s, 1H), 3.64 (s, 3H), 3.34 (dd, 13.5, 3.9 Hz, 1H), 2.99 (d, J = 17.7 Hz, 1H), 2.35-2.00 (m, 3H), 1.86-1.70 (m, 1H) |
| 111 | (structure) ·HCl | 404 | ¹H NMR (DMSO-d₆, 300 MHz) δ 9.58-9.33 (br s, 2H), 9.02 (br s, 1H), 8.67 (d, J = 7.5 Hz, 1H), 8.61 (d, J = 6.0 Hz, 1H), 8.54-8.44 (m, 3H), 7.95 (t, J = 8.1 Hz, 1H), 7.70-7.58 (m, 2H), 5.38 (br s, 1H), 4.46 (br s, 1H), 3.65 (s, 3H), 3.34 (dd, J = 12.6, 4.5 Hz, 1H), 2.99 (d, J = 17.4 Hz, 1H), 2.31-2.00 (m, 3H), 1.83-1.70 (m, 1H) |
| 112 | (structure) ·HCl | 371 | ¹H NMR (CD₃OD, 300 MHz) δ 8.29 (s, 1H), 8.13-8.08 (m, 1H), 7.76-7.72 (m, 1H), 7.66-7.56 (m, 2H), 7.43-7.37 (m, 1H), 7.21-7.15 (m, 1H), 5.30 (d, J = 4.8 Hz, 1H), 4.54 (br s, 1H), 3.73 (s, 3H), 3.49 (dd, J = 17.4, 4.5 Hz, 1H), 3.08 (d, J = 17.4 Hz, 1H), 2.55-2.18 (m, 3H), 1.99-1.88 (m, 1H) |
| 113 | (structure) ·HCl | 404 | ¹H NMR (CD₃OD, 300 MHz) δ 8.93 (s, 1H), 8.70 (d, J = 7.5 Hz, 1H), 8.50 (s, 1H), 8.48-8.37 (m, 1H), 8.26 (d, J = 8.1 Hz, 1H), 7.96-7.86 (m, 1H), 7.81 (t, J = 8.1 Hz, 1H), 7.64-7.52 (m, 1H), 7.50 (d, J = 8.7 Hz, 1H), 5.30 (br s, 1H), 4.53 (br s, 1H), 3.68 (s, 3H), 3.46 (dd, J = 12.6, 4.8 Hz, 1H), 3.04 (d, J = 17.1 Hz, 1H), 2.51-2.21 (m, 3H), 2.02-1.90 (m, 1H) |

TABLE 1-continued

| Ex. No. | Structure | Mass Spec | ¹H NMR Data |
|---|---|---|---|
| 114 | 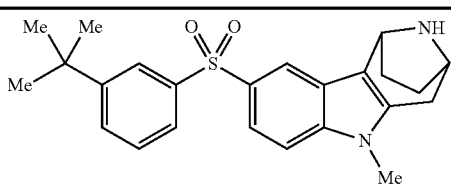 ·HCl | 409 | ¹H NMR (CD$_3$OD, 300 MHz) δ 8.27 (d, J = 1.5 Hz, 1H), 7.95 (t, J = 2.1 Hz, 1H), 7.77-7.69 (m, 2H), 7.67-7.63 (m, 1H), 7.58 (d, J = 9.0 Hz, 1H), 7.46 (t, J = 7.8 Hz, 1H), 5.28 (br s, 1H), 4.54 (br s, 1H), 3.71 (s, 3H), 3.47 (dd, J = 17.4, 4.2 Hz, 1H), 3.05 (d, J = 17.1 Hz, 1H), 2.47-2.21 (m, 3H), 2.02-1.94 (m, 1H), 1.32 (s, 9H) |
| 115 | 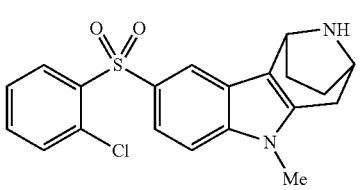 ·HCl | 387 | ¹H NMR (DMSO-d$_6$, 300 MHz) δ 9.30 (br s, 2H), 8.34 (d, J = 1.5 Hz, 1H), 8.29-8.22 (m, 1H), 7.70-7.62 (m, 2H), 7.61-7.55 (m, 3H), 5.35 (d, J = 3.9 Hz, 1H), 4.46 (br s, 1H), 3.69 (s, 3H), 3.41 (dd, J = 17.4, 5.7 Hz, 1H), 3.01 (d, J = 17.1 Hz, 1H), 2.32-2.21 (m, 2H), 2.09-2.01 (m, 1H), 1.85-1.75 (m, 1H) |
| 116 | 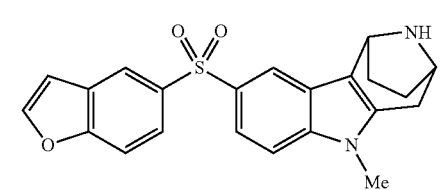 ·HCl | 393 | ¹H NMR (DMSO-d$_6$, 300 MHz) δ 9.56 (br s, 1H), 9.13 (br s, 1H), 8.38 (d, J = 1.2 Hz, 1H), 8.32 (d, J = 1.8 Hz, 1H), 8.17 (d, J = 2.1 Hz, 1H), 7.86 (dd, J = 6.6, 2.1 Hz, 1H), 7.78 (d, J = 8.7 Hz, 1H), 7.72-7.58 (m, 2H), 7.12-7.11 (m, 1H), 5.35 (d, J = 4.2 Hz, 1H), 4.46 (br s, 1H), 3.66 (s, 3H), 3.37 (dd, J = 17.4, 4.5 Hz, 1H), 3.00 (d, J = 17.1 Hz, 1H), 2.35-2.15 (m, 2H), 2.13-2.02 (m, 1H), 1.88-1.70 (m, 1H) |
| 117 | 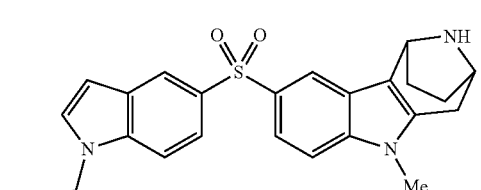 ·HCl | 434 | ¹H NMR (DMSO-d$_6$, 300 MHz) δ 9.23 (br s, 2H), 8.33 (d, J = 1.5 Hz, 1H), 8.20 (d, J = 1.5 Hz, 1H), 7.70-7.55 (m, 5H), 6.66 (d, J = 3.3 Hz, 1H), 5.34 (d, J = 3.6 Hz, 1H), 4.85-4.70 (m, 1H), 4.45 (br s, 1H), 3.65 (s, 3H), 3.42-3.30 (m, 1H), 2.99 (d, J = 17.1 Hz, 1H), 2.32-2.17 (m, 2H), 2.10-1.98 (m, 1H), 1.82-1.70 (m, 1H), 1.42 (d, J = 6.6 Hz, 6H) |
| 118 | 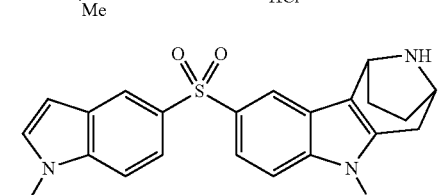 ·HCl | 420 | ¹H NMR (DMSO-d$_6$, 300 MHz) δ 9.24 (br s, 2H), 8.33 (s, 1H), 8.20 (s, 1H), 7.62-7.55 (m, 5H), 6.63 (d, J = 3.3 Hz, 1H), 5.34 (d, J = 3.9 Hz, 1H), 4.45 (br s, 1H), 4.23 (q, J = 7.2 Hz, 2H), 3.65 (s, 3H), 3.45-3.35 (m, 1H), 2.99 (d, J = 17.4 Hz, 1H), 2.33-2.18 (m, 2H), 2.13-2.00 (m, 1H), 1.86-1.70 (m, 1H), 1.32 (t, J = 7.2 Hz, 3H) |
| 119 | 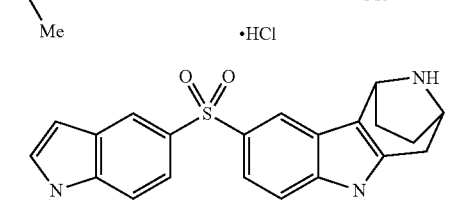 ·HCl | 436 | ¹H NMR (DMSO-d$_6$, 300 MHz) δ 9.80 (br s, 1H), 9.17 (br s, 1H), 8.33 (d, J = 1.2 Hz, 1H), 8.19 (s, 1H), 7.68-7.50 (m, 5H), 6.62 (d, J = 3.0 Hz, 1H), 5.33 (s, 1H), 4.88 (t, J = 5.4 Hz, 1H), 4.44 (s, 1H), 4.23 (t, J = 5.4 Hz, 2H), 3.72-3.62 (m, 5H), 3.42-3.31 (m, 1H), 2.98 (d, J = 17.1 Hz, 1H), 2.38-1.98 (m, 3H), 1.85-1.65 (m, 1H) |
| 120 | 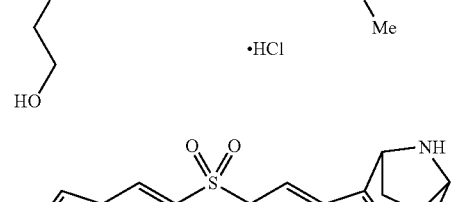 ·HCl | 450 | ¹H NMR (DMSO-d$_6$, 300 MHz) δ 9.53 (br s, 1H), 9.11 (br s, 1H), 8.33 (d, J = 1.5 Hz, 1H), 8.19 (d, J = 1.2 Hz, 1H), 7.67-7.50 (m, 5H), 6.63 (d, J = 3.0 Hz, 1H), 5.35 (d, J = 3.9 Hz, 1H), 4.45 (br s, 1H), 4.36 (t, J = 5.1 Hz, 2H), 3.65 (s, 3H), 3.61 (t, J = 5.1 Hz, 2H), 3.42-3.30 (m, 1H), 3.16 (s, 3H), 2.94 (d, J = 17.1 Hz, 1H), 2.35-2.20 (m, 3H), 1.85-1.70 (m, 1H) |

TABLE 1-continued

| Ex. No. | Structure | Mass Spec | ¹H NMR Data |
|---|---|---|---|
| 121 | 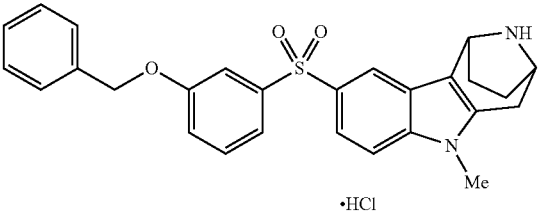 [SMILES: Cn1c2c(c3cc(S(=O)(=O)c4cccc(OCc5ccccc5)c4)ccc31)C1CCC(C2)N1 ; Cl] •HCl | 459 | ¹H NMR (CD$_3$OD, 300 MHz) δ 8.24 (d, 1H), 7.68 (dd, J = 6.9, 1.8 Hz, 1H), 7.54-7.26 (m, 9H), 7.22-7.15 (m, 1H), 5.28 (d, J = 4.8 Hz, 1H), 5.12 (s, 2H), 4.53-4.45 (m, 1H), 3.72 (s, 3H), 3.53-3.43 (m, 1H), 3.07 (d, J = 17.4 Hz, 1H), 2.46-2.19 (m, 3H), 2.02-1.89 (m, 1H) |
| 122 | 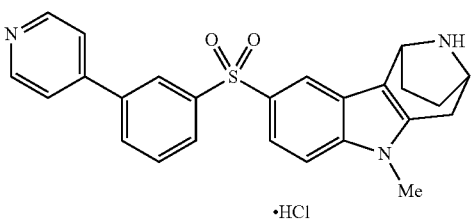 [SMILES: Cn1c2c(c3cc(S(=O)(=O)c4cccc(-c5ccncc5)c4)ccc31)C1CCC(C2)N1 ; Cl] •HCl | 430 | ¹H NMR (CD$_3$OD, 300 MHz) δ 8.94 (d, J = 6.9 Hz, 2H), 8.56 (t, J = 1.8 Hz, 1H), 8.51-8.43 (m, 2H), 8.38 (d, J = 1.5 Hz, 1H), 8.24-8.15 (m, 2H), 7.87-7.77 (m, 2H), 7.60 (d, J = 9.0 Hz, 1H), 5.32 (d, J = 4.5 Hz, 1H), 4.61-4.50 (m, 1H), 3.72 (s, 3H), 3.50 (dd, J = 17.7, 4.8 Hz, 1H), 3.08 (d, J = 17.4 Hz, 1H), 2.50-2.20 (m, 3H), 2.00-1.86 (m, 1H) |
| 123 | 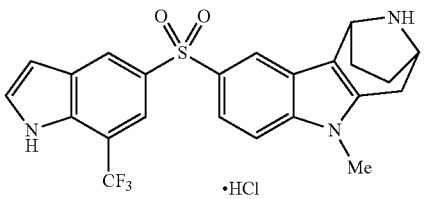 •HCl | 460 | ¹H NMR (DMSO-d$_6$, 300 MHz) δ 12.05 (s, 1H), 9.20 (br s, 2H), 8.53 (s, 1H), 8.41 (d, J = 1.4 Hz, 1H), 7.88 (br s, 1H), 7.72 (dd, J = 8.8, 1.7 Hz, 1H), 7.67-7.63 (m, 2H), 6.85 (dd, J = 3.1, 1.5 Hz, 1H), 5.36 (br s, 1H), 4.46 (br s, 1H), 3.66 (s, 3H), 3.32-3.30 (m, 1H), 3.00 (d, J = 15.0 Hz, 1H), 2.28-2.20 (m, 2H), 2.09 (t, J = 9.0 Hz, 1H), 1.81-1.78 (m, 1H) |
| 124 | 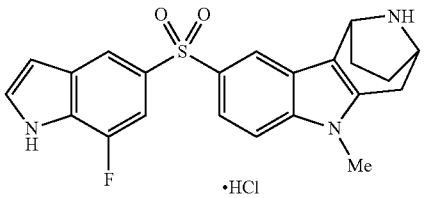 [SMILES: Cn1c2c(c3cc(S(=O)(=O)c4cc(F)c5[nH]ccc5c4)ccc31)C1CCC(C2)N1 ; Cl] •HCl | 410 | ¹H NMR (DMSO-d$_6$, 400 MHz) δ 12.18 (s, 1H), 9.58 (br s, 1H), 9.09 (br s, 1H), 8.37 (s, 1H), 8.08 (s, 1H), 7.70-7.60 (m, 3H), 7.43 (d, J = 10.8 Hz, 1H), 6.73 (br s, 1H), 5.36 (br s, 1H), 4.47 (br s, 1H), 3.66 (s, 3H), 3.38-3.32 (m, 1H), 2.99 (d, J = 17.7 Hz, 1H), 2.27 (br s, 2H), 2.11-2.09 (m, 1H), 1.81-1.79 (m, 1H) |
| 125 | 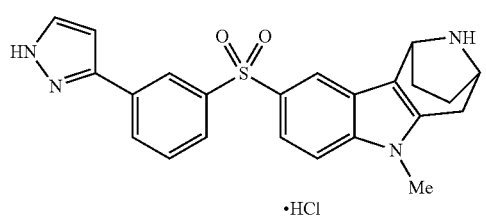 [SMILES: Cn1c2c(c3cc(S(=O)(=O)c4cccc(-c5cc[nH]n5)c4)ccc31)C1CCC(C2)N1 ; Cl] •HCl | 419 | ¹H NMR (DMSO-d$_6$, 400 MHz) δ 9.55 (br s, 1H), 9.07 (br s, 1H), 8.42 (s, 1H), 8.33 (s, 1H), 8.02 (d, J = 5.4 Hz, 1H), 7.84-7.61 (m, 6H), 6.83 (s, 1H), 5.37 (br s, 1H), 4.47 (br s, 1H), 3.67 (s, 3H), 3.37 (d, J = 16.4 Hz, 1H), 3.00 (d, J = 17.6 Hz, 1H), 2.37-2.27 (m, 2H), 2.11-2.04 (m, 1H), 1.90-1.88 (m, 1H) |
| 126 | 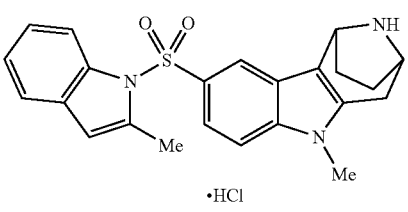 [SMILES: Cc1cc2ccccc2n1S(=O)(=O)c1ccc2c(c1)c1c(n2C)CC2CCC1N2 ; Cl] •HCl | 406 | ¹H NMR (DMSO-d$_6$, 300 MHz) δ 9.28 (br s, 2H), 8.40 (s, 1H), 8.09 (d, J = 8.4 Hz, 1H), 7.57 (d, J = 9.0 Hz, 1H), 7.50-7.40 (m, 2H), 7.28-7.13 (m, 2H), 6.50 (s, 1H), 5.35 (d, J = 3.9 Hz, 1H), 4.44 (br s, 1H), 3.62 (s, 3H), 3.35 (d, J = 4.5 Hz, 1H), 2.97 (d, J = 17.4 Hz, 1H), 2.64 (s, 3H), 2.32-2.18 (m, 2H), 2.08-1.91 (m, 1H), 1.82-1.70 (m, 1H) |
| 127 | 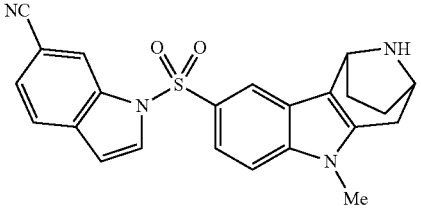 •HCl | 417 | ¹H NMR (DMSO-d$_6$, 300 MHz) δ 9.28 (br s, 2H), 8.67 (d, J = 1.6 Hz, 1H), 8.43 (s, 1H), 8.11 (d, J = 3.6 Hz, 1H), 7.80-7.72 (m, 2H), 7.65 (s, 1H), 7.60 (d, J = 8.4 Hz, 1H), 6.93 (d, J = 3.6 Hz, 1H), 5.37 (d, J = 4.5 Hz, 1H), 4.47 (br s, 1H), 3.64 (s, 3H), 3.36 (d, J = 5.4 Hz, 1H), 2.98 (d, J = 17.1 Hz, 1H), 2.34-2.20 (m, 2H), 2.05-1.90 (m, 1H), 1.80-1.71 (m, 1H) |

TABLE 1-continued

| Ex. No. | Structure | Mass Spec | $^1$H NMR Data |
|---|---|---|---|
| 128 | 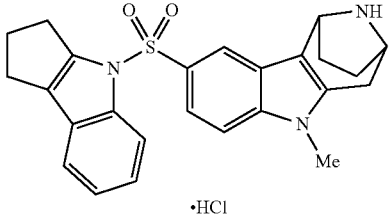 [SMILES: Cn1c2c(c3cc(S(=O)(=O)n4c5c(c6ccccc64)CCC5)ccc31)C1CCC(C2)N1 ; Cl] •HCl | 432 | $^1$H NMR (DMSO-d$_6$, 300 MHz) δ 9.37 (br s, 1H), 8.99 (br s, 1H), 8.40 (d, J = 1.5 Hz, 1H), 7.99 (d, J = 7.5 Hz, 1H), 7.61-7.51 (m, 2H), 7.35-7.30 (m, 1H), 7.25-7.13 (m, 2H), 5.37 (br s, 1H), 4.46 (br s, 1H), 3.62 (s, 3H), 3.42-3.12 (m, 3H), 2.98 (d, J = 17.1 Hz, 1H), 2.72-2.62 (m, 3H), 2.30-2.21 (m, 3H), 2.08-1.98 (m, 1H), 1.82-1.71 (m, 1H) |
| 129 | 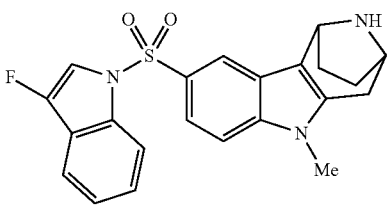 •HCl | 410 | $^1$H NMR (DMSO-d$_6$, 300 MHz) δ 9.31 (br s, 2H), 8.46 (s, 1H), 8.07 (d, J = 8.4 Hz, 1H), 7.90 (d, J = 1.8 Hz, 1H), 7.69-7.51 (m, 3H), 7.43 (t, J = 7.2 Hz, 1H), 7.30 (t, J = 7.5 Hz, 1H), 5.31 (br s, 1H), 4.46 (br s, 1H), 3.63 (s, 3H), 3.35-3.20 (m, 1H), 2.97 (d, J = 17.4 Hz, 1H), 2.32-2.20 (m, 2H), 2.10-1.94 (m, 1H), 1.82-1.70 (m, 1H) |
| 130 | 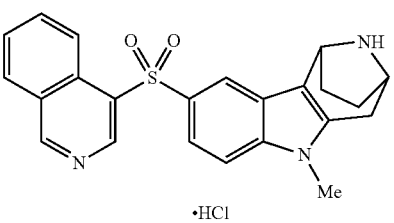 [SMILES: Cn1c2c(c3cc(S(=O)(=O)c4cncc5ccccc45)ccc31)C1CCC(C2)N1 ; Cl] •HCl | 404 | $^1$H NMR (DMSO-d$_6$, 300 MHz) δ 9.76 (s, 1H), 9.61 (s, 1H), 9.23 (s, 1H), 9.10 (d, J = 9.6 Hz, 1H), 8.61 (d, J = 8.4 Hz, 1H), 8.54 (d, J = 1.5 Hz, 1H), 8.29 (d, J = 7.8 Hz, 1H), 7.96-7.91 (m, 1H), 7.82-7.73 (m, 2H), 7.65-7.62 (d, J = 8.7 Hz, 1H), 5.37 (s, 1H), 4.45 (s, 1H), 3.65 (s, 3H), 3.35 (dd, J = 17.2, 4.5 Hz, 1H), 2.98 (d, J = 17.7 Hz, 1H), 2.32-2.23 (m, 2H), 2.07-2.02 (m, 1H), 1.79-1.74 (m, 1H) |
| 131 | 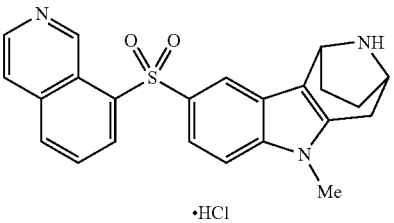 [SMILES: Cn1c2c(c3cc(S(=O)(=O)c4cccc5ccncc45)ccc31)C1CCC(C2)N1 ; Cl] •HCl | 404 | $^1$H NMR (DMSO-d$_6$, 300 MHz) δ 10.01 (s, 1H), 9.63 (d, J = 5.4 Hz, 1H), 9.11 (d, J = 10.5 Hz, 1H), 8.65 (d, J = 5.7 Hz, 1H), 8.59 (s, 1H), 8.55-8.53 (d, J = 6.9 Hz, 1H), 8.39-8.36 (d, J = 8.4 Hz, 1H), 8.09-8.04 (m, 2H), 7.65 (s, 2H), 5.41 (s, 1H), 4.46 (s, 1H), 3.75 (s, 3H), 3.35 (dd, J = 17.5, 4.5 Hz, 1H), 2.99 (d, J = 17.1 Hz, 1H), 2.31-2.23 (m, 2H), 2.09-2.03 (m, 1H), 1.78-1.75 (m, 1H) |
| 132 | 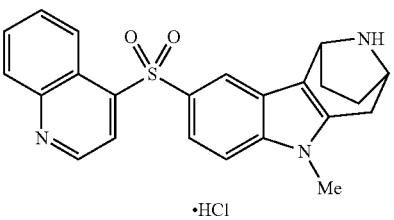 [SMILES: Cn1c2c(c3cc(S(=O)(=O)c4ccnc5ccccc45)ccc31)C1CCC(C2)N1 ; Cl] •HCl | 404 | $^1$H NMR (DMSO-d$_6$, 300 MHz) δ 9.55-9.65 (m, 1H), 9.20 (d, J = 4.5 Hz, 1H), 9.07 (d, J = 10.2 Hz, 1H), 8.71-8.63 (m, 1H), 8.54 (d, J = 1.5 Hz, 1H), 8.18-8.14 (m, 2H), 7.88-7.82 (m, 1H), 7.76-7.70 (m, 2H), 7.68-7.65 (m, 1H), 5.38 (s, 1H), 4.46 (s, 1H), 3.63 (s, 3H), 3.32 (d, J = 4.5 Hz, 1H), 3.02-2.96 (d, J = 17.7 Hz, 1H), 2.31-2.20 (m, 2H), 2.10-2.03 (m, 1H), 1.79-1.75 (m, 1H) |
| 133 | 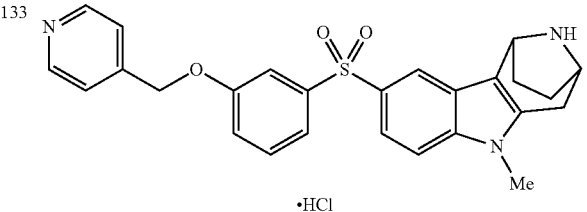 •HCl | 460 | $^1$H NMR (CD$_3$OD, 300 MHz) δ 8.78 (d, J = 6.3 Hz, 2H), 8.27 (d, J = 1.5 Hz, 1H), 8.03 (d, J = 6.0 Hz, 2H), 7.72 (dd, J = 10.5, 1.8 Hz, 1H), 7.65-7.48 (m, 4H), 7.32-7.28 (m, 1H), 5.51 (s, 2H), 5.30 (d, J = 4.8 Hz, 1H), 4.57-4.55 (m, 1H), 3.75 (s, 3H), 3.49 (dd, J = 11.2, 5.1 Hz, 1H), 3.11-3.05 (m, 1H), 2.53-2.25 (m, 3H), 2.09-1.91 (m, 1H) |

TABLE 1-continued

| Ex. No. | Structure | Mass Spec | ¹H NMR Data |
|---|---|---|---|
| 134 | 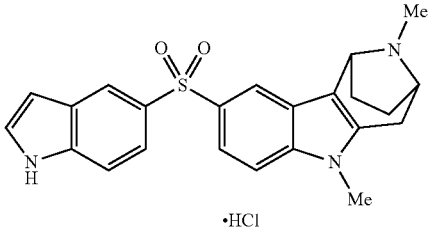 [SMILES: CN1C2CCC1c1c(n(C)c3ccc(S(=O)(=O)c4ccc5[nH]ccc5c4)cc13)C2 ; Cl] •HCl | 406 | ¹H NMR (DMSO-d$_6$, 300 MHz) δ 11.6 (br s, 1H), 10.89-10.22 (m, 1H), 8.23 (s, 1H), 8.20 (s, 1H), 7.69-7.64 (m, 1H), 7.63 (s, 1H), 7.61-7.56 (m, 1H), 7.55-7.51 (m, 2H), 6.63-6.61 (m, 1H), 5.24 (s, 1H), 4.34-4.22 (m, 1H), 3.67 (s, 3H), 3.52-3.39 (m, 1H), 3.13-2.98 (m, 1H), 2.83-2.61 (m, 3H), 2.43-2.28 (m, 2H), 2.15-2.03 (m, 1H), 1.88-1.78 (m, 1H) |
| 135 | 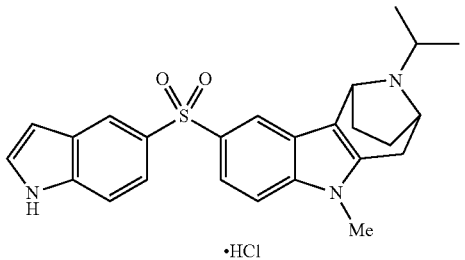 [SMILES: CC(C)N1C2CCC1c1c(n(C)c3ccc(S(=O)(=O)c4ccc5[nH]ccc5c4)cc13)C2 ; Cl] •HCl | 434 | ¹H NMR (DMSO-d$_6$, 300 MHz) δ 11.6 (s, 1H), 10.64-9.54 (m, 1H), 8.44 (d, J = 15.3 Hz, 1H), 8.20 (s, 1H), 7.67-7.55 (m, 3H), 7.54-7.49 (m, 2H), 6.62 (s, 1H), 5.61-5.52 (m, 1H), 4.62-4.43 (m, 1H), 3.66 (s, 3H), 3.44-3.34 (m, 1H), 3.17-3.07 (m, 1H), 3.00 (d, J = 17.7 Hz, 1H), 2.48-2.27 (m, 2H), 2.12-1.98 (m, 1H), 1.92-1.78 (m, 1H), 1.43-1.34 (m, 4H), 2.00 (d, J = 6.3 Hz, 2H) |
| 136 | 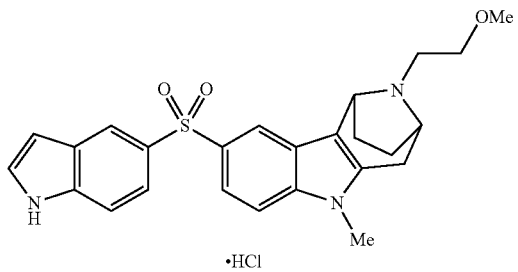 [SMILES: COCCN1C2CCC1c1c(n(C)c3ccc(S(=O)(=O)c4ccc5[nH]ccc5c4)cc13)C2 ; Cl] •HCl | 450 | ¹H NMR (DMSO-d$_6$, 400 MHz) δ 11.6 (br s, 1H), 10.50 (br s, 0.6H), 10.10 (br s, 0.4H), 8.28 (dd, J = 12.0, 1.6 Hz, 1H), 8.20 (s, 1H), 7.67-7.58 (m, 3H), 7.57-7.51 (m, 2H), 6.62-6.61 (m, 1H), 5.37 (s, 1H), 4.47-4.35 (m, 1H), 3.83-3.64 (m, 1H), 3.66 (s, 3H), 3.64-3.40 (m, 2H), 3.23 (s, 3H), 3.19-3.01 (m, 2H), 2.45-2.32 (m, 3H), 2.15-2.03 (m, 1H), 1.87-1.82 (m, 1H) |
| 137 | 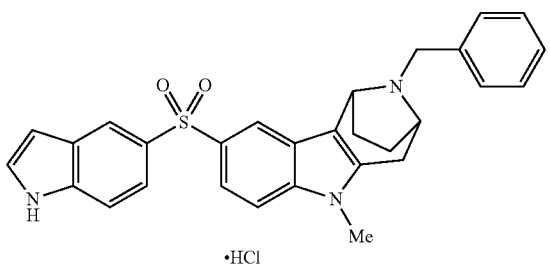 [SMILES: Cn1c2c(c3cc(S(=O)(=O)c4ccc5[nH]ccc5c4)ccc31)C1CCC(C2)N1Cc1ccccc1 ; Cl] •HCl | 482 | ¹H NMR (DMSO-d$_6$, 300 MHz) δ 11.61 (d, J = 5.1 Hz, 1H), 10.79-10.35 (m, 1H), 8.23 (d, J = 12.6 Hz, 1H), 8.18 (s, 1H), 8.18-7.62 (m, 3H), 7.59-7.50 (m, 4H), 7.40-7.35 (m, 1H), 7.32-7.30 (m, 2H), 6.65-6.61 (m, 1H), 5.13-5.00 (m, 1H), 4.43-4.30 (m, 2H), 4.25-4.01 (m, 1H), 3.65 (d, J = 15.0 Hz, 3H), 3.57-3.38 (m, 1H), 3.13-3.05 (m, 1H), 2.73-2.57 (m, 1H), 2.40-2.38 (m, 1H), 2.27-2.07 (m, 2H) |
| 138 | 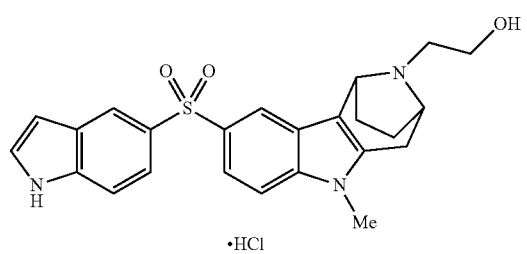 [SMILES: Cn1c2c(c3cc(S(=O)(=O)c4ccc5[nH]ccc5c4)ccc31)C1CCC(C2)N1CCO ; Cl] •HCl | 436 | ¹H NMR (DMSO-d$_6$, 300 MHz) δ 11.62 (s, 1H), 10.62-10.10 (m, 1H), 8.27 (s, 1H), 8.20 (s, 1H), 7.63-7.58 (m, 3H), 7.54-7.51 (m, 2H), 6.63-6.62 (m, 1H), 5.42-5.26 (m, 2H), 4.50-4.38 (m, 1H), 3.86-3.80 (m, 1H), 3.73-3.61 (m, 5H), 3.51-3.37 (m, 1H), 3.25-3.15 (m, 1H), 3.13-2.97 (m, 2H), 2.48-2.27 (m, 1H), 2.18-2.00 (m, 1H), 1.91-1.78 (m, 1H) |
| 139 | 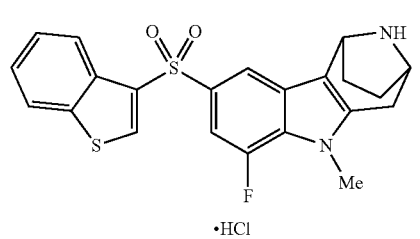 [SMILES: Cn1c2c(c3cc(S(=O)(=O)c4csc5ccccc45)cc(F)c31)C1CCC(C2)N1 ; Cl] •HCl | 427 | ¹H NMR (DMSO-d$_6$, 300 MHz) δ 9.54 (br s, 1H), 9.08 (br s, 1H), 8.83 (s, 1H), 8.40 (s, 1H), 8.25-8.06 (m, 2H), 7.54-7.40 (m, 3H), 5.41 (d, J = 3.6 Hz, 1H), 4.48 (br s, 1H), 3.79 (s, 3H), 3.40-3.35 (m, 1H), 2.99 (d, J = 17.4 Hz, 1H), 2.35-2.18 (m, 2H), 2.16-1.97 (m, 1H), 1.89-1.69 (m, 1H) |

TABLE 1-continued

| Ex. No. | Structure | Mass Spec | ¹H NMR Data |
|---|---|---|---|
| 140 | 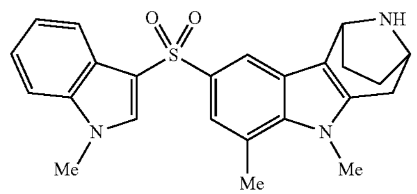 | 420 | ¹H NMR (DMSO-d$_6$, 400 MHz) δ 9.20 (br s, 2H), 8.19 (d, J = 1.6 Hz, 1H), 8.14 (s, 1H), 7.80 (d, J = 7.6 Hz, 1H), 7.53 (d, J = 8.4 Hz, 1H), 7.35 (d, J = 0.8 Hz, 1H), 7.30-7.16 (m, 2H), 5.28 (d, J = 4.0 Hz, 1H), 4.50-4.41 (m, 1H), 3.86 (s, 3H), 3.83 (s, 3H), 3.35-3.26 (m, 1H), 2.94 (d, J = 16.4 Hz, 1H), 2.72 (s, 3H), 2.30-2.20 (m, 2H), 2.08-1.98 (m, 1H), 1.82-1.70 (m, 1H) |
| 141 | 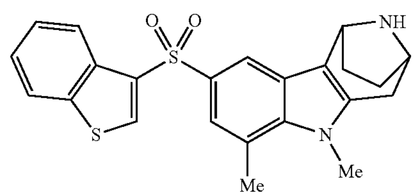 | 423 | ¹H NMR (DMSO-d$_6$, 400 MHz) δ 9.45 (br s, 1H), 9.02 (br s, 1H), 8.75 (s, 1H), 8.33 (d, J = 2.0 Hz, 1H), 8.21-8.15 (m, 1H), 8.13-8.07 (m, 1H), 7.51-7.38 (m, 3H), 5.37 (d, J = 4.0 Hz, 1H), 4.52-4.42 (m, 1H), 3.84 (s, 3H), 3.36-3.26 (m, 1H), 2.95 (d, J = 17.2, 1H), 2.74 (s, 3H), 2.31-2.19 (m, 2H), 2.09-1.99 (m, 1H), 1.82-1.70 (m, 1H) |
| 142 | 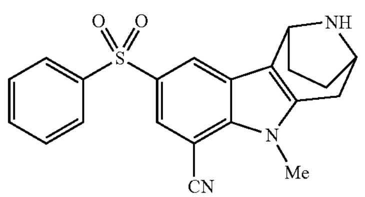 | 378 | ¹H NMR (DMSO-d$_6$, 400 MHz) δ 9.76 (br s, 1H), 9.20 (br s, 1H), 8.73 (d, J = 1.6 Hz, 1H), 8.19 (d, J = 2.0 Hz, 1H), 8.06-7.98 (m, 2H), 7.70-7.56 (m, 3H), 5.42 (s, 1H), 4.49 (br s, 1H), 3.94 (s, 3H), 3.37-3.32 (m, 1H), 3.05 (d, J = 17.2 Hz, 1H), 2.35-2.20 (m, 2H), 2.14-2.01 (m, 1H), 1.85-1.69 (m, 1H) |
| 143 | 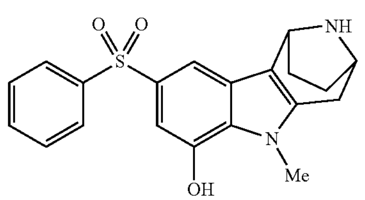 | 369 | ¹H NMR (CD$_3$OD, 300 MHz) δ 7.92 (d, J = 7.5 Hz, 2H), 7.73 (d, J = 1.2 Hz, 1H), 7.62-7.49 (m, 3H), 7.00 (d, J = 1.5 Hz, 1H), 5.21 (s, 1H), 4.53 (br s, 1H), 3.96 (s, 3H), 2.99 (d, J = 17.1 Hz, 1H), 3.00 (d, J = 17.1 Hz, 1H), 2.51-2.20 (m, 2H), 2.29-2.19 (m, 1H), 2.01-1.90 (m, 1H) |
| 144 | 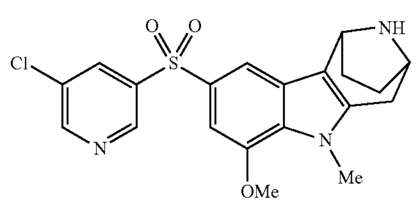 | 418 | ¹H NMR (DMSO-d$_6$, 300 MHz) δ 9.20 (br s, 2H), 9.10 (br s, 1H), 8.89 (d, J = 2.1 Hz, 1H), 8.53 (t, J = 2.1 Hz, 1H), 8.10 (d, J = 1.2 Hz, 1H), 7.21 (d, J = 1.2 Hz, 1H), 5.24 (d, J = 3.6 Hz, 1H), 4.49-4.42 (m, 1H), 3.99 (s, 3H), 3.87 (s, 3H), 3.32-3.23 (m, 1H), 2.95 (d, J = 16.8 Hz, 1H), 2.30-2.21 (m, 2H), 2.12-2.03 (m, 1H), 1.84-1.71 (m, 1H) |
| 145 | 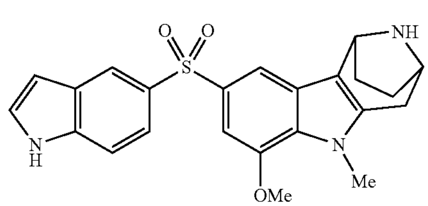 | 422 | ¹H NMR (CD$_3$OD, 300 MHz) δ 8.25 (d, J = 1.5 Hz, 1H), 7.84 (d, J = 1.5 Hz, 1H), 7.65 (dd, J = 8.7, 1.8 Hz, 1H), 7.49 (d, J = 8.7 Hz, 1H), 7.40 (d, J = 3.0 Hz, 1H), 7.14 (d, J = 1.5 Hz, 1H), 6.62 (dd, J = 3.3, 0.6 Hz, 1H), 5.21 (d, J = 4.8 Hz, 1H), 4.55-4.46 (m, 1H), 3.95 (s, 3H), 3.91 (s, 3H), 3.39 (dd, J = 17.1, 4.5 Hz, 1H), 2.97 (dd, J = 17.4, 1.2 Hz, 1H), 2.49-2.20 (m, 3H), 2.01-1.88 (m, 1H) |

TABLE 1-continued

| Ex. No. | Structure | Mass Spec | $^1$H NMR Data |
|---|---|---|---|
| 146 | 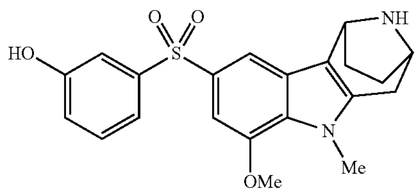 | 399 | $^1$H NMR (CD$_3$OD, 300 MHz) δ 7.84 (s, 1H), 7.41-7.28 (m, 3H), 7.11 (s, 1H), 6.97 (d, J = 6.9 Hz, 1H), 5.24 (br s, 1H), 4.55 (br s, 1H), 3.97 (s, 3H), 3.93 (s, 3H), 3.42 (d, J = 15.6 Hz, 1H), 3.01 (d, J = 16.2 Hz, 1H), 2.50-2.30 (m, 2H), 2.29-2.20 (m, 1H), 2.01-1.90 (m, 1H) |
| 147 | 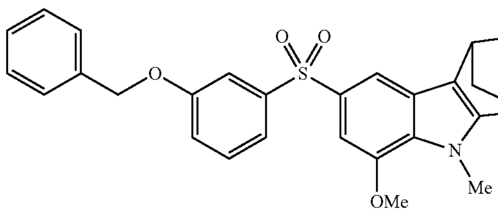 | 489 | $^1$H NMR (DMSO-d$_6$, 300 MHz) δ 9.55 (br s, 1H), 9.10 (br s, 1H), 7.97 (s, 1H), 7.59-7.21 (m, 9H), 7.09 (s, 1H), 5.29 (s, 1H), 5.17 (s, 2H), 4.45 (s, 1H), 3.94 (s, 3H), 3.86 (s, 3H), 2.95 (d, J = 17.7 Hz, 2H), 2.32-2.17 (m, 2H), 2.12-1.97 (m, 1H), 1.84-1.70 (m, 1H) |
| 148 | 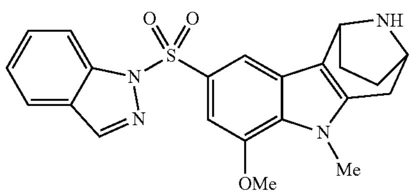 | 423 | $^1$H NMR (DMSO-d$_6$, 300 MHz) δ 9.23 (br s, 2H), 8.49 (s, 1H), 8.22 (d, J = 8.4 Hz, 1H), 8.03 (d, 1.5 Hz, 1H), 7.83 (d, J = 8.1 Hz, 1H), 7.65 (t, J = 7.2 Hz, 1H), 7.39 (t, J = 7.5 Hz, 1H), 6.98 (d, J = 1.5 Hz, 1H), 5.28 (d, J = 3.6 Hz, 1H), 4.42 (s, 1H), 3.84 (s, 3H), 3.81 (s, 3H), 3.24 (d, J = 4.2 Hz, 1H), 2.91 (d, J = 16.8 Hz, 1H), 2.31-2.19 (m, 2H), 2.11-1.92 (m, 1H), 1.81-1.69 (m, 1H) |
| 149 | 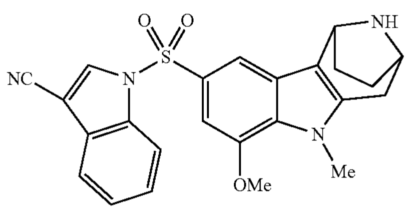 | 447 | $^1$H NMR (DMSO-d$_6$, 400 MHz) δ 9.08 (br s, 2H), 8.89 (s, 1H), 8.26 (d, J = 1.6 Hz, 1H), 8.14 (d, J = 8.4 Hz, 1H), 7.71-7.66 (m, 1H), 7.51-7.38 (m, 2H), 7.17 (d, J = 1.6 Hz, 1H), 5.29 (br s, 1H), 4.45 (br s, 1H), 3.94 (s, 3H), 3.82 (s, 3H), 3.25 (dd, J = 16.8, 4.4 Hz, 1H), 2.93 (d, J = 17.2 Hz, 1H), 2.28-2.18 (m, 2H), 2.06-1.97 (m, 1H), 1.80-1.70 (m, 1H) |
| 150 | 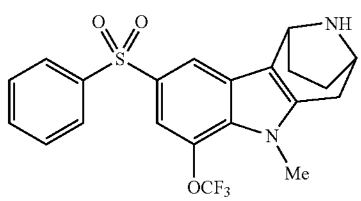 | 437 | $^1$H NMR (CD$_3$OD, 300 MHz) δ 8.28 (d, J = 1.8 Hz, 1H), 8.01-7.98 (m, 1H), 7.97-7.95 (m, 1H), 7.66-7.58 (m, 3H), 7.57-7.53 (m, 1H), 5.29 (d, J = 4.8 Hz, 1H), 4.57-4.50 (m, 1H), 3.87 (s, 3H), 3.44 (dd, J = 17.4, 4.5 Hz, 1H), 3.06 (d, J = 17.4 Hz, 1H), 2.51-2.21 (m, 3H), 2.02-1.91 (m, 1H) |
| 151 | 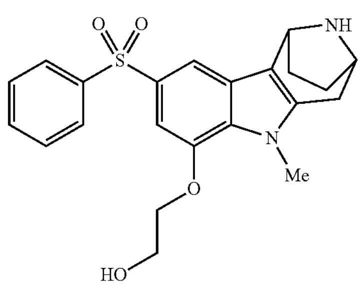 | 413 | $^1$H NMR (DMSO-d$_6$, 400 MHz) δ 9.39 (br s, 1H), 9.09 (br s, 1H), 7.97-7.93 (m, 3H), 7.65-7.55 (m, 3H), 7.10 (d, J = 1.2 Hz, 1H), 5.30 (d, J = 4.0 Hz, 1H), 4.93 (t, J = 5.2 Hz, 1H), 4.54 (br s, 1H), 4.22-4.13 (m, 2H), 3.89 (s, 3H), 3.82-3.77 (m, 2H), 2.95 (d, J = 16.8 Hz, 1H), 2.28-2.22 (m, 2H), 2.09-2.01 (m, 1H), 1.72-1.62 (m, 1H) |

TABLE 1-continued

| Ex. No. | Structure | Mass Spec | ¹H NMR Data |
|---|---|---|---|
| 152 | 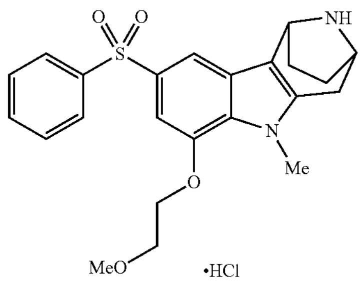 [SMILES: COCCOc1cc(S(=O)(=O)c2ccccc2)cc2c3c(n(C)c12)CC1CCC3N1 ; Cl] | 427 | ¹H NMR (DMSO-d₆, 300 MHz) δ 9.48-9.09 (m, 2H), 7.98-7.93 (m, 3H), 7.64-7.54 (m, 3H), 7.13 (d, J = 2.0 Hz, 1H), 5.29 (d, J = 3.9 Hz, 1H), 4.48-4.41 (m, 1H), 4.36-4.23 (m, 2H), 3.87 (s, 3H), 3.74 (t, J = 4.5 Hz, 2H), 3.36-3.33 (m, 1H), 3.32 (s, 3H), 2.94 (d, J = 16.8 Hz, 1H), 2.31-2.19 (m, 2H), 2.08-1.99 (m, 1H), 1.83-1.71 (m, 1H) |
| 153 | 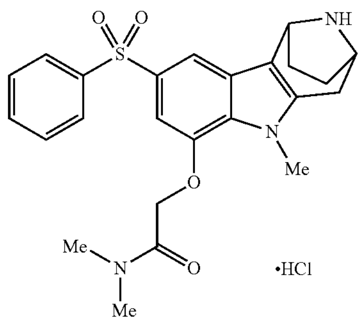 [SMILES: CN(C)C(=O)COc1cc(S(=O)(=O)c2ccccc2)cc2c3c(n(C)c12)CC1CCC3N1 ; Cl] | 454 | ¹H NMR (DMSO-d₆, 400 MHz) δ 9.52 (br s, 1H), 9.09 (br s, 1H), 7.96-7.91 (m, 3H), 7.65-7.54 (m, 3H), 7.15 (d, J = 1.6 Hz, 1H), 5.30 (d, J = 4.0 Hz, 1H), 5.07 (s, 2H), 4.46 (br s, 1H), 3.94 (s, 3H), 3.42-3.33 (m, 1H), 3.06 (s, 3H), 2.96 (d, J = 16.8 Hz, 1H), 2.83 (s, 3H), 2.31-2.21 (m, 2H), 2.11-2.01 (m, 1H), 1.81-1.72 (m, 1H) |
| 154 | 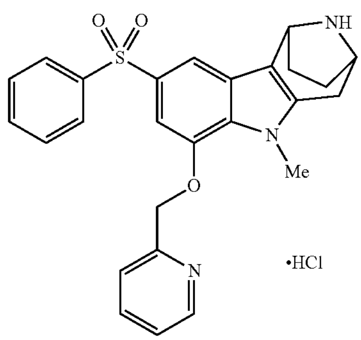 [SMILES: Cn1c2c(c3cc(S(=O)(=O)c4ccccc4)cc(OCc4ccccn4)c31)C1CCC(C2)N1 ; Cl] | 460 | ¹H NMR (DMSO-d₆, 300 MHz) δ 9.82-9.73 (m, 1H), 9.20 (d, J = 9.3 Hz, 1H), 8.71 (d, J = 4.5 Hz, 1H), 8.06-8.00 (m, 1H), 7.99 (d, J = 1.5 Hz, 1H), 7.88-7.85 (m, 2H), 7.72 (d, J = 7.8 Hz, 1H), 7.65-7.52 (m, 3H), 7.26 (t, J = 5.1 Hz, 1H), 7.18 (d, J = 1.5 Hz, 1H), 5.55 (s, 2H), 5.30 (br s, 1H), 4.43 (br s, 1H), 3.90 (s, 3H), 3.33 (dd, J = 17.1, 4.5 Hz, 1H), 3.00 (d, J = 17.1 Hz, 1H), 2.39-2.21 (m, 2H), 2.09-1.99 (m, 1H), 1.82-1.71 (m, 1H) |
| 155 | 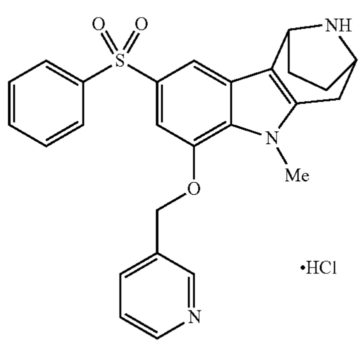 [SMILES: Cn1c2c(c3cc(S(=O)(=O)c4ccccc4)cc(OCc4cccnc4)c31)C1CCC(C2)N1 ; Cl] | 460 | ¹H NMR (DMSO-d₆, 300 MHz) δ 9.71-9.61 (m, 1H), 9.21-9.09 (m, 1H), 8.89 (s, 1H), 8.71 (d, J = 5.1 Hz, 1H), 8.26 (d, J = 7.8 Hz, 1H), 8.01 (d, J = 7.8 Hz, 1H), 7.94-7.89 (m, 2H), 7.74-7.67 (m, 1H), 7.64-7.54 (m, 3H), 7.24 (d, J = 1.5 Hz, 1H), 5.46 (d, J = 1.8 Hz, 2H), 5.30 (br s, 1H), 4.45 (br s, 1H), 3.83 (s, 3H), 3.32 (dd, J = 17.1, 4.5 Hz, 1H), 2.94 (d, J = 17.1 Hz, 1H), 2.29-2.21 (m, 2H), 2.09-2.01 (m, 1H), 1.82-1.71 (m, 1H) |
| 156 | 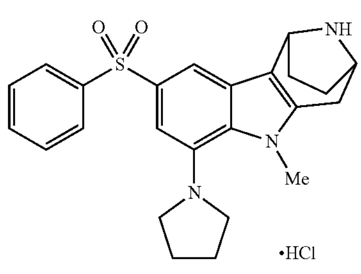 [SMILES: Cn1c2c(c3cc(S(=O)(=O)c4ccccc4)cc(N4CCCC4)c31)C1CCC(C2)N1 ; Cl] | 422 | ¹H NMR (DMSO-d₆, 400 MHz) δ 9.61 (d, J = 8.0 Hz, 1H), 9.07 (d, J = 9.6 Hz, 1H), 8.04 (d, J = 2.0 Hz, 1H), 7.95-7.91 (m, 2H), 7.65-7.55 (m, 3H), 7.32 (d, J = 1.6 Hz, 1H), 5.30 (s, 1H), 4.45 (br s, 1H), 3.90 (s, 3H), 3.32 (dd, J = 17.2, 4.4 Hz, 1H), 3.09-2.91 (m, 5H), 2.29-2.22 (m, 2H), 2.11-2.02 (m, 1H), 1.97-1.89 (m, 4H), 1.84-1.75 (m, 1H) |

TABLE 1-continued

| Ex. No. | Structure | Mass Spec | ¹H NMR Data |
|---|---|---|---|
| 157 | 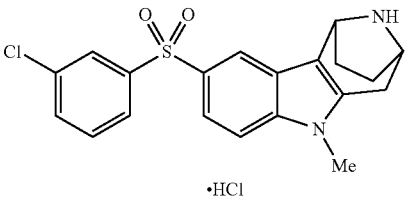<br>•HCl<br>Enantiomer 1 | 387 | ¹H NMR (DMSO-d$_6$, 300 MHz) δ 9.55 (br s, 1H), 9.09 (br s, 1H), 8.42 (d, J = 1.2 Hz, 1H), 7.95 (t, J = 1.8 Hz, 1H), 7.89 (dt, J = 7.8, 1.2 Hz, 1H), 7.73-7.69 (m, 2H), 7.68 (s, 1H), 7.61 (t, J = 8.1 Hz, 1H), 5.36 (br s, 1H), 4.48 (br s, 1H), 3.68 (s, 3H), 3.37 (dd, J = 17.4, 4.5 Hz, 1H), 3.01 (d, J = 17.4 Hz, 1H), 2.32-2.23 (m, 2H), 2.12-2.04 (m, 1H), 1.82-1.74 (m, 1H) |
| 158 | 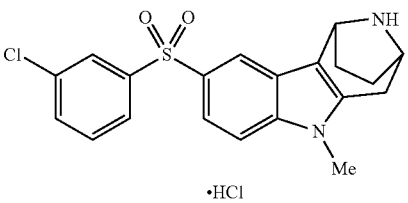<br>•HCl<br>Enantiomer 2 | 387 | ¹H NMR (DMSO-d$_6$, 300 MHz) δ 9.72-9.55 (m, 1H), 9.11 (br s, 1H), 8.42 (d, J = 1.5 Hz, 1H), 7.95 (t, J = 1.8 Hz, 1H), 7.89 (dt, J = 7.8, 1.2 Hz, 1H), 7.74-7.58 (m, 4H), 5.36 (br s, 1H), 4.47 (br s, 1H), 3.68 (s, 3H), 3.33-3.46 (m, 1H), 3.01 (d, J = 17.4 Hz, 1H), 2.34-2.23 (m, 2H), 2.12-2.04 (m, 1H), 1.82-1.74 (m, 1H) |
| 159 | 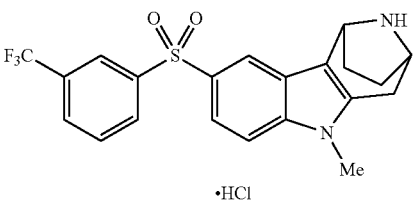<br>•HCl<br>Enantiomer 1 | 421 | ¹H NMR (DMSO-d$_6$, 300 MHz) δ 9.31 (br s, 2H), 8.47 (d, J = 1.5 Hz, 1H), 8.26 (d, J = 8.4 Hz, 1H), 8.21 (s, 1H), 8.04 (d, J = 7.8 Hz, 1H), 7.84 (t, J = 7.8 Hz, 1H), 7.77-7.66 (m, 2H), 5.35 (d, J = 3.9 Hz, 1H), 4.51-4.42 (m, 1H), 3.68 (s, 3H), 3.37 (dd, J = 17.4, 4.5 Hz, 1H), 3.00 (d, J = 17.4 Hz, 1H), 2.32-2.21 (m, 2H), 2.14-2.04 (m, 1H), 1.84-1.72 (m, 1H) |
| 160 | 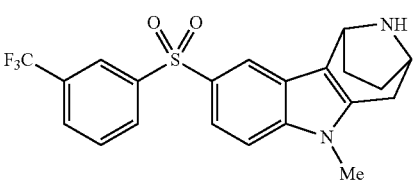<br>•HCl<br>Enantiomer 2 | 421 | ¹H NMR (DMSO-d$_6$, 500 MHz) δ 9.47 (br s, 1H), 9.05 (br s, 1H), 8.47 (d, J = 1.6 Hz, 1H), 8.26 (d, J = 7.9 Hz, 1H), 8.21 (s, 1H), 8.04 (d, J = 7.9 Hz, 1H), 7.85 (t, J = 7.9 Hz, 1H), 7.75 (dd, J = 8.8, 1.8 Hz, 1H), 7.69 (d, J = 8.8 Hz, 1H), 5.36 (br s, 1H), 4.51-4.48 (br s, 1H), 3.68 (s, 3H), 3.37 (dd, J = 15.0, 2.7 Hz, 1 H, partially masked by solvent), 3.01 (d, J = 17.3 Hz, 1H), 2.26 (m, 2H), 2.09 (t, J = 9.8 Hz, 1H), 1.80 (m, 1H) |
| 161 | 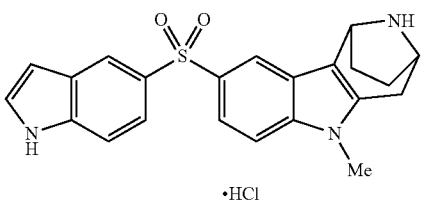<br>•HCl<br>Enantiomer 1 | 392 | ¹H NMR (CD$_3$OD, 300 MHz) δ 8.25 (s, 1H), 8.24 (s, 1H), 7.73 (dd, J = 8.7, 1.8 Hz, 1H), 7.64 (dd, J = 8.7, 1.8 Hz, 1H), 7.57-7.45 (m, 2H), 7.43-7.37 (m, 1H), 6.61 (dd, J = 3.3, 0.6 Hz, 1H), 5.28 (d, J = 4.8 Hz, 1H), 4.57-4.48 (m, 1H), 3.69 (s, 3H), 3.46 (dd, J = 17.4, 4.5 Hz, 1H), 3.05 (dd, J = 17.4, 0.9 Hz, 1H), 2.51-2.22 (m, 3H), 2.02-1.90 (m, 1H) |
| 162 | 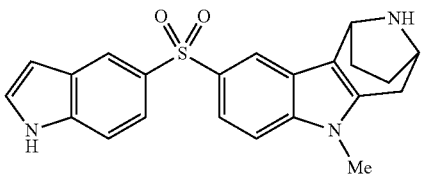<br>•HCl<br>Enantiomer 2 | 392 | ¹H NMR (CD$_3$OD, 300 MHz) δ 8.25 (s, 1H), 8.24 (s, 1H), 7.72 (dd, J = 8.7, 1.8 Hz, 1H), 7.64 (dd, J = 8.7, 1.8 Hz, 1H), 7.56-7.46 (m, 2H), 7.43-7.37 (m, 1H), 6.61 (dd, J = 3.3, 0.6 Hz, 1H), 5.27 (d, J = 4.5 Hz, 1H), 4.57-4.48 (m, 1H), 3.69 (s, 3H), 3.45 (dd, J = 17.4, 4.8 Hz, 1H), 3.04 (dd, J = 17.4, 1.2 Hz, 1H), 2.51-2.22 (m, 3H), 2.02-1.90 (m, 1H) |

TABLE 1-continued

| Ex. No. | Structure | Mass Spec | $^1$H NMR Data |
|---|---|---|---|
| 163 | 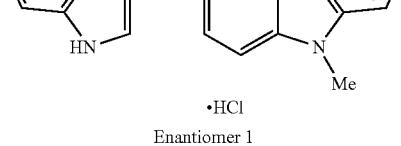 ·HCl Enantiomer 1 | 392 | $^1$H NMR (DMSO-$d_6$, 300 MHz) δ 12.13 (s, 1H), 9.12 (br s, 2H), 8.38 (d, J = 1.8 Hz, 1H), 8.10 (d, J = 3.0 Hz, 1H), 7.78 (d, J = 7.5 Hz, 1H), 7.68 (dd, J = 8.7, 1.8 Hz, 1H), 7.57 (d, J = 8.7 Hz, 1H), 7.46 (d, J = 7.8 Hz, 1H), 7.25-7.10 (m, 2H), 5.35 (d, J = 3.9 Hz, 1H), 4.50-4.40 (m, 1H), 3.64 (s, 3H), 3.40-3.30 (m, 1H), 2.97 (d, J = 17.1 Hz 1H), 2.32-2.18 (m, 2H), 2.12-2.01 (m, 1H), 1.86-1.71 (m, 1H) |
| 164 | 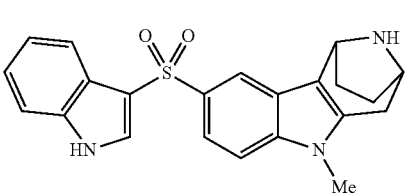 ·HCl Enantiomer 2 | 392 | $^1$H NMR (DMSO-$d_6$, 300 MHz) δ 12.14 (s, 1H), 9.10 (br s, 2H), 8.38 (d, J = 1.8 Hz, 1H), 8.10 (d, J = 3.0 Hz, 1H), 7.78 (d, J = 7.5 Hz, 1H), 7.68 (dd, J = 9.0, 1.8 Hz, 1H), 7.57 (d, J = 8.7 Hz, 1H), 7.46 (d, J = 7.8 Hz, 1H), 7.25-7.10 (m, 2H), 5.35 (d, J = 3.9 Hz, 1H), 4.50-4.40 (m, 1H), 3.64 (s, 3H), 3.40-3.30 (m, 1H), 2.97 (d, J = 17.1 Hz 1H), 2.32-2.18 (m, 2H), 2.12-2.01 (m, 1H), 1.86-1.71 (m, 1H) |
| 165 |  ·HCl Enantiomer 1 | 406 | $^1$H NMR (DMSO-$d_6$, 400 MHz) δ 9.12 (br s, 2H), 8.37 (d, J = 1.6 Hz, 1H), 8.17 (s, 1H), 7.83-7.78 (m, 1H), 7.67 (dd, J = 8.4, 1.6 Hz, 1H), 7.61-7.51 (m, 2H), 7.30-7.17 (m, 2H), 5.35 (d, J = 4.4 Hz, 1H), 4.50-4.42 (m, 1H), 3.86 (s, 3H), 3.64 (s, 3H), 3.38-3.30 (m, 1H), 2.98 (d, J = 16.4 Hz, 1H), 2.30-2.20 (m, 2H), 2.11-2.02 (m, 1H), 1.84-1.72 (m, 1H) |
| 166 | 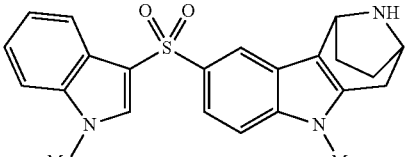 ·HCl Enantiomer 2 | 406 | $^1$H NMR (DMSO-$d_6$, 400 MHz) δ 9.12 (br s, 2H), 8.37 (d, J = 1.6 Hz, 1H), 8.17 (s, 1H), 7.83-7.78 (m, 1H), 7.67 (dd, J = 8.8, 2.0 Hz, 1H), 7.61-7.51 (m, 2H), 7.30-7.17 (m, 2H), 5.36 (d, J = 4.4 Hz, 1H), 4.50-4.42 (m, 1H), 3.86 (s, 3H), 3.64 (s, 3H), 3.38-3.30 (m, 1H), 2.98 (d, J = 16.8 Hz, 1H), 2.30-2.20 (m, 2H), 2.11-2.02 (m, 1H), 1.84-1.72 (m, 1H) |
| 167 | 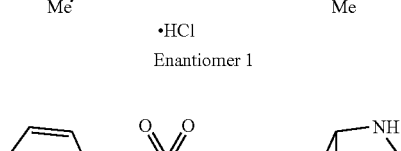 ·HCl Enantiomer 1 | 409 | $^1$H NMR (DMSO-$d_6$, 300 MHz) δ 9.30 (br s, 2H), 8.53 (d, J = 1.5 Hz, 1H), 8.39 (d, J = 1.2 Hz, 1H), 8.21 (d, J = 8.4 Hz, 1H), 7.97 (d, J = 5.4 Hz, 1H), 7.82 (dd, J = 8.7, 1.8 Hz, 1H), 7.72-7.62 (m, 3H), 5.33 (d, J = 3.6 Hz, 1H), 4.45 (br s, 1H), 3.66 (s, 3H), 3.43-3.35 (m, 1H), 2.99 (d, J = 17.4 Hz, 1H), 2.36-2.18 (m, 2H), 2.17-1.99 (m, 1H), 1.86-1.69 (m, 1H) |
| 168 | 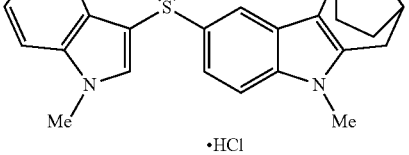 ·HCl Enantiomer 2 | 409 | $^1$H NMR (DMSO-$d_6$, 400 MHz) δ 9.25 (br s, 2H), 8.53 (d, J = 1.6 Hz, 1H), 8.39 (d, J = 1.6 Hz, 1H), 8.21 (d, J = 8.4 Hz, 1H), 7.97 (d, J = 5.6 Hz, 1H), 7.82 (dd, J = 8.4, 2.0 Hz, 1H), 7.12-1.60 (m, 3H), 5.34 (d, J = 4.0 Hz, 1H), 4.46 (br s, 1H), 3.66 (s, 3H), 3.43-3.34 (m, 1H), 2.99 (d, J = 17.2 Hz, 1H), 2.36-2.19 (m, 2H), 2.17-1.99 (m, 1H), 1.85-1.69 (m, 1H) |

TABLE 1-continued

| Ex. No. | Structure | Mass Spec | ¹H NMR Data |
|---|---|---|---|
| 169 | Enantiomer 1 (·HCl) | 404 | ¹H NMR (DMSO-$d_6$, 400 MHz) δ 9.35 (br s, 1H), 9.09 (br s, 1H), 8.96-8.90 (m, 1H), 8.62 (dd, J = 6.0, 1.2 Hz, 1H), 8.51 (d, J = 2.0 Hz, 1H), 8.48 (dd, J = 6.4, 2.0 Hz, 1H), 8.33 (dd, J = 6.8, 1.6 Hz, 1H), 7.88-7.80 (m, 2H), 7.63-7.53 (m, 2H), 5.36 (br s, 1H), 4.46 (br s, 1H), 3.64 (s, 3H), 3.36-3.26 (m, 1H), 2.98 (d, J = 17.2 Hz, 1H), 2.34-1.98 (m, 3H), 1.82-1.70 (m, 1H) |
| 170 | Enantiomer 2 (·HCl) | 404 | ¹H NMR (DMSO-$d_6$, 300 MHz) δ 9.44 (br s, 1H), 9.07 (br s, 1H), 8.96-8.89 (m, 1H), 8.62 (dd, J = 6.3, 1.2 Hz, 1H), 8.54-8.42 (m, 2H), 8.33 (dd, J = 6.9, 1.5 Hz, 1H), 7.90-7.80 (m, 2H), 7.64-7.52 (m, 2H), 5.36 (br s, 1H), 4.46 (br s, 1H), 3.64 (s, 3H), 3.35 (dd, J = 13.2, 4.5 Hz, 1H), 2.98 (d, J = 17.4 Hz, 1H), 2.35-1.98 (m, 3H), 1.81-1.70 (m, 1H) |
| 171 | Enantiomer 1 (·HCl) | 409 | ¹H NMR (DMSO-$d_6$, 300 MHz) δ 9.53 (br s, 1H), 9.06 (br s, 1H), 8.78 (s, 1H), 8.50 (d, J = 2.4 Hz, 1H), 8.21-8.05 (m, 2H), 7.71 (dd, J = 8.7, 2.8 Hz, 1H), 7.64 (d, J = 12.0 Hz, 1H), 7.50-7.40 (m, 2H), 5.38 (br s, 1H), 4.47 (br s, 1H), 3.65 (s, 3H), 3.40-3.25 (m, 1H), 2.99 (d, J = 17.1 Hz, 1H), 2.35-2.18 (m, 2H), 2.14-2.01 (m, 1H), 1.90-1.71 (m, 1H) |
| 172 | Enantiomer 2 (·HCl) | 400 | ¹H NMR (DMSO-$d_6$, 300 MHz) δ 9.31 (br s, 1H), 9.10 (br s, 1H), 8.77 (s, 1H), 8.50 (d, J = 1.5 Hz, 1H), 8.21-8.05 (m, 2H), 7.72 (dd, J = 8.7, 1.8 Hz, 1H), 7.64 (d, J = 9.0 Hz, 1H), 7.50-7.40 (m, 2H), 5.39 (d, J = 3.0 Hz, 1H), 4.47 (br s, 1H), 3.65 (s, 3H), 3.41-3.32 (m, 1H), 2.99 (d, J = 17.7 Hz, 1H), 2.32-2.18 (m, 1H), 2.13-2.14 (m, 2H), 1.85-1.70 (m, 1H) |
| 173 | Enantiomer 1 (·HCl) | 420 | ¹H NMR (DMSO-$d_6$, 300 MHz) δ 9.39 (br s, 1H), 9.01 (br s, 1H), 8.33 (d, J = 1.2 Hz, 1H), 8.20 (s, 1H), 7.68-7.55 (m, 5H), 6.63 (d, J = 3.0 Hz, 1H), 5.35 (br s, 1H), 4.46 (br s, 1H), 4.23 (q, J = 7.2 Hz, 2H), 3.65 (s, 3H), 3.41-3.32 (m, 1H), 2.99 (d, J = 17.1 Hz, 1H), 2.32-2.00 (m, 3H), 1.83-1.68 (m, 1H), 1.31 (t, J = 7.2 Hz, 3H) |
| 174 | Enantiomer 2 (·HCl) | 420 | ¹H NMR (DMSO-$d_6$, 300 MHz) δ 9.53 (br s, 1H), 9.06 (br s, 1H), 8.33 (d, J = 1.2 Hz, 1H), 8.20 (s, 1H), 7.68-7.53 (m, 5H), 6.63 (d, J = 3.3 Hz, 1H), 5.35 (d, J = 3.9 Hz, 1H), 4.46 (br s, 1H), 4.23 (q, J = 7.2 Hz, 2H), 3.65 (s, 3H), 3.41-3.32 (m, 1H), 2.99 (d, J = 17.1 Hz, 1H), 2.32-2.00 (m, 3H), 1.83-1.68 (m, 1H), 1.31 (t, J = 7.2 Hz, 3H) |

TABLE 1-continued

| Ex. No. | Structure | Mass Spec | ¹H NMR Data |
|---|---|---|---|
| 175 | [Structure: 4-(trifluoromethyl)phenylsulfonyl-substituted N-methyl carbazole fused with azabicyclic amine] ·HCl Enantiomer 1 | 421 | ¹H NMR (MeOD, 300 MHz) δ 8.31 (d, J = 1.8 Hz, 1H), 8.15 (d, J = 8.4 Hz, 2H), 7.85 (d, J = 8.4 Hz, 2H), 7.77 (dd, J = 9.0, 1.8 Hz, 1H), 7.60 (d, J = 8.7 Hz, 1H), 5.28 (d, J = 4.8 Hz, 1H), 4.55-4.51 (m, 1H), 3.75 (s, 3H), 3.53-3.37 (m, 1H), 3.09-3.03 (m, 1H), 2.52-2.50 (m, 3H), 2.01-1.92 (m, 1H) |
| 176 | [Structure: same 4-(trifluoromethyl)phenylsulfonyl-substituted N-methyl carbazole fused with azabicyclic amine] ·HCl Enantiomer 2 | 421 | ¹H NMR (DMSO-d₆, 300 MHz) δ 9.38 (s, 2H), 8.42 (s, 1H), 8.14 (d, J = 8.4 Hz, 2H), 7.97 (d, J = 8.7 Hz, 2H), 7.69 (s, 2H), 5.33 (d, J = 3.9 Hz, 1H), 4.46-4.44 (m, 1H), 3.63 (s, 3H), 3.40 (d, J = 17.1 Hz, 1H), 3.00 (d, J = 17.1 Hz, 1H), 2.29-2.27 (m, 2H), 2.11-2.05 (m, 1H), 1.80-1.76 (m, 1H) |
| 177 | [Structure: 4-cyanophenylsulfonyl-substituted N-methyl carbazole fused with azabicyclic amine] ·HCl Enantiomer 1 | 378 | ¹H NMR (DMSO-d₆, 300 MHz) δ 9.38 (s, 2H), 8.42 (s, 1H), 8.12-8.04 (m, 4H), 7.69 (s, 2H), 5.32 (d, J = 3.9 Hz, 1H), 4.46-4.41 (m, 1H), 3.68 (s, 3H), 3.43-3.42 (m, 1H), 3.00 (d, J = 17.4 Hz, 1H), 2.33-2.26 (m, 2H), 2.11-2.05 (m, 1H), 1.85-1.76 (m, 1H) |
| 178 | [Structure: same 4-cyanophenylsulfonyl-substituted N-methyl carbazole fused with azabicyclic amine] ·HCl Enantiomer 2 | 378 | ¹H NMR (DMSO-d₆, 300 MHz) δ 9.38 (s, 2H), 8.42 (s, 1H), 8.12-8.00 (m, 4H), 7.69 (s, 2H), 5.32 (d, J = 3.9 Hz, 1H), 4.46-4.41 (m, 1H), 3.68 (s, 3H), 3.43 (d, J = 10.2 Hz, 1H), 3.00 (d, J = 17.4 Hz, 1H), 2.33-2.26 (m, 2H), 2.11-2.05 (m, 1H), 1.85-1.76 (m, 1H) |
| 179 | [Structure: isoquinolin-4-ylsulfonyl-substituted N-methyl carbazole fused with azabicyclic amine] ·HCl Enantiomer 1 | 404 | ¹H NMR (DMSO-d₆, 300 MHz) δ 9.62 (m, 2H), 9.24 (s, 1H), 9.07 (d, J = 9.9 Hz, 1H), 8.61 (d, J = 8.4 Hz, 1H), 8.55 (d, J = 1.8 Hz, 1H), 8.29 (d, J = 8.1 Hz, 1H), 7.96-7.90 (m, 1H), 7.82-7.74 (m, 2H), 7.63 (d, J = 8.7 Hz, 1H), 5.38 (s, 1H), 4.46 (s, 1H), 3.65 (s, 3H), 3.33 (dd, J = 17.2, 4.5 Hz, 1H), 2.99 (d, J = 17.1 Hz, 1H), 2.30-2.23 (m, 2H), 2.09-2.02 (m, 1H), 1.78-1.74 (m, 1H) |
| 180 | [Structure: same isoquinolin-4-ylsulfonyl-substituted N-methyl carbazole fused with azabicyclic amine] ·HCl Enantiomer 2 | 404 | ¹H NMR (DMSO-d₆, 300 MHz) δ 9.62 (m, 2H), 9.24 (s, 1H), 9.07 (d, J = 9.9 Hz, 1H), 8.61 (d, J = 8.4 Hz, 1H), 8.55 (d, J = 1.8 Hz, 1H), 8.29 (d, J = 8.1 Hz, 1H), 7.96-7.90 (m, 1H), 7.82-7.74 (m, 2H), 7.63 (d, J = 8.7 Hz, 1H), 5.38 (s, 1H), 4.46 (s, 1H), 3.65 (s, 3H), 3.33 (dd, J = 17.2, 4.5 Hz, 1H), 2.99 (d, J = 17.1 Hz, 1H), 2.30-2.23 (m, 2H), 2.09-2.02 (m, 1H), 1.78-1.74 (m, 1H) |

TABLE 1-continued

| Ex. No. | Structure | Mass Spec | $^1$H NMR Data |
|---|---|---|---|
| 181 | 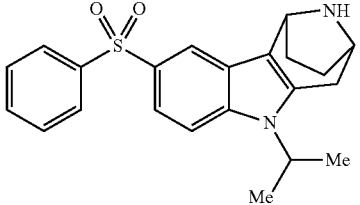<br>·HCl<br>Enantiomer 1 | 381 | $^1$H NMR (DMSO-d$_6$, 300 MHz) δ 9.71 (br s, 1H), 9.19 (br s, 1H), 8.37 (d, J = 1.5 Hz, 1H), 7.98-7.88 (m, 2H), 7.80 (d, J = 9.0 Hz, 1H), 7.68-7.52 (m, 4H), 5.34 (d, J = 3.6 Hz, 1H), 4.76-4.57 (m, 1H), 4.43 (br s, 1H), 3.46 (dd, J = 16.8, 3.9 Hz, 1H), 3.03 (d, J = 17.1 Hz, 1H), 2.38-2.02 (m, 3H), 1.85-1.69 (m, 1H), 1.50 (d, J = 6.9 Hz, 3H), 1.46 (d, J = 6.9 Hz, 3H) |
| 182 | 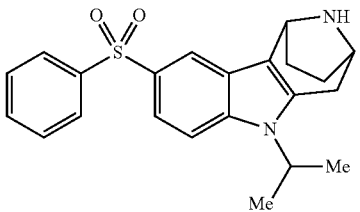<br>·HCl<br>Enantiomer 2 | 381 | $^1$H NMR (DMSO-d$_6$, 300 MHz) δ 9.37 (br s, 1H), 9.04 (br s, 1H), 8.36 (d, J = 1.8 Hz, 1H), 7.98-7.88 (m, 2H), 7.80 (d, J = 9.0 Hz, 1H), 7.68-7.52 (m, 4H), 5.35 (d, J = 3.9 Hz, 1H), 4.75-4.60 (m, 1H), 4.45 (br s, 1H), 3.48-3.35 (m, 1H), 3.05 (d, J = 17.1 Hz, 1H), 2.30-2.05 (m, 3H), 1.85-1.75 (m, 1H), 1.50 (d, J = 6.9 Hz, 3H), 1.46 (d, J = 6.9 Hz, 3H) |
| 183 | 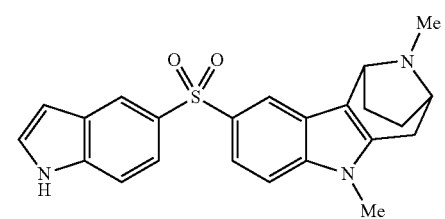<br>·HCl<br>Enantiomer 1 | 406 | $^1$H NMR (DMSO-d$_6$, 400 MHz) δ 11.60 (br s, 1H), 10.50 (br s, 0.4H), 10.00 (br s, 0.6H), 8.24 (d, J = 1.6 Hz, 1H), 8.22 (d, J = 1.6 Hz, 1H), 7.68-7.54 (m, 3H), 7.52 (d, J = 5.6 Hz, 2H), 6.63 (t, J = 6.0 Hz, 1H), 5.24-5.22 (m, 1H), 4.32-4.25 (m, 1H), 3.68 (s, 3H), 3.42-3.31 (m, 1H), 2.83 (s, 3H), 2.67-2.64 (m, 2H), 2.35-2.33 (m, 1H), 2.16-2.05 (m, 1H), 1.92-1.80 (m, 1H) |
| 184 | 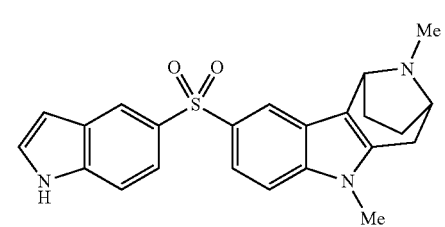<br>·HCl<br>Enantiomer 2 | 406 | $^1$H NMR (DMSO-d$_6$, 400 MHz) δ 11.50 (br s, 1H), 10.50 (br s, 0.4H), 10.10 (br s, 0.6H), 8.24 (d, J = 1.6 Hz, 1H), 8.22 (d, J = 1.6 Hz, 1H), 7.54-7.69 (m, 3H), 7.52 (d, J = 5.6 Hz, 2H), 6.63 (t, J = 6.0 Hz, 1H), 5.22-5.24 (m, 1H), 4.25-4.32 (m, 1H), 3.68 (s, 3H), 3.31-3.42 (m, 1H), 2.83 (s, 3H), 2.64-2.67 (m, 2H), 2.33-2.35 (m, 1H), 2.05-2.16 (m, 1H), 1.80-1.92 (m, 1H) |
| 185 | 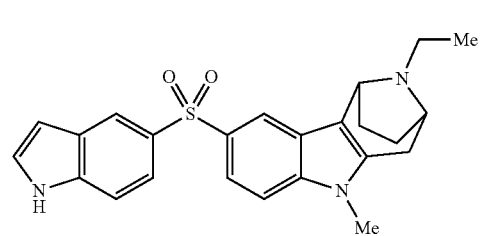<br>·HCl<br>Enantiomer 1 | 420 | $^1$H NMR (CD$_3$OD, 300 MHz) δ 8.25-8.24 (m, 2H), 7.73 (dd, J = 18.0, 1.5 Hz, 1H), 7.64 (dd, J = 18.0, 1.5 Hz, 1H), 7.54-7.47 (m, 2H), 7.39 (d, J = 3.3 Hz, 1H), 6.61 (d, J = 3.0 Hz, 1H), 5.18-5.10 (m, 1H), 4.29-4.26 (m, 1H), 3.70 (s, 3H), 3.42 (dd, J = 15.0, 4.0 Hz, 1H), 3.07-2.95 (m, 3H), 2.47-2.45 (m, 2H), 2.19-2.14 (m, 1H), 1.93-1.85 (m, 1H), 1.34 (t, J = 7.2 Hz, 3H) |

TABLE 1-continued

| Ex. No. | Structure | Mass Spec | ¹H NMR Data |
|---|---|---|---|
| 186 | Enantiomer 2 · HCl | 420 | ¹H NMR (CD₃OD, 300 MHz) δ 8.25-8.24 (m, 2H), 7.72 (dd, J = 11.0, 1.5 Hz, 1H), 7.64 (dd, J = 10.0, 1.5 Hz, 1H), 7.54-7.47 (m, 2H), 7.39 (d, J = 3.3 Hz, 1H), 6.61 (d, J = 3.0 Hz, 1H), 5.14-5.11 (m, 1H), 4.29-4.25 (m, 1H), 3.70 (s, 3H), 3.42 (dd, J = 16.0, 4.5 Hz, 1H), 3.10-2.94 (m, 3H), 2.48-2.44 (m, 2H), 2.22-2.15 (m, 1H), 1.93-1.89 (m, 1H), 1.36-1.29 (m, 3H) |
| 187 | Enantiomer 1 · HCl | 410 | ¹H NMR (CD₃OD, 300 MHz) δ 8.32 (d, J = 1.5 Hz, 1H), 7.73 (dd, J = 8.9, 2.4 Hz, 1H), 7.70-7.65 (m, 2H), 7.53-7.45 (m, 2H), 6.96 (td, J = 9.6, 2.4 Hz, 1H), 6.67 (dd, J = 3.9, 0.6 Hz, 1H), 5.29 (dd, J = 5.1 Hz, 1H), 4.52 (t, J = 4.8 Hz, 1H), 3.67 (s, 3H), 3.43 (dd, J = 17.4, 4.5 Hz, 1H), 3.03 (d, J = 17.7 Hz, 1H), 2.50-2.31 (m, 2H), 2.30-2.19 (m, 1H), 2.01-1.90 (m, 1H) |
| 188 | Enantiomer 2 · HCl | 410 | ¹H NMR (CD₃OD, 300 MHz) δ 8.32 (d, J = 1.5 Hz, 1H), 7.73 (dd, J = 8.9, 2.4 Hz, 1H), 7.70-7.65 (m, 2H), 7.53-7.45 (m, 2H), 6.96 (td, J = 9.6, 2.4 Hz, 1H), 6.67 (dd, J = 3.9, 0.6 Hz, 1H), 5.29 (dd, J = 5.1 Hz, 1H), 4.52 (t, J = 4.8 Hz, 1H), 3.67 (s, 3H), 3.43 (dd, J = 17.4, 4.5 Hz, 1H), 3.03 (d, J = 17.7 Hz, 1H), 2.50-2.31 (m, 2H), 2.30-2.19 (m, 1H), 2.01-1.90 (m, 1H) |
| 189 | Enantiomer 1 · HCl | 392 | ¹H NMR (CD₃OD, 300 MHz) δ 8.28 (d, J = 1.5 Hz, 1H), 8.00 (d, J = 8.4 Hz, 1H), 7.71-7.63 (m, 2H), 7.52-7.43 (m, 2H), 7.29-7.21 (m, 1H), 7.19-7.17 (m, 1H), 6.67 (d, J = 3.6 Hz, 1H), 5.27 (d, J = 4.8 Hz, 1H), 4.56-4.45 (m, 1H), 3.65 (s, 3H), 3.43 (dd, J = 17.4, 4.5 Hz, 1H), 3.02 (d, J = 17.7 Hz, 1H), 2.48-2.30 (m, 3H), 2.00-1.86 (m, 1H) |
| 190 | Enantiomer 2 · HCl | 392 | ¹H NMR (CD₃OD, 300 MHz) δ 8.28 (d, J = 1.8 Hz, 1H), 8.01 (d, J = 8.1 Hz, 1H), 7.72-7.63 (m, 2H), 7.53-7.43 (m, 2H), 7.30-7.22 (m, 1H), 7.19-7.11 (m, 1H), 6.67 (d, J = 3.6 Hz, 1H), 5.27 (d, J = 4.8 Hz, 1H), 4.57-4.46 (m, 1H), 3.65 (s, 3H), 3.43 (dd, J = 17.4, 4.5 Hz, 1H), 3.02 (d, J = 17.7 Hz, 1H), 2.51-2.13 (m, 3H), 2.00-1.87 (m, 1H) |
| 191 | Enantiomer 1 · HCl | 410 | ¹H NMR (CD₃OD, 300 MHz) δ 8.29 (s, 1H), 8.00 (dd, J = 9.0, 4.2 Hz, 1H), 7.75 (d, J = 3.9 Hz, 1H), 7.70-7.63 (m, 2H), 7.49 (d, J = 8.7 Hz, 1H), 7.19 (dd, J = 9.3, 2.7 Hz, 1H), 7.03 (dt, J = 9.0, 2.4 Hz, 1H), 6.67 (d, J = 3.6 Hz, 1H), 5.27 (br s, 1H), 4.51 (br s, 1H), 3.66 (s, 3H), 3.48-3.35 (m, 1H), 3.10-2.96 (m, 1H), 2.51-2.17 (m, 3H), 2.00-1.88 (m, 1H) |

TABLE 1-continued

| Ex. No. | Structure | Mass Spec | ¹H NMR Data |
|---|---|---|---|
| 192 | •HCl Enantiomer 2 | 410 | ¹H NMR (CD$_3$OD, 300 MHz) δ 8.29 (d, J = 1.5 Hz, 1H), 8.00 (dd, J = 9.0, 4.2 Hz, 1H), 7.75 (d, J = 3.9 Hz, 1H), 7.67 (dd, J = 9.0, 1.8 Hz, 1H), 7.49 (d, J = 9.0 Hz, 1H), 7.19 (dd, J = 8.7, 2.4 Hz, 1H), 7.03 (dt, J = 9.0, 2.4 Hz, 1H), 6.67 (d, J = 3.6 Hz, 1H), 5.28 (d, J = 4.8 Hz, 1H), 4.53 (br s, 1H), 3.66 (s, 3H), 3.43 (dd, J = 17.7, 4.8 Hz, 1H), 3.03 (d, J = 17.4 Hz, 1H), 2.52-2.17 (m, 3H), 2.02-1.89 (m, 1H) |
| 193 | •HCl Enantiomer 1 | 426 | ¹H NMR (CD$_3$OD, 300 MHz) δ 8.32 (s, 1H), 7.99 (s, 1H), 7.72 (d, J = 3.6 Hz, 1H), 7.66 (d, J = 9.0 Hz, 1H), 7.55-7.43 (m, 2H), 7.16 (d, J = 8.4 Hz, 1H), 6.68 (d, J = 3.6 Hz, 1H), 5.27 (d, J = 4.5 Hz, 1H), 4.53 (br s, 1H), 3.66 (s, 3H), 3.45 (dd, J = 17.4, 4.2 Hz, 1H), 3.03 (d, J = 17.4 Hz, 1H), 2.50-2.41 (m, 2H), 2.30-2.16 (m, 1H), 2.00-1.89 (m, 1H) |
| 194 | •HCl Enantiomer 2 | 426 | ¹H NMR (CD$_3$OD, 300 MHz) δ 8.33 (s, 1H), 8.00 (s, 1H), 7.72 (d, J = 3.3 Hz, 1H), 7.66 (d, J = 9.0 Hz, 1H), 7.53-7.45 (m, 2H), 7.17 (d, J = 8.4 Hz, 1H), 6.68 (d, J = 3.3 Hz, 1H), 5.30 (d, J = 4.2 Hz, 1H), 4.53 (br s, 1H), 3.67 (s, 3H), 3.45 (dd, J = 17.3, 4.2 Hz, 1H), 3.03 (d, J = 17.1 Hz, 1H), 2.46-2.37 (m, 2H), 2.27-2.20 (m, 1H), 1.97-1.93 (m, 1H) |
| 195 | •HCl Enantiomer 1 | 426 | ¹H NMR (CD$_3$OD, 300 MHz) δ 8.30 (s, 1H), 7.99 (d, J = 8.7 Hz, 1H), 7.74 (d, J = 3.6 Hz, 1H), 7.67 (dd, J = 8.7, 1.5 Hz, 1H), 7.52-7.48 (m, 2H), 7.25 (dd, J = 9.0, 1.8 Hz, 1H), 6.65 (d, J = 3.6 Hz, 1H), 5.28 (d, J = 4.8 Hz, 1H), 4.52 (br s, 1H), 3.66 (s, 3H), 3.43 (dd, J = 17.4, 4.5 Hz, 1H), 3.03 (d, J = 17.7 Hz, 1H), 2.52-2.31 (m, 2H), 2.28-2.19 (m, 1H), 1.99-1.89 (m, 1H) |
| 196 | •HCl Enantiomer 2 | 426 | ¹H NMR (CD$_3$OD, 300 MHz) δ 8.30 (s, 1H), 7.99 (d, J = 9.0 Hz, 1H), 7.74 (d, J = 3.3 Hz, 1H), 7.68 (d, J = 8.4 Hz, 1H), 7.51-7.48 (m, 2H), 7.25 (dd, J = 9.0, 1.8 Hz, 1H), 6.66 (d, J = 3.3 Hz, 1H), 5.28 (d, J = 4.5 Hz, 1H), 4.52 (br s, 1H), 3.66 (s, 3H), 3.43 (dd, J = 17.5, 4.8 Hz, 1H), 3.03 (d, J = 17.4 Hz, 1H), 2.46-2.36 (m, 2H), 2.27-2.20 (m, 1H), 1.97-1.94 (m, 1H) |

TABLE 1-continued

| Ex. No. | Structure | Mass Spec | ¹H NMR Data |
|---|---|---|---|
| 197 | 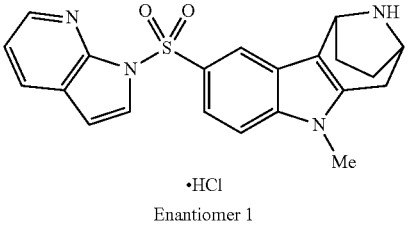 [SMILES: Cn1c2c(c3cc(S(=O)(=O)n4ccc5cccnc54)ccc31)C1CCC(C2)N1 ; Cl] ·HCl Enantiomer 1 | 393 | ¹H NMR (CD₃OD, 300 MHz) δ 8.51 (d, J = 1.8 Hz, 1H), 8.34 (dd, J = 5.1, 1.5 Hz, 1H), 8.09 (dd, J = 8.1, 1.2 Hz, 1H), 7.91 (d, J = 3.9 Hz, 1H), 7.86 (dd, J = 9.0, 1.8 Hz, 1H), 7.53 (d, J = 9.0 Hz, 1H), 7.32 (dd, J = 7.8, 5.1 Hz, 1H), 6.76 (d, J = 3.9 Hz, 1H), 5.29 (d, J = 4.8 Hz, 1H), 4.55 (br s, 1H), 3.68 (s, 3H), 3.45 (dd, J = 17.7, 4.8 Hz, 1H), 3.05 (d, J = 17.4 Hz, 1H), 2.51-2.31 (m, 2H), 2.29-2.21 (m, 1H), 2.01-1.90 (m, 1H) |
| 198 | 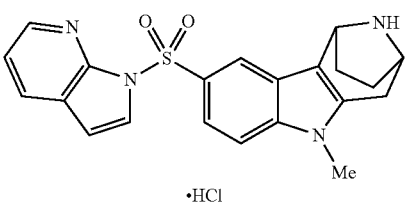 ·HCl Enantiomer 2 | 393 | ¹H NMR (CD₃OD, 300 MHz) δ 8.49 (d, J = 1.8 Hz, 1H), 8.31 (dd, J = 5.1, 1.5 Hz, 1H), 8.01 (dd, J = 7.8, 1.5 Hz, 1H), 7.89-7.84 (m, 2H), 7.52 (d, J = 9.0 Hz, 1H), 7.26 (dd, J = 7.8, 4.8 Hz, 1H), 6.73 (d, J = 4.2 Hz, 1H), 5.29 (d, J = 4.8 Hz, 1H), 4.54 (br s, 1H), 3.68 (s, 3H), 3.45 (dd, J = 17.4, 4.5 Hz, 1H), 3.04 (dd, J = 17.4, 1.2 Hz, 1H), 2.43-2.37 (m, 2H), 2.29-2.22 (m, 1H), 1.99-1.94 (m, 1H) |
| 199 | 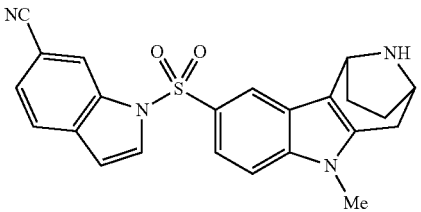 ·HCl Enantiomer 1 | 417 | ¹H NMR (CD₃OD, 300 MHz) δ 8.42 (d, J = 1.5 Hz, 1H), 8.37 (s, 1H), 7.98 (d, J = 3.9 Hz, 1H), 7.71-7.68 (m, 2H), 7.54 (d, J = 9.0 Hz, 1H), 7.48 (dd, J = 8.2, 1.2 Hz, 1H), 6.82 (d, J = 3.6 Hz, 1H), 5.32 (d, J = 4.5 Hz, 1H), 4.53 (br s, 1H), 3.67 (s, 3H), 3.44 (dd, J = 17.7, 4.5 Hz, 1H), 3.04 (d, J = 17.4 Hz, 1H), 2.46-2.31 (m, 2H), 2.28-2.21 (m, 1H), 1.97-1.93 (m, 1H) |
| 200 | 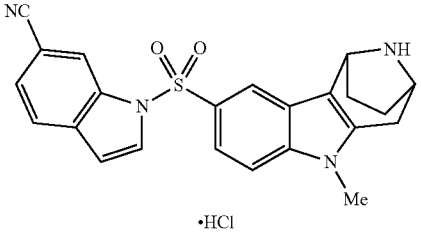 ·HCl Enantiomer 2 | 417 | ¹H NMR (CD₃OD, 300 MHz) δ ¹H NMR (CD₃OD, 300 MHz) δ 8.41 (d, J = 1.8 Hz, 1H), 8.37 (d, J = 0.6 Hz, 1H), 7.98 (d, J = 3.6 Hz, 1H), 7.70-7.67 (m, 2H), 7.54 (d, J = 9.0 Hz, 1H), 7.47 (dd, J = 8.1, 1.2 Hz, 1H), 6.82 (d, J = 3.6 Hz, 1H), 5.32 (d, J = 4.8 Hz, 1H), 4.53 (br s, 1H), 3.67 (s, 3H), 3.44 (dd, J = 17.4, 4.5 Hz, 1H), 3.03 (dd, J = 17.5, 0.9 Hz, 1H), 2.46-2.34 (m, 2H), 2.31-2.21 (m, 1H), 1.98-1.92 (m, 1H) |
| 201 | 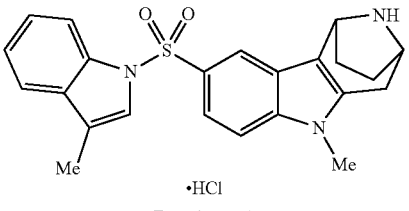 ·HCl Enantiomer 1 | 406 | ¹H NMR (CD₃OD, 300 MHz) δ 8.23 (d, J = 1.8 Hz, 1H), 7.99 (d, J = 8.1 Hz, 1H), 7.63 (dd, J = 8.7, 1.8 Hz, 1H), 7.47-7.41 (m, 3H), 7.27 (t, J = 8.4 Hz, 1H), 7.18 (t, J = 7.8 Hz, 1H), 5.22 (d, J = 4.8 Hz, 1H), 4.53-4.47 (m, 1H), 3.64 (s, 3H), 3.41 (dd, J = 17.4, 4.8 Hz, 1H), 3.00 (d, J = 17.4 Hz, 1H), 2.31-2.48 (m, 2H), 2.21 (d, J = 1.5 Hz, 3H), 2.23-2.19 (m, 1H), 1.97-1.88 (m, 1H) |
| 202 | 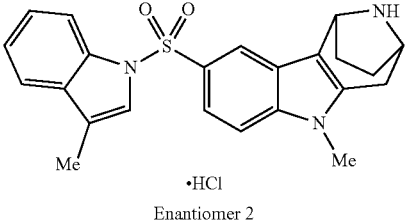 [SMILES: Cc1cn(S(=O)(=O)c2ccc3c(c2)c2c(n3C)CC3CCC2N3)c2ccccc12 ; Cl] ·HCl Enantiomer 2 | 406 | ¹H NMR (DMSO-d₆, 400 MHz) δ 9.22-8.94 (m, 2H), 8.41 (s, 1H), 7.97 (d, J = 8.1 Hz, 1H), 7.60 (d, J = 1.6 Hz, 2H), 7.56 (d, J = 1.2 Hz, 1H), 7.49 (d, J = 7.6 Hz, 1H), 7.30 (t, J = 7.2 Hz, 1H), 7.21 (t, J = 8.0 Hz, 1H), 5.28 (d, J = 4.0 Hz, 1H), 4.45-4.40 (m, 1H), 3.61 (s, 3H), 3.31-3.26 (m, 1H), 2.94 (d, J = 17.2 Hz, 1H), 2.27-2.21 (m, 2H), 2.20 (d, J = 1.2 Hz, 3H), 2.04-1.98 (m, 1H), 1.76-1.72 (m, 1H) |

TABLE 1-continued

| Ex. No. | Structure | Mass Spec | $^1$H NMR Data |
|---|---|---|---|
| 203 | 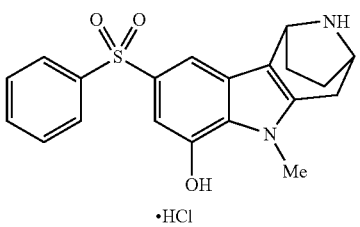<br>·HCl<br>Enantiomer 1 | 369 | $^1$H NMR (DMSO-d$_6$, 300 MHz) δ 10.56 (br s, 1H), 9.49-9.11 (m, 2H), 7.86 (dd, J = 4.8, 2.7 Hz, 2H), 7.79 (d, J = 1.8 Hz, 1H), 7.65-7.55 (m, 3H), 6.97 (d, J = 1.5 Hz, 1H), 5.23 (d, J = 3.6 Hz, 1H), 4.47-4.39 (m, 1H), 3.87 (s, 3H), 3.25 (d, J = 4.2 Hz, 1H), 2.92 (d, J = 16.8 Hz, 1H), 2.29-2.20 (m, 2H), 2.09-2.01 (m, 1H), 1.83-1.72 (m, 1H) |
| 204 | 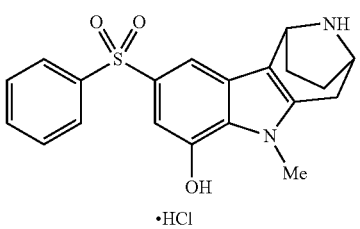<br>·HCl<br>Enantiomer 2 | 369 | $^1$H NMR (DMSO-d$_6$, 300 MHz) δ 10.49 (br s, 1H), 9.21-8.81 (m, 2H), 7.86 (dd, J = 7.8, 1.5 Hz, 2H), 7.79 (d, J = 1.8 Hz, 1H), 7.64-7.57 (m, 3H), 6.97 (d, J = 1.5 Hz, 1H), 5.23 (d, J = 3.6 Hz, 1H), 4.47-4.39 (m, 1H), 3.87 (s, 3H), 3.25 (d, J = 5.1 Hz, 1H), 2.92 (d, J = 16.8 Hz, 1H), 2.29-2.19 (m, 2H), 2.09-2.01 (m, 1H), 1.82-1.72 (m, 1H) |
| 205 | 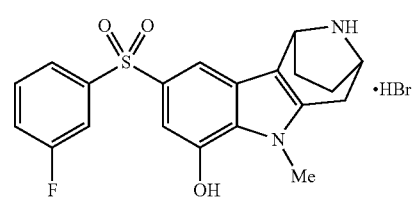<br>(−)-Enantiomer | 387 | $^1$H NMR (DMSO-d$_6$, 300 MHz) δ 10.54 (s, 1H), 9.15 (br s, 1H), 8.97 (br s, 1H), 7.87 (d, J = 1.6 Hz, 1H), 7.68 (m, 3H), 7.52 (m, 1H), 6.98 (d, J = 1.7 Hz, 1H), 5.30 (br d, J = 3.8 Hz, 1H), 4.48 (br s, 1H), 3.88 (s, 3H), 3.29 (dd, J = 18.6, 4.0 Hz, 1 H, partially masked by solvent), 2.96 (d, J = 17.2 Hz, 1H), 2.24 (m, 2H), 2.08 (t, J = 9.8 Hz, 1H), 1.80 (t, J = 8.1 Hz, 1H) |
| 206 | 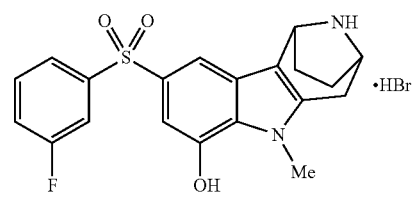<br>(+)-Enantiomer | 387 | $^1$H NMR (DMSO-d$_6$, 300 MHz) δ 10.53 (s, 1H), 9.10 (br s, 1H), 8.95 (br s, 1H), 7.87 (d, J = 1.7 Hz, 1H), 7.67 (m, 3H), 7.52 (m, 1H), 6.98 (d, J = 1.7 Hz, 1H), 5.30 (br d, J = 3.0 Hz, 1H), 4.48 (br s, 1H), 3.88 (s, 3H), 3.29 (dd, J = 16.2, 3.4 Hz, 1 H, partially masked by solvent), 2.96 (d, J = 17.0 Hz, 1H), 2.24 (m, 2H), 2.08 (t, J = 9.5 Hz, 1H), 1.81 (m, 1H) |
| 207 | 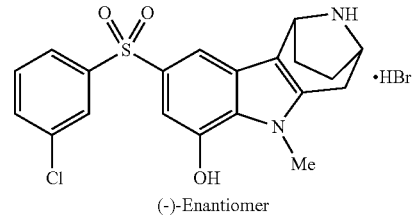 [SMILES: Cn1c2c(c3cc(S(=O)(=O)c4cccc(Cl)c4)cc(O)c31)C1CCC(C2)N1 ; Br]<br>(−)-Enantiomer | 403 | $^1$H NMR (DMSO-d$_6$, 300 MHz) δ 10.55 (s, 1H), 9.15 (br s, 1H), 8.97 (br s, 1H), 7.87 (m, 2H), 7.83 (td, J = 7.6, 1.4 Hz, 1H), 7.73 (m, 1H), 7.63 (t, J = 7.9 Hz, 1H), 6.98 (d, J = 1.7 Hz, 1H), 5.30 (br d, J = 3.8 Hz, 1H), 4.48 (br s, 1H), 3.88 (s, 3H), 3.29 (dd, J = 16.6, 3.9 Hz, 1 H, partially masked by solvent), 2.96 (d, J = 17.0 Hz, 1H), 2.24 (m, 2H), 2.10 (m, 1H), 1.80 (t, J = 7.8 Hz, 1H) |
| 208 | 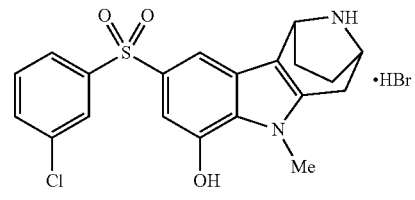<br>(+)-Enantiomer | 403 | $^1$H NMR (DMSO-d$_6$, 300 MHz) δ 10.54 (s, 1H), 9.13 (br s, 1H), 8.97 (br s, 1H), 7.87 (m, 2H), 7.83 (td, J = 7.6, 1.5 Hz, 1H), 7.74 (m, 1H), 7.63 (t, J = 8.0 Hz, 1H), 6.98 (d, J = 1.8 Hz, 1H), 5.31 (br d, J = 3.7 Hz, 1H), 4.49 (br s, 1H), 3.89 (s, 3H), 3.29 (dd, J = 16.7, 3.6 Hz, 1 H, partially masked by solvent), 2.96 (d, J = 16.9 Hz, 1H), 2.25 (m, 2H), 2.08 (t, J = 9.5 Hz, 1H), 1.81 (t, J = 8.1 Hz, 1H) |

TABLE 1-continued

| Ex. No. | Structure | Mass Spec | ¹H NMR Data |
|---|---|---|---|
| 209 | (+)-Enantiomer, ·HBr | 437 | ¹H NMR (DMSO-d₆, 300 MHz) δ 10.57 (s, 1H), 9.06 (br s, 1H), 8.95 (br s, 1H), 8.17 (d, J = 8.2 Hz, 1H), 8.12 (s, 1H), 5.06 (d, J = 7.6 Hz, 1H), 7.92 (t, J = 1.7 Hz, 1H), 7.86 (t, J = 7.9 Hz, 1H), 6.99 (d, J = 1.7 Hz, 1H), 5.30 (br d, J = 3.7 Hz, 1H), 4.48 (br s, 1H), 3.88 (s, 3H), 3.28 (dd, J = 15.9, 3.9 Hz, 1 H, partially masked by solvent), 2.96 (d, J = 17.1 Hz, 1H), 2.23 (m, 2H), 2.05 (m, 1H), 1.77 (m, 1H) |
| 210 | (−)-Enantiomer, ·HBr | 387 | ¹H NMR (DMSO-d₆, 300 MHz) δ 10.53 (s, 1H), 9.08 (br s, 1H), 8.94 (br s, 1H), 7.98 (dt, J = 3.8, 1.7 Hz, 1H), 7.78 (s, 1H), 7.73 (m, 1H), 7.46 (dt, J = 3.8, 0.9 Hz, 1H), 7.37 (dd, J = 10.5, 8.4 Hz, 1H), 7.00 (s, 1H), 5.30 (br d, J = 4.3 Hz, 1H), 4.47 (br s, 1H), 3.89 (s, 3H), 3.29 (dd, J = 15.8, 3.1 Hz, 1 H, partially masked by solvent), 2.96 (d, J = 16.9 Hz, 1H), 2.24 (m, 2H), 2.05 (t, J = 9.5 Hz, 1H), 1.82 (m, 1H) |
| 211 | (+)-Enantiomer, ·HBr | 387 | ¹H NMR (DMSO-d₆, 300 MHz) δ 10.53 (s, 1H), 9.08 (br s, 1H), 8.94 (br s, 1H), 7.98 (dt, J = 3.8, 1.7 Hz, 1H), 7.78 (s, 1H), 7.73 (m, 1H), 7.46 (dt, J = 3.8, 0.8 Hz, 1H), 7.37 (dd, J = 10.7, 8.8 Hz, 1H), 7.00 (s, 1H), 5.30 (br d, J = 4.2 Hz, 1H), 4.47 (br s, 1H), 3.89 (s, 3H), 3.29 (dd, J = 15.3, 3.2 Hz, 1 H, partially masked by solvent), 2.96 (d, J = 16.9 Hz, 1H), 2.22 (m, 2H), 2.05 (t, J = 9.4 Hz, 1H), 1.81 (m, 1H) |
| 212 | Enantiomer 1, ·HCl | 383 | ¹H NMR (CD₃OD, 300 MHz) δ 7.99-7.96 (m, 1H), 7.95 (d, J = 1.5 Hz, 1H), 7.87 (d, J = 1.5 Hz, 1H), 7.61-7.51 (m, 3H), 7.13 (d, J = 1.5 Hz, 1H), 5.24 (d, J = 4.8 Hz, 1H), 4.53 (t, J = 4.8 Hz, 1H), 3.97 (s, 3H), 3.93 (s, 3H), 3.41 (dd, J = 17.1, 4.5 Hz, 1H), 3.00 (d, J = 17.1 Hz, 1H), 2.50-2.21 (m, 3H), 2.01-1.91 (m, 1H) |
| 213 | Enantiomer 2, ·HCl | 383 | ¹H NMR (CD₃OD, 300 MHz) δ 7.96 (dd, J = 8.1, 1.5 Hz, 2H), 7.87 (d, J = 1.5 Hz, 1H), 7.61-7.51 (m, 3H), 7.13 (d, J = 1.5 Hz, 1H), 5.24 (d, J = 4.8 Hz, 1H), 4.53 (t, J = 5.7 Hz, 1H), 3.97 (s, 3H), 3.93 (s, 3H), 3.41 (dd, J = 17.1, 4.5 Hz, 1H), 3.00 (d, J = 17.1 Hz, 1H), 2.50-2.20 (m, 3H), 2.01-1.90 (m, 1H) |
| 214 | Enantiomer 2, ·HCl | 449 | ¹H NMR (DMSO-d₆, 300 MHz) δ 9.27 (br s, 2H), 8.02 (d, J = 1.5 Hz, 1H), 7.83 (d, J = 8.1 Hz, 1H), 7.74 (s, 1H), 7.64 (t, J = 8.1 Hz, 1H), 7.44 (dd, J = 8.1, 2.1 Hz, 1H), 7.36 (t, J = 73.5 Hz, 1H), 7.13 (d, J = 1.5 Hz, 1H), 5.29 (d, J = 3.9 Hz, 1H), 4.45 (br s, 1H), 3.96 (s, 3H), 3.86 (s, 3H), 3.28 (d, J = 3.5 Hz, 1H), 2.94 (d, J = 17.1 Hz, 1H), 2.32-2.18 (m, 2H), 2.11-1.98 (m, 1H), 1.84-1.70 (m, 1H) |

TABLE 1-continued

| Ex. No. | Structure | Mass Spec | ¹H NMR Data |
|---|---|---|---|
| 215 | 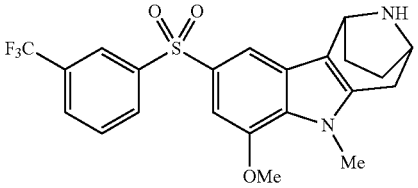 Enantiomer 1 | 451 | ¹H NMR (DMSO-$d_6$, 300 MHz) δ 9.30 (br s, 2H), 8.36-8.23 (m, 2H), 8.17-8.07 (m, 1H), 8.04 (d, J = 7.5 Hz, 1H), 7.84 (t, J = 7.8 Hz, 1H), 7.18 (d, J = 1.5 Hz, 1H), 5.30 (d, J = 3.9 Hz, 1H), 4.45 (s, 1H), 3.96 (s, 3H), 3.86 (s, 3H), 3.28 (d, J = 3.5 Hz, 1H), 2.95 (d, J = 17.1 Hz, 1H), 2.32-2.18 (m, 2H), 2.12-1.98 (m, 1H), 1.84-1.70 (m, 1H) |
| 216 | 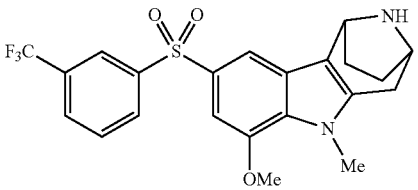 Enantiomer 2 | 451 | ¹H NMR (DMSO-$d_6$, 300 MHz) δ 9.65-9.10 (m, 2H), 8.36-8.23 (m, 2H), 8.09 (d, J = 1.5 Hz, 1H), 8.04 (d, J = 7.5 Hz, 1H), 7.84 (t, J = 7.8 Hz, 1H), 7.18 (d, J = 1.5 Hz, 1H), 5.30 (d, J = 3.9 Hz, 1H), 4.45 (s, 1H), 3.96 (s, 3H), 3.86 (s, 3H), 3.43-3.22 (m, 1H), 2.95 (d, J = 17.1 Hz, 1H), 2.32-2.18 (m, 2H), 2.12-1.98 (m, 1H), 1.84-1.70 (m, 1H) |
| 217 | 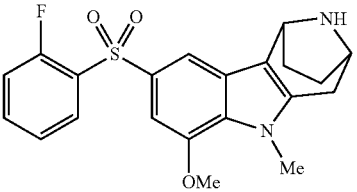 Enantiomer 1 | 401 | ¹H NMR (CD$_3$OD, 300 MHz) δ 8.09 (dt, J = 7.8, 1.8 Hz, 1H), 7.93-7.87 (m, 1H), 7.71-7.61 (m, 1H), 7.40 (t, J = 7.5 Hz, 1H), 7.26-7.16 (m, 2H), 5.23 (br s, 1H), 4.53 (br s, 1H), 3.97 (s, 3H), 3.95 (s, 3H), 3.50-3.36 (m, 1H), 3.01 (d, J = 17.4 Hz, 1H), 2.58-2.30 (m, 3H), 2.05-1.88 (m, 1H) |
| 218 | 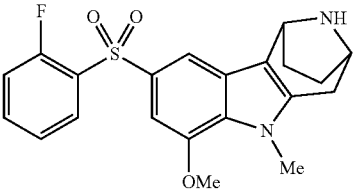 Enantiomer 2 | 401 | ¹H NMR (CD$_3$OD, 300 MHz) δ 8.09 (dt, J = 7.8, 1.8 Hz, 1H), 7.92-7.86 (m, 1H), 7.72-7.61 (m, 1H), 7.45-7.36 (m, 1H), 7.26-7.15 (m, 2H), 5.22 (br s, 1H), 4.53 (br s, 1H), 3.97 (s, 3H), 3.95 (s, 3H), 3.49-3.36 (m, 1H), 3.01 (d, J = 17.1 Hz, 1H), 2.52-2.17 (m, 3H), 2.02-1.88 (m, 1H) |
| 219 | 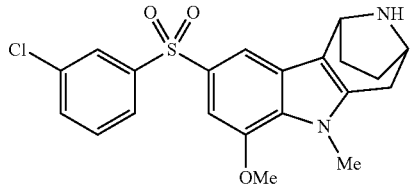 Enantiomer 1 | 417 | ¹H NMR (CD$_3$OD, 300 MHz) δ 7.95 (t, J = 1.5 Hz, 1H), 7.92-7.88 (m, 2H), 7.63-7.59 (m, 1H), 7.53 (t, J = 7.8 Hz, 1H), 7.15 (d, J = 1.5 Hz, 1H), 5.23 (d, J = 4.8 Hz, 1H), 4.51 (br s, 1H), 3.99 (s, 3H), 3.94 (s, 3H), 3.42 (dd, J = 17.4, 4.8 Hz, 1H), 3.00 (d, J = 17.1 Hz, 1H), 2.50-2.20 (m, 3H), 2.01-1.90 (m, 1H) |

TABLE 1-continued

| Ex. No. | Structure | Mass Spec | ¹H NMR Data |
|---|---|---|---|
| 220 | [3-chlorophenylsulfonyl-methoxy-N-methyl carbazole fused bicyclic amine] ·HCl Enantiomer 2 | 417 | ¹H NMR (CD$_3$OD, 300 MHz) δ 7.95 (t, J = 1.5 Hz, 1H), 7.92-7.88 (m, 2H), 7.63-7.59 (m, 1H), 7.53 (t, J = 7.8 Hz, 1H), 7.15 (d, J = 1.5 Hz, 1H), 5.23 (d, J = 4.8 Hz, 1H), 4.51 (br s, 1H), 3.99 (s, 3H), 3.94 (s, 3H), 3.42 (dd, J = 17.4, 4.8 Hz, 1H), 3.00 (d, J = 17.1 Hz, 1H), 2.50-2.20 (m, 3H), 2.01-1.90 (m, 1H) |
| 221 | [3-fluorophenylsulfonyl-methoxy-N-methyl carbazole fused bicyclic amine] ·HCl Enantiomer 1 | 401 | ¹H NMR (CD$_3$OD, 300 MHz) δ 7.90 (d, J = 1.5 Hz, 1H), 7.80 (d, J = 9.3 Hz, 1H), 7.74-7.68 (m, 1H), 7.62-7.53 (m, 1H), 7.39-7.31 (m, 1H), 7.15 (d, J = 1.5 Hz, 1H), 5.25 (d, J = 5.1 Hz, 1H), 4.53 (br s, 1H), 3.99 (s, 3H), 3.94 (s, 3H), 3.42 (dd, J = 17.4, 4.8 Hz, 1H), 3.01 (d, J = 17.4 Hz, 1H), 2.49-2.21 (m, 3H), 2.03-1.90 (m, 1H) |
| 222 | [3-fluorophenylsulfonyl-methoxy-N-methyl carbazole fused bicyclic amine] ·HCl Enantiomer 2 | 401 | ¹H NMR (CD$_3$OD, 300 MHz) δ 7.90 (d, J = 1.5 Hz, 1H), 7.80 (d, J = 10.5 Hz, 1H), 7.74-7.68 (m, 1H), 7.62-7.53 (m, 1H), 7.39-7.31 (m, 1H), 7.15 (d, J = 1.5 Hz, 1H), 5.25 (d, J = 4.8 Hz, 1H), 4.53 (br s, 1H), 3.99 (s, 3H), 3.93 (s, 3H), 3.42 (dd, J = 17.1, 4.2 Hz, 1H), 2.99 (d, J = 16.8 Hz, 1H), 2.49-2.20 (m, 3H), 2.01-1.89 (m, 1H) |
| 223 | [1-methylindol-3-yl-sulfonyl-methoxy-N-methyl carbazole fused bicyclic amine] ·HCl Enantiomer 1 | 436 | ¹H NMR (DMSO-d$_6$, 300 MHz) δ 9.11 (br s, 2H), 8.17 (s, 1H), 7.98 (d, J = 1.5 Hz, 1H), 7.86 (d, J = 7.5 Hz, 1H), 7.54 (d, J = 8.1 Hz, 1H), 7.31-7.17 (m, 2H), 7.12 (d, J = 1.5 Hz, 1H), 5.29 (d, J = 3.6 Hz, 1H), 4.49-4.40 (m, 1H), 3.91 (s, 3H), 3.86 (s, 3H), 3.82 (s, 3H), 3.31-3.21 (m, 1H), 2.92 (d, J = 16.8 Hz, 1H), 2.31-2.18 (m, 2H), 2.07-1.96 (m, 1H), 1.81-1.70 (m, 1H) |
| 224 | [1-methylindol-3-yl-sulfonyl-methoxy-N-methyl carbazole fused bicyclic amine] ·HCl Enantiomer 2 | 436 | ¹H NMR (DMSO-d$_6$, 300 MHz) δ 9.11 (br s, 2H), 8.17 (s, 1H), 7.97 (d, J = 1.5 Hz, 1H), 7.87 (d, J = 7.5 Hz, 1H), 7.54 (d, J = 8.1 Hz, 1H), 7.31-7.17 (m, 2H), 7.12 (d, J = 1.5 Hz, 1H), 5.29 (d, J = 4.2 Hz, 1H), 4.49-4.40 (m, 1H), 3.91 (s, 3H), 3.86 (s, 3H), 3.82 (s, 3H), 3.31-3.21 (m, 1H), 2.91 (d, J = 17.1 Hz, 1H), 2.31-2.18 (m, 2H), 2.07-1.97 (m, 1H), 1.81-1.70 (m, 1H) |

TABLE 1-continued

| Ex. No. | Structure | Mass Spec | ¹H NMR Data |
|---|---|---|---|
| 225 | (+)-Enantiomer | 431 | ¹H NMR (CD₃OD, 300 MHz) δ 7.92 (m, 3H), 7.62 (td, J = 8.1, 1.6 Hz, 1H), 7.54 (t, J = 7.9 Hz, 1H), 7.17 (t, J = 2.0 Hz, 1H), 5.15 (2xd, J = 4.5 Hz, 1H), 4.34 (m, 1H), 4.00 (s, 1.2H), 3.99 (s, 1.8H), 3.97 (s, 1.2H), 3.95 (s, 1.8H), 3.48 (m, 1H), 3.06 (m, 1H), 2.96 (s, 1.8H), 2.80 (s, 1.2H), 2.55 (2xm, 2H), 2.28 (m, 1H), 2.05 (m, 1H) |
| 226 | (−)-Enantiomer | 431 | ¹H NMR (CD₃OD, 500 MHz) δ 7.95 (s, 1H), 7.90 (td, J = 7.9, 1.3 Hz, 1H), 7.88 (s, 1H), 7.61 (m, 1H), 7.54 (t, J = 7.9 Hz, 1H), 7.17 (s, 1H), 5.15 (m, 1H), 4.34 (br s, 1H), 4.00 (s, 3H), 3.97 (s, 1.2H), 3.95 (s, 1.8H), 3.46 (m, 1H), 3.08 (m, 1H), 2.96 (s, 1.8H), 2.80 (s, 1.2H), 2.55 (2xm, 2H), 2.28 (m, 1H), 2.04 (m, 1H) |
| 227 | (−)-Enantiomer | 397 | ¹H NMR (CD₃OD, 500 MHz) δ 7.96 (m, 2H), 7.85 (t,, J = 1.7 Hz, 1H), 7.60 (m, 1H), 7.55 (t, J = 7.6 Hz, 2H), 7.16 (m, 1H), 5.14 (2xd, J = 5.4 Hz, 1H), 4.32 (m, 1H), 3.99 (s, 1.2H), 3.98 (s, 1.8H), 3.96 (s, 1.2H), 3.94 (s, 1.8H), 3.47 (m, 1H), 3.05 (m, 1H), 2.96 (s, 1.8H), 2.80 (s, 1.2H), 2.53 (2xm, 2H), 2.27 (m, 1H), 2.03 (m, 1H) |
| 228 | Enantiomer 1 | 406 | ¹H NMR (DMSO-d₆, 300 MHz) δ 8.92 (br s, 2H), 8.28 (d, J = 1.5 Hz, 1H), 7.99 (d, J = 8.4 Hz, 1H), 7.79 (d, J = 3.9 Hz, 1H), 7.56 (d, J = 7.5 Hz, 1H), 7.37-7.16 (m, 3H), 6.78 (dd, J = 3.9, 0.6 Hz, 1H), 5.29-5.22 (m, 1H), 4.42 (br s, 1H), 3.81 (s, 3H), 3.31-3.20 (m, 1H), 2.90 (d, J = 17.4 Hz, 1H), 2.70 (s, 3H), 2.28-2.18 (m, 2H), 2.03-1.91 (m, 1H), 1.78-1.67 (m, 1H) |
| 229 | Enantiomer 2 | 406 | ¹H NMR (DMSO-d₆, 300 MHz) δ 9.27 (br s, 2H), 8.30 (d, J = 1.8 Hz, 1H), 7.99 (d, J = 7.8 Hz, 1H), 7.79 (d, J = 3.6 Hz, 1H), 7.56 (d, J = 7.5 Hz, 1H), 7.38-7.16 (m, 3H), 6.78 (d, J = 3.9 Hz, 1H), 5.30 (d, J = 4.4 Hz, 1H), 4.43 (br s, 1H), 3.81 (s, 3H), 3.30-3.24 (m, 1H), 2.92 (d, J = 17.1 Hz, 1H), 2.70 (s, 3H), 2.31-2.20 (m, 2H), 2.03-1.91 (m, 1H), 1.78-1.67 (m, 1H) |
| 230 | Enantiomer 1 | 436 | ¹H NMR (DMSO-d₆, 300 MHz) δ 9.59 (br s, 1H), 9.06 (d, J = 8.1 Hz, 1H), 8.06-7.88 (m, 2H), 7.59 (d, J = 1.5 Hz, 1H), 7.50 (d, J = 7.8 Hz, 1H), 7.32 (dt, J = 7.5, 1.2 Hz, 1H), 7.22 (t, J = 6.6 Hz, 1H), 7.00 (d, J = 1.5 Hz, 1H), 5.27 (br s, 1H), 4.43 (br s, 1H), 3.86 (s, 3H), 3.79 (s, 3H), 3.26 (dd, J = 17.4, 4.5 Hz, 1H), 2.90 (d, J = 17.1 Hz, 1H), 2.32-2.18 (m, 5H), 2.02-1.93 (m, 1H), 1.80-1.68 (m, 1H) |

TABLE 1-continued

| Ex. No. | Structure | Mass Spec | $^1$H NMR Data |
|---|---|---|---|
| 231 | (structure) ·HCl Enantiomer 2 | 436 | $^1$H NMR (DMSO-d$_6$, 300 MHz) δ 9.65-9.55 (m, 1H), 9.06 (d, J = 9.3 Hz, 1H), 8.06-7.88 (m, 2H), 7.59 (d, J = 0.9 Hz, 1H), 7.50 (d, J = 7.5 Hz, 1H), 7.32 (dt, J = 8.1, 0.9 Hz, 1H), 7.22 (t, J = 7.8 Hz, 1H), 7.00 (d, J = 1.5 Hz, 1H), 5.27 (br s, 1H), 4.43 (br s, 1H), 3.86 (s, 3H), 3.79 (s, 3H), 3.26 (dd, J = 17.1, 4.2 Hz, 1H), 2.90 (d, J = 17.1 Hz, 1H), 2.32-2.18 (m, 5H), 2.02-1.93 (m, 1H), 1.80-1.68 (m, 1H) |
| 232 | (structure) ·HCl Enantiomer 1 | 434 | $^1$H NMR (DMSO-d$_6$, 300 MHz) δ 9.66 (s, 1H), 9.61 (s, 1H), 9.22 (s, 1H), 9.07 (d, J = 9.3 Hz, 1H), 8.67 (d, J = 8.4 Hz, 1H), 8.29 (d, J = 8.1 Hz, 1H), 8.15 (d, J = 1.5 Hz, 1H), 7.98-7.93 (m, 1H), 7.83-7.78 (m, 1H), 7.17 (d, J = 1.5 Hz, 1H), 5.32 (s, 1H), 4.45 (s, 1H), 3.96 (s, 3H), 3.78 (s, 3H), 3.28 (dd, J = 17.2, 4.5 Hz, 1H), 2.92 (d, J = 17.1 Hz, 1H), 2.29-2.18 (m, 2H), 2.04-1.95 (m, 1H), 1.82-1.72 (s, 1H) |
| 233 | (structure) ·HCl Enantiomer 2 | 434 | $^1$H NMR (DMSO-d$_6$, 300 MHz) δ 9.61 (s, 1H), 9.43 (m, 1H), 9.21 (s, 1H), 9.01 (d, J = 9.0 Hz, 1H), 8.66 (d, J = 9.0 Hz, 1H), 8.29 (d, J = 8.1 Hz, 1H), 8.15 (d, J = 1.5 Hz, 1H), 7.98-7.92 (m, 1H), 7.83-7.78 (m, 1H), 7.17 (d, J = 1.5 Hz, 1H), 5.32 (s, 1H), 4.45 (s, 1H), 3.96 (s, 3H), 3.78 (s, 3H), 3.27 (dd, J = 17.2, 4.8 Hz, 1H), 2.93 (d, J = 16.8 Hz, 1H), 2.26-2.22 (m, 2H), 2.05-1.98 (m, 1H), 1.82-1.70 (s, 1H) |
| 234 | (structure) ·HCl Enantiomer 1 | 397 | $^1$H NMR (DMSO-d$_6$, 400 MHz) δ 9.51-9.12 (m, 2H), 7.97-7.93 (m, 3H), 7.65-7.55 (m, 3H), 7.08 (d, J = 1.6 Hz, 1H), 5.28 (d, J = 4.0 Hz, 1H), 4.44 (br s, 1H), 4.25-4.17 (m, 2H), 3.87 (s, 3H), 3.31-3.25 (m, 1H), 2.94 (d, J = 16.4 Hz, 1H), 2.28-2.17 (m, 2H), 2.07-2.00 (m, 1H), 1.80-1.74 (m, 1H), 1.41 (t, J = 7.2 Hz, 3H) |
| 235 | (structure) ·HCl Enantiomer 2 | 397 | $^1$H NMR (DMSO-d$_6$, 400 MHz) δ 9.51-9.12 (m, 2H), 7.97-7.93 (m, 3H), 7.65-7.55 (m, 3H), 7.08 (d, J = 1.6 Hz, 1H), 5.28 (d, J = 4.0 Hz, 1H), 4.44 (br s, 1H), 4.25-4.17 (m, 2H), 3.87 (s, 3H), 3.31-3.24 (m, 1H), 2.94 (d, J = 16.4 Hz, 1H), 2.28-2.15 (m, 2H), 2.07-2.01 (m, 1H), 1.74-1.80 (m, 1H), 1.41 (t, J = 7.2 Hz, 3H) |

TABLE 1-continued

| Ex. No. | Structure | Mass Spec | ¹H NMR Data |
|---|---|---|---|
| 236 | 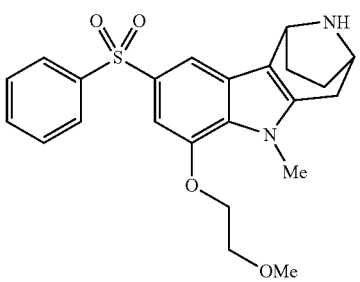 ·HCl Enantiomer 1 | 427 | ¹H NMR (CD$_3$OD, 400 MHz) δ 8.00-7.94 (m, 2H), 7.88 (s, 1H), 7.63-7.51 (m, 3H), 7.16 (s, 1H), 5.23 (d, J = 4.8 Hz, 1H), 4.52 (t, J = 5.2 Hz, 1H), 4.29 (t, J = 4.4 Hz, 2H), 3.96 (s, 3H), 3.82 (t, J = 4.4 Hz, 2H), 3.45-3.37 (m, 4H), 3.00 (d, J = 17.2 Hz, 1H), 2.50-2.30 (m, 2H), 2.20-2.13 (m, 1H), 2.00-1.88 (m, 1H) |
| 237 | 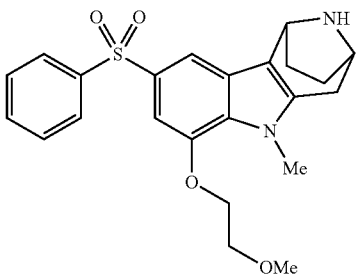 ·HCl Enantiomer 2 | 427 | ¹H NMR (CD$_3$OD, 400 MHz) δ 8.00-7.93 (m, 2H), 7.88 (s, 1H), 7.63-7.50 (m, 3H), 7.16 (s, 1H), 5.23 (d, J = 5.2 Hz, 1H), 4.52 (t, J = 5.6 Hz, 1H), 4.29 (t, J = 4.4 Hz, 2H), 3.96 (s, 3H), 3.82 (t, J = 4.4 Hz, 2H), 3.45-3.36 (m, 4H), 3.00 (d, J = 17.2 Hz, 1H), 2.49-2.29 (m, 2H), 2.29-2.19 (m, 1H), 2.01-1.88 (m, 1H) |
| 238 | 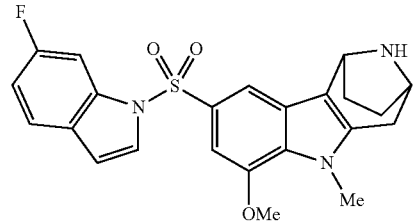 ·HCl Enantiomer 1 | 440 | ¹H NMR (DMSO-d$_6$, 400 MHz) δ 9.29 (br s, 2H), 8.18 (s, 1H), 7.89-7.73 (m, 2H), 7.63-7.50 (m, 1H), 7.15-7.02 (m, 2H), 6.80 (br s, 1H), 5.35-5.25 (m, 1H), 4.50-4.37 (m, 1H), 3.89 (s, 3H), 3.81 (s, 3H), 3.25 (dd, J = 17.6, 4.8 Hz, 1H), 2.92 (d, J = 16.2 Hz, 1H), 2.29-2.13 (m, 2H), 2.03-1.93 (m, 1H), 1.79-1.70 (m, 1H) |
| 239 | 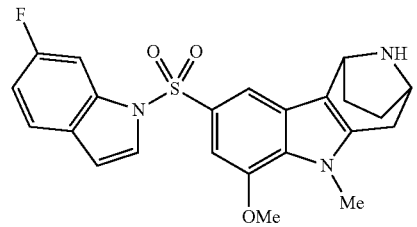 ·HCl Enantiomer 2 | 440 | ¹H NMR (DMSO-d$_6$, 400 MHz) δ 9.22 (br s, 2H), 8.18 (s, 1H), 7.87 (d, J = 3.6 Hz, 1H), 7.81 (dd, J = 10.0, 2.4 Hz, 1H), 7.59 (dd, J = 8.4, 5.2 Hz, 1H), 7.13-7.05 (m, 2H), 6.79 (dd, J = 3.6, 0.6 Hz, 1H), 5.31 (s, 1H), 4.44 (s, 1H), 3.89 (s, 3H), 3.81 (s, 3H), 3.25 (dd, J = 17.6, 4.8 Hz, 1H), 2.92 (d, J = 16.8 Hz, 1H), 2.28-2.15 (m, 2H), 2.03-1.94 (m, 1H), 1.79-1.70 (m, 1H) |
| 240 | 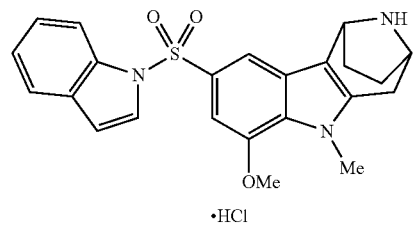 ·HCl Enantiomer 1 | 422 | ¹H NMR (CD$_3$OD, 400 MHz) δ 8.03 (d, J = 6.0 Hz, 1H), 7.88 (d, J = 1.2 Hz, 1H), 7.68 (d, J = 3.0 Hz, 1H), 7.50 (d, J = 6.0 Hz, 1H), 7.27 (t, J = 6.3 Hz, 1H), 7.17 (t, J = 6.0 Hz, 1H), 7.01 (d, J = 1.2 Hz, 1H), 6.68 (d, J = 3.3 Hz, 1H), 5.21 (d, J = 3.6 Hz, 1H), 4.51-4.48 (m, 1H), 3.87 (s, 3H), 3.86 (s, 3H), 3.46-3.43 (m, 1H), 2.96 (d, J = 13.8 Hz, 1H), 2.48-2.30 (m, 2H), 2.24-2.15 (m, 1H), 1.97-1.87 (m, 1H) |

TABLE 1-continued

| Ex. No. | Structure | Mass Spec | ¹H NMR Data |
|---|---|---|---|
| 241 | (structure) ·HCl Enantiomer 2 | 422 | ¹H NMR (CD₃OD, 400 MHz) δ 8.03 (d, J = 6.3 Hz, 1H), 7.88 (d, J = 1.2 Hz, 1H), 7.68 (d, J = 2.7 Hz, 1H), 7.50 (d, J = 6.0 Hz, 1H), 7.27 (t, J = 6.3 Hz, 1H), 7.17 (t, J = 6.0 Hz, 1H), 7.01 (d, J = 1.6 Hz, 1H), 6.68 (dd, J = 4.0, 0.8 Hz, 1H), 5.21 (d, J = 5.2 Hz, 1H), 4.51-4.48 (m, 1H), 3.87 (s, 3H), 3.86 (s, 3H), 3.46-3.43 (m, 1H), 2.96 (d, J = 14.1 Hz, 1H), 2.48-2.30 (m, 2H), 2.24-2.15 (m, 1H), 1.97-1.87 (m, 1H) |
| 242 | (structure) ·HCl Enantiomer 1 | 447 | ¹H NMR (DMSO-d₆, 300 MHz) δ 9.27 (br s, 2H), 8.47 (s, 1H), 8.31 (d, J = 1.8 Hz, 1H), 8.17 (d, J = 3.6 Hz, 1H), 7.78 (d, J = 8.1 Hz, 1H), 7.61 (dd, J = 8.1, 1.2 Hz, 1H), 7.13 (d, J = 1.5 Hz, 1H), 6.93 (d, J = 3.6 Hz, 1H), 5.33 (d, J = 4.5 Hz, 1H), 4.45 (br s, 1H), 3.91 (s, 3H), 3.81 (s, 3H), 3.28-3.23 (m, 1H), 2.92 (d, J = 17.1 Hz, 1H), 2.30-2.22 (m, 2H), 2.01-1.91 (m, 1H), 1.77-1.71 (m, 1H) |
| 243 | (structure) ·HCl Enantiomer 2 | 447 | ¹H NMR (DMSO-d₆, 300 MHz) δ 9.28 (br s, 2H), 8.47 (s, 1H), 8.31 (d, J = 1.5 Hz, 1H), 8.17 (d, J = 3.6 Hz, 1H), 7.78 (d, J = 8.1 Hz, 1H), 7.61 (dd, J = 8.1, 1.2 Hz, 1H), 7.13 (d, J = 1.5 Hz, 1H), 6.93 (d, J = 3.6 Hz, 1H), 5.33 (d, J = 4.5 Hz, 1H), 4.45 (br s, 1H), 3.93 (s, 3H), 3.81 (s, 3H), 3.29-3.23 (m, 1H), 2.91 (d, J = 17.1 Hz, 1H), 2.30-2.18 (m, 2H), 2.02-1.95 (m, 1H), 1.75-1.71 (m, 1H) |
| 244 | (structure) ·HCl Enantiomer 1 | 419 | ¹H NMR (CD₃OD, 300 MHz) δ 8.42-8.28 (m, 3H), 8.01-7.92 (m, 1H), 7.88 (d, J = 6 Hz, 1H), 7.70-7.56 (m, 2H), 7.31 (dd, J = 8.7, 1.8 Hz, 1H), 6.56 (t, J = 2.1 Hz, 1H), 5.31 (d, J = 4.2 Hz, 1H), 4.59-4.49 (m, 1H), 3.71 (s, 3H), 3.50 (dd, J = 17.4, 4.5 Hz, 1H), 3.06 (d, J = 17.4 Hz, 1H), 2.52-2.24 (m, 3H), 2.03-1.92 (m, 1H) |
| 245 | (structure) ·HCl Enantiomer 2 | | ¹H NMR (DMSO-d₆, 300 MHz) δ 9.20-8.70 (br s, 2H), 8.64 (d, J = 2.4 Hz, 1H), 8.42 (d, J = 1.5 Hz, 1H), 8.39-8.34 (m, 1H), 8.14-8.06 (m, 1H), 7.87-7.78 (m, 2H), 7.77-7.65 (m, 3H), 6.63-6.56 (m, 1H), 5.38-5.28 (m, 1H), 4.52-4.38 (m, 1H), 3.67 (s, 3H), 3.39-3.33 (m, 1H), 2.98 (d, J = 17.1 Hz, 1H), 2.33-2.16 (m, 2H), 2.15-2.02 (m, 1H), 2.35-1.72 (m, 1H). |

TABLE 1-continued

| Ex. No. | Structure | Mass Spec | $^1$H NMR Data |
|---|---|---|---|
| 246 | 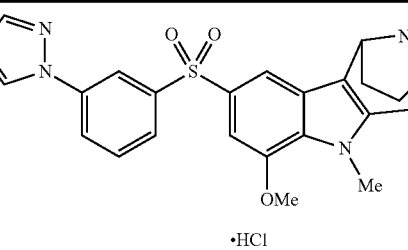<br>·HCl<br>Enantiomer 1 | 449 | $^1$H NMR (DMSO-d$_6$, 400 MHz) δ 9.52-9.42 (m, 1H), 9.05 (d, J = 9.2 Hz, 1H), 8.69-8.62 (m, 1H), 8.41-8.36 (m, 1H), 8.13-8.08 (m, 1H), 8.07-8.04 (m, 1H) 7.91-7.85 (m, 1H), 7.80 (d, J = 1.6 Hz, 1H), 7.70 (t, J = 8 Hz, 1H), 7.16 (d, J = 1.6 Hz, 1H), 6.62-6.58 (m, 1H), 5.38-5.25 (m, 1H), 4.52-4.41 (m, 1H), 3.96 (s, 3H), 3.85 (s, 3H), 3.34-3.24 (m, 1H), 2.94 (d, J = 16.8 Hz, 1H), 2.32-2.18 (m, 2H), 2.05 (t, J = 10 Hz, 1H), 1.85-1.70 (m, 1H) |
| 247 | 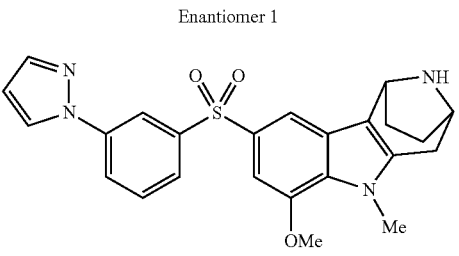<br>·HCl<br>Enantiomer 2 | 449 | $^1$H NMR (DMSO-d$_6$, 400 MHz) δ 9.50 (br s, 1H), 9.05 (br s, 1H), 8.69-8.62 (m, 1H), 8.41-8.36 (m, 1H), 8.13-8.08 (m, 1H), 8.07-8.04 (m, 1H) 7.91-7.85 (m, 1H), 7.80 (d, J = 1.6 Hz, 1H), 7.70 (t, J = 8 Hz, 1H), 7.16 (d, J = 1.6 Hz, 1H), 6.62-6.58 (m, 1H), 5.31 (d, J = 4.0 Hz, 1H), 4.52-4.41 (m, 1H), 3.96 (s, 3H), 3.85 (s, 3H), 3.34-3.24 (m, 1H), 2.94 (d, J = 16.8 Hz, 1H), 2.32-2.18 (m, 2H), 2.05 (t, J = 10 Hz, 1H), 1.85-1.70 (m, 1H) |

Example 248

Binding Assay Procedures

The relative affinities of the various compounds for the 5-HT$_6$ receptor were measured in a radioligand binding assay, using a scintillation proximity assay (SPA) format. Test compounds were dissolved to 10 mM in 100% DMSO, then serially diluted at 4× assay concentrations into assay buffer containing 16% DMSO in 96-well poly-propylene plates.

For binding analysis vs. the human receptor, samples were incubated in 50 mM Tris-HCl, pH 7.5, 5 mM MgCl$_2$, 1 mM EDTA (4% DMSO final) with 10 nM [N-methyl-$^3$H]-LSD (Perkin Elmer), 2.5 µg of human 5-HT$_6$ receptor membranes (Millipore) and 50 µg SPA beads (PVT-PEI-WGA, GE Healthcare) per well in a final volume of 0.2 mL. For binding analysis vs. the rat receptor, samples were incubated in the same buffer with 3.5 nM [N-methyl-$^3$H]-LSD, 50 µg of rat 5-HT$_6$ receptor membranes (Perkin Elmer) and 0.4 mg SPA beads (PVT-PEI-WGA Type B, GE Healthcare) per well also in a final volume of 0.2 mL. Binding reactions were performed in PicoPlate96 microtiter plates (Perkin Elmer) by consecutively adding 50 µL of each competing compound or buffer, SPA beads, radioligand, and 5-HT$_6$ receptor membranes. After an overnight incubation at room temperature on a Nutator mixer, plates were centrifuged for 15 min at 1,500 rpm, followed by incubation in the dark for 10 min. Radioactivity was counted in either a TopCountNXT microplate counter (Perkin Elmer) or a Wallac Trilux 1450 Microbeta microplate reader (Perkin Elmer) for 5 min per well. Total binding control contained compound dilution buffer only; nonspecific binding is determined in the presence of 100 µM 5-hydroxytryptamine. Specific binding was determined by subtracting nonspecific binding from total binding.

All experiments were performed in duplicate using ten concentrations of competing ligand. IC$_{50}$ values were determined from specific binding data using XLfit4.1 curve fitting software from IDBS Ltd. The inhibition constant (K$_i$) was calculated using the Cheng-Prusoff equation: $K_i = IC_{50}/(1+(L/K_D))$, where L=concentration of radioligand in the assay, and $K_D$=affinity of the radioligand for the receptor.

Example 249

Cell-Based Functional Assay Procedures

The functional activities of the various compounds on the 5-HT$_6$ receptor were determined in a cell-based functional assay by measuring the production of cAMP using HTRF™ assay technology (CisBio International). Test compounds were dissolved to 10 mM in 100% DMSO, then serially diluted at 1000× assay concentrations into 100% DMSO in 96-well polypropylene plates. Compounds were further diluted to 4× assay concentrations with serum free media containing IBMX. For functional analysis vs. the human 5-HT$_6$ receptor expressing cell lines, samples were incubated in serum free DMEM with 1 mM IBMX (0.25% DMSO final) with 60,000 cells/well in a final volume of 100 µL for a total of 30 minutes at room temperature.

Antagonist activity was determined after a 20 minute incubation by the addition of a 5-hydroxytryptamine challenge at the EC$_{80}$ (30 nM 5-HT) and an additional incubation of 10 minutes. Cells were lysed by addition of HTRF™ reagents (CisBio International) and after another 30 minute incubation, the plates were read on an AnalystGT (MDS) or SynergyHT (BioTek) microplate reader. Basal cAMP accumulation levels were measured in the presence of 0.25% DMSO only. Antagonist activity was expressed as the ratio of cAMP produced in a test well to the average cAMP produced in the EC$_{80}$ challenge control wells.

Agonist activity was determined after a full 30 minutes of incubation at room temperature, using 10 µM 5-HT as the E$_{max}$ control. Cells were lysed by addition of HTRF™ reagents (CisBio International) and after another 30 minute incubation, the plates were read on an AnalystGT (MDS) or SynergyHT (BioTek) microplate reader. Basal cAMP accumulation levels were measured in the presence of 0.25%

DMSO only. Agonist activity was expressed as the ratio of cAMP produced in a test well to the average cAMP produced in the $E_{max}$ control wells.

All cell-based experiments were performed in duplicate using ten concentrations of test compound with 5-HT (agonist mode) or a known antagonist (antagonist mode) included as additional controls in every run. $IC_{50}/EC_{50}$ values were determined using XLfit4.1 curve fitting software from IDBS Ltd. For antagonists, the apparent dissociation constant ($K_b$) was calculated using a modified Cheng-Prusoff equation: $K_b=IC_{50}/(1+(A/EC_{50A}))$, where A=concentration of reference agonist in the assay and $EC_{50}A=EC_{50}$ value of the reference agonist.

TABLE 2

Biological activity of the compounds of the present invention.

| Compound | human $5HT_6$ Ki (nM) |
|---|---|
| Compound of Example 27 | 7.8 |
| Compound of Example 28 | 60 |
| Compound of Example 29 | 136 |
| Compound of Example 30 | 410 |
| Compound of Example 31 | 44 |
| Compound of Example 32 | 11 |
| Compound of Example 33 | 15 |
| Compound of Example 34 | 4.8 |
| Compound of Example 35 | 4.2 |
| Compound of Example 36 | 1.8 |
| Compound of Example 37 | 3.7 |
| Compound of Example 38 | 2.1 |
| Compound of Example 39 | 3.8 |
| Compound of Example 40 | 5.8 |
| Compound of Example 41 | 17 |
| Compound of Example 42 | 11 |
| Compound of Example 43 | 35 |
| Compound of Example 44 | 6.3 |
| Compound of Example 45 | 14 |
| Compound of Example 46 | 6.5 |
| Compound of Example 47 | 11 |
| Compound of Example 48 | 2.0 |
| Compound of Example 49 | 1.4 |
| Compound of Example 50 | 37 |
| Compound of Example 51 | 37 |
| Compound of Example 52 | 11 |
| Compound of Example 53 | 13 |
| Compound of Example 54 | 10 |
| Compound of Example 55 | 8.5 |
| Compound of Example 56 | 51 |
| Compound of Example 57 | 2.6 |
| Compound of Example 58 | 44 |
| Compound of Example 59 | 139 |
| Compound of Example 60 | 193 |
| Compound of Example 61 | 156 |
| Compound of Example 62 | 0.85 |
| Compound of Example 63 | 1.43 |
| Compound of Example 64 | 5.6 |
| Compound of Example 65 | 0.59 |
| Compound of Example 66 | 18 |
| Compound of Example 67 | 4.1 |
| Compound of Example 68 | 1.2 |
| Compound of Example 69 | 7.8 |
| Compound of Example 70 | 8.2 |
| Compound of Example 71 | 3.3 |
| Compound of Example 72 | 8.1 |
| Compound of Example 73 | 3.0 |
| Compound of Example 74 | 7.1 |
| Compound of Example 75 | 3.6 |
| Compound of Example 76 | 6.9 |
| Compound of Example 77 | 4.9 |
| Compound of Example 78 | 794 |
| Compound of Example 79 | 1.6 |
| Compound of Example 80 | 17 |
| Compound of Example 81 | 13 |
| Compound of Example 82 | 22 |
| Compound of Example 83 | 0.96 |
| Compound of Example 84 | 1.0 |

TABLE 2-continued

Biological activity of the compounds of the present invention.

| Compound | human $5HT_6$ Ki (nM) |
|---|---|
| Compound of Example 85 | 14 |
| Compound of Example 86 | 14 |
| Compound of Example 87 | 350 |
| Compound of Example 88 | 350 |
| Compound of Example 89 | 432 |
| Compound of Example 90 | 52 |
| Compound of Example 91 | 115 |
| Compound of Example 92 | 150 |
| Compound of Example 94 | 0.32 |
| Compound of Example 95 | 5.8 |
| Compound of Example 96 | 341 |
| Compound of Example 97 | 104 |
| Compound of Example 98 | 1.3 |
| Compound of Example 99 | 4.5 |
| Compound of Example 100 | 1.2 |
| Compound of Example 101 | 2.9 |
| Compound of Example 102 | 0.71 |
| Compound of Example 103 | 9.3 |
| Compound of Example 104 | 5.0 |
| Compound of Example 105 | 100 |
| Compound of Example 106 | 3.9 |
| Compound of Example 107 | 78 |
| Compound of Example 108 | 15 |
| Compound of Example 109 | 0.72 |
| Compound of Example 110 | 148 |
| Compound of Example 111 | 22 |
| Compound of Example 112 | 4.6 |
| Compound of Example 113 | 23 |
| Compound of Example 115 | 4.8 |
| Compound of Example 116 | 20 |
| Compound of Example 117 | 4.4 |
| Compound of Example 118 | 5.8 |
| Compound of Example 119 | 228 |
| Compound of Example 120 | 64 |
| Compound of Example 121 | 1.9 |
| Compound of Example 122 | 48 |
| Compound of Example 123 | 0.47 |
| Compound of Example 124 | 0.33 |
| Compound of Example 125 | 244 |
| Compound of Example 126 | 7.2 |
| Compound of Example 127 | 1.5 |
| Compound of Example 128 | 24 |
| Compound of Example 129 | 2.7 |
| Compound of Example 130 | 3.6 |
| Compound of Example 131 | 13 |
| Compound of Example 132 | 39 |
| Compound of Example 133 | 11 |
| Compound of Example 134 | 0.26 |
| Compound of Example 135 | 3.2 |
| Compound of Example 136 | 1.4 |
| Compound of Example 137 | 1.2 |
| Compound of Example 138 | 1.2 |
| Compound of Example 139 | 0.47 |
| Compound of Example 140 | 0.56 |
| Compound of Example 141 | 0.29 |
| Compound of Example 142 | 115 |
| Compound of Example 143 | 3.4 |
| Compound of Example 144 | 21 |
| Compound of Example 145 | 0.31 |
| Compound of Example 146 | 2.3 |
| Compound of Example 147 | 1.4 |
| Compound of Example 148 | 1.3 |
| Compound of Example 149 | 1.2 |
| Compound of Example 150 | 70 |
| Compound of Example 151 | 44 |
| Compound of Example 152 | 9.2 |
| Compound of Example 153 | 581 |
| Compound of Example 154 | 80 |
| Compound of Example 155 | 129 |
| Compound of Example 156 | 52 |
| Compound of Example 157 | 2.7 |
| Compound of Example 158 | 1.9 |
| Compound of Example 159 | 1.4 |
| Compound of Example 160 | 4.5 |
| Compound of Example 161 | 0.37 |
| Compound of Example 162 | 0.28 |

TABLE 2-continued

Biological activity of the compounds of the present invention.

| Compound | human 5HT$_6$ Ki (nM) |
|---|---|
| Compound of Example 163 | 1.2 |
| Compound of Example 164 | 0.74 |
| Compound of Example 165 | 0.81 |
| Compound of Example 166 | 0.41 |
| Compound of Example 167 | 7.5 |
| Compound of Example 168 | 3.3 |
| Compound of Example 169 | 27 |
| Compound of Example 170 | 17 |
| Compound of Example 171 | 0.36 |
| Compound of Example 172 | 0.28 |
| Compound of Example 173 | 15 |
| Compound of Example 174 | 5.1 |
| Compound of Example 175 | 151 |
| Compound of Example 176 | 46 |
| Compound of Example 177 | 747 |
| Compound of Example 178 | 454 |
| Compound of Example 179 | 3.7 |
| Compound of Example 180 | 1.9 |
| Compound of Example 181 | 284 |
| Compound of Example 182 | 365 |
| Compound of Example 183 | 0.42 |
| Compound of Example 184 | 0.35 |
| Compound of Example 185 | 1.5 |
| Compound of Example 186 | 0.77 |
| Compound of Example 187 | 1.1 |
| Compound of Example 188 | 0.50 |
| Compound of Example 189 | 1.2 |
| Compound of Example 190 | 0.68 |
| Compound of Example 191 | 1.9 |
| Compound of Example 192 | 1.1 |
| Compound of Example 193 | 0.86 |
| Compound of Example 194 | 0.50 |
| Compound of Example 195 | 4.6 |
| Compound of Example 196 | 1.2 |
| Compound of Example 197 | 4.3 |
| Compound of Example 198 | 4.7 |
| Compound of Example 199 | 1.8 |
| Compound of Example 200 | 0.75 |
| Compound of Example 201 | 1.4 |
| Compound of Example 202 | 0.72 |
| Compound of Example 203 | 2.9 |
| Compound of Example 204 | 4.8 |
| Compound of Example 205 | 1.8 |
| Compound of Example 206 | 1.6 |
| Compound of Example 207 | 0.91 |
| Compound of Example 208 | 0.69 |
| Compound of Example 209 | 0.53 |
| Compound of Example 210 | 1.0 |
| Compound of Example 211 | 1.6 |
| Compound of Example 212 | 0.57 |
| Compound of Example 213 | 4.8 |
| Compound of Example 214 | 3.0 |
| Compound of Example 215 | 1.8 |
| Compound of Example 216 | 0.80 |
| Compound of Example 217 | 4.7 |
| Compound of Example 218 | 0.46 |
| Compound of Example 219 | 1.7 |
| Compound of Example 220 | 0.50 |
| Compound of Example 221 | 3.3 |
| Compound of Example 222 | 0.56 |
| Compound of Example 223 | 2.4 |
| Compound of Example 224 | 0.99 |
| Compound of Example 225 | 0.53 |
| Compound of Example 226 | 1.0 |
| Compound of Example 227 | 0.68 |
| Compound of Example 228 | 0.96 |
| Compound of Example 229 | 1.8 |
| Compound of Example 230 | 1.3 |
| Compound of Example 231 | 0.31 |
| Compound of Example 232 | 9.6 |
| Compound of Example 233 | 3.7 |
| Compound of Example 234 | 4.9 |
| Compound of Example 235 | 0.42 |
| Compound of Example 236 | 18 |
| Compound of Example 237 | 7.1 |
| Compound of Example 238 | 0.85 |

TABLE 2-continued

Biological activity of the compounds of the present invention.

| Compound | human 5HT$_6$ Ki (nM) |
|---|---|
| Compound of Example 239 | 0.43 |
| Compound of Example 240 | 0.85 |
| Compound of Example 241 | 0.35 |
| Compound of Example 242 | 2.4 |
| Compound of Example 243 | 0.58 |
| Compound of Example 244 | 14 |
| Compound of Example 245 | 9.0 |
| Compound of Example 246 | 10 |
| Compound of Example 247 | 1.5 |

This table illustrates representative compounds tested for 5HT$_6$ affinity in the human binding assay. All compounds tested in the cell based assay showed antagonism against the human 5HT$_6$ receptor. Example 158 had 42% occupancy of the 5HT$_6$ receptor after oral dosing at 30 mg/kg using ex vivo receptor occupancy measurements in Sprague-Dawley rats.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed:
1. A compound of formula (I):

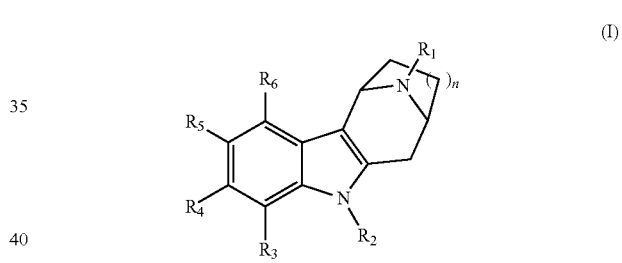

wherein:
n is an integer from 1 to 2; and
R$_1$ is independently H, C$_1$-C$_6$ alkyl, C$_2$-C$_6$ alkenyl, C$_2$-C$_6$ alkynyl, C$_1$-C$_6$ alkoxy, C$_3$-C$_6$ cycloalkyl, cycloalkylalkyl, aryl C$_1$-C$_6$ alkyl, mono or polycyclic aryl, or mono or polycyclic heteroaryl containing from 1 to 5 heteroatoms selected from the group consisting of nitrogen, sulfur, and oxygen, each one of R$_1$ optionally substituted from 1 to 3 times with substituents selected from the group consisting of halogen, OH, OR$_8$, —C(O)R$_8$, —C(O)OR$_8$, —C(O)NR$_8$R$_9$, —NR$_8$R$_9$, —SR$_8$, —S(O)R$_8$, —S(O)$_2$R$_8$, NH$_2$, CN, NO$_2$, C$_1$-C$_6$ alkyl, C$_2$-C$_6$ alkenyl, C$_2$-C$_6$ alkynyl, C$_3$-C$_6$ cycloalkyl, cycloalkylalkyl, mono or polycyclic aryl, and mono or polycyclic heteroaryl containing from 1 to 5 heteroatoms selected from the group consisting of nitrogen, sulfur, and oxygen;
R$_2$ is independently —S(O)R$_8$, —S(O)$_2$R$_8$, C$_1$-C$_6$ alkyl, straight or branched C$_2$-C$_6$ alkenyl, C$_3$-C$_6$ cycloalkyl, mono or polycyclic aryl, or mono or polycyclic heteroaryl containing from 1 to 5 heteroatoms selected from the group consisting of nitrogen, sulfur, and oxygen, each optionally substituted from 1 to 3 times with substituents selected from the group consisting of halogen, OH, NO$_2$, C$_1$-C$_6$ linear alkyl, and C$_2$-C$_6$ alkenyl;

$R_3$ and $R_6$ are independently H, halogen, $CF_3$, $CHF_2$, $CH_2F$, OH, $OR_8$, —$C(O)R_8$, —$C(O)OR_8$, —$C(O)NR_8R_9$, —O—$(CH_2)_p$—$C(O)NR_8R_9$, —$NR_8R_9$, —$SR_8$, —$S(O)R_8$, —$S(O)_2R_8$, $NH_2$, CN, $NO_2$, $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, mono or polycyclic aryl, wherein p is an integer from 0 to 6;

$R_4$ and $R_5$ are independently H, $C_1$-$C_6$ alkyl, halogen, or $R_7SO_2$—;

$R_7$ is independently a substituted or unsubstituted mono or polycyclic aryl or substituted or unsubstituted mono or polycyclic heteroaryl containing from 1 to 5 heteroatoms selected from the group consisting of oxygen, nitrogen, and sulfur, each one of $R_7$ optionally substituted from 1 to 4 times for each cyclic ring with substituents selected from the group consisting of H, OH, $OR_8$, —$C(O)R_8$, —$C(O)OR_8$, —$C(O)NR_8R_9$, —$NHR_8$, —$NR_8R_9$, —$SR_8$, —$S(O)R_8$, —$S(O)_2R_8$, $NH_2$, CN, $NO_2$, halogen, $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, mono or polycyclic aryl, and mono or polycyclic heteroaryl, each one of $R_7$ substitutents optionally substituted from 1 to 3 times with substitutents selected from the group consisting of halogen, H, OH, $OR_8$, —$C(O)R_8$, —$C(O)OR_8$, —$C(O)NR_8R_9$, —$NHR_8$, —$NR_8R_9$, —$SR_8$, —$S(O)R_8$, —$S(O)_2R_8$, $NH_2$, CN, $NO_2$, $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, and mono or polycyclic aryl;

$R_8$ and $R_9$ are independently H, $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, a monocyclic aryl or a monocyclic heteroaryl containing from 1-5 heteroatoms selected from the group consisting of nitrogen, oxygen, and sulfur each one of $R_8$ and $R_9$ optionally substituted from 1 to 3 times with substituents selected from the group consisting of halogen, OH, CN, $NO_2$, $NH_2$, H, $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, a monocyclic aryl, and a monocyclic heteroaryl; or $R_8$ and $R_9$ can combine to form a 4- to 7-membered heterocyclyl or a mono heteroaryl each containing from 1 to 5 heteroatoms selected from the group consisting of nitrogen, sulfur, and oxygen, wherein the heterocyclyl or heteroaryl are optionally substituted from 1 to 3 times with substituents selected from the group consisting of halogen, OH, CN, $NO_2$, $NH_2$, H, $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, and a monocyclic aryl, with the proviso that at least one of $R_4$ and $R_5$, but not both, is $R_7SO_2$—;

or an oxide thereof, or a pharmaceutically acceptable salt thereof.

2. The compound according to claim 1, wherein n is 1.

3. The compound according to claim 2, wherein
$R_1$ is H or $C_1$-$C_6$ alkyl;
$R_2$ is $C_1$-$C_6$ linear alkyl;
$R_3$ is H, $C_1$-$C_6$ alkyl, or $OR_8$;
$R_4$ and $R_6$ are H;
$R_5$ is $R_7SO_2$—;
$R_7$ is substituted or unsubstituted phenyl, substituted or unsubstituted heteroaryl, substituted or unsubstituted polycyclic aryl, or substituted or unsubstitued polycyclic heteroaryl; and
$R_8$ is $C_1$-$C_6$ alkyl.

4. The compound according to claim 3, wherein
$R_3$ is H, methyl, or ethyl.

5. The compound according to claim 2, wherein
$R_1$ is H or $C_1$-$C_6$ alkyl;
$R_2$ is $C_1$-$C_6$ linear alkyl;

$R_3$, $R_4$, and $R_6$ are H; and
$R_5$ is $R_7SO_2$—.

6. The compound according to claim 5, wherein $R_1$ is methyl.

7. The compound according to claim 5, wherein $R_1$ is H.

8. The compound according to claim 2, wherein
$R_1$ is H or $C_1$-$C_6$ alkyl;
$R_2$ is $C_1$-$C_6$ linear alkyl;
$R_3$ is Br, Cl, F, or I;
$R_4$ and $R_6$ are H; and
$R_5$ is $R_7SO_2$—.

9. The compound according to claim 1, wherein n is 2.

10. The compound according to claim 9, wherein
$R_1$ is H or $C_1$-$C_6$ alkyl;
$R_2$ is $C_1$-$C_6$ alkyl;
$R_3$, $R_4$, and $R_6$ are H, $C_1$-$C_6$ alkyl, or $OR_8$; and
$R_5$ is $R_7SO_2$—.

11. The compound according to claim 1, wherein
n is 1
$R_1$ is H or $C_1$-$C_6$ alkyl;
$R_2$ is $C_1$-$C_6$ linear alkyl;
$R_3$, $R_5$ and $R_6$ are H; and
$R_4$ is $R_7SO_2$—.

12. The compound according to claim 1, wherein
n is 2
$R_1$ is H or $C_1$-$C_6$ alkyl;
$R_2$ is $C_1$-$C_6$ linear alkyl;
$R_3$, $R_5$ and $R_6$ are H; and
$R_4$ is $R_7SO_2$—.

13. The compound according to claim 1 which has the formula (Ia):

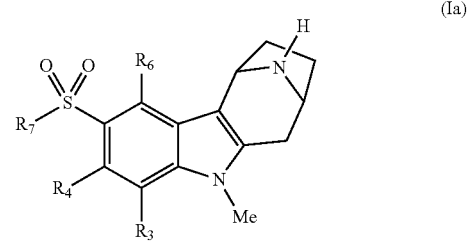

(Ia)

wherein
$R_3$ is H, Me, Et, or $OR_8$,
$R_4$ is H;
$R_6$ is H;
$R_7$ is substituted or unsubstituted phenyl, substituted or unsubstituted heteroaryl, substituted or unsubstituted polycyclic aryl, or substituted or unsubstituted polycyclic heteroaryl; and
$R_8$ is Me or Et.

14. The compound according to claim 1, wherein $R_7$ is a substituted or unsubstituted monocyclic aryl.

15. The compound according to claim 14, wherein the monocyclic aryl is a substituted or unsubstituted phenyl.

16. The compound according to claim 1, wherein $R_7$ is a substituted or unsubstituted polycyclic aryl.

17. The compound according to claim 16, wherein the substituted or unsubstituted polycyclic aryl is selected from the group consisting of naphthyl, azulenyl, fluorenyl, phenanthrenyl, anthracenyl, pyrenyl, triphenylenyl, chrysenyl, and naphthacenyl.

18. The compound according to claim 1, wherein $R_7$ is a substituted or unsubstituted monocyclic heteroaryl.

19. The compound according to claim 18, wherein the substituted or unsubstituted monocyclic heteroaryl is selected from the group consisting of pyrrolyl, pyrazolyl, imidazolyl, triazolyl, furyl, thiophenyl, oxazolyl, isoxazolyl, thiazolyl, isothiazolyl, oxadiazolyl, thiadiazolyl, pyridyl, pyrazinyl, pyrimidinyl, pyridazinyl, and triazinyl.

20. The compound according to claim 1 wherein $R_7$ is a substituted or unsubstituted polycyclic heteroaryl.

21. The compound according to claim 20, wherein the substituted or unsubstituted polycyclic heteroaryl is selected from the group consisting of thienopyrrolyl, furopyrrolyl, indolyl, azaindolyl, isoindolyl, indolinyl indolizinyl, indazolyl, benzimidazolyl, imidazopyridinyl, benzotriazolyl, benzoxazolyl, benzoxadiazolyl, benzothiazolyl, pyrazolopyridinyl, triazolopyridinyl, thienopyridinyl, benzothiadiazolyl, benzofuyl, benzothiophenyl, quinolinyl, isoquinolinyl, tetrahydroquinolinyl, tetrahydroisoquinolinyl, cinnolinyl, quinazolinyl, quinolizilinyl, phthalazinyl, benzotriazinyl, chromenyl, and naphthyridinyl.

22. The compound according to claim 1, wherein the compound is present in the form of a pharmaceutical acceptable salt.

23. The compound according to claim 1, wherein the compound is present in the form of an oxide.

24. The compound according to claim 1, wherein the compound is a (+)-stereoisomer.

25. The compound according to claim 1, wherein the compound is a (−)-stereoisomer.

26. A process for preparation of a product compound of formula (I):

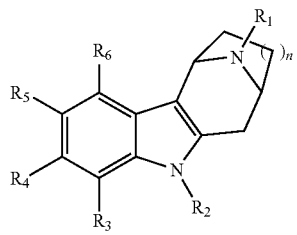

wherein n is an integer from 1 to 2; and $R_1$ is independently H, $C_1$-$C_6$ alkyl, $C_2$-$C_6$ alkenyl, $C_2$-$C_6$ alkynyl, $C_1$-$C_6$ alkoxy, $C_3$-$C_6$ cycloalkyl, $C_4$-$C_7$ cycloalkylalkyl, aryl $C_1$-$C_6$ alkyl, mono or polycyclic aryl, or mono or polycyclic heteroaryl containing from 1 to 5 heteroatoms selected from the group consisting of nitrogen, sulfur, and oxygen, each one of $R_1$ optionally substituted from 1 to 3 times with substituents selected from the group consisting of halogen, OH, $OR_8$, —C(O)$R_8$, —C(O)O$R_8$, —C(O)N$R_8R_9$, —NH$R_8$, —N$R_8R_9$, —S$R_8$, —S(O)$R_8$, —S(O)$_2R_8$, NH$_2$, CN, NO$_2$, $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, mono or polycyclic aryl, and mono or polycyclic heteroaryl containing from 1 to 5 heteroatoms selected from the group consisting of nitrogen, sulfur, and oxygen;

$R_2$ is independently —C(O)$R_8$, —C(O)O$R_8$, —C(O)N$R_8R_9$, —S(O)$R_8$, —S(O)$_2R_8$, $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, aryl $C_1$-$C_6$ alkyl, mono or polycyclic aryl, or mono or polycyclic heteroaryl containing from 1 to 5 heteroatoms selected from the group consisting of nitrogen, sulfur, and oxygen, each optionally substituted from 1 to 3 times with substituents selected from the group consisting of halogen, OH, NH$_2$, CN, NO$_2$, $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, mono or polycyclic aryl, and mono or polycyclic heteroaryl;

$R_3$ and $R_6$ are independently H, halogen, CF$_3$, CHF$_2$, CH$_2$F, OH, $OR_8$, —C(O)$R_8$, —C(O)O$R_8$, —C(O)N$R_8R_9$, —O—(CH$_2$)$_p$—C(O)N$R_8R_9$, —NH$R_8$, —N$R_8R_9$, —S$R_8$, —S(O)$R_8$, —S(O)$_2R_8$, NH$_2$, CN, NO$_2$, $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, mono or polycyclic aryl, wherein p is an integer from 0 to 6;

$R_4$ and $R_5$ are independently H, $C_1$-$C_6$ alkyl, halogen, or $R_7SO_2$—;

$R_7$ is independently a substituted or unsubstituted mono or polycyclic aryl or substituted or unsubstituted mono or polycyclic heteroaryl containing from 1 to 5 heteroatoms selected from the group consisting of oxygen, nitrogen, and sulfur, each one of $R_7$ optionally substituted from 1 to 4 times for each cyclic ring with substituents selected from the group consisting of H, OH, $OR_8$, —C(O)$R_8$, —C(O)O$R_8$, —C(O)N$R_8R_9$, —NH$R_8$, —N$R_8R_9$, —S$R_8$, —S(O)$R_8$, —S(O)$_2R_8$, NH$_2$, CN, NO$_2$, halogen, $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, mono or polycyclic aryl, and a mono or polycyclic heteroaryl, each one of substituents optionally substituted from 1 to 3 times with substitutents selected from the group consisting of halogen, H, OH, $OR_8$, —C(O)$R_8$, —C(O)O$R_8$, —C(O)N$R_8R_9$, —NH$R_8$, —N$R_8R_9$, —S$R_8$, —S(O)$R_8$, —S(O)$_2R_8$, NH$_2$, CN, NO$_2$, $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, and mono or polycyclic aryl;

$R_8$ and $R_9$ are independently H, $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, a monocyclic aryl or a monocyclic heteroaryl containing from 1-5 heteroatoms selected from the group consisting of nitrogen, oxygen, and sulfur each one of $R_8$ and $R_9$ optionally substituted from 1 to 3 times with substituents selected from the group consisting of halogen, OH, CN, NO$_2$, NH$_2$, H, $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, a monocyclic aryl, and a monocyclic heteroaryl; or $R_8$ and $R_9$ can combine to form a 4- to 7-membered heterocyclyl or a mono heteroaryl each containing from 1 to 5 heteroatoms selected from the group consisting of nitrogen, sulfur, and oxygen, wherein the heterocyclyl or heteroaryl are optionally substituted from 1 to 3 times with substituents selected from the group consisting of halogen, OH, CN, NO$_2$, NH$_2$, H, $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, and a monocyclic aryl, with the proviso that at least one of $R_4$ and $R_5$, but not both, is $R_7SO_2$—;

or an oxide thereof, or a pharmaceutically acceptable salt thereof said process comprising:

providing a first intermediate having the structure:

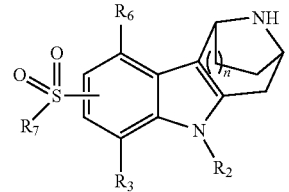

and
reacting a first intermediate with an electrophile R₁Z under conditions effective to form the compound of formula (I), wherein Z is a leaving group.

27. The process according to claim 26 further comprising:
providing a sulfonyl epiminocycloalkyl[b]indole having the structure:

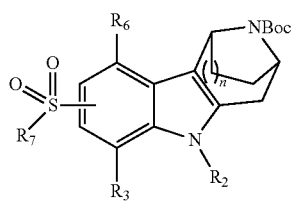

and
deprotecting the bridged amino group of a sulfonyl epiminocycloalkyl[b]indole under acidic conditions effective to form the first intermediate.

28. The process according to claim 27, wherein said deprotecting under the acidic conditions is carried out with hydrochloric acid, hydrobromic acid, hydrofluoric acid, hydroboric acid, trifluoroacetic acid, or sulfuric acid.

29. The process according to claim 27, wherein said providing a sulfonyl epiminocycloalkyl[b]indole comprises:
reacting a second intermediate having the structure:

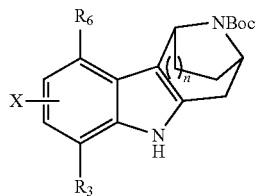

with R₂Y, wherein Y is a leaving group, and a base to produce a third intermediate having the structure:

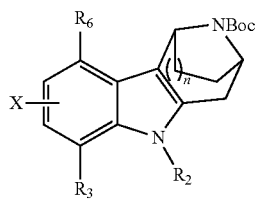

and
subjecting the third intermediate to a reaction with arylsulfonyl salt under conditions effective to produce the sulfonyl epiminocycloalkyl[b]indole, wherein X is a leaving group.

30. The process according to claim 29, wherein said subjecting is carried out with a palladium catalyst selected from the group consisting of bis(benzonitrile) palladium (II) chloride, palladium diacetate, palladium dibenzylidene acetone, tetrakis(triphenylphosphine) palladium, bis(triphenylphosphine) palladium (II) dichloride, bis(diphenylphosphineferrocene) palladium (II) dichloride, and bis(diphenylphosphineferrocene) palladium.

31. The process according to claim 29, wherein the aryl sulfonyl salt is prepared by reacting an arylsulfonyl chloride having the structure:

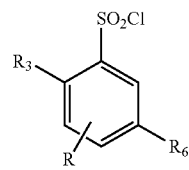

with Na₂SO₃ in presence of a base.

32. The process according to claim 31, wherein the base is selected from the group consisting of sodium hydroxide and sodium bicarbonate.

33. The process according to claim 29, wherein Y is a radical selected from the group consisting of halo, mesylate, tosylate, triflate, and acetate.

34. The process according to claim 29 further comprising:
selectively protecting a fourth intermediate having the structure:

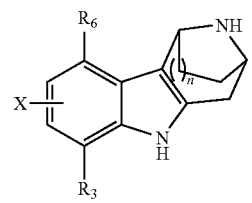

by reacting it with Boc group containing compound under conditions effective to form the second intermediate.

35. The process according to claim 34 further comprising:
reacting a hydrazine having the structure:

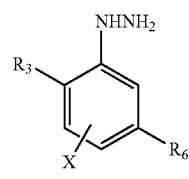

with a ketone having structure:

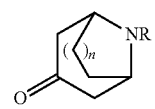

wherein R is H or a protective group under conditions effective to form the fourth intermediate.

36. The process according to claim 35 further comprising:
reacting an aniline having the structure:

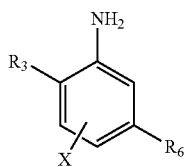

with a nitrite under conditions effective to form the hydrazine.

37. The process according to claim 36, wherein said reacting is carried out with a Lewis acid selected from the group consisting of titanium tetrachloride, aluminum chloride, boron trifluoride, boron tribromide, dimethylboron bromide, phosphorous pentachloride, tin dichloride, and tin tetrachloride.

38. The method according to claim 36, wherein the nitrite is selected from the group consisting of sodium nitrite, potassium nitrite, and lithium nitrite.

39. The process according to claim 36 further comprising:
reacting a nitroarene having the structure:

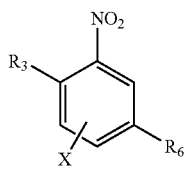

with a reducing agent under conditions effective to form the amine.

40. The process according to claim 27 further comprising:
sulfonylating a third intermediate having the structure:

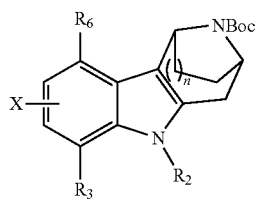

in presence of an organolithium and sulfur dioxide under conditions effective to produce a lithium sulfinate intermediate having the structure:

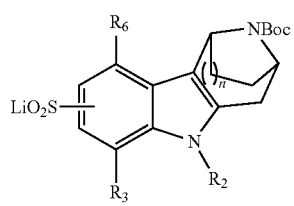

and subjecting the lithium sulfinate-intermediate to an acylation or heteroarylation with $R_7X$ in presence of a palladium catalyst under conditions effective to produce the sulfonyl epiminocycloalkyl[b]indole.

41. The process according to claim 40, wherein the organolithium is selected from the group, n-butyllithium, t-butyllithium, sec-butyllithium, phenyl lithium, and lithium disopropyl amide.

42. The process according to claim 40, wherein X is selected from the group consisting of chloro, bromo, iodo, and triflyl.

43. The process according to claim 27 further comprising:
halogenating a lithium sulfinate-intermediate having the structure:

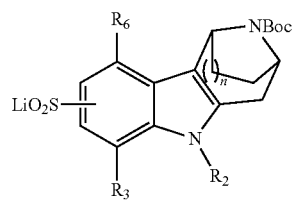

under conditions effective to produce a halosulfonyl epiminocycloalkyl[b]indole having the structure:

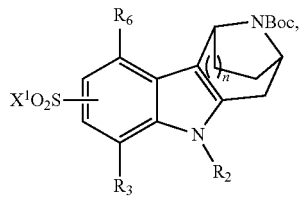

wherein $X^1$ is Cl, Br, or I;
and
arylating the halosulfonyl epiminocycloalkyl[b]indole under conditions effective to produce the sulfonyl epiminocycloalkyl[b]indole.

44. The process according to claim 43, wherein said halogenating is carried out with an agent selected from the group consisting of N-bromosuccinimide, N-chlorosuccinimide, and N-iodosuccinimide.

45. The process according to claim 43, wherein said halogenating is carried out in an organic solvent which is polar, non polar, protic or aprotic.

46. The process according to claim 26, wherein Z is selected from the group consisting of halo, mesylate, tosylate, triflate, and acetate.

47. A process for resolution of diastereomers comprising:
providing a mixture of the diastereomers of the compound of formula (II)

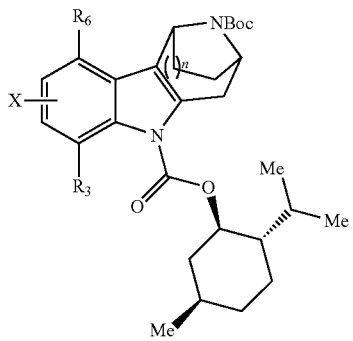

(II)

wherein:

R₃ and R₆ are independently H, halogen, CF₃, CHF₂, CH₂F, OH, OR₈, —C(O)R₈, —C(O)OR₈, —C(O)NR₈R₉, —NR₈R₉, —SR₈, —S(O)R₈, —S(O)₂R₈, NH₂, CN, NO₂, $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, mono or polycyclic aryl; and X is independently chloro, bromo, iodo, or triflyl; and subjecting the mixture to a resolution procedure under conditions effective to separate the diastereomers of the compound of formula (II) from one another.

48. The process according to claim 47, wherein said providing comprises:

reacting a compound of formula (III):

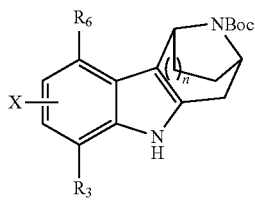

(III)

and a cyclohexyl chloroformate having the structure:

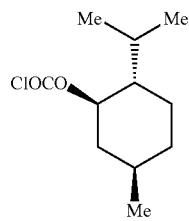

under conditions effective to form the mixture of the diastereomers of the compound of formula (II).

49. The process according to claim 47 further comprising:

reacting one of the diastereomers of the compound of formula (II) under conditions effective to form the (−) enantiomer of a compound of formula (III)

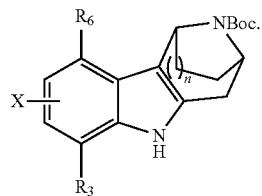

(III)

50. The process according to claim 47 further comprising:

reacting one of the diastereomers of the compound of formula (II) under conditions effective to form a single diastereomer of the compound of formula (IV):

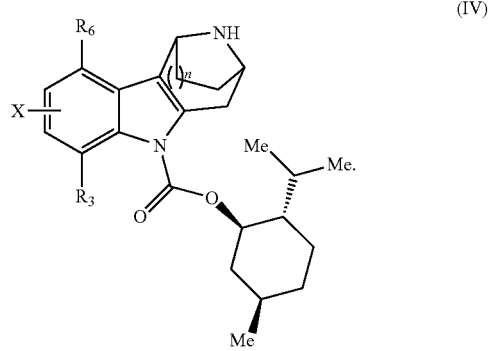

(IV)

51. The process according to claim 50 further comprising:

protecting the single diastereomer of the compound of formula (IV) under conditions effective to form a single diastereomer of the compound of formula (II).

52. The process according to claim 51 further comprising:

reacting the single diastereomer of the compound of formula (II) under conditions effective to form the (+) enantiomer of the compound of formula (III)

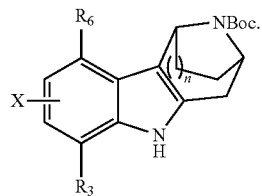

(III)

53. The process of claim 26, wherein R₂ is independently —S(O)R₈, —S(O)₂R₈, $C_1$-$C_6$ linear alkyl, straight or branched $C_2$-$C_6$ alkenyl, $C_3$-$C_6$ cycloalkyl, mono or polycyclic aryl, or mono or polycyclic heteroaryl containing from 1 to 5 heteroatoms selected from the group consisting of nitrogen, sulfur, and oxygen, each optionally substituted from 1 to 3 times with substituents selected from the group consisting of halogen, OH, NO₂, $C_1$-$C_6$ alkyl, and $C_2$-$C_6$ alkenyl.

\* \* \* \* \*